(12) United States Patent
Himmelsbach et al.

(10) Patent No.: US 8,859,580 B2
(45) Date of Patent: Oct. 14, 2014

(54) ARYL- AND HETEROARYLCARBONYL DERIVATIVES OF BENZOMORPHANES AND RELATED SCAFFOLDS, MEDICAMENTS CONTAINING SUCH COMPOUNDS AND THEIR USE

(75) Inventors: Frank Himmelsbach, Mittelbiberach (DE); Matthias Eckhardt, Biberach (DE); Bradford S. Hamilton, Biberach (DE); Armin Heckel, Biberach (DE); Joerg Kley, Mittelbiberach (DE); Thorsten Lehmann-Lintz, Ochsenhausen (DE); Herbert Nar, Ochsenhausen (DE); Stefan Peters, Biberach (DE); Annette Schuler-Metz, Ulm (DE); Matthias Zentgraf, Biberach (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 568 days.

(21) Appl. No.: 12/742,680

(22) PCT Filed: Nov. 14, 2008

(86) PCT No.: PCT/EP2008/065577
§ 371 (c)(1),
(2), (4) Date: Jul. 12, 2010

(87) PCT Pub. No.: WO2009/063061
PCT Pub. Date: May 22, 2009

(65) Prior Publication Data
US 2011/0190262 A1    Aug. 4, 2011

(30) Foreign Application Priority Data

Nov. 16, 2007 (EP) .................................. 07120914
Dec. 21, 2007 (EP) .................................. 07123942
Apr. 24, 2008 (EP) .................................. 08155137

(51) Int. Cl.
| | |
|---|---|
| C07D 221/26 | (2006.01) |
| C07D 417/06 | (2006.01) |
| C07D 401/06 | (2006.01) |
| C07D 471/08 | (2006.01) |
| C07D 498/08 | (2006.01) |
| C07D 413/14 | (2006.01) |
| C07D 413/06 | (2006.01) |
| C07D 405/06 | (2006.01) |
| C07D 401/14 | (2006.01) |
| C07D 451/06 | (2006.01) |
| C07D 403/06 | (2006.01) |

(52) U.S. Cl.
CPC ............ *C07D 221/26* (2013.01); *C07D 417/06* (2013.01); *C07D 401/06* (2013.01); *C07D 471/08* (2013.01); *C07D 498/08* (2013.01); *C07D 413/14* (2013.01); *C07D 413/06* (2013.01); *C07D 405/06* (2013.01); *C07D 401/14* (2013.01); *C07D 451/06* (2013.01); *C07D 403/06* (2013.01)
USPC .............................................. 514/295; 546/97

(58) Field of Classification Search
CPC ........................... C07D 221/26; C07D 451/00
USPC .............................................. 514/295; 546/97
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 3,474,106 A | 10/1969 | Ziering et al. | |
| 3,539,637 A | 11/1970 | Clarke, Jr. et al. | |
| 3,703,529 A | 11/1972 | Cavalla et al. | |
| 3,823,150 A | 7/1974 | Merz et al. | |
| 3,856,795 A | 12/1974 | Yardley | |
| 3,919,047 A * | 11/1975 | Vidic et al. | 435/122 |
| 3,931,194 A | 1/1976 | Merz et al. | |
| 3,981,874 A | 9/1976 | Merz et al. | |
| 4,009,171 A | 2/1977 | Albertson | |
| 4,043,927 A | 8/1977 | Duling et al. | |

(Continued)

FOREIGN PATENT DOCUMENTS

| | | | |
|---|---|---|---|
| CA | 1049008 A1 | 2/1979 | |
| CA | 1049511 A1 | 2/1979 | |

(Continued)

OTHER PUBLICATIONS

Gutkowska et al. (Acta Poloniae Pharmaceutica 1982, 39, p. 61-64).*

(Continued)

*Primary Examiner* — Bong-Sook Baek
(74) *Attorney, Agent, or Firm* — Michael P. Morris; David L. Kershner

(57) ABSTRACT

The present invention relates to compounds defined by formula I

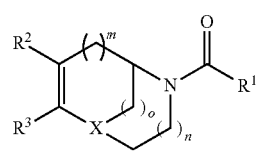

wherein the groups $R^1$ to $R^3$, X, m, n and o are defined as in claim 1, possessing valuable pharmacological activity. Particularly the compounds are inhibitors of 11β-hydroxysteroid dehydrogenase (HSD) 1 and thus are suitable for treatment and prevention of diseases which can be influenced by inhibition of this enzyme, such as metabolic diseases, in particular diabetes type 2, obesity and dyslipidemia.

9 Claims, No Drawings

(56) References Cited

U.S. PATENT DOCUMENTS

| | | | |
|---|---|---|---|
| 4,108,857 A * | 8/1978 | Albertson | 546/97 |
| 4,166,174 A | 8/1979 | Tanaka et al. | |
| 4,268,673 A | 5/1981 | Akkerman et al. | |
| 5,354,758 A | 10/1994 | Lawson et al. | |
| 5,607,941 A | 3/1997 | Merz et al. | |
| 6,145,103 A | 11/2000 | Typaldos et al. | |
| 6,368,816 B2 | 4/2002 | Walker et al. | |
| 6,838,253 B2 | 1/2005 | Walker et al. | |
| 6,946,487 B2 | 9/2005 | Walker et al. | |
| 7,087,400 B2 | 8/2006 | Walker et al. | |
| 7,122,531 B2 | 10/2006 | Walker et al. | |
| 7,122,532 B2 | 10/2006 | Walker et al. | |
| 7,129,231 B2 | 10/2006 | Walker et al. | |
| 7,897,773 B2 | 3/2011 | Aletru et al. | |
| 8,048,825 B2 | 11/2011 | Hino et al. | |
| 2006/0089349 A1 | 4/2006 | Gundertofte et al. | |
| 2006/0194780 A1 | 8/2006 | Nargund et al. | |
| 2009/0170894 A1 | 7/2009 | Aletru et al. | |
| 2010/0256363 A1 | 10/2010 | Xu | |
| 2011/0015157 A1 | 1/2011 | Claremon et al. | |
| 2011/0028445 A1 | 2/2011 | Eckhardt et al. | |
| 2011/0112062 A1 | 5/2011 | Claremon et al. | |
| 2011/0136800 A1 | 6/2011 | Eckhardt et al. | |
| 2011/0190262 A1 | 8/2011 | Himmelsbach et al. | |
| 2011/0263583 A1 | 10/2011 | Claremon et al. | |
| 2011/0269736 A1 | 11/2011 | Eckhardt et al. | |
| 2011/0269791 A1 | 11/2011 | Peters et al. | |
| 2011/0275595 A1 | 11/2011 | Eckhardt et al. | |
| 2012/0108579 A1 | 5/2012 | Renz et al. | |
| 2012/0115853 A1 | 5/2012 | Eckhardt et al. | |
| 2012/0172357 A1 | 7/2012 | Himmelsbach | |

FOREIGN PATENT DOCUMENTS

| | | |
|---|---|---|
| CA | 1056377 A1 | 6/1979 |
| CA | 1107280 A1 | 8/1981 |
| DE | 2105743 A1 | 8/1972 |
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 10034623 A1 | 1/2002 |
| EP | 0847275 A1 | 6/1998 |
| EP | 1864971 A1 | 12/2007 |
| EP | 1935420 A1 | 6/2008 |
| FR | 2796940 A1 | 2/2001 |
| GB | 1077711 A | 8/1967 |
| JP | 2003057815 A | 2/2003 |
| JP | 2006342093 A | 12/2006 |
| JP | 2007015930 A | 1/2007 |
| JP | 2007016223 A | 1/2007 |
| JP | 2007140188 A | 6/2007 |
| JP | 2007254409 A | 10/2007 |
| JP | 2007269721 A | 10/2007 |
| JP | 2011519374 A | 7/2011 |
| WO | 9413641 A1 | 6/1994 |
| WO | 9637494 A1 | 11/1996 |
| WO | 9707789 A1 | 3/1997 |
| WO | 9822462 A1 | 5/1998 |
| WO | 9852940 A1 | 11/1998 |
| WO | 0155063 A1 | 8/2001 |
| WO | 03097608 A2 | 11/2003 |
| WO | 2004089896 A1 | 10/2004 |
| WO | 2005108360 A1 | 11/2005 |
| WO | 2005108361 A1 | 11/2005 |
| WO | 2006024628 A1 | 3/2006 |
| WO | 2006040329 A1 | 4/2006 |
| WO | 2006044174 A2 | 4/2006 |
| WO | 2007051810 A2 | 5/2007 |
| WO | 2007076055 A2 | 7/2007 |
| WO | 2007081570 A2 | 7/2007 |
| WO | 2007124337 A1 | 11/2007 |
| WO | 2007127693 A1 | 11/2007 |
| WO | 2007127763 A2 | 11/2007 |
| WO | 2008000951 A2 | 1/2008 |
| WO | 2008059948 A1 | 5/2008 |
| WO | 2008106128 A2 | 9/2008 |
| WO | 2009017664 A1 | 2/2009 |
| WO | 2009017671 A1 | 2/2009 |
| WO | 2009061498 A1 | 5/2009 |
| WO | 2009063061 A2 | 5/2009 |
| WO | 2009100872 A1 | 8/2009 |
| WO | 2009102428 A2 | 8/2009 |
| WO | 2009102460 A2 | 8/2009 |
| WO | 2009117109 A1 | 9/2009 |
| WO | 2009134400 A1 | 11/2009 |
| WO | 2009138386 A2 | 11/2009 |
| WO | 2010010157 A2 | 1/2010 |
| WO | 2010010174 A1 | 1/2010 |
| WO | 2010011314 A1 | 1/2010 |
| WO | 2010023161 A1 | 3/2010 |
| WO | 2010046445 A2 | 4/2010 |
| WO | 2010139673 A1 | 12/2010 |
| WO | 2011057054 A1 | 5/2011 |
| WO | 2012061708 A1 | 5/2012 |

OTHER PUBLICATIONS

Kametani et al. (Chem Pharm Bull, 13(3):295-299, 1965).*
Serajuddin (Advanced Drug Delivery Reviews 59:603-616, 2007).*
Abstract in English for JP2007140188 publication date 2007.
International Search Report for PCT/EP2008/065577 mailed May 8, 2009.
Caplus-133:4656—Anantanarayan, A. et. al., "Preparation of heteroarylpyrazoles as P38 kinase inhibitors". 2000.
Caplus-147:134403, Hembrough, T.A., et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
ChemAbstract—Accession No. 958599-31-0, Chemical Abstracts Service, Columbus, Ohio, Source: Emory MLSC database, Dec. 2007.
ChemAbstract—Accession No. 958625-83-7, Chemical Abstracts Service, Columbus, Ohio, Source: Emory MLSC database, Dec. 2007.
ChemAbstract—Accession No. 958629-14-6, Chemical Abstracts Service, Columbus, Ohio, Source: Emory MLSC database, Dec. 2007.
ChemAbstract—Accession No. 958629-22-6, Chemical Abstracts Service, Columbus, Ohio, Source: Emory MLSC database, Dec. 2007.
ChemAbstract—Accession No. 958629-39-5, Chemical Abstracts Service, Columbus, Ohio, Source: Emory MLSC database, Dec. 2007.
ChemAbstract—Accession No. 958696-32-7, Chemical Abstracts Service, Columbus, Ohio, Source: Emory MLSC database, Dec. 2007.
ChemAbstract—Accession No. 958696-39-4, Chemical Abstracts Service, Columbus, Ohio, Source: Emory MLSC database, Dec. 2007.
ChemAbstract—Accession No. 958700-63-5, Chemical Abstracts Service, Columbus, Ohio, Source: Emory MLSC database, Dec. 2007.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
WO09017664 Published Feb. 5, 2009. Applicant: Vitae Pharmaceuticals, Inc. Inventor: D. A. Claremon et al. Also published as US Publication US2011015157 and US201025636.
International Search Report and Written Opinion for PCT/US2012/050679 mailed Oct. 31, 2012.
Olesen, Preben H.; the Use of Bioisosteric Groups in Lead Optimization; Current Opinion in Drug Discovery & Development (2001) vol. 4, No. 4 pp. 471-478.

(56) References Cited

OTHER PUBLICATIONS

Thornber, C.W.; Isosterism and Molecular Modification in Drug Design; Chem. Soc, Rev (1979) vol. 8 pp. 563-580.

De Luis et al., Control of Metabolic Syndrome with Metformin in Obese Type 2 Diabetes Mellitus Patients, Diabetes Research and Clinical Practice, 2000, vol. 50, Suppl. 1, pp. S51-S52.

Patani, George A. et al., "Bioisosterism: a Rational Approach in Drug Design" Chem. Rev. (1996) vol. 96, pp. 3147-3176.

Abstract in English for German DE10034623, publication date Jan. 31, 2002.

Abstract in English for German DE2105743, publication date Aug. 31, 1972.

Abstract in English for German DE2108954, publication date Sep. 7, 1972.

Abstract in English for JP2003057815, publication date Feb. 28, 2003.

Abstract in English for JP2006342093, publication date Dec. 21, 2006.

Abstract in English for JP2007016223, publication date Jan. 25, 2007.

Abstract in English for JP2007269721, publication date Oct. 18, 2007.

Bosch, J. et al., "Benzomorphan Related Compounds. A Versatile Method for the Synthesis of Heteromorphans." Heterocycles, 1980, vol. 14, No. 12, pp. 1983-1988.

Demarinis, R. M. et al., "a-Adrenergic Agents, 1. Direct-Acting a1 Agonists Related to Methoxannine." Journal of Medicinal Chemistry, 1981, vol. 24, No. 12, pp. 1432-1437.

Eberle, M. K. et al., "Carbocyclic Phenylhydrazines in the Fischer Indole Synthesis-II." Tetrahedron, 1973, vol. 29, No. 24, pp. 4049-4052.

Harno, E. et al., "Will treating diabetes with 11b-HSD1 inhibitors affect the HPA axis?" Trends in Endocrinology and Metabolism, 2010, vol. 21, No. 10, pp. 619-627.

Kametani, T. et al., "Azabenzomorphane and Related Compounds." Chem. Pharma. Bull., 1965, vol. 13, No. 3, pp. 295-299.

Ma, Z. et al., "A Concise Formal Synthesis of Unnatural (+)-Aphanorphine from (2S,4R)-4-Hydroxyproline." Synlett, 2007, No. 1, pp. 161-163.

Ma, Z. et al., "Formal Syntheses of (−)- and (+)-aphanorphine from (2S,4R)-4-hydroxyproline." Tetrahedron, 2007, 63, pp. 7523-7531.

Masamune, T. et al., "The Synthesis and the Exhaustive Methylation of the cis and trans Isomers of 1,2,3,4,4a,5,6,10b-Octahydrophenanthridine and 1,2,3,4,4a,5,6,10b-Octahydrobenzo[f]quinoline." Journal of Organic Chemistry, 1964, vol. 29, No. 6, pp. 1419-1424.

Mehta, P. et al., "Synthesis of cis & trans-1-substituted 1,2,3,4,4a,5,11,11a-octahydro-6H-pyrido[3,2-b]carbazoles, 4-substituted 1,2,3,4,4a,5,6,11c-octa-hydro-7H-pyrido[2,3,-c]carbazoles, cis-4-methyl-1,2,3,4,4a,5,6,12b-octa-hydro-7H-pyrido[2,3-c]acridine & cis-1-methyl-1,2,3,4,4a,5,12,12a-octa-hydro-6H-pyrido[3,2-b]-acridine—A new class of potential antiparkinsonian agents." Indian Journal of Chemistry, 1991, vol. 30B, No. 2, pp. 213-221.

Rosenstock, J. "The 11-b-Hydroxysteroid Dehydrogenase Type 1 Inhibitor INCB13739 Improves Hyperglycemia in Patients With Type 2 Diabetes Inadequately Controlled by Metformin Monotherapy." Diabetes Care, 2010, vol. 33, No. 7, pp. 1516-1522.

Stewart, P. et al., "11b-Hydroxysteroid Dehydrogenase." Advances in Research and Applications, 1999, vol. 57, pp. 249-324.

Tadayyon, M. et al., "Insulin sensitisation in the treatment of Type 2 diabetes." Expert Opinion on Investigational Drugs, 2003, vol. 12, No. 3, pp. 307-324.

Yokoyama, N. et al., "Syntheses, Analgetic Activity, and Physical Dependence Capacity of 5-Phenyl-6,7-benzomorphan Derivatives." Journal of Medicinal Chemistry, 1979, vol. 22, No. 5, pp. 537-553.

* cited by examiner

ARYL- AND HETEROARYLCARBONYL DERIVATIVES OF BENZOMORPHANES AND RELATED SCAFFOLDS, MEDICAMENTS CONTAINING SUCH COMPOUNDS AND THEIR USE

The present invention relates to compounds derived from the following chemical scaffold which is structurally defined by the formula I

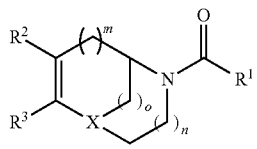

wherein the groups $R^1$ to $R^3$, X, m, n and o are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the enzyme 11β-hydroxysteroid dehydrogenase (HSD) 1 are proposed for the treatment of the metabolic syndrome, in particular diabetes type 2, obesity and dyslipidemia.

In the scientific publications *Acta Poloniae Pharmaceutica* 1982, 39, p. 61-64 and *Acta Poloniae Pharmaceutica* 1986, 43, p. 403-405 the syntheses of the following benzomorphanes, that may have various pharmacological activities, particularly analgetic activity, are described:

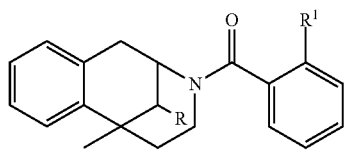

R = H, Me
$R^1$ = OAc, 2,3-dimethylphenylamino, phenylamino, ethylamino, 3-methylsulfanylphenylamino The scientific publication *Chem. Ber.* 1976, 109, p. 2657-2669 reports the following microbiological transformations of a benzomorphane:

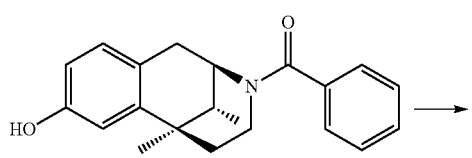

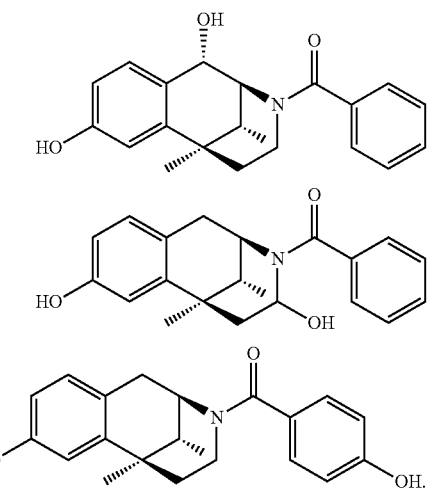

The scientific publication *Heterocycles* 1980, 14, p. 1983-1988 describes a method for the synthesis of the following heteromorphanes:

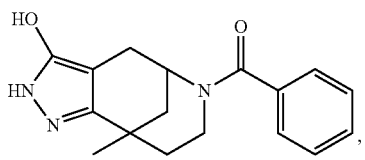

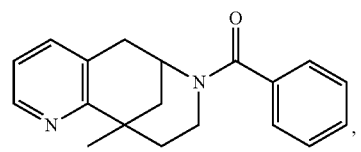

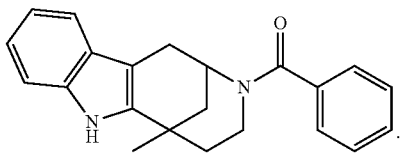

In the scientific publications *Tetrahedron* 2007, 63, p. 7523-7531 and *Synthesis* 2007, p. 161-163 the formal syntheses of (+)- and (−)-aphanorphine are reported that leads via the pure enantiomers of the following benzomorphane as intermediates:

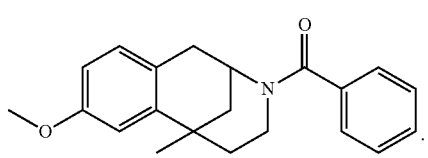 [SMILES: COc1ccc2c(c1)C1(C)CCN(C(=O)c3ccccc3)C(C2)C1]

The patent DE 23 38 369 describes a microbiological hydroxylation method for the preparation of benzomorphanes of the general formula

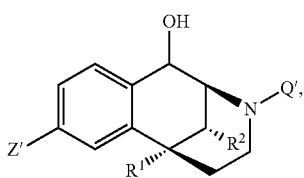

wherein $R^1$, $R^2$, Q', and Z' are as described therein.

In the WO 03/097608 opioid and opioid-like compounds of the general formula R-A-X wherein R, A and X are as defined therein, are described for the treatment and prevention of septic shock and other disorders. Inter alia A denotes benzomorphanes of the general formula

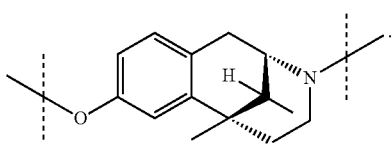

In the U.S. Pat. No. 4,108,857 derivatives of benzomorphanes of the general formula

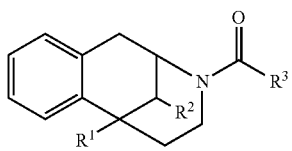

$R^1$ = lower alkyl
$R^2$ = H, lower alkyl
$R^3$ = inter alia pyridyl are described as compounds having anticonvulsant, central nervous system depressant and diuretic activity.

In the DE 23 54 002 derivatives of benzomorphanes of the general formula

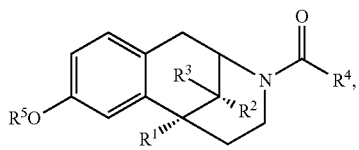

wherein $R^1$, $R^2$, $R^3$, and $R^5$ are as defined therein and $R^4$ is 2-methoxymethylfuran-3-yl or 3-methoxymethylfuran-2-yl, are described as intermediates for the preparation of the corresponding N-furanylmethyl-benzomorphanes.

In the DE 2 229 695 derivatives of benzomorphanes of the general formula

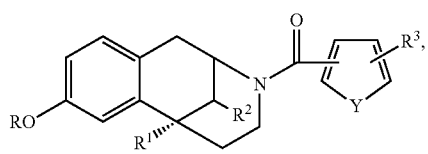

wherein R, $R^1$, $R^2$, $R^3$, and Y are as defined therein, are described as intermediates for the preparation of benzomorphanes that may be useful as analgesics and antitussives.

In the DE 2 108 954 derivatives of benzomorphanes of the general formula

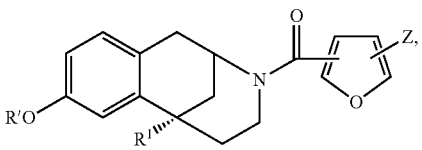

wherein R', $R^1$, and Z are as defined therein, are principally described as possible intermediates for the preparation of benzomorphanes that may have valuable therapeutic properties.

In the DE 2 105 743 derivatives of benzomorphanes of the general formula

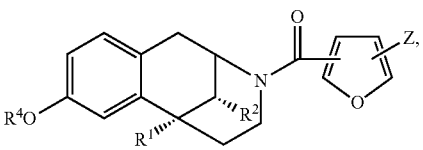

wherein $R^1$, $R^2$, $R^4$, and Z are as defined therein, are described as principle intermediates for the preparation of benzomorphanes that may have analgetic activity.

In the U.S. Pat. No. 3,703,529 tricyclic nitrogen-containing compounds of the general formula

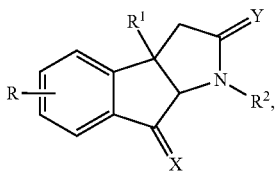

wherein R, $R^1$, $R^2$, X, and Y are as defined therein, that may be useful as anti-inflammatory and analgesic agents, are described.

The inventors are not aware that N-aryl- or heteroarylcarbonyl derivatives of benzomorphanes have been described as inhibitors of 11β-hydroxysteroid dehydrogenase (HSD) 1.

AIM OF THE INVENTION

The aim of the present invention is to find new benzomorphanes or related compounds, particularly those which are active with regard to the enzyme 11β-hydroxysteroid dehydrogenase (HSD) 1. A further aim of the present invention is to discover benzomorphanes or related compounds which have an inhibitory effect on the enzyme 11β-hydroxysteroid dehydrogenase (HSD) 1 in vitro and/or in vivo and possess suitable pharmacological and pharmacokinetic properties to use them as medicaments.

A further aim of the present invention is to provide new pharmaceutical compositions which are suitable for the prevention and/or treatment of metabolic disorders, particularly diabetes and dyslipidemia.

Other aims of the present invention will become apparent to the skilled man directly from the foregoing and following remarks.

OBJECT OF THE INVENTION

In a first aspect the present invention relates in its broadest embodiment to compounds derived from the following chemical scaffolds which are structurally defined by the formula I

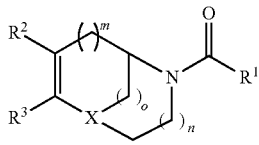

wherein $R^1$ denotes aryl or heteroaryl,
  while by aryl is meant phenyl or naphthyl and
  by heteroaryl is meant pyrrolyl, furanyl, thienyl, pyridyl, indolyl, benzofuranyl, benzothiophenyl, quinolinyl, isoquinolinyl, or
  pyrrolyl, furanyl, thienyl, pyridyl in which 1 or 2 CH are replaced by N, or
  indolyl, benzofuranyl, benzothiophenyl, quinolinyl, or isoquinolinyl, wherein 1 to 3 CH are replaced by N, or
  1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, indanyl, 1-oxo-indanyl, 2,3-dihydro-indolyl, 2,3-dihydro-1H-isoindolyl, 2,3-dihydro-2-oxo-indolyl, 2,3-dihydro-1-oxo-isoindolyl, 2,3-dihydrobenzo-furanyl, 2,3-dihydro-2-oxo-1H-benzimidazolyl, 2,3-dihydro-2-oxo-benzoxazolyl, benzo[1,3]dioxolyl, 2-oxo-benzo[1,3]dioxolyl, 1,2,3,4-tetrahydro-naphthyl, 1,2,3,4-tetrahydro-quinolinyl, 1,2,3,4-tetrahydro-2-oxo-quinolinyl, 1,2-dihydro-2-oxo-quinolinyl, 1,4-dihydro-4-oxo-quinolinyl, 1,2,3,4-tetrahydro-isoquinolinyl, 1,2,3,4-tetrahydro-1-oxo-isoquinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quina-zolinyl, 1,2,3,4-tetrahydro-2,4-dioxo-quinazolinyl, 1,2-dihydro-2-oxoquinoxalinyl, 1,2,3,4-tetrahydro-3-oxoquinoxalinyl, 1,2,3,4-tetrahydro-2,3-dioxoquinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxin-yl, or 3,4-dihydro-3-oxo-2H-benzo[1,4]oxazinyl,
  wherein the above-mentioned aryl or heteroaryl rings are optionally substituted with one $R^4$, one to four identical or different $R^5$, and one $R^6$, and all heteroaryl rings are attached to the carbonyl group via a carbon atom, $R^2$ and $R^3$ together with the double bond to which they are attached denote
  a benzo ring optionally substituted with $R^7$, $R^8$ and $R^9$,
  a pyrido ring optionally substituted with $R^7$, $R^8$ and $R^9$,
  a pyrrolo, furo, thieno, pyridazino, pyrimido or pyrazino ring optionally substituted with two substituents selected from $R^7$, $R^8$ and $R^9$,
  a pyrazolo, imidazo, oxazolo, thiazolo, isoxazolo, or isothiazolo ring optionally substituted with $R^7$, or
  a 1,2,3-triazolo ring optionally substituted with $C_{1-4}$-alkyl or with phenyl that is optionally additionally substituted with one to three $R^{10}$, $R^4$ denotes fluorine, chlorine, bromine, iodine,
  $C_{1-6}$-alkyl, $C_{2-6}$-alkenyl, $C_{2-6}$-alkynyl, hydroxy, $C_{1-4}$-alkyloxy,
  nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl,
  $C_{1-3}$-alkyl-carbonylamino, (het)aryl-carbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di -($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl) -piperazin-1-yl-carbonylamino, $C_{1-3}$-alkyl-sulfonylamino, aminosulfonylamino, $C_{1-3}$-alkyl -amino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonyl -amino, 4-($C_{1-3}$-alkyl)-piperazin-1-yl-sulfonylamino, ($C_{1-3}$-alkyloxy-carbonylamino)carbonylamino, (het)arylsulfonylamino, (het)aryl-$C_{1-3}$-alkyl-sulfonylamino,
  N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N -(aminocarbonyl)-$C_{1-3}$-alkylamino, N—($C_{1-3}$-alkyl-aminocarbonyl)-$C_{1-3}$-alkylamino, N-[di -($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino,
  oxo-imidazolidin-1-yl, 2,4-dioxo-imidazolidin-1-yl, 2,5-dioxo-imidazolidin-1-yl, 2-oxo -hexahydropyrimidin-1-yl, wherein the nitrogen atom in position 3 of the aforementioned groups is optionally substituted with methyl or ethyl,
  cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl -carbonyl, piperazin-1-yl-carbonyl, 4-($C_{1-3}$-alkyl)-piperazin-1-yl-carbonyl, (het)arylamino -carbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl,
  $C_{1-3}$-alkyl-carbonyl, (het)aryl-carbonyl,
  carboxy-$C_{1-3}$-alkyl, $C_{1-3}$-alkyloxy-carbonyl-$C_{1-3}$-alkyl, cyano-$C_{1-3}$-alkyl, aminocarbonyl -$C_{1-3}$-alkyl, $C_{1-3}$-alkyl-aminocarbonyl-$C_{1-3}$-alkyl, di-($C_{1-3}$-alkyl)-aminocarbonyl -$C_{1-3}$-alkyl, pyrrolidin-1-yl-carbonyl-$C_{1-3}$-alkyl, piperidin-1-yl-carbonyl-$C_{1-3}$-alkyl, morpholin-4-yl -carbonyl-$C_{1-3}$-alkyl, piperazin-1-yl-carbonyl-$C_{1-3}$-alkyl, 4-($C_{1-3}$-alkyl)-piperazin-1-yl -carbonyl-$C_{1-3}$-alkyl,
  carboxy-$C_{1-3}$-alkyloxy, $C_{1-3}$-alkyloxy-carbonyl-$C_{1-3}$-alkyloxy, cyano-$C_{1-3}$-alkyloxy, amino -carbonyl-$C_{1-3}$-alkyloxy, $C_{1-3}$-alkyl-aminocarbonyl-$C_{1-3}$-alkyloxy, di-($C_{1-3}$-alkyl)-amino -carbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, $C_{1-3}$-alkylsulfonyloxy, (het)aryl-sulfonyl, (het)arylsulfonyloxy, trifluoromethylsulfanyl, trifluoromethylsulfinyl, trifluoro-methylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yl-oxy, tetrahydro-furanyl-$C_{1-3}$-alkyloxy, tetrahydropyranyl-$C_{1-3}$-alkyloxy, wherein the above-mentioned azetidin-1-yl, pyrrolidin-1-yl and piperidin-1-yl moieties are optionally substituted with one or two groups selected from methyl, ethyl, methoxymethyl, hydroxy or methoxy, and, wherein the above-mentioned piperazin-1-yl and morpholin-4-yl moieties are optionally substituted with one or two groups selected from methyl, ethyl or methoxymethyl, and wherein the above-mentioned (het)aryl is phenyl, naphthyl, pyrrolyl, furanyl, thienyl, tetrazolyl, pyridyl, indolyl, benzofuranyl, benzothiophenyl, quinolinyl, isoquinolinyl, or pyrrolyl, furanyl, thienyl, pyridyl in which 1 or 2 CH are replaced by N, or indolyl, benzofuranyl, benzothiophenyl, quinolinyl, isoquinolinyl in which 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzo-furanyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, 3,4-dihydro-3-oxo-2H-benzo[1,4]oxazinyl, and wherein the above-mentioned (het)aryl groups are optionally substituted with one or two $R^{10}$ which may be identical or different, $R^5$ and $R^6$, which may be identical or different, denote halogen, $C_{1-3}$-alkyl, $C_{2-3}$-alkynyl, trifluormethyl, hydroxy, $C_{1-3}$-alkyloxy, cyano, or $R^5$ together with $R^6$, if bound to adjacent carbon atoms, may additionally be methylenedioxy, difluoromethylenedioxy, ethylenedioxy, $C_{3-5}$-alkylene, or $R^5$ together with $R^6$, if bound to adjacent carbon atoms, may form together with the carbon atoms to which they are attached, a pyrazolo, imidazo, oxazolo, thiazolo, isoxazolo, or isothiazolo ring, that optionally are substituted with $C_{1-3}$-alkyl, trifluoromethyl, amino, $C_{1-3}$-alkylamino, di-($C_{1-3}$-alkyl)amino, hydroxy, $C_{1-3}$-alkyloxy, $R^7$ denotes fluorine, chlorine, bromine, iodine, $C_{1-4}$-alkyl, hydroxy, $C_{1-4}$-alkyloxy, nitro, amino, $C_{1-4}$-alkylamino, di-($C_{1-4}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkyl)-pi-perazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-4}$-alkyl)-piperazin-1-yl, 3-oxo-4-($C_{1-4}$-alkyl)-piperazin-1-yl, $C_{1-4}$-alkyl-carbonylamino, (het)aryl-carbonylamino, (het)aryl-$C_{1-4}$-alkyl-carbonylamino, $C_{1-4}$-alkyloxy-carbonylamino, aminocarbonylamino, $C_{1-4}$-alkyl-aminocarbonylamino, di-($C_{1-4}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-4}$-alkyl)-piperazin-1-yl-carbonylamino, $C_{1-4}$-alkyl-sulfonylamino, aminosulfonylamino, $C_{1-4}$-alkyl-amino-sulfonylamino, di-($C_{1-4}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonyl-amino, 4-($C_{1-4}$-alkyl)-piperazin-1-yl-sulfonylamino, ($C_{1-4}$-alkyloxy-carbonylamino)-carbonylamino, (het)arylsulfonylamino, (het)aryl-$C_{1-4}$-alkyl-sulfonylamino, N—($C_{1-4}$-alkyl)-$C_{1-4}$-alkyl-carbonylamino, N—($C_{1-4}$-alkyl)-(het)arylcarbonylamino, N—($C_{1-4}$-alkyl)-(het)aryl-$C_{1-4}$-alkyl-carbonylamino, N—($C_{1-4}$-alkyl)-$C_{1-4}$-alkyloxy-carbonylamino, N-(aminocarbonyl)-$C_{1-4}$-alkylamino, N—($C_{1-4}$-alkyl-aminocarbonyl)-$C_{1-4}$-alkylamino, N—[di-($C_{1-4}$-alkyl)aminocarbonyl]-$C_{1-4}$-alkylamino, N—($C_{1-4}$-alkyl)-$C_{1-4}$-alkyl-sulfonylamino, N—($C_{1-4}$-alkyl)-(het)arylsulfonylamino, N—($C_{1-4}$-alkyl)-(het)aryl-$C_{1-4}$-alkyl-sulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl, cyano, (hydroxyimino)aminomethyl, ($C_{1-4}$-alkyloxyimino)aminomethyl, carboxy, $C_{1-4}$-alkyloxy-carbonyl, aminocarbonyl, $C_{1-4}$-alkyl-aminocarbonyl, di-($C_{1-4}$-alkyl)-amino-carbonyl, pyrrolidin-1-yl-carbonyl, piperidin-1-yl-carbonyl, morpholin-4-yl-carbonyl, piperazin-1-yl-carbonyl, 4-($C_{1-4}$-alkyl)-piperazin-1-yl-carbonyl, $C_{1-4}$-alkyl-carbonyl, (het)aryl-carbonyl, carboxy-$C_{1-4}$-alkyl, $C_{1-4}$-alkyloxy-carbonyl-$C_{1-4}$-alkyl, cyano-$C_{1-4}$-alkyl, aminocarbonyl-$C_{1-4}$-alkyl, $C_{1-4}$-alkyl-aminocarbonyl-$C_{1-4}$-alkyl, di-($C_{1-4}$-alkyl)-aminocarbonyl-$C_{1-4}$-alkyl, pyrrolidin-1-yl-carbonyl-$C_{1-4}$-alkyl, piperidin-1-yl-carbonyl-$C_{1-4}$-alkyl, morpholin-4-yl-carbonyl-$C_{1-4}$-alkyl, piperazin-1-yl-carbonyl-$C_{1-4}$-alkyl, 4-($C_{1-4}$-alkyl)-piperazin-1-yl-carbonyl-$C_{1-4}$-alkyl, carboxy-$C_{1-4}$-alkyloxy, $C_{1-4}$-alkyloxy-carbonyl-$C_{1-4}$-alkyloxy, cyano-$C_{1-4}$-alkyloxy, amino-carbonyl-$C_{1-4}$-alkyloxy, $C_{1-4}$-alkyl-aminocarbonyl-$C_{1-4}$-alkyloxy, di-($C_{1-4}$-alkyl)-amino-carbonyl-$C_{1-4}$-alkyloxy, pyrrolidin-1-yl-carbonyl-$C_{1-4}$-alkyl-oxy, piperidin-1-yl-carbonyl-$C_{1-4}$-alkyloxy, morpholin-4-yl-carbonyl-$C_{1-4}$-alkyl-oxy, piperazin-1-yl-carbonyl-$C_{1-4}$-alkyloxy, 4-($C_{1-4}$-alkyl)-piperazin-1-yl-carbonyl-$C_{1-4}$-alkyloxy, hydroxy-$C_{1-4}$-alkyl, $C_{1-4}$-alkyloxy-$C_{1-4}$-alkyl, amino-$C_{1-4}$-alkyl, $C_{1-4}$-alkylamino-$C_{1-4}$-alkyl, di-($C_{1-4}$-alkyl)-amino-$C_{1-4}$-alkyl, pyrrolidin-1-yl-$C_{1-4}$-alkyl, $C_{1-4}$-alkylcarbonyl-amino-$C_{1-4}$-alkyl, N—($C_{1-4}$-alkyl)-$C_{1-4}$-alkylcarbonyl-amino-$C_{1-4}$-alkyl, 2-oxo-pyrrolidin-1-yl-$C_{1-4}$-alkyl, piperidin-1-yl-$C_{1-4}$-alkyl, 2-oxo-piperidin-1-yl-$C_{1-4}$-alkyl, morpholin-4-yl-$C_{1-4}$-alkyl, 3-oxo-morpholin-4-yl-$C_{1-4}$-alkyl, piperazin-1-yl-$C_{1-4}$-alkyl, 2-oxo-piperazin-1-yl-$C_{1-4}$-alkyl, 3-oxo-piperazin-1-yl-$C_{1-4}$-alkyl, 4-($C_{1-4}$-alkyl)-piperazin-1-yl-$C_{1-4}$-alkyl, 2-oxo-4-($C_{1-4}$-alkyl)-piperazin-1-yl-$C_{1-4}$-alkyl, 3-oxo-4-($C_{1-4}$-alkyl)-piperazin-1-yl-$C_{1-4}$-alkyl, hydroxy-$C_{1-4}$-alkyloxy, $C_{1-4}$-alkyloxy-$C_{1-4}$-alkyloxy, $C_{1-4}$-alkylsulfanyl-$C_{1-4}$-alkyloxy, $C_{1-4}$-alkylsulfinyl-$C_{1-4}$-alkyloxy, $C_{1-4}$-alkylsulfonyl-$C_{1-4}$-alkyloxy, amino-$C_{1-4}$-alkyloxy, $C_{1-4}$-alkylamino-$C_{1-4}$-alkyloxy, di-($C_{1-4}$-alkyl)-amino-$C_{1-4}$-alkyloxy, pyrrolidin-1-yl-$C_{1-4}$-alkyloxy, 2-oxo-pyrrolidin-1-yl-$C_{1-4}$-alkyloxy, piperidin-1-yl-$C_{1-4}$-alkyloxy, 2-oxo-piperidin-1-yl-$C_{1-4}$-alkyloxy, morpholin-4-yl-$C_{1-4}$-alkyloxy, 3-oxo-morpholin-4-yl-$C_{1-4}$-alkyloxy, piperazin-1-yl-$C_{1-4}$-alkyloxy, 2-oxo-piperazin-1-yl-$C_{1-4}$-alkyloxy, 3-oxo-piperazin-1-yl-$C_{1-4}$-alkyloxy, 4-($C_{1-4}$-alkyl)-piperazin-1-yl-$C_{1-4}$-alkyloxy, 2-oxo-4-($C_{1-4}$-alkyl)-piperazin-1-yl-$C_{1-4}$-alkyloxy, 3-oxo-4-($C_{1-4}$-alkyl)-piperazin-1-yl-$C_{1-4}$-alkyloxy, $C_{1-4}$-alkylsulfanyl, $C_{1-4}$-alkysulfinyl, $C_{1-4}$-alkylsulfonyl, $C_{1-4}$-alkylsulfonyloxy, (het)arylsulfonyl, (het)arylsulfonyloxy, trifluoromethylsulfanyl, trifluoromethylsulfinyl, trifluoro-methylsulfonyl, $C_{3-6}$-cycloalkylsulfanyl, $C_{3-6}$-cycloalkylsulfinyl, $C_{3-6}$-cycloalkylsulfonyl, $C_{3-6}$-cycloalkyl-$C_{1-3}$-alkylsulfanyl, $C_{3-6}$-cycloalkyl-$C_{1-3}$-alkylsulfinyl, $C_{3-6}$-cycloalkyl-$C_{1-3}$-alkylsulfonyl, aminosulfonyl, $C_{1-4}$-alkyl-aminosulfonyl, di-($C_{1-4}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-4}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, hydroxy-$C_{4-6}$-cycloalkyl, $C_{1-3}$-alkyloxy-$C_{3-6}$-cycloalkyl, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydro-furanyl-$C_{1-3}$-alkyloxy, tetrahydropyranyl-$C_{1-3}$-alkyloxy, wherein the above-mentioned (het)aryl is defined as described hereinbefore, $R^8$ and $R^9$, which may be identical or different, are halogen, $C_{1-3}$-alkyl, trifluoromethyl, hydroxy, $C_{1-3}$-alkyloxy, cyano, or $R^8$ together with $R^9$, if bound to adjacent carbon atoms, may additionally be methylenedioxy, difluoromethylenedioxy, ethylenedioxy, $C_{3-5}$-alkylene, or $R^8$ together with $R^9$, if bound to adjacent carbon atoms, may also form together with the carbon atoms to which they are attached, a benzo, pyrido, pyrimido, pyrazino, pyridazino, pyrazolo, imidazo, triazolo, oxazolo, thiazolo, isoxazolo, or isothiazolo ring, that all optionally are substituted with one L and/or one or two substituents independently selected from halogen, $C_{1-3}$-alkyl, trifluoromethyl, amino, $C_{1-3}$-alkylamino, di-($C_{1-3}$-alkyl)amino, hydroxy, $C_{1-3}$-alkyloxy, L is $L^1$ or $L^2$ and $L^1$ denotes halogen, $C_{1-6}$-alkyl, hydroxy-$C_{1-4}$-alkyl, $C_{1-3}$-alkyloxy-$C_{1-3}$-alkyl, $C_{3-6}$-cycloalkyl, hydroxy-$C_{4-6}$-cycloalkyl, $C_{1-3}$-alkyloxy-$C_{3-6}$-cycloalkyl, azetidinyl, 1-($C_{1-3}$-alkyl)-azetidinyl, 1-($C_{1-3}$-alkylcarbonyl)-azetidinyl, pyrrolidinyl, 1-($C_{1-3}$-alkyl)-pyrrolidinyl, 1-($C_{1-3}$-alkylcarbonyl)-pyrrolidinyl, piperidinyl, 1-($C_{1-3}$-alkyl)-piperidinyl, 1-($C_{1-3}$-alkylcarbonyl)-piperidinyl, tetrahydrofuranyl, tetrahydropyranyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, or trifluoromethoxy, $L^2$ denotes phenyl, or pyrrolyl, furanyl, thienyl, pyridyl, where in any of these groups 1 or 2 CH are optionally replaced by N atoms, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, or 1,2-dihydro-2-oxo-pyrazinyl, wherein each of the groups mentioned hereinbefore under $L^2$ is optionally substituted with one or two groups independently selected from fluorine, chlorine, $C_{1-3}$-alkyl, difluoromethyl, trifluoromethyl, cyano, amino, acetylamino, methylsulfonylamino, carboxy, $C_{1-4}$-alkyl-oxycarbonyl, aminocarbonyl, $C_{1-3}$-alkylaminocarbonyl, di-($C_{1-3}$-alkyl)-aminocarbonyl, hydroxy, $C_{1-3}$-alkyloxy, difluoromethoxy, and trifluoromethoxy, $R^{10}$ is $R^{10'}$ or $R^{10''}$ and $R^{10'}$ denotes halogen, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, or trifluoromethoxy, $R^{10'''}$ denotes pyrrolyl, furanyl, thienyl, pyridyl, wherein in any of these groups 1 or 2 CH optionally are replaced by N atoms, or indolyl, benzofuranyl, benzothiophenyl, quinolinyl, isoquinolinyl, wherein in any of these groups 1 to 3 CH optionally are replaced by N atoms, or phenyl, naphthyl, tetrazolyl, 1,2-dihydro-2-oxo-pyridinyl, 1,4-dihydro-4-oxo-pyridinyl, 2,3-di-hydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydro-benzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, or 3,4-dihydro-3-oxo-2H-benzo[1,4]oxazinyl, and wherein any of the groups mentioned hereinbefore under $R^{10'''}$ optionally are substituted independently with one or two groups selected from halogen, $C_{1-3}$-alkyl, difluoromethyl, trifluoromethyl, cyano, nitro, amino, acetylamino, methylsulfonylamino, carboxy, $C_{1-4}$-alkyl-oxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, and trifluoromethoxy, X denotes CH or N, m, n, o denote 0, 1 or 2, and wherein the bicyclic core structure of general formula I is optionally substituted independently with $R^{11}$ to $R^{14}$, wherein $R^{11}$ denotes fluorine, $C_{1-4}$-alkyl, (het)aryl, hydroxy, $C_{1-4}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, wherein (het)aryl is as described hereinbefore, $R^{12}$ denotes fluorine or $C_{1-4}$-alkyl, and $R^{13}$ and $R^{14}$, which may be identical or different, denote $C_{1-4}$-alkyl, and whilst the above-mentioned alkyl or alkylene moieties are branched or unbranched, the tautomers, the stereoisomers thereof, the mixtures thereof, and the salts thereof, while the compounds comprised by the formulae II.1 to II.8

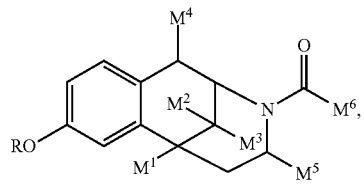

II.1 wherein

R is any substituent, $M^1$ is $C_{1-4}$-alkyl, $M^2$ and $M^3$ independently of each other are hydrogen or $C_{1-4}$-alkyl, $M^4$ is hydrogen or hydroxy, $M^5$ is hydrogen or hydroxy, and $M^6$ denotes phenyl, which may be substituted with one to three substituents selected from the group consisting of halogen, hydroxy, alkyl, nitro, cyano, trifluoromethyl, methoxy, naphthyl or biphenylyl, which may be substituted with one to three substituents selected from the group consisting of halogen, alkyl, nitro, cyano, trifluoromethyl, methoxy, pyridyl, which may be substituted with halogen, alkyl, nitro, cyano, trifluoromethyl, methoxy, and NR'R", where R' and R" are each independently hydrogen or alkyl, or form together with the nitrogen atom a 3- to 7-membered alicyclic ring optionally having a double bond, quinolinyl, isoquinolinyl, 4-cyclohexylphenyl, 4-oxo-4H-chromenyl, indolyl, benzothiophenyl, benzofuranyl, 5,6,7,8-tetrahydro-naphthalen-1-yl, 5,6,7,8-tetrahydro-naphthalen-2-yl, furanyl, methylfuranyl, ethylfuranyl, methoxymethylfuranyl, thienyl, methylthienyl, or ethylthienyl,

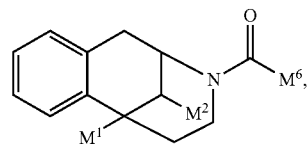

II.2 wherein $M^1$ is $C_{1-4}$-alkyl, $M^2$ is hydrogen or $C_{1-4}$-alkyl, $M^6$ denotes 2-acetoxy-phenyl, 2-ethylamino-phenyl, 2-phenylamino-phenyl, 2-(2,3-dimethyl-phenylamino)-phenyl, 2-(3-methylsulfanylphenylamino)-phenyl, or pyridyl,

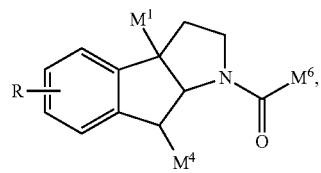

II-3 wherein

R is hydrogen, $C_{1-6}$-alkyl $M^1$ is hydrogen or $C_{1-4}$-alkyl, $M^4$ is hydrogen or hydroxy, $M^6$ is phenyl, methylphenyl, or methoxyphenyl,

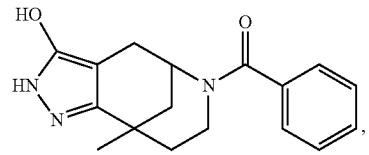

II.4

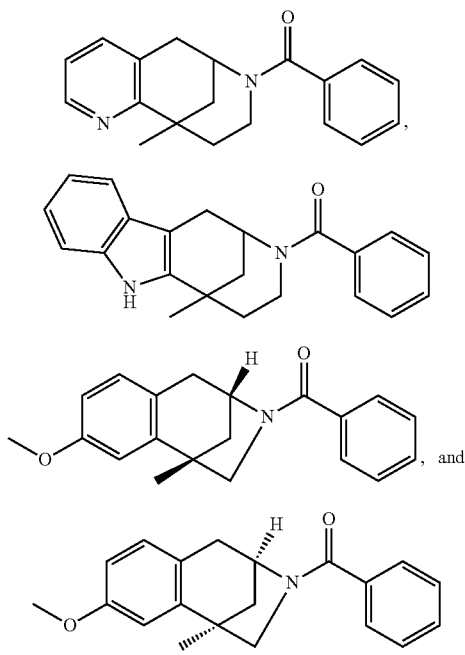

are excluded.

The compounds of general formula I according to the invention and the physiologically acceptable salts thereof have valuable pharmacological properties, particularly an inhibitory effect on the enzyme 11β-hydroxysteroid dehydrogenase (HSD) 1.

The first aspect of the invention also relates to the physiologically acceptable salts of the compounds of general formula I with inorganic or organic acids, except for the salts of the compounds comprised by the formulae II.1 to II.8.

In a second aspect this invention relates to pharmaceutical compositions, containing at least one compound of general formula I, except for the compounds comprised by the formulae II.1 to II.8, or a physiologically acceptable salt according to the invention, optionally together with one or more inert carriers and/or diluents.

In a third aspect this invention relates to the compounds according to general formula I, including the compounds comprised by the formulae II.1 to II.8, or the physiologically acceptable salts thereof, for treatment or prevention of diseases or conditions which can be influenced by inhibiting the enzyme 11β-hydroxysteroid dehydrogenase (HSD) 1, such as metabolic disorders.

In a fourth aspect this invention relates to the use of at least one compound according to general formula I, including the compounds comprised by the formulae II.1 to II.8, or one of the physiologically acceptable salts thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

In a fifth aspect the invention relates to a process for preparing a pharmaceutical composition according to the invention, characterized in that a compound of general formula I, except for the compounds comprised by the formulae II.1 to II.8, or one of the physiologically acceptable salts thereof is incorporated in one or more inert carriers and/or diluents by a non-chemical method.

In a sixth aspect the present invention relates to a process for preparing the compounds of general formula I, except for the compounds comprised by the formulae II.1 to II.8, characterized in that
in order to prepare compounds of general formula I which are defined as hereinbefore and hereinafter,
a compound of general formula III

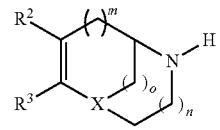

wherein
the groups $R^2$, $R^3$ and X, m, n and o are defined as hereinbefore and hereinafter;
is reacted with $R^1$—CO—Y, optionally prepared in situ from the corresponding carboxylic acid, wherein
Y is a leaving group and in particular
denotes fluorine, chlorine, bromine, cyano, $C_{1-10}$-alkoxy, $C_{1-6}$-alkylsulfanyl, $C_{2-4}$-alkenyl-oxy, $C_{2-4}$-alkynyloxy, oxyarylotriazol, oxyheteroarylotriazol, heteroaryl, succinyl-N-oxy, $C_{1-4}$-alkylcarbonyloxy, di-($C_{1-4}$-alkyl)aminocarbonyloxy, pyrrolylcarbonyloxy, piperidinylcarbonyloxy, morpholinylcarbonyloxy, tri-($C_{1-4}$-alkyl)carbamimidoyloxy, N,N,N',N'-tetra-($C_{1-4}$-alkyl)uronyl, N,N'-dicyclohexyluronyl, di-($C_{1-4}$-alkyloxy)-phosphoryloxy, di-(di-$C_{1-4}$-alkylamino)-phosphoryloxy, dipyrrolidinophosphoryloxy, arylsulfanyl, heteroarylsulfanyl, aryloxy, or heteroaryloxy,
while the alkyl, alkenyl, and alkynyl groups mentioned in the definition of the above groups, either alone or as part of another group, may be mono- or polysubstituted with fluorine, chlorine, $C_{1-3}$-alkyl, or $C_{1-3}$-alkoxy,
while the aryl groups mentioned in the definition of the above groups, either alone or as part of another group, denote phenyl or naphthyl groups and the heteroaryl groups mentioned in the definition of the above groups, either alone or as part of another group, denote pyridinyl, pyrimidinyl, triazinyl, imidazolyl, pyrazolyl, triazolyl, tetrazolyl, whilst both the aryl and heteroaryl groups optionally are independently mono or polysubstituted with fluorine, chlorine, bromine, $C_{1-3}$-alkyl, $C_{1-3}$-alkyloxy, nitro, cyano, or di-($C_{1-3}$-alkyl)amino groups,
and $R^1$ is defined as hereinbefore and hereinafter,
optionally in the presence of a base or another additive;
and, if necessary any protective group used in the reactions described above is cleaved concurrently or subsequently;
if desired a compound of general formula I obtained as described above is resolved into its stereoisomers;
if desired a compound of general formula I thus obtained is converted into the salts thereof, particularly for pharmaceutical use into the physiologically acceptable salts thereof.

In a seventh aspect the present invention relates to novel compounds of formulae IIIa to IIIg, representing subgeneric structures of formula III, including their tautomers, their stereoisomers, and the salts thereof, which are suitable as intermediates in the synthesis of compounds of formula I, characterised by
formula

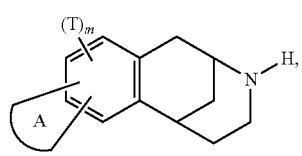

wherein the bicyclic substructure of formula IIIa (2-aza-bicyclo[3.3.1]non-6-ene, comprised by the core structure of formula I) is optionally substituted with one to three methyl groups and wherein A denotes an heteroarylo ring that is annelated to the polycyclic scaffold in formula IIIa via two adjacent carbon atoms of the benzo ring and wherein heteroarylo denotes triazolo or $C_{1-3}$-alkyl-triazolo or pyrido, pyrimido, pyrazino, pyridazino, each of them being optionally substituted with one L and/or one or two substituents independently selected from fluorine, chlorine, $C_{1-3}$-alkyl, trifluoromethyl, hydroxy, $C_{1-3}$-alkyloxy, or pyrazolo, imidazo, N—$C_{1-3}$-alkyl-imidazo, oxazolo, thiazolo, isoxazolo, or isothiazolo, each of them being optionally substituted with one L, preferably, heteroarylo denotes triazolo or methyl-triazolo, or pyrazino optionally substituted with one L and/or one substituent selected from fluorine, methyl, and methoxy, or imidazo, N-methyl-imidazo, or oxazolo, each of them being optionally substituted with one L, T denotes fluorine, chlorine, hydroxy, $C_{1-3}$-alkyl, $C_{1-3}$-alkyloxy, preferably, fluorine, methyl, hydroxy, and methoxy, m denotes 0, 1, or 2, preferably, 0 or 1, and wherein L is as defined hereinbefore and hereinafter; and formula

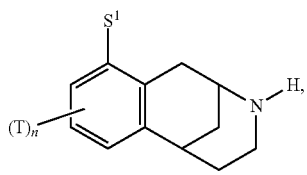

IIIb wherein the bicyclic substructure of formula IIIb (2-aza-bicyclo[3.3.1]non-6-ene) is optionally substituted with one to three methyl groups and wherein $S^1$ denotes fluorine, chlorine, ethyl, propyl, isopropyl, trifluoromethyl, hydroxy-$C_{1-3}$-alkyl, cyano, carboxy, $C_{1-3}$-alkyloxycarbonyl, aminocarbonyl, $C_{1-3}$-alkylaminocarbonyl, di-($C_{1-3}$-alkyl)aminocarbonyl, $C_{1-3}$-alkylsulfonyl, preferably, $S^1$ denotes fluorine, cyano, carboxy, $C_{1-3}$-alkyloxycarbonyl, aminocarbonyl, methylaminocarbonyl, dimethylaminocarbonyl, methylsulfonyl, n denotes 0, 1, 2, or 3, preferably, 0 or 1, and T is as defined hereinbefore; and formula

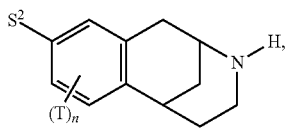

IIIc wherein the bicyclic substructure of formula IIIc (2-aza-bicyclo[3.3.1]non-6-ene) is optionally substituted with one to three methyl groups and wherein $S^2$ denotes fluorine, $C_{1-3}$-alkyl, amino-$C_{1-3}$-alkyl, acetylamino-$C_{1-3}$-alkyl, hydroxy-$C_{1-3}$-alkyl, $C_{1-3}$-alkylcarbonyl, cyano, carboxy, $C_{1-3}$-alkyloxycarbonyl, aminocarbonyl, $C_{1-3}$-alkylamino carbonyl, di-($C_{1-3}$-alkyl) aminocarbonyl, amino, $C_{1-3}$-alkylcarbonylamino, $C_{1-3}$-alkylsulfonylami no, di-($C_{1-3}$-alkyl)-aminosulfonyl, or phenyl, pyridinyl, pyrimidinyl, pyrazinyl, pyridazinyl, oxazolyl, thiazolyl, or N-methyl-pyridin-2-onyl, each of them being optionally substituted with one or two groups independently selected from fluorine, $C_{1-3}$-alkyl, trifluoromethyl, and $C_{1-3}$-alkyloxy, or oxadiazolyl optionally substituted with $C_{1-4}$-alkyl, preferably, $S^2$ denotes fluorine, methyl, aminomethyl, acetylaminomethyl, hydroxyethyl, methylcarbonyl, cyano, carboxy, $C_{1-3}$-alkyloxycarbonyl, aminocarbonyl, methylaminocarbonyl, dimethylaminocarbonyl, amino, acetylamino, methylsulfonylamino, dimethylaminosulfonyl, or phenyl or oxadiazolyl, each of them being optionally monosubstituted with methyl, and T and n are as defined hereinbefore; and formula

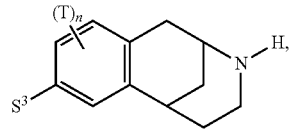

IIId wherein the bicyclic substructure of formula IIId (2-aza-bicyclo[3.3.1]non-6-ene) is optionally substituted with one to three methyl groups and wherein $S^3$ denotes $C_{1-3}$-alkyl, amino-$C_{1-3}$-alkyl, hydroxy-$C_{1-4}$-alkyl, hydroxy-trifluoromethyl-$C_{1-3}$-alkyl, $C_{1-4}$-alkylcarbonyl, cyano, carboxy, $C_{1-3}$-alkyloxycarbonyl, aminocarbonyl, $C_{1-3}$-alkylamino carbonyl, di-($C_{1-3}$-alkyl)aminocarbonyl, $C_{1-3}$-alkylsulfonyl, aminosulfonyl, $C_{1-3}$-alkylamino sulfonyl, di-($C_{1-3}$-alkyl)-aminosulfonyl, tetrazolyl, or phenyl, pyridinyl, pyrimidinyl, pyrazinyl, pyridazinyl, oxazolyl, thiazolyl, triazolyl, N—($C_{1-3}$-alkyl)-pyridin-2-onyl, N—($C_{1-3}$-alkyl)-pyridazin-3-onyl, each of them being optionally mono- or disubstituted with substituents independently selected from fluorine, $C_{1-3}$-alkyl, trifluorome thyl, and $C_{1-3}$-alkyloxy, or oxadiazolyl optionally substituted with $C_{1-4}$-alkyl, preferably, $S^3$ denotes aminomethyl, hydroxy-$C_{1-3}$-alkyl, hydroxy-trifluoromethyl-ethyl, methyl carbonyl, cyano, carboxy, $C_{1-3}$-alkyloxycarbonyl, aminocarbonyl, methylaminocarbonyl, dimethylaminocarbonyl, methylsulfonyl, aminosulfonyl, methylaminosulfonyl, dimethylamino sulfonyl, tetrazolyl, or phenyl, pyridinyl, pyrimidinyl, pyrazinyl, pyridazinyl, triazolyl, each of them being optionally mono- or disubstituted with methyl, or N-methyl-pyridin-2-onyl, N-methyl-pyridazin-3-onyl, oxadiazolyl, each of them being optionally additionally substituted with methyl, and T and n are as defined hereinbefore; and formula

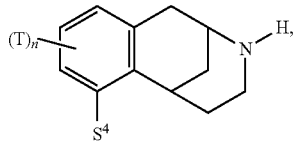

IIIe wherein the bicyclic substructure of formula IIIe (2-aza-bicyclo[3.3.1]non-6-ene) is optionally substituted with one to three methyl groups and wherein $S^4$ denotes fluorine, ethyl, propyl, isopropyl, trifluoromethyl, hydroxy-$C_{1-3}$-alkyl, cyano, carboxy, $C_{1-3}$-alkyloxycarbonyl, aminocarbonyl, $C_{1-3}$-alkylaminocarbonyl, di-($C_{1-3}$-alkyl)aminocarbonyl, nitro, amino, $C_{1-3}$-alkylcarbonylamino, $C_{1-3}$-alkylsulfonylamino, or phenyl, pyridinyl, pyrimidinyl, pyrazinyl, pyridazinyl, oxazolyl, thiazolyl, pyrrol-1-yl, N—($C_{1-3}$-alkyl)-pyridin-2-onyl, each of them being optionally mono- or disubstituted with substituents independently selected from fluorine, $C_{1-3}$-alkyl, trifluoromethyl, and $C_{1-3}$-alkyloxy, or preferably, $S^4$ denotes cyano, nitro, amino, methylsulfonylamino, pyridinyl, pyrrol-1-yl, and T and n are as defined hereinbefore; and formulae

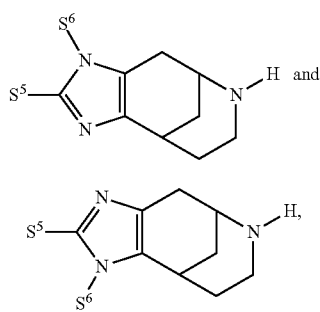

wherein the bicyclic substructure of formula IIIf and IIIg (2-aza-bicyclo[3.3.1]non-6-ene) is optionally substituted with one to three methyl groups and wherein $S^5$ denotes hydrogen, $C_{1-4}$-alkyl, preferably, hydrogen or methyl, and $S^6$ denotes hydrogen, $C_{1-4}$-alkyl, preferably, hydrogen or methyl.

Compounds according to the invention obtained by the synthetic routes described may be subsequently converted into other compounds of the invention by routine processes applicable for conversion of functional groups. Examples for subsequent conversion processes are provided in the following paragraphs.

If according to the invention a compound of general formula I is obtained which contains an amino, alkylamino or imino group, this may be converted by acylation or sulfonylation into a corresponding acyl or sulfonyl compound of general formula I;

if a compound of general formula I is obtained which contains a hydroxy group, this may be converted by acylation or sulfonylation into a corresponding acyl or sulfonyl compound of general formula I;

if a compound of general formula I is obtained which contains an amino, alkylamino or imino group, this may be converted by alkylation or reductive alkylation into a corresponding alkyl compound of general formula I;

if a compound of general formula I is obtained which contains a nitro group, this may be converted by reduction into a corresponding amino compound;

if a compound of general formula I is obtained which contains an imino group, this may be converted by nitrosation and subsequent reduction into a corresponding N-amino-imino compound;

if a compound of general formula I is obtained which contains a $C_{1-3}$-alkyloxycarbonyl group, this may be converted by cleavage of the ester into the corresponding carboxy compound;

if a compound of general formula I is obtained which contains a carboxy group, this may be converted by esterification into a corresponding ester of general formula I;

if a compound of general formula I is obtained which contains a carboxy or ester group, this may be converted by reaction with an amine into a corresponding amide of general formula I;

if a compound of general formula I is obtained which contains an aromatic substructure, this may be derivatized with a chlorine, bromine, or iodine atom or a nitro, sulfonic acid, or acyl group to a corresponding compound of general formula I by an electrophilic substitution reaction;

if a compound of general formula I is obtained which contains an aromatic amino group, this may be transformed into a corresponding cyano, fluoro, chloro, bromo, iodo, hydroxy, mercapto, or azido compound of general formula I by diazotization and subsequent replacement of the diazo group with cyanide, fluoride, chloride, bromide, iodide, hydroxide, alkyl or hydrogen sulfide, or azide, respectively;

if a compound of general formula I is obtained which contains an aromatic amino group, this may be converted into a corresponding aryl derivatized aromatic compound of general formula I by diazotization and subsequent replacement of the diazo group with an appropriate aryl nucleophile mediated by a suited transition metal species; if a compound of general formula I is obtained which contains an aromatic chloro, bromo, iodo, trifluoromethylsulfonyloxy, mesyloxy, or tosyloxy group, this may be converted into a corresponding aryl, alkenyl, alkynyl, or alkyl derivatized compound of general formula I by replacement of the respective group by aryl, alkenyl, alkynyl, or alkyl using a transition metal species mediated process;

if a compound of general formula I is obtained which contains an aromatic chloro, bromo, iodo, trifluoromethylsulfonyloxy, mesyloxy, or tosyloxy group, this may be replaced for hydrogen to give a corresponding aromatic compound of general formula I;

if a compound of general formula I is obtained which contains two adjacent heteroatoms that are amino and hydroxy, amino, or mercapto, these heteroatoms may be linked via a carboxy carbon atom to form a cyclic amidine, imino ester, or imino thioester substructure that may be part of an aromatic ring;

if a compound of general formula I is obtained which contains a cyano group, this may be converted into an amino alkyl derivatized compound of general formula I by reduction;

if a compound of general formula I is obtained which contains a cyano group, this may be converted into a N-hydroxycarbamimidoyl group by the treatment with hydroxylamine;

if a compound of general formula I is obtained which contains an N-hydroxycarbamimidoyl group, this may be converted to an oxadiazole derivatized compound of general formula I by the treatment with a carboxylic or related group;

if a compound of general formula I is obtained which contains an aminocarbonyl group, this may be converted by dehydration into a corresponding cyano compound of general formula I;

if a compound of general formula I is obtained which contains a keto or aldehydic group, this may be converted by reaction with a carbon nucleophile into a corresponding hydroxy alkyl compound of general formula I;

if a compound of general formula I is obtained which contains a keto or aldehydic group, this may be converted by reduction into a corresponding hydroxyl compound of general formula I;

if a compound of general formula I is obtained which contains a cyano group, this may be converted into a corresponding tetrazolyl compound of general formula I by reacting with an azide salt or derivative;

if a compound of general formula I is obtained which contains a nitro group, this may be converted by reduction into a corresponding amino compound; and/or if a compound of general formula I is obtained which contains an amino group, this may be converted to a corresponding pyrrolyl substituted compound of general formula I by reaction with an 1,4-dicarbonyl compound or a synthon thereof.

The subsequent esterification is optionally carried out in a solvent or mixture of solvents such as methylene chloride, dimethylformamide, benzene, toluene, chlorobenzene, tetrahydro-furan, benzene/tetrahydrofuran or dioxane or particularly advantageously in the corresponding alcohol optionally in the presence of an acid such as hydrochloric acid or in the presence of a dehydrating agent, e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxy-succinimide or 1-hydroxy-benzotriazole and optionally additionally in the presence of 4-dimethylamino-pyridine, N,N'-carbonyldiimidazole or triphenylphosphine/carbon tetrachloride, conveniently at temperatures between 0 and 150° C., preferably between 0 and 80° C.

The subsequent ester formation may also be carried out by reacting a compound which contains a carboxy group with a corresponding alkyl halide.

The subsequent acylation or sulfonylation is optionally carried out in a solvent or mixture of solvents such as methylene chloride, dimethylformamide, benzene, toluene, chlorobenzene, tetrahydrofuran, benzene/tetrahydrofuran or dioxane with a corresponding acyl or sulfonyl derivative optionally in the presence of a tertiary organic base or in the presence of an inorganic base or in the presence of a dehydrating agent, e.g. in the presence of isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexyl-carbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, at temperatures between 0 and 150° C., preferably between 0 and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxane with an alkylating agent such as a corresponding halide or sulfonic acid ester, e.g. methyl iodide, ethyl bromide, dimethylsulfate, or benzyl chloride, optionally in the presence of a tertiary organic base or in the presence of an inorganic base at temperatures between 0 and 150° C., preferably between 0 and 100° C.

The subsequent reductive alkylation is carried out with a corresponding carbonyl compound such as e.g. formaldehyde, acetaldehyde, propionaldehyde, acetone or butyraldehyde in the presence of a complex metal hydride such as sodium borohydride, lithium borohydride, sodium triacetoxyborohydride or sodium cyanoborohydride conveniently at a pH of 6-7 and at ambient temperature or using hydrogen in the presence of a transition metal catalyst, e.g. palladium/charcoal at a hydrogen pressure of 1 to 5 bar. The methylation may also be carried out in the presence of formic acid as reducing agent at elevated temperature, e.g. between 60 and 120° C.

The subsequent reduction of a nitro group is carried out, for example, with hydrogen and a catalyst such as palladium on carbon, platinum dioxide or Raney nickel, or using other reducing agents such as iron or zinc in the presence of an acid such as acetic acid.

The subsequent nitrosation of an imino group followed by reduction to obtain the N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-3}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide.

The subsequent amide formation is carried out by reacting a corresponding reactive carboxylic acid derivative with a corresponding amine optionally in a solvent or mixture of sol-vents such as methylene chloride, dimethylformamide, benzene, toluene, chlorobenzene, tetrahydrofuran, benzene/tetrahydrofuran or dioxane, while the amine used may also serve as solvent, optionally in the presence of a tertiary organic base or in the presence of an inorganic base or with a corresponding carboxylic acid in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclo-hexylcarbodiimide/N-hydroxysuccinimide or 1-hydroxy-benzotriazole and optionally additionally in the presence of 4-dimethylamino-pyridine, N,N'-carbonyldiimidazole or triphenyl-phosphine/carbon tetrachloride, conveniently at temperatures between 0 and 150° C., preferably between 0 and 80° C.

The subsequent introduction of a chlorine, bromine, or iodine atom onto an aromatic sub-structure may be carried out by reacting the aromatic compound with an appropriate electrophile of the halogen atom. Suited chlorine and bromine electrophiles may be e.g. N-halo-succinimide, HOCl, HOBr, tertBuOCl, tertBuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, borontrifluoride hydrate, borontrifluoride etherate, or aluminum halide. Further useful combinations may be LiBr and ceric ammonium nitrate, KCl or KBr with Oxone®, or KBr and sodium per-borate. Suited iodine electrophiles may be generated from iodine combined with an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles may be used without an additive or in the presence of an acid such as e.g. acetic acid, trifluoroacetic acid, or sulfuric acid, or a Lewis acid such as borontrifluoride hydrate, or copper salts. If a nitro group is to be introduced appropriate nitro electrophiles may be generated from, for example, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Acylating the aromatic part is conducted using an acyl electrophile that may be generated from the respective acyl halide, e.g. chloride, or acyl anhydride and a Lewis acid such as e.g. aluminum halide, diethylaluminum halide, indium halide, iron(III) halide, tin(IV) halide, borontrifluoride, titanium(IV) halide, or a Brønsted acid, e.g. sulfuric acid or triflic acid. The formyl group is best introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, dichloroethane, chlorobenzene, dichlorobenzene, ether, fluorinated hydrocarbons, hexanes, quinoline, or acetonitrile. The temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoro-borate, or an alkylnitrite, e.g. tertbutylnitrite or isoamylnitrite. The diazotization is optionally carried out in methylene chloride, dichloroethane, dimethylformamide, N-methylpyrrolidinone, benzene, toluene, chlorobenzene, tetrahydrofuran, water, ethyl acetate, alcohol, ether, dimethoxyethane, dioxane or mixtures thereof at temperatures between –10° C. and 100° C. (diazotization of amino groups is detailed in, for example, *Angew. Chem. Int. Ed.* 1976, 15, 251). The subsequent displacement of the diazo group for a cyano group, chlorine, or bromine using cuprous cyanide, chloride, or bromide, respectively, is known as the Sand-meyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between –10° C. and 120° C. in one of the solvents or mixtures mentioned above. The replacement of the diazo group for a fluorine atom may be achieved with a tetrafluoroborate salt or acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced for hydroxy using water or an aqueous solvent mixture at temperatures between 0 and 180° C. The reaction usually works without further additives but the addition of cuprous oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be carried out via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. In these reactions the diazo compound is preferably employed as its tetrafluoroborate salt optionally in methylene chloride, dimethylformamide, N-methylpyrrolidinone, benzene, toluene, tetrahydrofuran, water, ethyl acetate, alcohol, ether, dimethoxyethane, dioxane, or mixtures thereof at temperatures between 10° C. and 180° C., preferably between 20° C. and 140° C.

The subsequent replacement of an aromatic chloro, bromo, iodo atom or an aromatic trifluoromethylsulfonyloxy, mesyloxy, or tosyloxy group for an aryl, alkenyl, alkynyl, or alkyl residue is preferably mediated by a transition metal species derived from palladium, nickel, rhodium, copper, or iron. The active catalyst may be a complex of the transition metal with ligands such as e.g. phosphines (e.g. tritertbutylphosphine, tricyclohexylphosphine, substituted biphenyldicyclohexylphosphines, substituted biphenylditertbutylphosphines, triphenyl-phosphine, tritolylphosphine, trifurylphosphine, 1,1'-bis(diphenylphosphino)ferrocene), phosphites, imdiazole carbenes, imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as it is or as the zinc acetylide derivative. Depending on the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, copper salts such as copper chloride or copper thiophenecarboxylate may be advantageous or even essential. Copper iodide is a preferred additive in the coupling with a terminal alkyne group (Sonogashira reaction). The coupling reactions are optionally conducted in methylene chloride, dimethylformamide, N-methylpyrrolidinone, benzene, toluene, tetra-hydrofuran, water, ethyl acetate, alcohol, ether, dimethylsulfoxide, dimethoxyethane, dioxane, or mixtures thereof, though, depending on the nucleophile some of them are less or not suited at all. Preferred temperatures are in the range from –10° C. to 180° C.

The subsequent replacement of an aromatic chlorine, bromine, iodine atom or an aromatic trifluoromethylsulfonyloxy, mesyloxy, or tosyloxy group for a hydrogen atom is preferably mediated by a transition metal species derived from palladium, nickel, platinum, rhodium, or ruthenium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 5 bar, silanes, e.g. trialkoxysilane, boranes, hydrides, e.g. alkali metal borohydride, formic acid, or formates, e.g. ammonium formate. The reactions are preferably carried out in methylene chloride, dimethylformamide, dimethylacetamide, N-methylpyrrolidinone, benzene, toluene, tetrahydrofuran, water, ethyl acetate, alcohol, ether, dimethoxyethane, dioxane, or mixtures thereof at –10° C. to 180° C., more preferably at 20° C. to 140° C.

The subsequent cyclization of two adjacent heteroatoms is optionally conducted with a carboxy equivalent such as nitrile, carboxylic chloride or fluoride, carboxylic acid, ketene, carboxylic ester, or carboxylic thioester. The overall transformation consists of two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tertbutoxide. The use of dehydrating reagents such as anhydrides, e.g. acetic anhydride, orthoesters, e.g. trimethylorthoformate, thionyl-chloride, phosgene, diphosgene, triphosgene, phosphorous oxychloride, phosphorous pentachloride, dialkylcarbodiimides, combinations of phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, dichloroethane, benzene, toluene, tetrahydrofuran, ether, or combinations thereof, though, cyclization in the presence of an acid or a base may also be conducted in water or an alcohol, e.g. methanol, ethanol, isopropanol, or tertbutanol, or combinations with these solvents. The reactions are carried out at temperatures between 0° C. and 200° C., preferably between 20° C. and 140° C.

The subsequent reduction of a cyano group to obtain an aminomethyl group is optionally conducted with hydrogen in the presence of a transition metal species or with a hydride. Suited transition metals may be derived from palladium, nickel, platinum, rhodium, or ruthenium such as, for example, palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, dimethylformamide, or N-methylpyrrolidinone at hydrogen pressures between 1 and 10 bar, preferably between 1 and 5 bar, and at temperatures between 0 and 180° C., preferably between 20 and 120° C. Additives such as acids, e.g. hydrochloric acid, methanesulfonic acid, sulfuric acid, or acetic acid, may be beneficial for the hydrogenation. Appropriate hydride sources may be selected from e.g. borohydrides, e.g. sodium borohydride, potassium trisecbutylborohydride, borane, or lithium triethylborohydride, or alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, dioxane, 1,2-dimethoxyethane, dichloromethane, 1,2-dichloroethane, benzene, or toluene; some are also compatible with alcoholic solutions. Preferred reaction temperatures range from −80° C. to 160° C., more preferred from −40° C. to 60° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0° C. and 140° C.

The subsequent formation of an oxadiazole from an N-hydroxycarbamimidoyl is optionally conducted with a carboxy equivalent such as nitrile, carboxylic chloride or fluoride, carboxylic acid, ketene, carboxylic ester, or carboxylic thioester. The transformation is related to the formation of a ring starting from two adjacent heteroatoms described above and may be carried out analogously.

The subsequent formation of a cyano group from an amino carbonyl group is optionally con-ducted by using a dehydrating reagent such as e.g. anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloro-methane, 1,2-dibromotetrafluoroethane, or bromine. The reactions are preferably carried out in dichloromethane, 1,2-dichloroethane, hexanes, ether, dioxane, benzene, toluene, acetonitrile, mixtures thereof, or without a solvent at temperatures between 0° C. and 140° C. Additives such as amines, e.g. pyridine or triethylamine, or dimethylformamide may be beneficial.

The subsequent addition of a carbon nucleophile to a keto or an aldehydic group to obtain a tertiary or secondary alcohol may be carried out with an alkyl or aryl metal compound, preferably with a lithium or magnesium derivative. The reactions are preferably conducted in hexanes, ether, dioxane, tetrahydrofuran, 1,2-dimethoxyethane, benzene, toluene, or mixtures thereof between −80° C. and 50° C.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydide, or lithium aluminum hydride. The reductions may be conducted in e.g. dichloromethane, 1,2-dichloroethane, hexanes, ether, dioxane, tetrahydrofuran, dimethylformamide, N-methylpyrrolidinone, benzene, toluene, alcohols, e.g. methanol, water, or mixtures thereof, though, not all reducing agents are compatible with all of these solvents. Preferred temperatures are between −80° C. and 140° C. depending on the reducing power of the reagent. Alternatively, hydrogen in the presence of a transition metal catalyst may be used for the reduction.

The subsequent conversion of a cyano into a tetrazolyl group may be achieved by reacting the cyanide with sodium azide or trimethylsilyl azide in e.g. toluene, xylene, cyclohexane, dimethylformamide, dimethylacetamide, N-methylpyrrolidinone, tetrahydrofuran, dioxane, 1,2-dimethoxyethane, alcohol, water, or mixtures thereof. Beneficial additives may be $ZnBr_2$, $Bu_3SnCl$, $NH_4Cl$, $Bu_2SnO$, $AlCl_3$, $AlMe_3$, $HNEt_3Cl$, and $NEt_3$. The reactions are preferably conducted between 20° C. and 160° C.

The subsequent reduction of a nitro group is carried out, for example, with hydrogen and a catalyst such as palladium on carbon, platinum dioxide, or Raney nickel, or using other reducing agents such as iron or zinc in the presence of an acid such as acetic acid.

The subsequent formation of a pyrrolyl ring from an amino group may be accomplished, for instance, by reacting the amino compound with succinaldehyde or a derivative thereof, e.g. 2,5-dimethoxy-tetrahydrofuran or hexane-2,5-dione, in the presence of a Lewis acid, e.g. acetic acid, p-toluenesulfonic acid, or $Bi(OSO_2CF_3)_3$, in e.g. acetic acid, water, methanol, ethanol, acetonitrile, 1,4-dioxane, tetrahydrofuran, toluene, at 20 to 140° C. Additives such as molecular sieves or other dehydrating reagents such as acetic anhydride may be beneficial.

In the reactions described hereinbefore, any reactive group present such as hydroxy, carboxy, amino, alkylamino, or imino group may be protected during the reaction by conventional protecting groups which are cleaved again after the reaction.

For example, a protecting group for a hydroxy group may be a trimethylsilyl, tertbutyldimethylsilyl, triisopropylsilyl, acetyl, pivaloyl, benzoyl, methyl, ethyl, tert-butyl, allyl, trityl, benzyl, 4-methoxybenzyl, tetrahydropyranyl, methoxymethyl, ethoxymethyl, or 2-trimethylsilylethoxy-methyl group, protecting groups for a carboxy group may be trimethylsilyl, methyl, ethyl, tertbutyl, allyl, benzyl, or tetrahydropyranyl, protecting groups for a ketone or aldehyde may be a ketal or acetal, respectively, e.g. derived from methanol, glycol, or propane-1,3-diol, protecting groups for an amino, alkylamino, or imino group may be methyl, formyl, acetyl, trifluoroacetyl, ethoxycarbonyl, tert-butoxycarbonyl, benzyloxycarbonyl, benzyl, methoxy-benzyl, or 2,4-dimethoxybenzyl and additionally, for the amino group, phthalyl, and protecting groups for a terminal alkyne may be trimethylsilyl, trisopropylsilyl, tertbutyldimethylsilyl, or 2-hydroxy-isopropyl.

Any acyl protecting group may be cleaved, for example, hydrolytically in an aqueous solvent, e.g. in water, isopropanol/water, acetic acid/water, tetrahydrofuran/water, or dioxane/water, in the presence of an acid such as trifluoroacetic acid, hydrochloric acid, or sulfuric acid or in the presence of an alkali metal base such as lithium hydroxide, sodium hydroxide, or potassium hydroxide or aprotically, e.g. in the presence of iodotrimethylsilane, at temperatures between 0 and 120° C., preferably between 10 and 100° C. A trifluoroacetyl group is prefer-ably cleaved by treating with an acid such as hydrochloric acid, optionally in a solvent such as acetic acid, at temperatures between 50 and 120° C. or by treating with sodium hydroxide solution, optionally in an additional solvent such as tetrahydrofuran or methanol, at temperatures between 0 and 80° C.

Any acetal or ketal protecting group used may be cleaved, for example, hydrolytically in an aqueous solvent, e.g. in water, isopropanol/water, acetic acid/water, tetrahydrofuran/water, or dioxane/water, in the presence of an acid such as trifluoroacetic acid, hydrochloric acid, or sulfuric acid or aprotically, e.g. in the presence of iodotrimethylsilane, at temperatures between 0 and 120° C., preferably between 10 and 100° C.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide.

Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0° C. and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, dioxane, dimethoxyethane, toluene, benzene, dichloroethane, or dichloromethane, at temperatures between −20 and 100° C.

A benzyl, methoxybenzyl, or benzyloxycarbonyl group is advantageously cleaved hydro-genolytically, e.g. with hydrogen in the presence of a catalyst such as palladium on carbon, palladium hydroxide, or platinum oxide in a solvent such as methanol, ethanol, ethyl acetate, or glacial acetic acid, optionally in the presence of an acid, such as hydrochloric acid, at temperatures between 0 and 100° C., preferably between 20 and 60° C., and at hydrogen pressures of 1 to 7 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue, such as methoxybenzyl, may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tertbutyl or tertbutyloxycarbonyl group is preferably cleaved by treating with an acid such as trifluoroacetic acid, sulfuric acid, or hydrochloric acid or by treating with iodotrimethylsilane optionally using a solvent such as methylene chloride, dioxane, methanol, isopropanol, water, or diethyl-ether.

A methyl group at an tertiary amine may be cleaved by the treatment with 1-chloroethyl chloroformate. Hydrobromic acid and borontribromide are particularly suited for the cleavage of methylethers.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallisation from an optically active solvent or by reacting with an optically active sub-stance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts with inorganic or organic acids provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine, triethanolamine, N-methyl-D-glucamine, L-lysine, L-arginine, and piperazine.

DETAILED DESCRIPTION OF THE INVENTION

Unless otherwise stated, the groups, residues and substituents, particularly $R^1$ to $R^{14}$, L, X, m, n, and o are defined as above and hereinafter. If residues, substituents, or groups occur several times in a compound they may have the same or different meanings. Some preferred meanings of individual scaffolds, groups, and substituents of the compounds according to the invention will be given hereinafter.

First Aspect of the Invention

A first subgeneric embodiment of this invention is directed to compounds described by general formula I.1

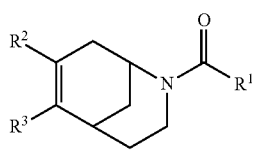

I.1 wherein the bicyclic core structure of general formula I.1 is optionally substituted with $R^{11}$ to $R^{14}$, and
wherein $R^1$ to $R^3$ and $R^{11}$ to $R^{14}$ are defined as hereinbefore and hereinafter, except for the compounds comprised by the formulae II.1 to II.8, their tautomers, their stereoisomers, mixtures thereof and the salts thereof.

A second subgeneric embodiment of this invention is directed to compounds described by general formula I.2

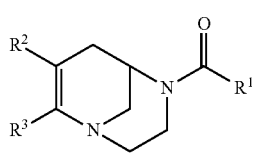

I.2 wherein the bicyclic core structure of general formula I.2 is optionally substituted with $R^{11}$ to $R^{14}$, and
wherein $R^1$ to $R^3$ and $R^{11}$ to $R^{14}$ are defined as hereinbefore and hereinafter, their tautomers, their stereoisomers, mixtures thereof and the salts thereof.

A third subgeneric embodiment of this invention is directed to compounds described by general formula I.3

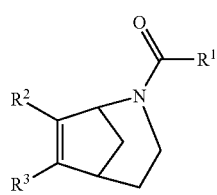

I.3 wherein the bicyclic core structure of general formula I.3 is optionally substituted with $R^{11}$ to $R^{14}$, and
wherein $R^1$ to $R^3$ and $R^{11}$ to $R^{14}$ are defined as hereinbefore and hereinafter, their tautomers, their stereoisomers, mixtures thereof and the salts thereof.

A fourth subgeneric embodiment of this invention is directed to compounds described by general formula I.4

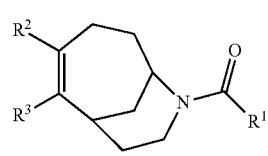

I.4 wherein the bicyclic core structure of general formula I.4 is optionally substituted with $R^{11}$ to $R^{14}$, and
wherein $R^1$ to $R^3$ and $R^1$ to $R^{14}$ are defined as hereinbefore and hereinafter, their tautomers, their stereoisomers, mixtures thereof and the salts thereof.

A fifth subgeneric embodiment of this invention is directed to compounds described by general formula I.5

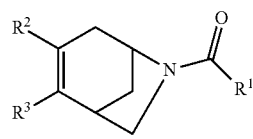

I.5 wherein the bicyclic core structure of general formula I.5 is optionally substituted with $R^{11}$ to $R^{14}$, and
wherein $R^1$ to $R^3$ and $R^{11}$ to $R^{14}$ are defined as hereinbefore and hereinafter, while the compounds of formulae II.7 and II.8 are excluded,
their tautomers, their stereoisomers, mixtures thereof and the salts thereof.

A sixth subgeneric embodiment of this invention is directed to compounds described by general formula I.6

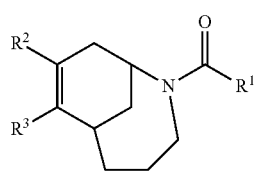

I.6 wherein the bicyclic core structure of general formula I.6 is optionally substituted with $R^{11}$ to $R^{14}$, and
wherein $R^1$ to $R^3$ and $R^{11}$ to $R^{14}$ are defined as hereinbefore and hereinafter, their tautomers, their stereoisomers, mixtures thereof and the salts thereof.

A seventh subgeneric embodiment of this invention is directed to compounds described by general formula I.7

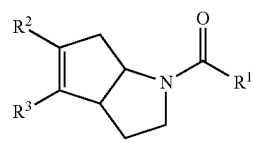

I.7 wherein the bicyclic core structure of general formula I.7 is optionally substituted with $R^{11}$ to $R^{14}$, and wherein $R^1$ to $R^3$ and $R^{11}$ to $R^{14}$ are defined as hereinbefore and hereinafter, while the compounds comprised by the formula II.3 are excluded, their tautomers, their stereoisomers, mixtures thereof and the salts thereof.

An eighth subgeneric embodiment of this invention is directed to compounds described by general formula I.8

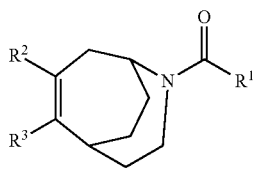

I.8 wherein the bicyclic core structure of general formula I.8 is optionally substituted with $R^{11}$ to $R^{14}$, and wherein $R^1$ to $R^3$ and $R^{11}$ to $R^{14}$ are defined as hereinbefore and hereinafter, their tautomers, their stereoisomers, mixtures thereof and the salts thereof.

A ninth subgeneric embodiment of this invention is directed to compounds described by general formula I.9

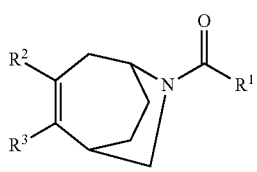

I.9 wherein the bicyclic core structure of general formula I.9 is optionally substituted with $R^{11}$ to $R^{14}$, and wherein $R^1$ to $R^3$ and $R^{11}$ to $R^{14}$ are defined as hereinbefore and hereinafter, their tautomers, their stereoisomers, mixtures thereof and the salts thereof.

A tenth subgeneric embodiment of this invention is directed to compounds described by general formula I.10

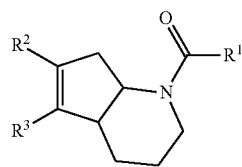

I.10 wherein the bicyclic core structure of general formula I.10 is optionally substituted with $R^{11}$ to $R^{14}$, and wherein $R^1$ to $R^3$ and $R^{11}$ to $R^{14}$ are defined as hereinbefore and hereinafter, their tautomers, their stereoisomers, mixtures thereof and the salts thereof.

Preferred compounds according to the invention are those of general formulae I.1 to I.10, wherein $R^1$ denotes aryl or heteroaryl,
while by aryl is meant phenyl or naphthyl and
by heteroaryl is meant pyrrolyl, furanyl, thienyl, pyridinyl, indolyl, benzofuranyl, benzo-thiophenyl, quinolinyl, isoquinolinyl, or pyrrolyl, furanyl, thienyl, pyridinyl wherein 1 or 2 CH are replaced by N, or indolyl, benzofuranyl, benzothiophenyl, quinolinyl, isoquinolinyl, wherein 1 or 2 CH are replaced by N, or 1-oxo-indanyl, 2,3-dihydro-indolyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, benzo[1,3]-dioxolyl, 1,2-dihydro-2-oxo-quinolinyl, 1,4-dihydro-4-oxo-quinolinyl, 1,2-dihydro-1-oxo-isoquinolinyl, 1,2-dihydro-2-oxo-quinazolinyl, 1,4-dihydro-4-oxo-quinazolinyl, 1,2-dihydro-2-oxoquinoxalinyl, or 1,2,3,4-tetrahydro-3-oxo-quinoxalinyl, wherein the above-mentioned aryl and heteroaryl rings are optionally independently substituted with one $R^4$, one to four identical or different $R^5$, and one $R^6$.

Preferably $R^1$ denotes phenyl, naphthyl, furanyl, pyrazolyl, imidazolyl, pyridinyl, pyrimidinyl, pyrazinyl, pyridazinyl, indolyl, benzimidazolyl, indazolyl, benzotriazolyl, benzoxazolyl, benzo-thiazolyl, quinolinyl, isoquinolinyl, quinazolinyl, naphthyridinyl, quinoxalinyl, 2,3-dihydro-2-oxo-indolyl, or 1,2,3,4-tetrahydro-3-oxo-quinoxalinyl, wherein any of these groups optionally are independently substituted with one $R^4$, one to four identical or different $R^5$, and one $R^6$.

More preferably, $R^1$ denotes phenyl, naphthyl, pyrazolyl, pyridinyl, pyrimidinyl, naphthyl, benzofuranyl, indolyl, benzothiophenyl, benzimidazolyl, indazolyl, benzotriazolyl, benzoxazolyl, benzothiazolyl, quinolinyl, isoquinolinyl, quinazolinyl, naphthyridinyl, quinoxalinyl, 2,3-dihydro-2-oxo-indolyl, or 1,2,3,4-tetrahydro-3-oxo-quinoxalinyl, wherein any of these groups optionally are independently substituted with one $R^4$ and one to four different or identical $R^5$.

Most preferably, $R^1$ denotes phenyl, pyrazolyl, pyridinyl, benzofuranyl, indolyl, benzimidazolyl, indazolyl, benzotriazolyl, benzothiazolyl, 2,3-dihydro-2-oxo-indolyl, or 1,2,3,4-tetrahydro-3-oxo-quinoxalinyl, wherein any of these groups optionally are independently substituted with one $R^4$ and one to four different or identical $R^5$.

Particularly preferred are 4-carbamoyl-phenyl, 4-(morpholin-4-ylmethyl)phenyl, 4-amino-phenyl, 4-hydroxyphenyl, 4-amino-3-fluoro-phenyl, 4-amino-3-chloro-phenyl, 4-amino-3,5-dichloro-phenyl, indol-3-yl, indol-5-yl, indol-6-yl, benzimidazol-5-yl, indazol-5-yl, benzothiazol-5-yl, and benzothiazol-6-yl.

$R^2$ and $R^3$, together with the double bond to which they are attached, denote a benzo or pyrido ring, optionally both independently substituted with $R^7$, $R^8$ and $R^9$, or denote a furo, pyrrolo, pyridazino, pyrimido, or pyrazino ring, wherein any of these groups optionally are independently substituted with $R^7$ and $R^8$ or $R^8$ and $R^9$, or denote a pyrazolo, imidazo, oxazolo, thiazolo, isoxazolo, or isothiazolo ring, wherein any of these groups optionally are independently substituted with $R^7$.

Preferably, $R^2$ and $R^3$, together with the double bond to which they are attached, denote a benzo or pyrido ring, both optionally independently substituted with $R^7$, $R^8$ and $R^9$, or denote a pyrrolo, pyridazino, pyrimido, or pyrazino ring, wherein any of these groups optionally are independently substituted with $R^7$ and $R^8$ or $R^8$ and $R^9$, or denote a pyrazolo or imidazo ring, both optionally substituted with $R^7$.

More preferably, $R^2$ and $R^3$, together with the double bond to which they are attached, denote a benzo or pyrido ring, both independently substituted with $R^7$, $R^8$ and $R^9$, or denote a pyrrolo ring optionally substituted independently with $R^7$ and $R^8$ or $R^8$ and $R^9$, particularly a benzo ring optionally substituted independently with $R^7$, $R^8$ and $R^9$.

$R^4$ denotes fluorine, chlorine, bromine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonyl-amino, morpholin-4-yl-carbonylamino, piperazin-1-yl-carbonylamino, 4-($C_{1-3}$-alkyl)-pi-perazin-1-yl-carbonylamino, $C_{1-3}$-alkyl-sulfonylamino, (het)arylsulfonylamino, (het)aryl-$C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-car-bonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, amino-carbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyl-oxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yl-oxy, tetrahydropyran-3-yl-oxy, tetrahydropyran-4-yl-oxy, tetra-hydrofuranyl-$C_{1-3}$-alkyloxy, tetrahydropyranyl-$C_{1-3}$-alkyloxy, wherein the above-mentioned (het)aryl groups are phenyl, naphthyl, or pyrrolyl, furanyl, thienyl, pyridyl, indolyl, benzofuranyl, benzothiophenyl, quinolinyl, isoquinolinyl, or pyrrolyl, furanyl, thienyl, pyridyl wherein 1 or 2 CH are replaced by N, or indolyl, benzofuranyl, benzothiophenyl, quinolinyl, isoquinolinyl wherein 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzo-furanyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quina-zolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, or 3,4-dihydro-3-oxo-2H-benzo[1,4]oxazin-yl, and wherein any of the groups mentioned for the (het)aryl groups are optionally substituted with one or two $R^{10}$ which may be identical or different.

Preferably $R^4$ denotes fluorine, chlorine, bromine, $C_{1-4}$-alkyl, hydroxy, $C_{1-4}$-alkyloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkyl-carbonyl)-piperazin-1-yl, 4-($C_{3-6}$-cycloalkylcarbonyl)-piperazin-1-yl, 4-($C_{1-4}$-alkyloxy-carbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonyl-amino, morpholin-4-yl-carbonylamino, piperazin-1-yl-carbonylamino, 4-($C_{1-3}$-alkyl)-piperazin-1-yl-carbonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, N—($C_{1-3}$-alkyl)-(het)arylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-trifluoromethyl-ethyl, aminosulfonyl, (het)aryl, (het)aryl-$C_{1-3}$-alkyl, or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups optionally are substituted with $R^{10}$.

More preferably, $R^4$ denotes fluorine, chlorine, $C_{1-4}$-alkyl, hydroxy, $C_{1-4}$-alkyloxy, amino, $C_{1-3}$-alkylamino, di-($C_{1-3}$-alkyl)amino, pyrrolidin-1-yl, piperidin-1-yl, morpholin-4-yl, $C_{1-3}$-alkyl-carbonylamino, aminocarbonyl, $C_{1-3}$-alkyl-aminocarbonyl, di-($C_{1-3}$-alkyl)-aminocarbonyl, (N-methyl)-benzylaminocarbonyl, (N-methyl)-phenylaminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, morpholin-4-yl-$C_{1-3}$-alkyl, (2-methyl-morpholin-4-yl)-$C_{1-3}$-alkyl, (2,6-dimethyl-morpholin-4-yl)-$C_{1-3}$-alkyl, 3-oxo-morpholin-4-yl-methyl, pyrrolidin-1-yl-$C_{1-3}$-alkyl, 2-oxo-pyrrolidin-1-yl-$C_{1-3}$-alkyl, $C_{1-3}$-alkylcarbonylamino-$C_{1-3}$-alkyl, phenylcarbonylamino-$C_{1-3}$-alkyl, imidazolyl-$C_{1-3}$-alkyl, triazolyl-$C_{1-3}$-alkyl, trifluoromethyl, difluoromethoxy, trifluoromethoxy, 2,2,2-trifluoro-1-hydroxyethyl, 2,2,2-trifluoro-1-hydroxy-1-methyl-ethyl, or 2,2,2-trifluoro-1-hydroxy-1-trifluoromethyl-ethyl, or aminosulfonyl.

Most preferably, $R^4$ denotes fluorine, chlorine, methyl, hydroxy, methoxy, methylamino, morpholin-4-yl, acetylamino, aminocarbonyl, (N-methyl)-propylaminocarbonyl, (N-methyl)-benzylaminocarbonyl, (N-methyl)-phenylaminocarbonyl, dimethylamino-carbonyl, diethylaminocarbonyl, piperidin-1-ylcarbonyl, morpholin-4-ylcarbonyl, pyrrolidin-1-yl-carbonyl, 2-(methoxymethyl)-pyrrolidin-1-yl-carbonyl, 1-hydroxy-ethyl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, acetylaminomethyl, phenylcarbonylaminomethyl, 2-oxo-pyrrolidin-1-yl-methyl, morpholin-4-yl-methyl, 3-oxo-morpholin-4-yl-methyl, imidazol-1-ylmethyl, triazol-1-ylmethyl, (2-methyl-morpholin-4-yl)-methyl, or aminosulfonyl.

$R^5$ and $R^6$ are independently selected from among fluorine, chlorine, bromine, $C_{1-3}$-alkyl, $C_{2-3}$-alkynyl, trifluoromethyl, hydroxy, $C_{1-3}$-alkyloxy, and cyano, preferably from hydrogen, fluorine, chlorine, methyl, ethyl, ethynyl, trifluoromethyl, hydroxy, methoxy, and ethoxy, more preferably from hydrogen, fluorine, chlorine, methyl, ethynyl, hydroxy, and methoxy.

If $R^5$ and $R^6$ are bound to adjacent carbon atoms they together may additionally denote methylenedioxy, difluoromethylenedioxy, ethylenedioxy, or $C_{3-5}$-alkylene, preferably methylenedioxy, ethylene-1,2-dioxy, propylene, or butylene, more preferably methylenedioxy or ethylene-1,2-dioxy, most preferably ethylene-1,2-dioxy.

Preferably $R^7$ denotes fluorine, chlorine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, 3-oxo-piperazin-1-yl, 4-($C_{1-4}$-alkylcarbonyl)-piperazin-1-yl, $C_{1-3}$-alkyl-carbonylamino, (het)aryl-carbonylamino, $C_{1-3}$-alkyloxy-carbonylamino, $C_{1-3}$-alkyl-aminocarbonylamino, di-($C_{1-3}$-alkyl)aminocarbonylamino, pyrrolidin-1-yl-carbonyl-amino, piperidin-1-yl-carbonylamino, morpholin-4-yl-carbonylamino, $C_{1-3}$-alkyl-sulfonyl-amino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, (het)aryl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-$C_{1-3}$-alkyloxy-carbonylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)aryl-sulfonylamino, cyano, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$- alkyl)-amino-carbonyl, pyrrolidin-1-yl-carbonyl, piperidin-1-yl-carbonyl, morpholin-4-yl-carbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-4}$-alkyl, $C_{1-3}$-alkyloxy-$C_{1-4}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-piperidin-1-yl-$C_{1-3}$-alkyl, 3-oxo-morpholin-4-yl-$C_{1-3}$-alkyl, hydroxy-$C_{1-4}$-alkyloxy, $C_{1-4}$-alkyloxy-$C_{1-4}$-alkyloxy, $C_{1-3}$-alkylsulfinyl-$C_{1-3}$-alkyloxy, $C_{1-3}$-alkylsulfonyl-$C_{1-3}$-alkyloxy, di-($C_{1-3}$-alkyl)-amino-$C_{1-3}$-alkyloxy, 2-oxo-pyrrolidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, $C_{1-4}$-alkylsulfanyl, $C_{1-4}$-alkysulfinyl, $C_{1-4}$-alkylsulfonyl, (het)arylsulfonyl, $C_{3-6}$-cycloalkylsulfanyl, $C_{3-6}$-cycloalkylsulfinyl, $C_{3-6}$-cycloalkylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkoxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydro-furanyl-$C_{1-3}$-alkyloxy, or tetrahydropyranyl-$C_{1-3}$-alkyloxy, wherein the above-mentioned (het)aryl groups are defined as described hereinbefore under $R^4$.

More preferably $R^7$ denotes fluorine, chlorine, $C_{1-4}$-alkyl, hydroxy, $C_{1-4}$-alkyloxy, nitro, amino, $C_{1-3}$-alkylamino, 2-oxo-pyrrolidin-1-yl, 2-oxo-piperidin-1-yl, morpholin-4-yl, 3-oxo-morpholin-4-yl, $C_{1-3}$-alkyl-carbonylamino, (het)aryl-carbonylamino, $C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-13}$-alkyl)-$C_{1-3}$-alkyl-sulfonylamino, N—($C_{1-3}$-alkyl)-(het)arylsulfonylamino, cyano, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, $C_{1-3}$-alkyl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, cyano-$C_{1-3}$-alkyloxy, aminocarbonyl-$C_{1-3}$-alkyloxy, $C_{1-3}$-alkyl-aminocarbonyl-$C_{1-3}$-alkyl-oxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-3}$-alkyl, $C_{1-3}$-alkyloxy-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-pyrrolidin-1-yl-$C_{1-3}$-alkyl, 2-oxo-piperid-in-1-yl-$C_{1-3}$-alkyl, 3-oxo-morpholin-4-yl-$C_{1-3}$-alkyl, hydroxy-$C_{1-3}$-alkyloxy, $C_{1-3}$-alkyloxy-$C_{1-3}$-alkyloxy, $C_{1-4}$-alkylsulfanyl, $C_{1-4}$-alkysulfinyl, $C_{1-4}$-alkylsulfonyl, $C_{3-6}$-cycloalkylsulfanyl, $C_{3-6}$-cycloalkylsulfinyl, $C_{3-6}$-cycloalkylsulfonyl, aminosulfonyl, $C_{1-3}$-alkyl-aminosulfonyl, di-($C_{1-3}$-alkyl)-aminosulfonyl, trifluoromethyl, difluoromethoxy, trifluoromethoxy, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl or (het)aryloxy, wherein the above-mentioned (het)aryl groups for $R^7$ denote phenyl, furanyl, thienyl, oxazolyl, thiazolyl, isoxazolyl, imidazolyl, pyrazolyl, oxadiazolyl, triazolyl, tetrazolyl, pyridinyl, pyrimidinyl, pyrazinyl, pyridazinyl, or triazinyl, wherein any of these groups are optionally mono- or disubstituted with $R^{10}$. Most preferably $R^7$ denotes fluorine, chlorine, $C_{1-3}$-alkyl, hydroxy, $C_{1-3}$-alkyloxy, amino, $C_{1-3}$-alkyl-carbonylamino, $C_{1-3}$-alkyl-sulfonylamino, cyano, (hydroxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, hydroxy-$C_{1-3}$-alkyl, trifluoromethyl-hydroxy-$C_{1-3}$-alkyl, $C_{1-3}$-alkyloxy-$C_{1-3}$-alkyl, $C_{1-3}$-alkyl-carbonyl-amino-$C_{1-3}$-alkyl, hydroxy-$C_{1-3}$-alkyloxy, $C_{1-3}$-alkyloxy-$C_{1-3}$-alkyloxy, trifluoromethyl, difluoromethoxy, trifluoromethoxy, $C_{1-3}$-alkylcarbonyl, $C_{1-4}$-alkylsulfonyl, $C_{3-6}$-cycloalkylsulfonyl, aminosulfonyl, $C_{1-3}$-alkyl-aminosulfonyl, di-($C_{1-3}$-alkyl)-aminosulfonyl, or a (het)aryl group selected from phenyl, pyrrol-1-yl, 4-methyl-4H-[1,2,4]triazol-3-yl, oxadiazolyl, pyridinyl, 1,2-dihydro-1-methyl-2-oxo-pyridinyl, pyrimidinyl, pyridazinyl, and 2,3-dihydro-2-methyl-3-oxo-pyridazinyl, each of them being optionally monosubstituted with $R^{10}$;

particularly $R^7$ denotes fluorine, chlorine, methyl, hydroxy, methoxy, amino, acetylamino, methylsulfonylamino, cyano, (hydroxyimino)aminomethyl, carboxy, methoxycarbonyl, ethoxycarbonyl, aminocarbonyl, methylaminocarbonyl, dimethylaminocarbonyl, acetylaminomethyl, acetyl, 1-hydroxy-ethyl, 1-hydroxy-1-methyl-ethyl, 2,2,2-trifluoro-1-hydroxy-1-methyl-ethyl, methylsulfonyl, aminosulfonyl, methylaminosulfonyl, dimethylaminosulfonyl, phenyl, pyrrol-1-yl, pyridin-3-yl, pyridin-4-yl, 1,2-dihydro-1-methyl-2-oxo-pyridin-5-yl, 1,2-dihydro-1-methyl-2-oxo-pyridin-4-yl, pyrimidin-4-yl, 2-methyl-pyrimidin-4-yl, 2-methyl-pyrimidin-5-yl, 6-methyl-pyridazin-3-yl, 2,3-dihydro-2-methyl-3-oxo-pyridazin-6-yl, 4,5-dimethyl-4H-[1,2,4]triazol-3-yl, oxadiazolyl, or methyloxadiazolyl.

$R^8$ and $R^9$, which may be identical or different, denote fluorine, chlorine, bromine, $C_{1-3}$-alkyl, trifluoromethyl, hydroxy, $C_{1-3}$-alkyloxy, or cyano. More preferably $R^8$ and $R^9$ independently denote fluorine, chlorine, methyl, ethyl, isopropyl, trifluoromethyl, hydroxy, methoxy, ethoxy, or cyano. Most preferably, $R^8$ denotes hydroxyl, or methoxy.

If $R^8$ and $R^9$ are bound to adjacent carbon atoms they together may additionally denote methylenedioxy, difluoromethylenedioxy, ethylenedioxy, $C_{3-5}$-alkylene, or form together with the carbon atoms to which they are attached a benzo, pyrazino, pyrazolo, imidazo, N—($C_{1-3}$-alkyl)-pyrazolo, N—($C_{1-3}$-alkyl)-imidazo, triazolo, oxazolo, thiazolo, isoxazolo, or isothiazolo ring, wherein any of the five-membered aromatics are optionally additionally monosubstituted with L and any six-membered rings are optionally mono- or disubstituted with one L and/or one substituent selected from fluorine, $C_{1-3}$-alkyl, trifluoromethyl, amino, $C_{1-3}$-alkylamino, di-($C_{1-3}$-alkyl)amino, hydroxyl, or $C_{1-3}$-alkyloxy. Preferably, $R^8$ and $R^9$, if bound to adjacent carbon atoms, together may additionally denote methylenedioxy, ethylene-1,2-dioxy, propylene, butylene or together with the carbon atoms to which they are attached form a benzo, pyrazino, pyrazolo, imidazo, N—($C_{1-13}$-alkyl)-pyrazolo, N—($C_{1-3}$-alkyl)-imidazo, triazolo, oxazolo, thiazolo, isoxazolo, or isothiazolo ring, wherein any of the five-membered aromatics are optionally additionally monosubstituted with L and any six-membered rings are optionally mono- or disubstituted with one L and/or one substituent selected from fluorine, methyl, trifluoromethyl, methylamino, dimethylamino, hydroxyl, or methoxy.

More preferably, $R^8$ and $R^9$, if bound to adjacent carbon atoms, together may additionally denote methylenedioxy or ethylene-,12-dioxy or together with the carbon atoms to which they are attached form a benzo, pyrazino, imidazo, N—($C_{1-3}$-alkyl)-imidazo, triazolo, oxazolo, or thiazolo ring, wherein the benzo and pyrazino ring are optionally substituted with one or two methyl groups and the imidazo, N—$C_{1-3}$-alkylimidazo, oxazolo, and thiazolo ring are optionally additionally substituted with L.

Most preferably, $R^8$ and $R^9$, if bound to adjacent carbon atoms, together may additionally de-note methylenedioxy or together with the carbon atoms to which they are attached form an optionally additionally with methyl, tert-butyl, cyclopropyl, tetrahydrofuran-2-yl, 1-acetyl-piperidin-4-yl, pyridin-3-yl, 1,2-dihydro-1-methyl-2-oxo-pyridin-5-yl, pyridazin-4-yl, pyrazinyl, or 5-methyl-pyrazin-2-yl substituted oxazolo, imidazo, or N-methyl-imidazo group, an optionally with methyl substituted triazolo group, or an optionally methyl or dimethyl substituted benzo or pyrazino ring.

L preferably is fluorine, $C_{1-4}$-alkyl, $C_{3-6}$-cycloalkyl, pyrrolidinyl, 1-methyl-pyrrolidinyl, 1-acetyl-pyrrolidinyl, piperidinyl, 1-methyl-piperidinyl, 1-acetyl-piperidinyl, tetrahydrofuranyl, tetrahydropyranyl, trifluoromethyl, cyano, amino, acetylamino, methylsulfonylamino, carboxy, $C_{1-3}$-alkyloxycarbonyl, aminocarbonyl, methylaminocarbonyl, dimethylaminocarbonyl, aminosulfonyl, hydroxy, $C_{1-3}$-alkyloxy, or phenyl, pyridyl, pyridazinyl, pyrazinyl, pyrimidinyl, 1,2-dihydro-2-oxo-pyridinyl, which are optionally substituted with one or two groups independently selected from fluorine, chlorine, $C_{1-3}$-alkyl, difluoromethyl, trifluoromethyl, cyano, amino, acetylamino, methylsulfonylamino, carboxy, $C_{1-3}$-alkyloxycarbonyl, aminocarbonyl, methylaminocarbonyl, dimethylamino-carbonyl, hydroxy, methoxy, difluoromethoxy, and trifluoromethoxy.

More preferably, L is fluorine, methyl, ethyl, tert-butyl, $C_{3-6}$-cycloalkyl, pyrrolidinyl, 1-methyl-pyrrolidinyl, 1-acetyl-pyrrolidinyl, piperidinyl, 1-methyl-piperidinyl, 1-acetyl-piperidinyl, tetrahydrofuranyl, tetrahydropyranyl, trifluoromethyl, cyano, amino, acetylamino, methylsulfonylamino, carboxy, methoxycarbonyl, ethoxycarbonyl, aminocarbonyl, methylaminocarbonyl, dimethylaminocarbonyl, aminosulfonyl, hydroxy, methoxy, or phenyl, pyridyl, pyridazinyl, pyrazinyl, pyrimidinyl, 1,2-dihydro-2-oxo-pyridinyl, which are optionally substituted with one or two groups independently selected from fluorine, methyl trifluoromethyl, cyano, amino, acetylamino, methylsulfonylamino, carboxy, aminocarbonyl, methylaminocarbonyl, dimethylaminocarbonyl, hydroxy, and methoxy.

Most preferably, L is fluorine, methyl, cyclopropyl, 1-acetyl-piperidinyl, tetrahydrofuranyl, acetylamino, methylsulfonylamino, carboxy, hydroxy, methoxy, or pyridyl, pyridazinyl, pyrazinyl, 1,2-dihydro-2-oxo-pyridinyl, which are optionally substituted with one or two methyl groups; particularly, L is methyl, tert-butyl, cyclopropyl, tetrahydrofuran-2-yl, 1-acetyl-piperidin-4-yl, pyrid-3-yl, pyridazin-3-yl, pyrazinyl, 5-methylpyrazin-2-yl, 1,2-dihydro-2-oxo-pyridin-5-yl.

$R^{10}$ preferably denotes fluorine, chlorine, bromine, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, phenyl, hydroxy, $C_{1-3}$-alkyloxy, difluoromethoxy, or trifluoromethoxy.

More preferably, $R^{10}$ denotes fluorine, chlorine, methyl, difluoromethyl, trifluoromethyl, cyano, hydroxy, methoxy, difluoromethoxy, or trifluoromethoxy, most preferably, $R^{10}$ denotes methyl.

$R^{11}$ preferably denotes fluorine, $C_{1-3}$-alkyl, phenyl, hydroxy, $C_{1-3}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl, or $C_{1-3}$-alkyloxy-$C_{1-4}$-alkyl. More preferably $R^{11}$ denotes fluorine, $C_{1-3}$-alkyl, hydroxyl, or $C_{1-3}$-alkyloxy. Most preferably, $R^{11}$ denotes methyl, ethyl, propyl, hydroxy, or methoxy, particularly hydrogen, methyl, or methoxy.

$R^{12}$ preferably denotes fluorine, or $C_{1-3}$-alkyl, more preferably methyl or ethyl; and $R^{13}$ and $R^{14}$, which may be identical or different, preferably denote $C_{1-13}$-alkyl. More preferably, $R^{13}$ and $R^{14}$ denote methyl.

Some terms used above and hereinafter to describe the compounds according to the invention will now be defined more closely.

The term "substituted" as used herein, means that any one or more hydrogens on the designated atom is replaced with a selection from the indicated group, provided that the designated atom's normal valence is not exceeded, and that the substitution results in a stable compound.

The term halogen denotes an atom selected from the group consisting of F, Cl, Br and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{3-n}$-cycloalkenyl denotes a $C_{3-n}$-cycloalkyl group which is as hereinbefore defined and additionally has at least one C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

If groups or residues are optionally substituted, this applies to any form of the group or residue. For instance, if an alkyl group is optionally mono- or polyfluorinated this comprises also alkyl residues which are part of larger groups, e.g. alkyloxy, alkylcarbonyl, alkoxyalkyl, etc. or if a (het)aryl group is optionally mono- or polysubstituted with a certain substituent or a set of substituents this also includes (het)aryl groups which are part of larger groups, e.g. (het)aryl-$C_{1-n}$-alkyl, (het)aryloxy, (het)aryloxy-$C_{1-n}$-alkyl, (het)aryl-$C_{1-n}$-alkyloxy, etc. Accordingly, in cases where $R^4$ or $R^7$ have e.g. the meaning (het)aryloxy, while (het)aryl residues are optionally mono- or polyfluorinated and (het)aryl denotes inter alia phenyl, the meanings mono-, di-, tri-, tetra-, and pentafluorophenoxy are also comprised. The same applies to groups or residues in which a $CH_2$ group may be replaced by O, S, NR, CO, or $SO_2$. For instance, a residue having inter alia the meaning hydroxy-$C_{1-3}$-alkyl, in which a $CH_2$ group may be replaced by CO, this comprises carboxy, carboxymethyl, hydroxymethylcarbonyl, carboxyethyl, hydroxymethylcarbonylmethyl, and hydroxyethyl-carbonyl.

The compounds according to the invention may be obtained using methods of synthesis known in principle. Preferably the compounds are obtained by the following methods according to the invention which are described in more detail hereinafter.

A general strategy to access compounds of the invention is delineated in Scheme 1; $R^2$, $R^3$, X, m, n, and o have the meanings as defined hereinbefore and hereinafter. The key reaction to assemble the bicyclic framework is an intramolecular merger of an amino functionality with a carboxy group that results in the formation of an amide linkage. The fusion of the carboxylic acid function and the amino group may be carried out with or without an additive at elevated temperatures, preferably between 20 and 200° C. Additives that remove the water forming during the reaction, such as molecular sieves or orthoesters, or other additives such as bases, e.g. hexamethyldisilazides, or boronic acids may facilitate the reaction. Though, more preferably the reaction is done with a more reactive entity of the carboxy function such as an acyl halide, ester, thioester, anhydride, mixed anhydride, or ketene which may be generated in a separate preceding reaction step or in situ. Preferred acyl halides are acyl chloride and acyl fluoride. Preferred esters and thioesters are derived from e.g. methanol/methylthiol, ethanol/ethylthiol, 2,2,2-trifluoroethanol, phenol/thiophenol, substituted phenol/thiophenol such as 4-nitrophenol or pentafluorophenol, hydroxy heteroaryl such as hydroxybenzotriazol, hydroxypyridotriazol, or hydroxytriazines, or N-hydroxysuccinimid. Preferred mixed anhydrides are derived from alkylcarboxylic acids, e.g. pivalic acid, carbonates, e.g. methyl and ethyl carbonate, carbamates, e.g. N,N-dimethyl carbamate, phosphoric acids, e.g. dimethyl-phosphoric acid or $(Me_2N)_2P(O)$ OH, or ureas, e.g. dicyclohexylurea, dimethylurea, or tetramethylurea. Additionally, N acylated derivatives derived from azaheteroaromatics such as imidazole, triazole, tetrazole, or pyridine such as e.g. 4-dimethylaminopyridine may be used as well. Some of the more popular reagents used for the activation of the carboxylic acid function are N,N'-carbonyldiimidazol, dicyclohexylcarbodiimide, (benzotriazol-1-yloxy)-dipiperidinocarbenium hexafluorophospate or tetrafluoroborate, (benzotriazol-1-yloxy) dipyrrolidinocarbenium hexafluorophospate or tetrafluoroborate, 1-(3-dimethylaminopropyl)-3-ethylcarbodiimide methiodide, $POCl_3$, $SOCl_2$, $(COCl)_2$, $COCl_2$, arylboronic acid, $TiCl_4$, $(MeO)_2POCl$, cyanuric chloride, 1-hydroxybenzotriazol, 1-hydroxy-7-azabenzotriazol, benzoltriazol-1-yloxytris(dimethylamino)phosphonium hexafluorophospate or tetrafluoroborate, benzoltriazol-1-yloxytripyrrolidinophosphonium hexafluorophospate or tetrafluoroborate, (7-aza-benzoltriazol-1-yloxy)tripyrrolidinophosphonium hexafluorophosphate or tetrafluoroborate, O-(benzotriazol-1-yl)-N,N,N',N'-tetramethyluronium hexafluorophosphate or tetra-fluoroborate, O-(7-aza-1H-benzotriazol-1-yl)-1,1,3,3-tetramethyluronium hexafluorophosphate or tetrafluoroborate. This compilation of reagents represents only a few possibilities to activate an carboxylic acid function. A host of additional reagents is known and may be used here as well. The reactive carboxylic acid derivatives may also serve as intermediates for other acylating reagents also sufficiently reactive for this transformation. The activation step and the ensuing amide forming step are often best carried out in the presence of additional additives such as bases, e.g. ethyldiisopropylamine, triethylamine, alkali metal carbonate, pyridine, 4-dimethylaminopyridine, imidazole, dimethylaluminum amides, lithium amides, alkali metal cyanide, or alkali metal hexamethyldisilazide. The reactions are preferably con-ducted in organic solvents but may also be carried out in aqueous solvents. Among the organic solvents ordinarily used are dimethylformamide, dimethylacetamide, N-methyl-pyrrolidinone, dimethylsulfoxide, tetrahydrofuran, hexane, ether, dioxane, dimethoxyethane, dichloromethane, dichloroethane, toluene, benzene, ethyl acetate, quinoline, pyridine, or mixtures thereof. The reactions may be carried out at −80° C. to 220° C., preferably between −10° C. and 120° C. Subsequently, the lactam group is reduced to give the secondary amine. This transformation is a well established reaction that may be carried out, for example, using LiAlH$_4$, hydrogen in the presence of a catalyst, NaBH$_4$ in the presence of e.g. iodine, LiBH$_4$, borane, sodium in propanol, Cl$_3$SiH, silanes, e.g. Et$_3$SiH, in the presence of a transition metal such as rhenium, 9-BBN, LiBH$_3$NMe$_2$, or Et$_3$SiH combined with LiEt$_3$BH. Solvents such as e.g. tetrahydrofuran, ether, dimethoxyethane, dioxane, hexane, benzene, toluene, dichloro-methane, alcohols, water, or mixtures thereof may be employed at −78° C. to 200° C., preferably between −10° C. and 120° C.; though, in combination with some reducing reagents only a few of these solvents are usable. This strategy is well suited for the synthesis of the scaffolds I.1 to I.10.

Scheme 1. Strategy 1 to build the bicyclic skeleton

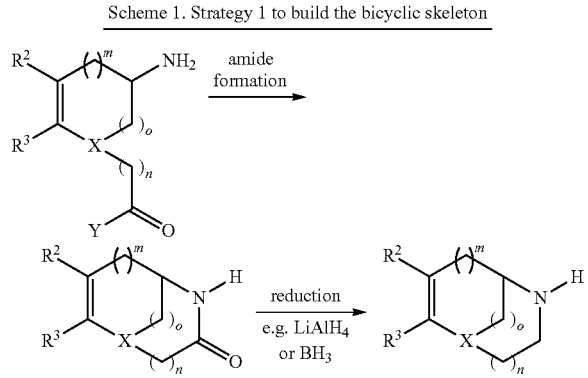

Y = see text

Another common synthetic route to acquire the compounds of the invention is summarized in Scheme 2; R$^2$, R$^3$, X, m, n, and o have the meanings as defined hereinbefore and hereinafter. The bicyclic framework is formed via an intramolecular reductive amination reaction of a primary amine with a ketone functionality. Reductive aminations have large precedence in organic chemistry and may be carried out e.g. using hydrogen in the presence of a transition metal catalyst such as one derived from Ni, Rh, Pd, or Pt, borohydride reagents, e.g. sodium borohydride, sodium cyanoborohydride, or sodium triacetoxyborohydide, zinc in combination with hydrochloric acid, PhSiH$_3$ with Bu$_2$SnCl$_2$, B$_{10}$H$_{14}$, or formic acid or salts thereof. Some of these reagents are preferably used in combination with an additive such as acid, e.g. acetic acid or mineral acid. The reactions are preferably conducted in organic solvents or aqueous mixtures, e.g. dimethylformamide, dimethylacetamide, N-methylpyrrolidinone, dimethylsulfoxide, tetrahydrofuran, hexane, ether, dioxane, dimethoxyethane, dichloromethane, dichloro-ethane, toluene, benzene, alcohols, water, or mixtures thereof. The reactions may be carried out at −80° C. to 200° C., preferably between −10° C. and 100° C.

Scheme 2. Strategy 2 to build the bicyclic skeleton

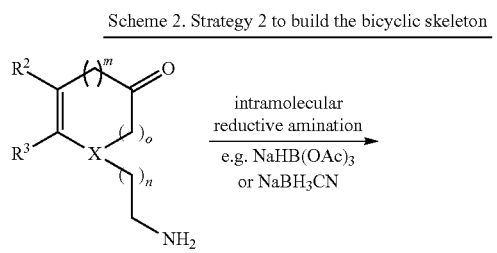

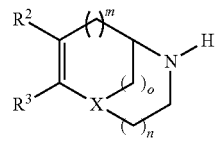

The strategy shown in Scheme 3, wherein R$^2$, R$^3$, X, m, n, and o have the meanings as defined hereinbefore and hereinafter, is another valid approach based on the reductive amination reaction already delineated in Scheme 2. Reaction conditions described there may analogously be employed here.

Scheme 3. Strategy 3 to build the bicyclic skeleton

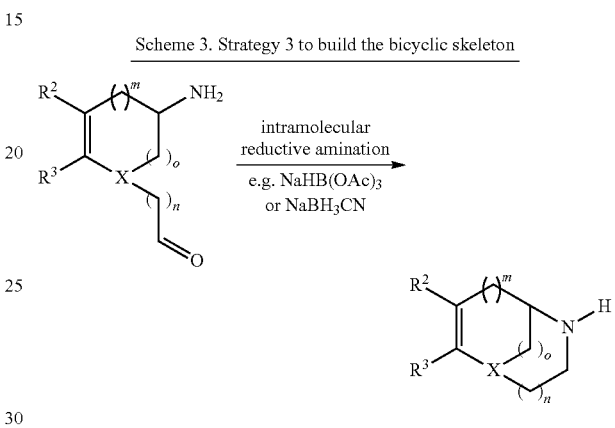

Scheme 4, wherein R$^2$, R$^3$, X, m, n, and o have the meanings as defined hereinbefore and hereinafter, shows another approach to assemble the bicyclic framework. This approach is an intramolecular alkylation of the nitrogen group with an appropriate electrophile of the side-chain. The nitrogen group may be an amino group, i.e. R$^a$ denotes e.g. hydrogen, methyl, allyl, benzyl, or dimethoxybenzyl, or an amide group, i.e. R$^a$ denotes e.g. methoxycarbonyl, benzyloxycarbonyl, allyloxycarbonyl, tertbutoxycarbonyl, trifluormethylcarbonyl, acetyl, 2,2,2-trichloroethoxycarbonyl, tolylsulfonyl, phenylsulfonyl, methoxyphenylsulfonyl, nitrophenyl-sulfonyl, 2,2,2-trichloroethylsulfonyl, or 2-trimethylsilylethylsulfonyl. The nitrogen function is reacted with an electrophilic C$_{sp3}$-center in the side-chain, i.e. LG in Scheme 4 denotes e.g. chlorine, bromine, iodine, mesyloxy, tosyloxy, or trifluoromethylsulfonyloxy, in the presence of a base such as e.g. triethylamine, ethyldiisopropylamine, diazabicycloundecene, alkali metal carbonate, alkali metal tertbutoxide, alkali metal diisopropylamide, butyllithium, or sodium hydride. The stronger bases among them are preferably used in combination with the amides in e.g. N-methylpyrrolidinone, dimethylsulfoxide, tetrahydrofuran, hexane, ether, dioxane, dimethoxyethane, toluene, benzene, tertbutanol, isopropanol, or mixtures thereof at temperatures between −70 and 100° C., preferably between −30 and 60° C. The milder bases listed are preferably used in combination with the amines in dichloromethane, dimethylformamide, N-methylpyrrolidinone, dimethylsulfoxide, tetrahydrofuran, hexane, ether, dioxane, dimethoxyethane, toluene, benzene, methanol, ethanol, tertbutanol, isopropanol, water, or mixtures thereof at temperatures between 0 and 140° C., preferably between 20 and 120° C. For the amides the conditions originally reported by Mitsunobu may be used as well. Accordingly, the side-chain leaving group LG is generated in situ from the hydroxy group (LG=OH) using a phosphine, e.g. triphenylphosphine or tributylphosphine, in combination with an azodicarboxylate, e.g. diethyl azodicarboxylate, diisopropyl azodicarboxylate, or azodicarboxylic dipiperidide. Suited solvents may be selected from among dimethylformamide, N-methylpyrrolidinone, dichloromethane, tetrahydrofuran, hexane, ether, dioxane, dimethoxyethane, toluene, benzene, and mixtures thereof. The reaction is preferably conducted at temperatures between 0 and 100° C. The opposite way around, i.e. LG denotes $NHR^a$ and $NHR^a$ denotes LG, may be applicable as well. Reaction conditions are equivalent to the original way around.

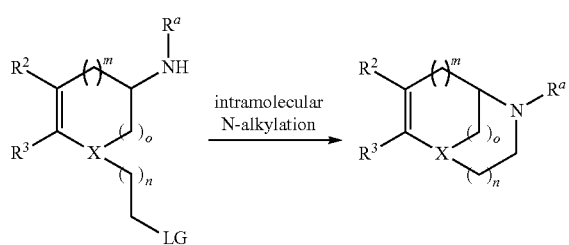

Scheme 4. Strategy 4 to build the bicyclic skeleton

A further generally applicable approach is based on an electrophilic aromatic substitution reaction (Scheme 5); $R^2$, $R^3$, m, n, and o have the meanings as defined hereinbefore and hereinafter. Thereby the aromatic part of the molecule reacts with an activated carbon atom of the azacycle to form the bicyclic framework. The reactive intermediate bears a (partially) positively charged carbon atom in the azacycle that may be generated by the addition of an acid to an olefinic bond or by the activation of an appropriately positioned leaving group. A huge number of Bronstedt and Lewis acids have been described for this classical reaction that may also be used here. The following enumeration is supposed to give a few more widely used of them: hydrobromic acid, hydroiodic acid, hydrochloric acid, sulfuric acid, phosphoric acid, $P_4O_{10}$, trifluoroacetic acid, methanesulfonic acid, toluenesulfonic acid, trifluormethanesulfonic acid, $Sc(OTf)_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. Depending on the inclination of the leaving group to be substituted and the electronic nature of the aromatic a more or less powerful acid catalyst has to be used. Besides the acid catalysts mentioned silver salts, e.g. AgOTf, may be useful in the reactions using halides as leaving group. Preferred solvents are hydrocarbons such as hexane or cyclohexane, chlorinated hydrocarbons such as dichloromethane or dichloro-ethane, perfluorinated hydrocarbons, nitrobenzene, chlorinated benzenes, heteroaromatics such as quinoline, dimethoxyethane, dioxane, ether, ionic liquids, or mixtures thereof. The reactions may be carried out between −10° C. and 220° C., preferably between 20° C. and 180° C. The reactions may also be conducted under microwave irradiation.

This synthetic strategy is particularly suited for the scaffolds I.1 and I.3 to I.10 bearing an electron rich aromatic.

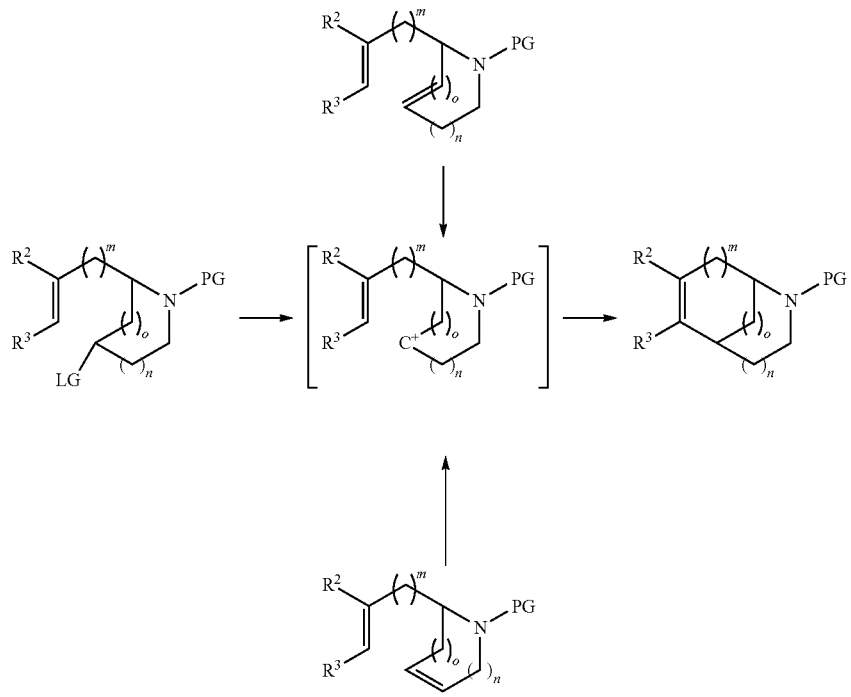

Scheme 5. Strategy 5 to build the bicyclic skeleton

LG = e.g. OH, $OSO_2Me$, $OSO_2Tol$, $OSO_2CF_3$, Cl, Br, I, $O(C_{1-3}$-alkyl), $OCO(C_{1-4}$-alkyl), PG = protective group, e.g. Me or Bn, or $COR^1$ The bicyclic scaffold may also be accessed via the route delineated in Scheme 6; m has the meaning as defined hereinbefore and hereinafter and PG and PG' are protective groups such as e.g. trialkylsilyl for PG and benzyl or methyl for PG'. The cyclization is realized by the addition of a radical intermediate, generated from the trichloromethyl group and a chlorine abstracting reagent, onto the double bond. Suited chlorine abstracting reagents are $Bu_3Sn\cdot$ and $(Me_3Si)_3Si\cdot$ that are formed in situ by a radical initiator, such as azobisisobutyronitrile or dibenzoylperoxide, from $Bu_3SnH$ and $(Me_3Si)_3SiH$, respectively. The reaction is preferably conducted in benzene, toluene, cyclohexane, or hexanes at elevated temperature. This approach is reported inter alia in *Tetrahedron: Asymmetry* 1999, 10, 2399-2410. Elaboration of the bicyclic scaffold to the desired compounds may be accomplished after reduction of the amide functionality to the amine and removal of the protecting group at the right-hand end of the molecule and transformation of the $CH_2C=O$ substructure in the left-hand part of the molecule to one of the aromatics described hereinbefore. These transformations are described hereinbefore and hereinafter and are known for similar compounds from the organic chemistry literature (see e.g. Thomas L. Gilchrist, *Heterocyclenchemie*, VCH, Weinheim, 1995).

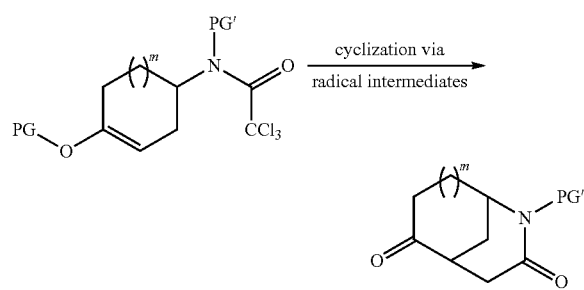

Scheme 6. Strategy 6 to build the bicyclic skeleton

Besides the strategies presented a host of additional approaches to construct the bicyclic systems of the present invention can be envisaged and are also reported in the literature (see e.g. *J. Med. Chem.* 1970, 13, 630-634; *Chem. Rev.* 1977, 77, 1-36; *J. Med. Chem.* 1979, 22, 537-553; *J. Org. Chem.* 1984, 49, 4033-4044; *J. Med. Chem.* 1996, 39, 1956-1966; *Heterocycles* 1996, 43, 15-22; *J. Med. Chem.* 2002, 45, 3755-3764; *J. Org. Chem.* 2006, 71, 2046-2055; and references quoted therein). Therefore, the preceding strategies are in no way meant to restrict the possible synthetic pathways to access the compounds of the invention but are only supposed to show a few routes by way of example.

The synthetic routes presented may rely on the use of protecting groups. Suitable protecting groups for the respective functionalities and their removal have been described hereinbefore and may analogously be employed (see also: *Protecting Groups*, Philip J. Kocienski, 3rd edition, Georg Thieme Verlag, Stuttgart, 2004 and references quoted therein).

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly an inhibitory effect on the enzyme 11β-hydroxysteroid dehydrogenase (HSD) 1.

The biological properties of the new compounds may be investigated as follows:

In vitro inhibition of 11β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contained incubations with vehicle controls instead of compound as controls for non-inhibited cortisol gene-ration (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal and $IC_{50}$ curves were generated.

The compounds of general formula I according to the invention may for example have $IC_{50}$ values below 10000 nM, particularly below 1000 nM, most preferably below 100 nM. In the Table 2 compounds of the invention (specified in Table 3) and their inhibitory activity determined as described above are compiled.

TABLE 2

| Ex. No. | 11β-HSD $IC_{50}$ (nM) | Ex. No. | 11β-HSD $IC_{50}$ (nM) | Ex. No. | 11β-HSD $IC_{50}$ (nM) | Ex. No. | 11β-HSD $IC_{50}$ (nM) |
|---|---|---|---|---|---|---|---|
| 1 | 285 | 80 | 40 | 168 | 561 | 249 | 265 |
| 2 | 741 | 81 | 463 | 169 | 950 | 250 | 53 |
| 3 | 85 | 82 | 56 | 170 | 626 | 251 | 66 |
| 4 | 56 | 84 | 139 | 171 | 1651 | 252 | 61 |
| 5 | 3099 | 85 | 89 | 172 | 1724 | 253 | 78 |
| 6 | 1058 | 86 | 2399 | 173 | 1694 | 254 | 742 |
| 7 | 262 | 87 | 622 | 174 | 406 | 255 | 742 |
| 8 | 3356 | 88 | 171 | 175 | 344 | 256 | 222 |
| 9 | 1979 | 89 | 62 | 176 | 603 | 257 | 209 |
| 10 | 1775 | 90 | 468 | 177 | 8906 | 258 | 33 |
| 11 | 530 | 91 | 711 | 178 | 159 | 259 | 115 |
| 12 | 792 | 92 | 1106 | 179 | 199 | 260 | 181 |
| 13 | 1609 | 93 | 2058 | 180 | 1318 | 261 | 47 |
| 14 | 734 | 94 | 6723 | 181 | 147 | 262 | 73 |
| 15 | 354 | 95 | 3842 | 183 | 155 | 263 | 71 |
| 16 | 360 | 96 | 95 | 184 | 1147 | 264 | 78 |
| 17 | 1378 | 97 | 1134 | 185 | 5375 | 265 | 22 |
| 18 | 3685 | 98 | 125 | 187 | 1957 | 266 | 42 |
| 19 | 658 | 99 | 285 | 188 | 2916 | 267 | 66 |
| 20 | 254 | 100 | 564 | 189 | 2273 | 268 | 931 |
| 21 | 669 | 102 | 1459 | 190 | 1651 | 269 | 63 |
| 22 | 5042 | 103 | 86 | 191 | 571 | 270 | 99 |
| 24 | 134 | 104 | 1388 | 192 | 434 | 271 | 50 |
| 25 | 686 | 105 | 1332 | 193 | 360 | 272 | 44 |
| 26 | 2889 | 106 | 2961 | 194 | 642 | 273 | 35 |
| 27 | 629 | 107 | 2546 | 195 | 2479 | 274 | 51 |
| 28 | 3684 | 108 | 140 | 196 | 781 | 275 | 25 |
| 29 | 1727 | 109 | 1457 | 197 | 3830 | 276 | 34 |
| 30 | 1398 | 111 | 1604 | 198 | 435 | 277 | 34 |
| 31 | 88 | 112 | 1234 | 199 | 137 | 278 | 438 |
| 32 | 915 | 113 | 3633 | 200 | 117 | 279 | 52 |
| 33 | 3493 | 115 | 1587 | 201 | 53 | 280 | 1264 |
| 34 | 3883 | 116 | 3854 | 202 | 66 | 281 | 918 |
| 35 | 672 | 117 | 1423 | 203 | 125 | 282 | 409 |

TABLE 2-continued

| Ex. No. | 11β-HSD IC$_{50}$ (nM) | Ex. No. | 11β-HSD IC$_{50}$ (nM) | Ex. No. | 11β-HSD IC$_{50}$ (nM) | Ex. No. | 11β-HSD IC$_{50}$ (nM) |
|---|---|---|---|---|---|---|---|
| 36 | 3665 | 118 | 72 | 204 | 27 | 283 | 55 |
| 37 | 998 | 119 | 1548 | 205 | 38 | 284 | 666 |
| 38 | 1444 | 120 | 3843 | 206 | 47 | 285 | 150 |
| 39 | 1590 | 121 | 4122 | 207 | 224 | 286 | 47 |
| 40 | 542 | 122 | 818 | 208 | 238 | 287 | 61 |
| 41 | 589 | 123 | 297 | 209 | 40 | 288 | 901 |
| 42 | 4527 | 124 | 658 | 210 | 68 | 289 | 121 |
| 43 | 1757 | 125 | 989 | 211 | 31 | 290 | 72 |
| 44 | 200 | 126 | 1270 | 212 | 1945 | 291 | 183 |
| 45 | 384 | 127 | 1466 | 213 | 2972 | 292 | 502 |
| 46 | 97 | 128 | 1291 | 214 | 5711 | 293 | 27 |
| 48 | 364 | 129 | 5848 | 215 | 1730 | 294 | 146 |
| 49 | 168 | 130 | 1608 | 216 | 1715 | 295 | 35 |
| 50 | 3002 | 131 | 361 | 217 | 410 | 296 | 32 |
| 51 | 629 | 132 | 958 | 218 | 2708 | 297 | 895 |
| 52 | 101 | 133 | 941 | 219 | 160 | 298 | 99 |
| 53 | 321 | 134 | 1228 | 220 | 549 | 299 | 352 |
| 54 | 529 | 135 | 3520 | 221 | 2433 | 300 | 115 |
| 55 | 746 | 137 | 3621 | 222 | 124 | 301 | 32 |
| 56 | 725 | 138 | 2805 | 223 | 106 | 302 | 35 |
| 57 | 137 | 139 | 92 | 224 | 21 | 303 | 717 |
| 58 | 62 | 140 | 48 | 225 | 98 | 304 | 251 |
| 59 | 36 | 141 | 59 | 226 | 1410 | 305 | 153 |
| 60 | 228 | 142 | 689 | 227 | 25 | 306 | 978 |
| 61 | 798 | 143 | 123 | 228 | 236 | 307 | 979 |
| 62 | 109 | 144 | 2561 | 229 | 68 | 308 | 210 |
| 63 | 216 | 145 | 108 | 231 | 146 | 309 | 184 |
| 64 | 753 | 146 | 384 | 232 | 132 | 310 | 214 |
| 65 | 29 | 147 | 1013 | 233 | 144 | 311 | 424 |
| 66 | 822 | 148 | 556 | 234 | 3119 | 312 | 103 |
| 67 | 32 | 149 | 374 | 235 | 95 | 313 | 61 |
| 68 | 372 | 150 | 438 | 236 | 189 | 314 | 162 |
| 69 | 105 | 151 | 426 | 237 | 916 | 315 | 61 |
| 70 | 362 | 152 | 4668 | 238 | 24 | 316 | 32 |
| 71 | 47 | 154 | 1657 | 239 | 24 | 317 | 217 |
| 72 | 148 | 155 | 354 | 240 | 51 | 318 | 31 |
| 73 | 88 | 156 | 340 | 241 | 204 | 319 | 446 |
| 74 | 69 | 157 | 335 | 242 | 547 | 320 | 165 |
| 75 | 395 | 160 | 2175 | 243 | 113 | 321 | 1167 |
| 76 | 166 | 161 | 1750 | 245 | 257 | 323 | 620 |
| 77 | 144 | 162 | 1091 | 246 | 637 | 324 | 121 |
| 78 | 67 | 163 | 249 | 247 | 190 | 325 | 771 |
| 79 | 1367 | 167 | 291 | 248 | 1514 | 330 | 44 |
| 331 | 439 | 332 | 64 | 333 | 84 | 334 | 104 |
| 335 | 115 | 336 | 198 | 337 | 52 | 338 | 63 |
| 339 | 1272 | 340 | 67 | 341 | 601 | 342 | 373 |
| 343 | 1524 | 344 | 35 | | | | |

In view of their ability to inhibit enzyme 11β-hydroxysteroid dehydrogenase (HSD) 1, the compounds of general formula I according to the invention and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor, and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an 11β-hydroxysteroid dehydrogenase (HSD) 1 inhibitor according to the invention with respect to one of the indications mentioned and/or which allow the dosage of an 11β-hydroxysteroid dehydrogenase (HSD) 1 inhibitor according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, sergliflozin), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, BI 1356), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

Preparation of the Starting Compounds

Example I

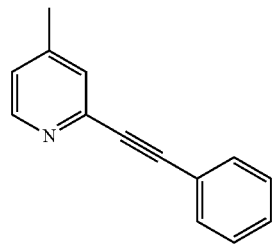

4-Methyl-2-phenylethynyl-pyridine

Phenylacetylene (15.4 mL) is added to a mixture of 2-bromo-4-methyl-pyridine (20.0 g), CuI (2.2 g), and Pd(PPh$_3$)$_2$Cl$_2$ (4.1 g) in triethylamine (600 mL) kept under argon atmosphere. The mixture is stirred at ambient temperature overnight. Then, water is added and the resulting mixture is extracted with diethylether. The combined organic extracts are washed with brine and dried (MgSO$_4$). The solvent is removed under reduced pressure and the residue is purified by chromatography on silica gel (cyclohexane/ethyl acetate 9:1->4:1) to give the product as an oil.

Yield: 18.6 g (83% of theory)

Mass spectrum (ESI$^+$): m/z=194 [M+H]$^+$

Example II

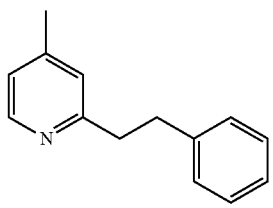

4-Methyl-2-phenethyl-pyridine

A mixture of 4-methyl-2-phenylethynyl-pyridine (18.2 g) and 10% palladium on carbon (2.0 g) in methanol (300 mL) is stirred under hydrogen atmosphere (50 psi) at ambient temperature until the triple bond is completely reduced (20 h). The mixture is filtered and the solvent is removed under reduced pressure.

Yield: 17.6 g (95% of theory)
Mass spectrum (ESI$^+$): m/z=198 [M+H]$^+$

Example III

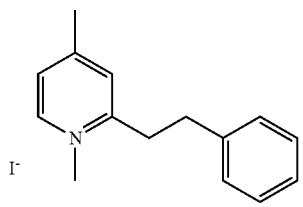

1,4-Dimethyl-2-phenethyl-pyridinium iodide

Iodomethane (8.3 mL) is added to a solution of 4-methyl-2-phenethyl-pyridine (17.5 g) in acetonitrile (70 mL). The resulting solution is stirred at room temperature overnight before another portion of iodomethane (2.8 mL) is added and the solution is further stirred at ca. 35° C. for another 14 h. After cooling to room temperature, the precipitate is separated by filtration, washed with acetonitrile, and dried at 50° C.

Yield: 20.9 g (69% of theory)
Mass spectrum (ESI$^+$): m/z=212 [1,4-dimethyl-2-phenethyl-pyridinium]$^+$

Example IV

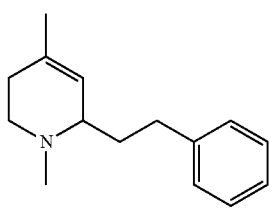

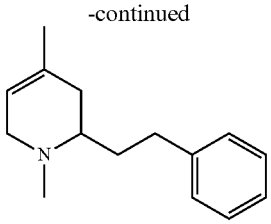

1,4-Dimethyl-6-phenethyl-1,2,3,6-tetrahydro-pyridine and 1,4-dimethyl-2-phenethyl-1,2,3,6-tetrahydro-pyridine Sodium borohydride (2.9 g) is added in one portion to a mixture of 1,4-dimethyl-2-phenethyl-pyridinium iodide (20.9 g) and sodium hydroxide (23.9 g) in water (60 mL) and methanol (75 mL). The mixture is stirred at 60° C. for 1 h and then cooled to room temperature. The reaction mixture is extracted with diethylether and the organic extracts are dried (MgSO$_4$). After removing the solvent, the residue is purified by chromatography on silica gel (dichloromethane/methanol 30:1->9:1) to give a mixture of the two title products (ca. 3:1).

Yield: 16.4 g (61% of theory)
Mass spectrum (ESI$^+$): m/z=216 [M+H]$^+$

Example V

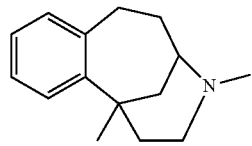 [SMILES: CN1CCC2(C)CC1CCc1ccccc12]

1,11-Dimethyl-11-aza-tricyclo[8.3.1.0*2,7*]tetradeca-2,4,6-triene

A mixture of 1,4-dimethyl-6-phenethyl-1,2,3,6-tetrahydro-pyridine and 1,4-dimethyl-2-phenethyl-1,2,3,6-tetrahydro-pyridine (ca. 3:1, 1.0 g) dissolved in polyphosphoric acid (5 mL) is stirred at 150° C. for 2 d. After cooling to ca. 80° C., water (30 mL) is added and the mixture is stirred vigorously for another 5 min. Then, the mixture is cooled in an ice bath, more water is added, and the mixture is basified using 40% NaOH in water. The resulting mixture is extracted with ethyl acetate, the combined organic extracts are washed with brine and dried (MgSO$_4$). The solvent is removed under reduced pressure to yield the title product.

Yield: 0.76 g (76% of theory)
Mass spectrum (ESI$^+$): m/z=216 [M+H]$^+$

The following compound is obtained analogously to Example V:

(1) 1-Methyl-10-aza-tricyclo[7.2.1.0*2,7*]dodeca-2,4,6-triene

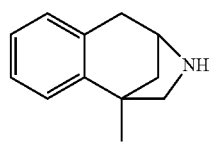

Mass spectrum (ESI$^+$): m/z=174 [M+H]$^+$
2-Benzyl-4-methyl-2,5-dihydro-pyrrole-1-carboxylic acid tert-butyl ester is used as the starting material.

Example VI

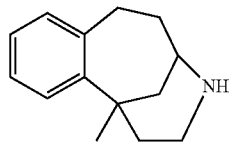

1-Methyl-11-aza-tricyclo[8.3.1.0*2,7*]tetradeca-2,4,6-triene

1-Chloroethyl chloroformate (3.8 mL) is added dropwise to a mixture of 1,11-dimethyl-11-aza-tricyclo[8.3.1.0*2,7*]tetradeca-2,4,6-triene (0.75 g) and NaHCO$_3$ (2.9 g) in 1,2-dichloroethane (3.5 mL) chilled in an ice bath. The reaction mixture is warmed to room temperature in the cooling bath and stirred overnight. Then, dichloromethane (20 mL) is added and the precipitate is removed by filtration. The filtrate is concentrated under reduced pressure and the residue is dissolved in methanol (20 mL). The resulting solution is stirred at reflux temperature for 2 h. The solution is concentrated and the residue is purified by HPLC on reversed phase (water/MeCN/NH$_3$) to give the title compound.

Yield: 0.11 g (16% of theory)

The following compounds are obtained analogously to Example VI:

(1) 11,11-Dimethyl-2,3,4,5-tetrahydro-1H-2,6-methano-benzo[d]azocin-6-ol

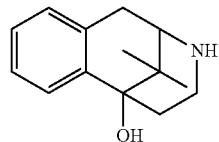 [SMILES: CC1(C)C2Cc3ccccc3C1(O)CCN2]

The starting material, 3,11,11-trimethyl-2,3,4,5-tetrahydro-1H-2,6-methano-benzo[d]azocin-6-ol, is obtained in analogy to EP 28717 (1981) from 2-benzyl-1,3,3-trimethyl-piperidinone.

(2) 8-Hydroxy-2,3,4,5-tetrahydro-1H-2,6-methano-benzo[d]azocine-6-carboxylic acid methyl ester

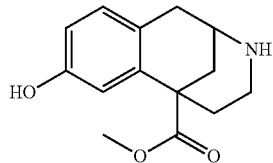 [SMILES: COC(=O)C12CCNC(Cc3ccc(O)cc31)C2]

The starting material, 8-hydroxy-3-methyl-2,3,4,5-tetrahydro-1H-2,6-methano-benzo[d]azocine-6-carboxylic acid methyl ester, may be obtained in analogy to *J. Med. Chem.* 1962, 5, 357-361 and U.S. Pat. No. 3,687,957 (1972) from 8-methoxy-3-methyl-1-oxo-2,3,4,5-tetrahydro-1H-2,6-methano-benzo[d]azocine-6-carbonitrile. The methoxy group on the aromatic ring may be cleaved by using boron tribromide in dichloromethane or hydrobromic acid in acetic acid (see e.g. *J. Med. Chem.* 1992, 35, 4135-4142; *J. Med. Chem.* 2004, 47, 165-174).

The starting material may also be obtained by reacting compound Example XXII(1) with boron tribromide according to Procedure J.

(3) 11,11-Dimethyl-6-phenyl-1,2,3,4,5,6-hexahydro-2,6-methano-benzo[d]azocin-8-ol

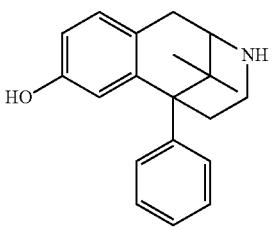 [SMILES: CC1(C)C2Cc3ccc(O)cc3C1(c1ccccc1)CCN2]

The starting material, 3,11,11-trimethyl-6-phenyl-1,2,3,4,5,6-hexahydro-2,6-methano-benzo[d]azocin-8-ol, may be obtained as described in DE 2027077 (1970).

(4) 6-Propyl-1,2,3,4,5,6-hexahydro-2,6-methano-benzo[d]azocin-8-ol

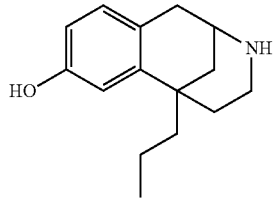

The starting material, 3-methyl-6-propyl-1,2,3,4,5,6-hexahydro-2,6-methano-benzo[d]azocin-8-ol, may be obtained as described in *J. Med. Chem.* 1963, 6, 322-5.

(5) 6-Methyl-1,2,3,4,5,6-hexahydro-2,6-methano-benzo[d]azocin-8-ol

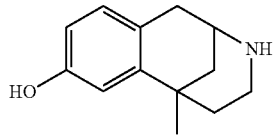

The starting material, 3,6-Dimethyl-1,2,3,4,5,6-hexahydro-2,6-methano-benzo[d]azocin-8-ol, may be obtained as described in *J. Org. Chem.* 1960, 25, 1386-8.

Example VII

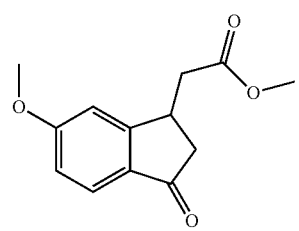 [SMILES: COC(=O)CC1CC(=O)c2ccc(OC)cc21]

(6-Methoxy-3-oxo-indan-1-yl)-acetic acid methyl ester

Concentrated sulfuric acid (3.0 mL) is added to 5-methoxy-1-indanone-3-acetic acid (13.0 g) dissolved in methanol (100 mL). The solution is stirred at reflux temperature for 4 h and then cooled to room temperature. About two third of the methanol is removed under reduced pressure and water (100 mL) and ethyl acetate (200 mL) are added to the remainder. The organic phase is separated and washed with water, 1 M NaOH solution, and brine. The organic phase is dried (MgSO$_4$) and the solvent is evaporated to give the product as a yellow oil.
Yield: 13.2 g (95% of theory)
Mass spectrum (ESI$^+$): m/z=235 [M+H]$^+$ Example VIII

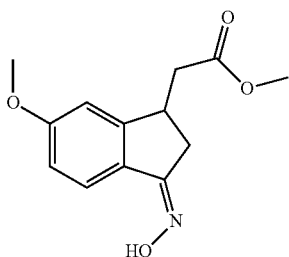 [SMILES: COC(=O)CC1C/C(=N/O)c2ccc(OC)cc21]

(3-Hydroxyimino-6-methoxy-indan-1-yl)-acetic acid methyl ester (6-Methoxy-3-oxo-indan-1-yl)-acetic acid methyl ester (12.0 g), hydroxylamine hydrochloride (4.6 g), and sodium acetate (5.5 g) dissolved in water (40 mL) and methanol (50 mL) are stirred at reflux temperature for 3 h. After cooling to room temperature, water (100 mL) is added and the solution is extracted with ethyl acetate. The combined organic extracts are washed with water and brine and dried (MgSO$_4$). The solvent is evaporated to give the product as a brown oil.
Yield: 12.5 g (98% of theory)
Mass spectrum (ESI$^+$): m/z=250 [M+H]$^+$ Example IX

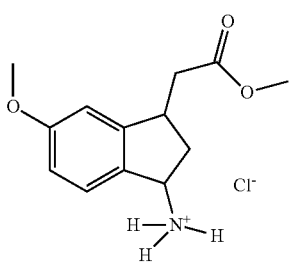 [SMILES: COC(=O)CC1CC([NH3+])c2ccc(OC)cc21 ; [Cl-]]

5-Methoxy-3-methoxycarbonylmethyl-indan-1-yl-ammonium chloride

A mixture of 10% palladium on carbon (3.0 g), (3-hydroxyimino-6-methoxy-indan-1-yl)-acetic acid methyl ester (12.5 g), and concentrated hydrochloric acid (4.7 mL) in methanol (150 mL) is stirred under hydrogen atmosphere at room temperature overnight. The mixture is filtered and the filtrate is concentrated under reduced pressure. The residue is azeotropically dried using toluene and washed with diisopropylether to give the product as a white solid after drying at 50° C.
Yield: 13.0 g (100% of theory)
Mass spectrum (ESI$^+$): m/z=236 [M+H](of amine)

Example X

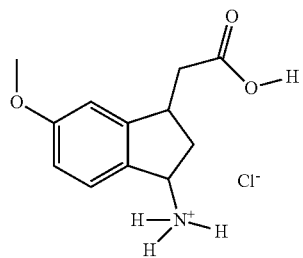 [SMILES: COc1ccc2c(c1)C(CC(=O)O)CC2[NH3+] ; [Cl-]]

3-Carboxymethyl-5-methoxy-indan-1-yl-ammonium chloride

5-Methoxy-3-methoxycarbonylmethyl-indan-1-yl-ammonium chloride (12.5 g) dissolved in 2 M hydrochloric acid (120 mL) is stirred at reflux temperature for 3 h. Then, the solvent is removed and the residue is azeotropically dried using toluene and further purified by washing with diisopropylether. The product is dried at 50° C.
Yield: 11.8 g (100% of theory)
Mass spectrum (ESI$^+$): m/z=220 [M+H]$^+$ (of amine)

Example XI

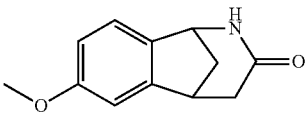

4-Methoxy-9-aza-tricyclo[6.3.1.0*2,7*]dodeca-2,4,6-trien-10-one

3-Carboxymethyl-5-methoxy-indan-1-yl-ammonium chloride (13.2 g) and 1-cyclohexyl-3-(2-morpholinoethyl) carbodiimide methyl-p-toluenesulfonate (21.7 g) dissolved in pyridine (500 mL) is stirred at room temperature for 7 d. Then, the pyridine is removed under reduced pressure and the residue is taken up in water (200 mL) and dichloromethane (200 mL). The organic phase is separated and the aqueous phase is extracted twice with dichloromethane. The combined organic phases are washed with 1 M hydrochloric acid, 1 M NaOH solution, and water. After drying (MgSO$_4$), the solvent is evaporated under reduced pressure to yield the product as a beige solid.
Yield: 3.0 g (29% of theory)
Mass spectrum (ESI$^+$): m/z=204 [M+H]$^+$

Example XII

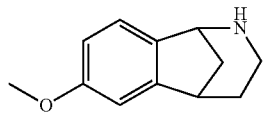

4-Methoxy-9-aza-tricyclo[6.3.1.0*2,7*]dodeca-2,4,6-triene

1 M Borane tetrahydrofuran complex (70 mL) is added dropwise to a solution of 4-methoxy-9-aza-tricyclo[6.3.1.0*2,7*]dodeca-2,4,6-trien-10-one (3.0 g) in THF (20 mL) chilled in an ice bath. The resulting solution is stirred at reflux temperature for 5 h and then at room temperature overnight. The solution is cooled to ca. −10° C. and half-concentrated hydrochloric acid (50 mL) is added carefully. The mixture is stirred at room temperature for 1 h and an additional hour at reflux temperature. The solvent is removed and 2 M NaOH solution (50 mL) is added to the residue. The resulting mixture is extracted with dichloromethane and the combined organic extracts are dried (MgSO$_4$). After removal of the solvent, the residue is taken up in ethanol (20 mL) and the resulting solution is treated with oxalic acid (3 mL) to obtain the oxalate salt of the title compound.

Yield: 0.8 g (19% of theory)
Mass spectrum (ESI$^+$): m/z=190 [M+H]$^+$

Example XIII

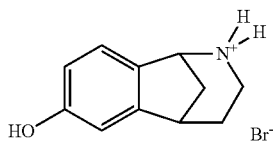

4-Hydroxy-9-azonia-tricyclo[6.3.1.0*2,7*]dodeca-2,4,6-triene bromide

A solution of 4-methoxy-9-aza-tricyclo[6.3.1.0*2,7*]dodeca-2,4,6-triene (0.50 g, oxalate salt) in hydrobromic acid (48% in water, 10 mL) is stirred at reflux temperature for 3 h. Then, the solution is concentrated under reduced pressure and the residue is azetropically dried using toluene and ethanol. The residue is washed with acetone and dried to give the product as a solid.

Yield: 0.23 g (49% of theory)
Mass spectrum (ESI$^+$): m/z=176 [M+H]$^+$ (of amine)

The following compound is obtained analogously to Example XIII:

(1) (2R,6S)-6,11,11-Trimethyl-1,2,3,4,5,6-hexahydro-2,6-methano-benzo[d]azocin-9-ol

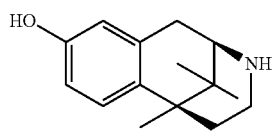

Mass spectrum (ESI$^+$): m/z=232 [M+H]$^+$

The compound is prepared from (2R,6S)-9-methoxy-6,11,11-trimethyl-1,2,3,4,5,6-hexahydro-2,6-methano-benzo[d]azocine [tartaric acid salt, for preparation see WO 9959976 (1999)] and isolated as the hydrogen bromide salt.

Example XIV

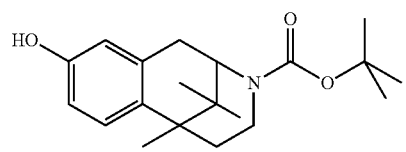 [SMILES: CC(C)(C)OC(=O)N1CCC2(C)c3ccc(O)cc3CC1C2(C)C]

9-Hydroxy-6,11,11-trimethyl-1,2,5,6-tetrahydro-4H-2,6-methano-benzo[d]azocine-3-carboxylic acid tert-butyl ester Di-tertbutyl dicarbonate (8.7 g) is added to a solution of 6,11,11-trimethyl-1,2,3,4,5,6-hexahydro-2,6-methano-benzo[d]azocin-9-ol (12.0 g) and triethylamine (8 ml) in dioxane (100 mL) and water (100 mL). The solution is stirred at room temperature overnight. Then, ethyl acetate is added and the organic phase is separated. The aqueous phase is extracted with ethyl acetate and the organic extract and phase are combined. The organic phase is washed with 1 M hydrochloric acid, water, and brine, and then dried (MgSO$_4$). After removal of the solvent under reduced pressure, the residue is crystallized from diisopropylether to give the title compound.

Yield: 6.5 g (51% of theory)
Mass spectrum (ESI$^+$: m/z=332 [M+H]$^+$

The following compounds are obtained analogously to Example XIV:

(1) (2R,6S)-10-Hydroxy-6,11,11-trimethyl-1,2,5,6-tetrahydro-4H-2,6-methano-benzo[d]azocine-3-carboxylic acid tert-butyl ester

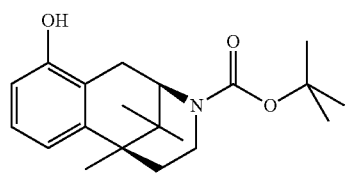

Mass spectrum (ESI$^+$): m/z=332 [M+H]$^+$ (2) (2R,6R,11S)-8-Hydroxy-6,11-dimethyl-1,2,5,6-tetrahydro-4H-2,6-methano-benzo[d]azocine-3-carboxylic acid tert-butyl ester

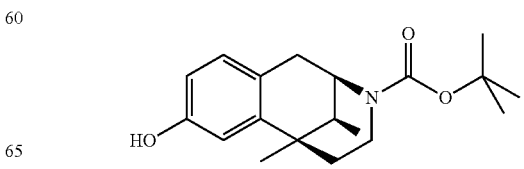

(3) (2S,6R)-8-Hydroxy-6,9,11,11-tetramethyl-1,2,5,6-tetrahydro-4H-2,6-methano-benzo[d]azocine-3-carboxylic acid tert-butyl ester

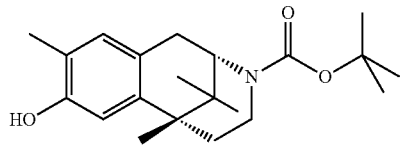 [SMILES: Cc1cc2c(cc1O)[C@@]1(C)CCN(C(=O)OC(C)(C)C)[C@@H](C2)C1(C)C]

The compound may be obtained by resolution of the racemic mixture by HPLC on chiral phase.

(4) (2R,6S)-8-Hydroxy-6,9,11,11-tetramethyl-1,2,5,6-tetrahydro-4H-2,6-methano-benzo[d]azocine-3-carboxylic acid tert-butyl ester

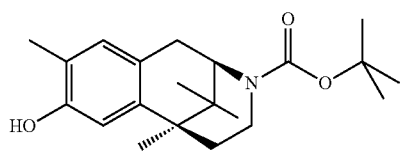 [SMILES: Cc1cc2c(cc1O)[C@]1(C)CCN(C(=O)OC(C)(C)C)[C@H](C2)C1(C)C]

The compound may be obtained by resolution of the racemic mixture by HPLC on chiral phase.

(5) (2S,6R)-9-Hydroxy-6,8,11,11-tetramethyl-1,2,5,6-tetrahydro-4H-2,6-methano-benzo[d]azocine-3-carboxylic acid tert-butyl ester

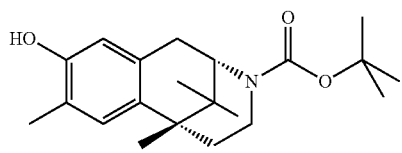 [SMILES: Cc1cc2c(cc1O)C[C@@H]1N(C(=O)OC(C)(C)C)CC[C@@]2(C)C1(C)C]

The compound may be obtained by resolution of the racemic mixture by HPLC on chiral phase.

(6) (2R,6S)-9-Hydroxy-6,8,11,11-tetramethyl-1,2,5,6-tetrahydro-4H-2,6-methano-benzo[d]azocine-3-carboxylic acid tert-butyl ester

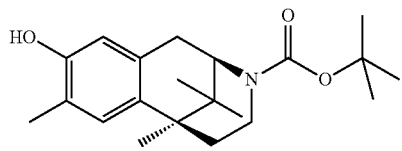 [SMILES: Cc1cc2c(cc1O)C[C@H]1N(C(=O)OC(C)(C)C)CC[C@]2(C)C1(C)C]

The compound may be obtained by resolution of the racemic mixture by HPLC on chiral phase.

(7) 8-Hydroxy-6,11,11-trimethyl-1,2,5,6-tetrahydro-4H-2,6-methano-benzo[d]azocine-3-carboxylic acid tert-butyl ester

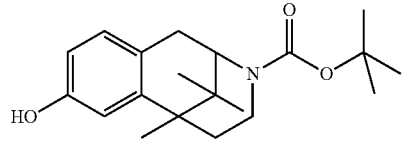 [SMILES: CC(C)(C)OC(=O)N1CCC2(C)c3cc(O)ccc3CC1C2(C)C]

(8) (2R,6S)-9-Hydroxy-6,11,11-trimethyl-1,2,5,6-tetrahydro-4H-2,6-methano-benzo[d]azocine-3-carboxylic acid tert-butyl ester

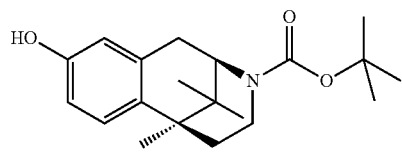 [SMILES: CC(C)(C)OC(=O)N1CC[C@@]2(C)c3ccc(O)cc3C[C@@H]1C2(C)C]

Mass spectrum (ESI$^+$): m/z=332 [M+H]$^+$

The compound may be obtained by resolution of the racemic mixture by HPLC on chiral phase or by using the enantiomerically pure starting material that in turn may be obtained as described in Example XIII(1) or by resolution of the racemic mixture by HPLC on chiral phase. The synthesis of the racemic starting material is described in EP 521422 (1993).

(9) 7-Hydroxy-6,11,11-trimethyl-1,2,5,6-tetrahydro-4H-2,6-methano-benzo[d]azocine-3-carboxylic acid tert-butyl ester

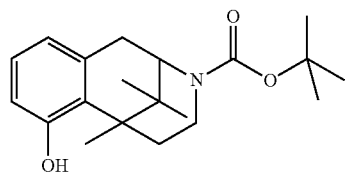 [SMILES: CC(C)(C)OC(=O)N1CCC2(C)c3c(O)cccc3CC1C2(C)C]

Mass spectrum (ESI$^+$): m/z=332 [M+H]+

(10) (2R,6S)-8-Acetyl-6,11,11-trimethyl-1,2,5,6-tetrahydro-4H-2,6-methano-benzo[d]azocine-3-carboxylic acid tert-butyl ester

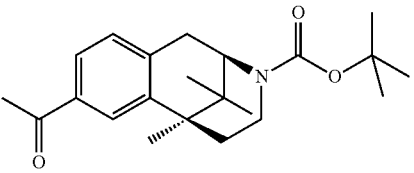 [SMILES: CC(=O)c1ccc2c(c1)[C@]1(C)CCN(C(=O)OC(C)(C)C)[C@H](C2)C1(C)C]

Mass spectrum (ESI$^+$): m/z=358 [M+H]$^+$

Example XV

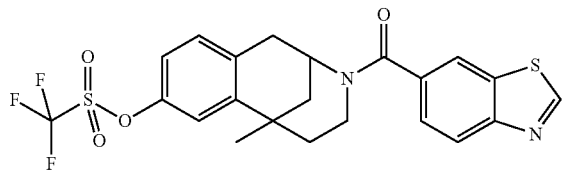 [SMILES: CC12CCN(C(=O)c3ccc4ncsc4c3)C(Cc3ccc(OS(=O)(=O)C(F)(F)F)cc31)C2]

Trifluoro-methanesulfonic acid 3-(benzothiazole-6-carbonyl)-6-methyl-1,2,3,4,5,6-hexahydro-2,6-methano-benzo[d]azocin-8-yl ester Trifluoromethanesulfonic anhydride (0.77 mL) is added to a solution of benzothiazol-6-yl-(8-hydroxy-6-methyl-1,2,5,6-tetrahydro-4H-2,6-methano-benzo[d]azocin-3-yl)-methanone (1.24 g; for synthesis see Example 92), triethylamine (3.4 mL), and 4-dimethylaminopyridine (10 mg) in dichloromethane (12 mL) chilled to −10° C. under argon atmosphere. The solution is stirred at ca. −5° C. for 30 min and then at room temperature overnight. The reaction solution is added to ice-cold water and then concentrated aqueous ammonia solution is added. The resulting mixture is extracted with dichloromethane, the combined organic extracts are washed with water and dried (MgSO$_4$). The solvent is removed under reduced pressure to give the crude product that is used without further purification.

Yield: 1.51 g (89% of theory)
Mass spectrum (ESI$^+$): m/z=497 [M+H]$^+$

The following compounds are obtained analogously to Example XV:

(1) (2R,6S)-Trifluoro-methanesulfonic acid 3-benzyl-6,11,11-trimethyl-1,2,3,4,5,6-hexahydro-2,6-methano-benzo[d]azocin-10-yl ester

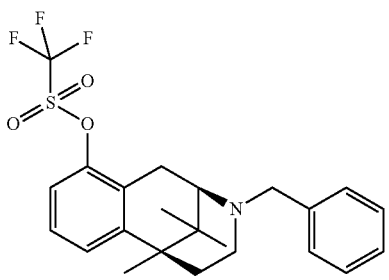 [SMILES: CC1(C)[C@H]2Cc3c(OS(=O)(=O)C(F)(F)F)cccc3[C@]1(C)CCN2Cc1ccccc1]

Mass spectrum (ESI$^+$: m/z=454 [M+H]$^+$ (2) 6,11,11-Trimethyl-9-trifluoromethanesulfonyloxy-1,2,5,6-tetrahydro-4H-2,6-methano-benzo[d]azocine-3-carboxylic acid tert-butyl ester

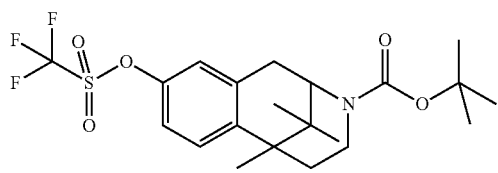 [SMILES: CC(C)(C)OC(=O)N1CCC2(C)c3ccc(OS(=O)(=O)C(F)(F)F)cc3CC1C2(C)C]

Mass spectrum (ESI$^+$): m/z=464 [M+H]$^+$ (3) (2R,6S)-6,11,11-Trimethyl-10-trifluoromethanesulfonyloxy-1,2,5,6-tetrahydro-4H-2,6-methanobenzo[d]azocine-3-carboxylic acid tert-butyl ester

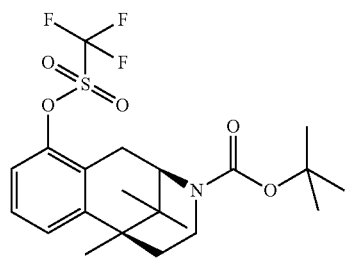 [SMILES: CC(C)(C)OC(=O)N1CC[C@@]2(C)c3cccc(OS(=O)(=O)C(F)(F)F)c3C[C@@H]1C2(C)C]

Mass spectrum (ESI$^+$): m/z=481 [M+NH$_4$]+

(4) (2R,6R)-6,11-Dimethyl-8-trifluoromethanesulfonyloxy-1,2,5,6-tetrahydro-4H-2,6-methano-benzo[d]azocine-3-carboxylic acid tert-butyl ester

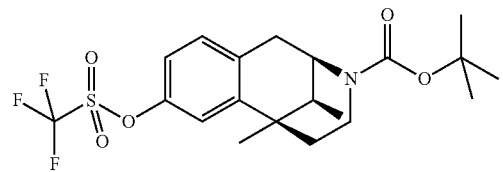 [SMILES: C[C@@H]1[C@H]2Cc3ccc(OS(=O)(=O)C(F)(F)F)cc3[C@]1(C)CCN2C(=O)OC(C)(C)C]

Mass spectrum (ESI$^+$): m/z=450 [M+H]$^+$ (5) 6,11,11-Trimethyl-8-trifluoromethanesulfonyloxy-1,2,5,6-tetrahydro-4H-2,6-methano-benzo[d]azocine-3-carboxylic acid tert-butyl ester

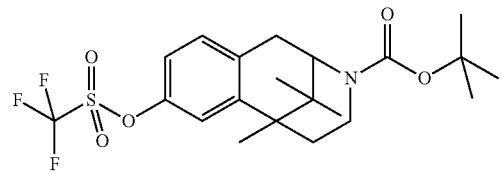 [SMILES: CC(C)(C)OC(=O)N1CCC2(C)c3cc(OS(=O)(=O)C(F)(F)F)ccc3CC1C2(C)C]

(6) (2R,6S)-6,11,11-Trimethyl-9-trifluoromethanesulfonyloxy-1,2,5,6-tetrahydro-4H-2,6-methanobenzo[d]azocine-3-carboxylic acid tert-butyl ester

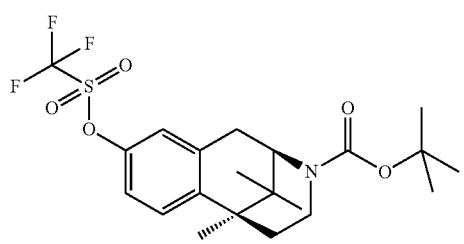 [SMILES: CC(C)(C)OC(=O)N1CC[C@@]2(C)c3ccc(OS(=O)(=O)C(F)(F)F)cc3C[C@@H]1C2(C)C]

Mass spectrum (ESI$^+$): m/z=464 [M+H]$^+$ (7) (2R,6R,11S)-Trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester

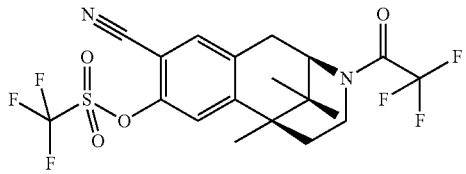

Mass spectrum (ESI⁺): m/z=488 [M+NH₄]⁺

(8) (2R,6R,11R)-Trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester

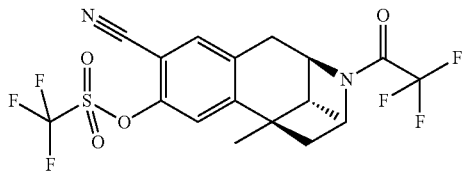 [SMILES: C[C@H]1[C@H]2Cc3cc(C#N)c(OS(=O)(=O)C(F)(F)F)cc3[C@]1(C)CCN2C(=O)C(F)(F)F]

Mass spectrum (ESI⁺): m/z=488 [M+NH₄]⁺

(9) 6,11,11-Trimethyl-7-trifluoromethanesulfonyloxy-1,2,5,6-tetrahydro-4H-2,6-methano-benzo[d]azocine-3-carboxylic acid tert-butyl ester

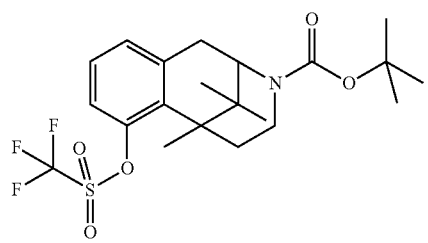 [SMILES: CC(C)(C)OC(=O)N1CCC2(C)c3c(cccc3OS(=O)(=O)C(F)(F)F)CC1C2(C)C]

Mass spectrum (ESI⁺): m/z=464 [M+H]⁺

(10) Trifluoro-methanesulfonic acid (2R,6R,11S)-6,11-dimethyl-3-(2,2,2-trifluoro-acetyl)-1,2,3,4,5,6-hexahydro-2,6-methano-benzo[d]azocin-8-yl ester

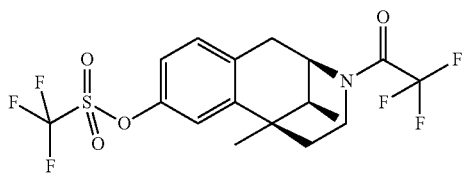 [SMILES: C[C@@H]1[C@H]2Cc3ccc(OS(=O)(=O)C(F)(F)F)cc3[C@]1(C)CCN2C(=O)C(F)(F)F]

Mass spectrum (ESI⁺): m/z=446 [M+H]⁺

Example XVI

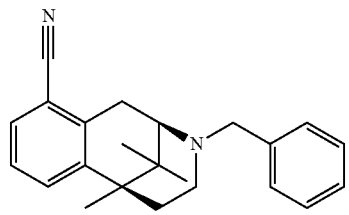 [SMILES: CC1(C)[C@H]2Cc3c(C#N)cccc3[C@]1(C)CCN2Cc1ccccc1]

(2R,6S)-3-Benzyl-6,11,11-trimethyl-1,2,3,4,5,6-hexahydro-2,6-methano-benzo[d]a zocine-10-carbonitrile Tetrakis(triphenylphosphine)palladium(0) (2.79 g) is added to a mixture of (2R,6S)-trifluoro-methanesulfonic acid 3-benzyl-6,11,11-trimethyl-1,2,3,4,5,6-hexahydro-2,6-methano-benzo[d]azocin-10-yl ester (7.30 g) and zinc cyanide (2.85 g) in dimethylformamide (35 mL) kept in argon atmosphere. The resulting mixture is stirred at 100° C. for 6 h. After cooling to room temperature, water (300 mL), concentrated ammonia solution (10 mL), and ethyl acetate (150 mL) are added and the forming precipitate is separated by filtration. The organic layer of the filtrate is separated and the aqueous layer is extracted twice with ethyl acetate. The combined organic phases are washed with brine and dried (MgSO₄). The solvent is removed under reduced pressure and the residue is purified by chromatography on silica gel (cyclohexane/ethyl acetate 19:1) to give the product.

Yield: 4.43 g (62% of theory)
Mass spectrum (ESI⁺: m/z=331 [M+H]⁺

The following compounds are obtained analogously to Example XVI:

(1) (2R,6R,11S)-8-Cyano-6,11-dimethyl-1,2,5,6-tetrahydro-4H-2,6-methano-benzo[d]azocine-3-carboxylic acid tert-butyl ester

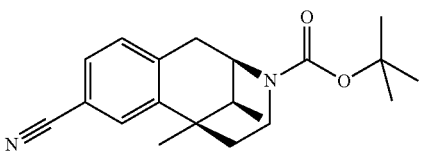 [SMILES: C[C@@H]1[C@H]2Cc3ccc(C#N)cc3[C@]1(C)CCN2C(=O)OC(C)(C)C]

Mass spectrum (ESI⁺): m/z=327 [M+H]⁺

(2) 9-Cyano-6,11,11-trimethyl-1,2,5,6-tetrahydro-4H-2,6-methano-benzo[d]azocine-3-carboxylic acid tert-butyl ester

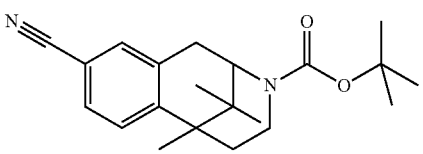 [SMILES: CC(C)(C)OC(=O)N1CCC2(C)c3ccc(C#N)cc3CC1C2(C)C]

Mass spectrum (ESI⁺): m/z=341 [M+H]⁺

(3) (2R,6S)-9-Cyano-6,11,11-trimethyl-1,2,5,6-tet-rahydro-4H-2,6-methano-benzo[d]azocine-3-car-boxylic acid tert-butyl ester

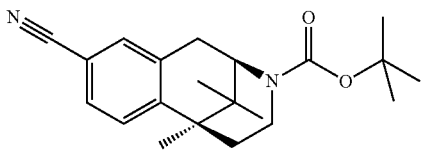 [SMILES: CC(C)(C)OC(=O)N1CC[C@@]2(C)c3ccc(C#N)cc3C[C@@H]1C2(C)C]

Mass spectrum (ESI⁺): m/z=341 [M+H]⁺

(4) 7-Cyano-6,11,11-trimethyl-1,2,5,6-tetrahydro-4H-2,6-methano-benzo[d]azocine-3-carboxylic acid tert-butyl ester

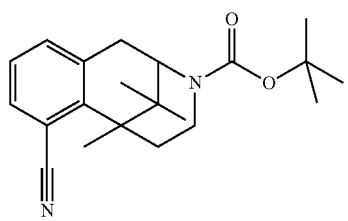 [SMILES: CC(C)(C)OC(=O)N1CCC2(C)c3c(C#N)cccc3CC1C2(C)C]

Mass spectrum (ESI⁺): m/z=341 [M+H]⁺

Example XVII

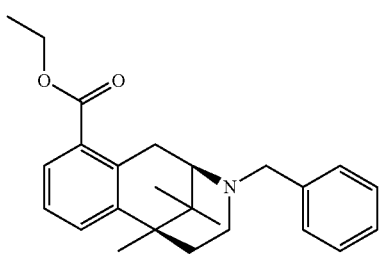 [SMILES: CCOC(=O)c1cccc2c1C[C@H]1N(Cc3ccccc3)CC[C@]2(C)C1(C)C]

(2R,6S)-3-Benzyl-6,11,11-trimethyl-1,2,3,4,5,6-hexahydro-2,6-methano-benzo[d]azocine-10-car-boxylic acid ethyl ester A solution of (2R,6S)-3-benzyl-6,11,11-trimethyl-1,2,3,4,5,6-hexahydro-2,6-methano-benzo[d]azocine-10-carboni-trile (1.14 g) in 80% sulfuric acid (4 mL) is stirred at 150° C. for 1 h. After cooling to room temperature, ethanol (30 mL) is added and the solution is stirred at 100° C. for 2 d. Then, the cooled solution is added to water (100 mL) and the mixture is basified using 40% aqueous NaOH solution. The resulting mixture is extracted twice with ethyl acetate and dried (MgSO₄). The solvent is removed under reduced pressure to give the crude product.

Yield: 1.14 g (87% of theory)
Mass spectrum (ESI⁺): m/z=378 [M+H]⁺

The following compounds are obtained analogously to Example XVII:

(1) 6,11,11-Trimethyl-1,2,3,4,5,6-hexahydro-2,6-methano-benzo[d]azocine-9-carboxylic acid ethyl ester

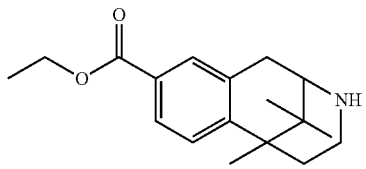 [SMILES: CCOC(=O)c1ccc2c(c1)CC1NCCC2(C)C1(C)C]

Mass spectrum (ESI⁺): m/z=288 [M+H]⁺

The compound is prepared from 6,11,11-trimethyl-1,2,3,4,5,6-hexahydro-2,6-methano-benzo[d]azocine-9-carboni-trile applying the procedure described above.

(2) (2R,6R,11S)-6,11-Dimethyl-1,2,3,4,5,6-hexahy-dro-2,6-methano-benzo[d]azocine-8-carboxylic acid ethyl ester

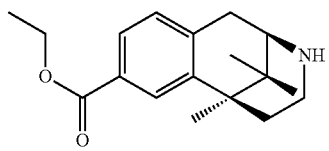

Mass spectrum (ESI⁺): m/z=274 [M+H]⁺

The compound is prepared from (2R,6R,11S)-6,11-dim-ethyl-1,2,3,4,5,6-hexahydro-2,6-methano-benzo[d]azocine-8-carbonitrile applying the procedure described above.

(3) 1-Hydroxy-8-methoxy-3-methyl-2,3,4,5-tetrahy-dro-1H-2,6-methano-benzo[d]azocine-6-carboxylic acid methyl ester

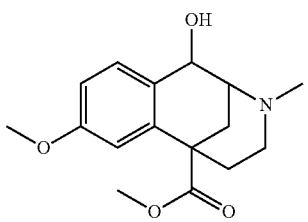

The compound may be prepared from 1-hydroxy-8-meth-oxy-3-methyl-2,3,4,5-tetrahydro-1H-2,6-methano-benzo[d]

azocine-6-carbonitrile [for synthesis see U.S. Pat. No. 3,687, 957 (1972)] as described above using methanol instead of ethanol.

Example XVIII

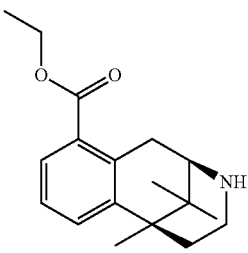 [SMILES: CCOC(=O)c1cccc2c1C[C@H]1NCC[C@]2(C)C1(C)C]

(2R,6S)-6,11,11-Trimethyl-1,2,3,4,5,6-hexahydro-2, 6-methano-benzo[d]azocine-10-carboxylic acid ethyl ester Pd(OH)$_2$ (0.20 g) is added to a solution of (2R,6S)-3-benzyl-6,11,11-trimethyl-1,2,3,4,5,6-hexahydro-2,6-methano-benzo[d]azocine-10-carboxylic acid ethyl ester (1.13 g) in ethanol (20 mL). The resulting mixture is stirred under hydrogen atmosphere (50 psi) at room temperature overnight. Then, the catalyst is separated by filtration and the filtrate is concentrated under reduced pressure to give the product.

Yield: 0.61 g (71% of theory)

Mass spectrum (ESI$^+$): m/z=288 [M+H]$^+$

The following compounds are obtained analogously to Example XVIII:

(1) (2R,6S)-6,11,11-Trimethyl-1,2,3,4,5,6-hexahydro-2,6-methano-benzo[d]azocine-10-carbonitrile

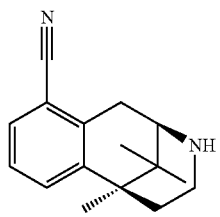 [SMILES: CC1(C)[C@H]2Cc3c(C#N)cccc3[C@]1(C)CCN2]

(2) 2,3,4,5,6,7-Hexahydro-2,6-methano-1H-azocino [5,4-b]indole (racemic mixture of the diastereomer shown)

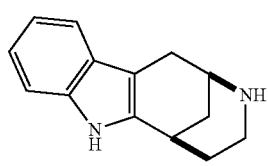 [SMILES: c1ccc2c3c([nH]c2c1)[C@@H]1CCN[C@H](C3)C1]

(3) 5,6,7,8,9,10-Hexahydro-6,10-methano-pyrido[3,2-d]azocine (racemic mixture of the diastereomer shown)

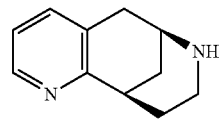 [SMILES: c1cnc2c(c1)C[C@@H]1C[C@H]2CCN1]

Mass spectrum (ESI$^+$): m/z=175 [M+H]$^+$

The debenzylation is carried out in the presence of 1 equivalent of 1 M hydrochloric acid as described above.

(4) 4-Methyl-3,5,9-triaza-tricyclo[6.3.1.0*2,6*] dodeca-2(6),4-diene (racemic mixture of the diastereomer shown)

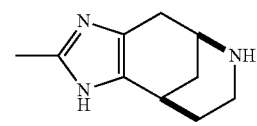

Mass spectrum (ESI$^+$): m/z=178 [M+H]$^+$

Example XIX

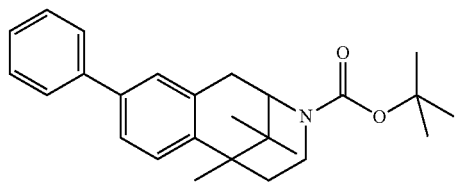 [SMILES: CC(C)(C)OC(=O)N1CCC2(C)c3ccc(-c4ccccc4)cc3CC1C2(C)C]

6,11,11-Trimethyl-9-phenyl-1,2,5,6-tetrahydro-4H-2, 6-methano-benzo[d]azocine-3-carboxylic acid tert-butyl ester Aqueous 2 M Na$_2$CO$_3$ solution (5 mL) is added to a mixture of 6,11,11-trimethyl-9-trifluoro-methanesulfonyloxy-1,2,5,6-tetrahydro-4H-2,6-methano-benzo[d]azocine-3-carboxylic acid tert-butyl ester (1.00 g) and phenylboronic acid (0.34 g) in dimethylformamide (5 mL) in argon atmosphere. The resulting mixture is flushed with argon and then 1,1'-bis (diphenyl-phosphino)ferrocene-palladium(II) dichloride dichloromethane complex (0.18 g) is added. The mixture is heated to 100° C. and stirred at this temperature for 4 h. After cooling to room temperature, water is added and the resulting mixture is extracted with ethyl acetate. The combined organic extracts are dried (MgSO$_4$) and the solvent is removed under reduced pressure. The residue is purified by chromatography on silica gel (cyclohexane/ethyl acetate 9:1->1:1) to give the product as a colorless oil.

Yield: 0.35 g (41% of theory)

Mass spectrum (ESI$^+$): m/z=392 [M+H]$^+$

The following compounds are obtained in analogy to Example XIX:

(1) (2R,6R,11S)-6,11-Dimethyl-8-phenyl-1,2,5,6-tetrahydro-4H-2,6-methano-benzo[d]azocine-3-carboxylic acid tert-butyl ester

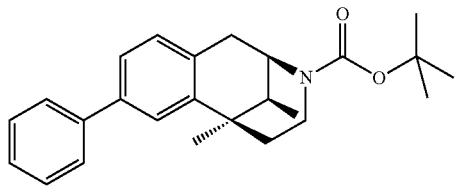 [SMILES: C[C@@H]1[C@H]2Cc3ccc(-c4ccccc4)cc3[C@]1(C)CCN2C(=O)OC(C)(C)C]

Mass spectrum (ESI$^+$): m/z=378 [M+H]$^+$ (2) (2R,6R,11S)-6,11-Dimethyl-8-pyridin-3-yl-1,2,5,6-tetrahydro-4H-2,6-methano-benzo[d]azocine-3-carboxylic acid tert-butyl ester

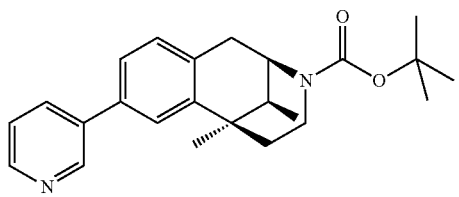 [SMILES: C[C@@H]1[C@H]2Cc3ccc(-c4cccnc4)cc3[C@]1(C)CCN2C(=O)OC(C)(C)C]

Mass spectrum (ESI$^+$): m/z=379 [M+H]$^+$ (3) (2R,6R,11S)-6,11-Dimethyl-8-pyridin-4-yl-1,2,5,6-tetrahydro-4H-2,6-methano-benzo[d]azocine-3-carboxylic acid tert-butyl ester

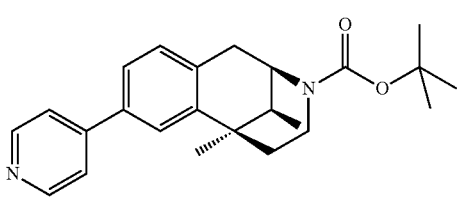 [SMILES: C[C@@H]1[C@H]2Cc3ccc(-c4ccncc4)cc3[C@]1(C)CCN2C(=O)OC(C)(C)C]

Mass spectrum (ESI$^+$): m/z=379 [M+H]$^+$ (4) (2R,6R,11S)-6,11-Dimethyl-8-pyrimidin-5-yl-1,2,5,6-tetrahydro-4H-2,6-methano-benzo[d]azocine-3-carboxylic acid tert-butyl ester

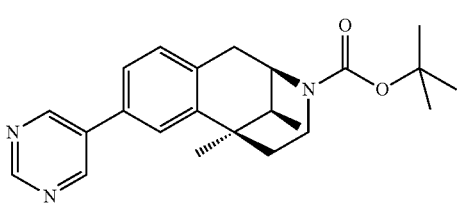 [SMILES: C[C@@H]1[C@H]2Cc3ccc(-c4cncnc4)cc3[C@]1(C)CCN2C(=O)OC(C)(C)C]

Mass spectrum (ESI$^+$): m/z=380 [M+H]$^+$ (5) 6,11,11-Trimethyl-7-pyridin-3-yl-1,2,5,6-tetrahydro-4H-2,6-methano-benzo[d]azocine-3-carboxylic acid tert-butyl ester

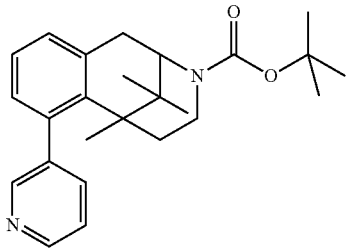 [SMILES: CC(C)(C)OC(=O)N1CCC2(C)c3c(cccc3-c3cccnc3)CC1C2(C)C]

Mass spectrum (ESI$^+$): m/z=393 [M+H]$^+$

Example XX

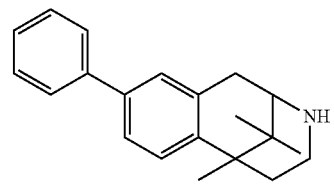 [SMILES: CC12CCNC(Cc3cc(-c4ccccc4)ccc31)C2(C)C]

6,11,11-Trimethyl-9-phenyl-1,2,3,4,5,6-hexahydro-2,6-methano-benzo[d]azocine

Trifluoroacetic acid (0.5 mL) is added to a solution of 6,11,11-trimethyl-9-phenyl-1,2,5,6-tetrahydro-4H-2,6-methano-benzo[d]azocine-3-carboxylic acid tert-butyl ester (0.30 g) in dichloromethane (2.5 mL). The solution is stirred at ambient temperature for 1 h and is then concentrated under reduced pressure. The crude trifluoroacetic acid salt of the title compound is used without further purification.

Yield: 0.31 g (100% of theory)

The following compounds are obtained analogously to Example XX:

(Alternatively, in cases in which the purity of the product is insufficient after applying the procedure described above the compounds are purified by HPLC on reversed phase (MeCN/water) to obtain the pure compounds)

(1) (2R,6R,11S)-6,11-Dimethyl-1,2,3,4,5,6-hexahydro-2,6-methano-benzo[d]azocine-8-carbonitrile

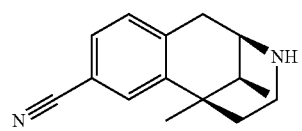 [SMILES: C[C@@H]1[C@H]2Cc3ccc(C#N)cc3[C@]1(C)CCN2]

Mass spectrum (ESI$^+$): m/z=227 [M+H]$^+$

The compound is obtained as its trifluoroacetic acid salt.

(2) 6,11,11-Trimethyl-1,2,3,4,5,6-hexahydro-2,6-methano-benzo[d]azocine-9-carbonitrile

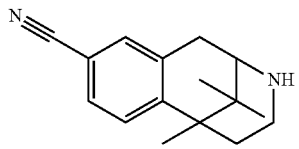 [SMILES: CC12CCNC(Cc3cc(C#N)ccc31)C2(C)C]

Mass spectrum (ESI⁺): m/z=241 [M+H]⁺

The compound is obtained as its trifluoroacetic acid salt.

(3) (2R,6S)-6,11,11-Trimethyl-1,2,3,4,5,6-hexahydro-2,6-methano-benzo[d]azocin-10-ylamine

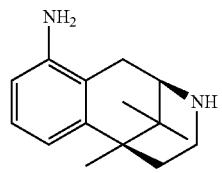 [SMILES: CC1(C)[C@H]2Cc3c(N)cccc3[C@]1(C)CCN2]

Mass spectrum (ESI⁺): m/z=231 [M+H]⁺

The compound is obtained as its double trifluoroacetic acid salt.

(4) 6,11,11-Trimethyl-1,2,3,4,5,6-hexahydro-2,6-methano-benzo[d]azocin-9-ylamine

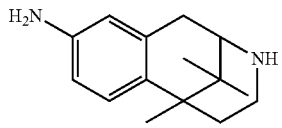 [SMILES: CC12CCNC(Cc3cc(N)ccc31)C2(C)C]

Mass spectrum (ESI⁺): m/z=231 [M+H]⁺

The compound is obtained as its double trifluoroacetic acid salt.

(5) (2S,6R)-8-Methoxy-6,9,11,11-tetramethyl-1,2,3,4,5,6-hexahydro-2,6-methano-benzo[d]azocine

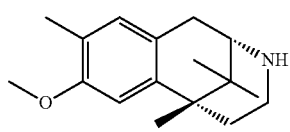 [SMILES: COc1cc2c(cc1C)C[C@@H]1NCC[C@@]2(C)C1(C)C]

The compound may be obtained by resolution of the racemic mixture by HPLC on chiral phase or by using the enantiomerically pure (2S,6R)-8-methoxy-6,9,11,11-tetramethyl-1,2,5,6-tetrahydro-4H-2,6-methano-benzo[d]azocine-3-carboxylic acid tert-butyl ester.

(6) (2R,6S)-8-Methoxy-6,9,11,11-tetramethyl-1,2,3,4,5,6-hexahydro-2,6-methano-benzo[d]azocine

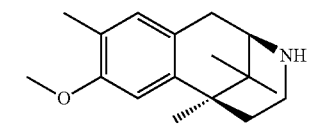 [SMILES: COc1cc2c(cc1C)C[C@H]1NCC[C@]2(C)C1(C)C]

The compound may be obtained by resolution of the racemic mixture by HPLC on chiral phase or by using the enantiomerically pure (2R,6S)-8-methoxy-6,9,11,11-tetramethyl-1,2,5,6-tetrahydro-4H-2,6-methano-benzo[d]azocine-3-carboxylic acid tert-butyl ester.

(7) (2S,6R)-9-Methoxy-6,8,11,11-tetramethyl-1,2,3,4,5,6-hexahydro-2,6-methano-benzo[d]azocine

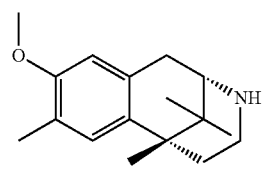 [SMILES: COc1cc2c(cc1C)[C@@]1(C)CCN[C@@H](C2)C1(C)C]

The compound may be obtained by resolution of the racemic mixture by HPLC on chiral phase or by using the enantiomerically pure (2S,6R)-9-methoxy-6,8,11,11-tetramethyl-1,2,5,6-tetrahydro-4H-2,6-methano-benzo[d]azocine-3-carboxylic acid tert-butyl ester.

(8) (2R,6S)-9-Methoxy-6,8,11,11-tetramethyl-1,2,3,4,5,6-hexahydro-2,6-methano-benzo[d]azocine

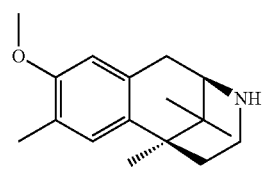 [SMILES: COc1cc2c(cc1C)[C@]1(C)CCN[C@H](C2)C1(C)C]

The compound may be obtained by resolution of the racemic mixture by HPLC on chiral phase or by using the enantiomerically pure (2R,6S)-9-methoxy-6,8,11,11-tetramethyl-1,2,5,6-tetrahydro-4H-2,6-methano-benzo[d]azocine-3-carboxylic acid tert-butyl ester.

(9) 8,9-Dimethoxy-6,11,11-trimethyl-1,2,3,4,5,6-hexahydro-2,6-methano-benzo[d]azocine

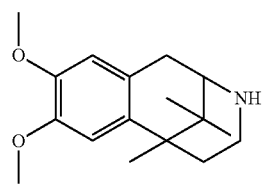 [SMILES: COc1cc2c(cc1OC)C1(C)CCNC(C2)C1(C)C]

(10) 8-Methoxy-6,11,11-trimethyl-1,2,3,4,5,6-hexahydro-2,6-methano-benzo[d]azocin-9-ol

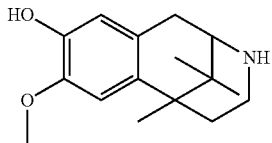

(11) 9-Methoxy-6,11,11-trimethyl-1,2,3,4,5,6-hexahydro-2,6-methano-benzo[d]azocin-8-ol

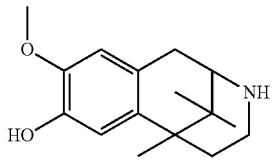 [SMILES: COc1cc2c(cc1O)C1(C)CCNC(C2)C1(C)C]

(12) (2R,6S)-6,11,11-Trimethyl-1,2,3,4,5,6-hexahydro-2,6-methano-benzo[d]azocine-9-carbonitrile

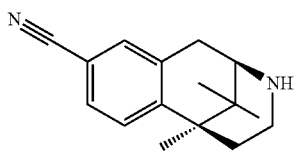 [SMILES: CC1(C)[C@H]2Cc3cc(C#N)ccc3[C@]1(C)CCN2]

Mass spectrum (ESI$^+$): m/z=241 [M+H]$^+$
The compound is obtained as its trifluoroacetic acid salt.

(13) (2S,6R)-9-Methoxy-6,11,11-trimethyl-1,2,3,4,5,6-hexahydro-2,6-methano-benzo[d]azocine

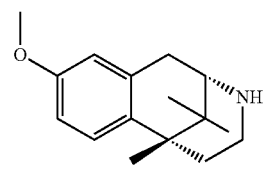

The compound may be obtained from the racemic mixture by separation from the enantiomer by HPLC on chiral phase.

(14) (2R,6R,11S)-6,11-Dimethyl-8-phenyl-1,2,3,4,5,6-hexahydro-2,6-methano-benzo[d]azocine

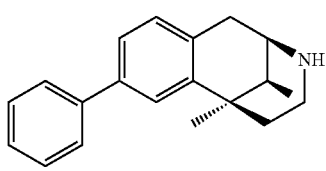 [SMILES: C[C@@H]1[C@H]2Cc3ccc(-c4ccccc4)cc3[C@]1(C)CCN2]

Mass spectrum (ESI$^+$): m/z=278 [M+H]$^+$

(15) (2R,6R,11S)-6,11-Dimethyl-8-pyridin-3-yl-1,2,3,4,5,6-hexahydro-2,6-methano-benzo[d]azocine

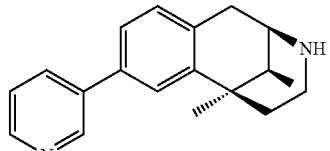

Mass spectrum (ESI$^+$): m/z=279 [M+H]$^+$

(16) (2R,6R,11S)-6,11-Dimethyl-8-pyridin-4-yl-1,2,3,4,5,6-hexahydro-2,6-methano-benzo[d]azocine

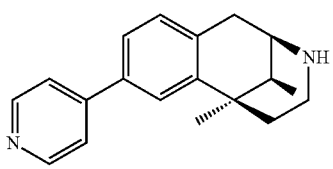 [SMILES: C[C@@H]1[C@H]2Cc3ccc(-c4ccncc4)cc3[C@]1(C)CCN2]

Mass spectrum (ESI$^+$): m/z=279 [M+H]$^+$

(17) (2R,6R,11S)-6,11-Dimethyl-8-pyrimidin-5-yl-1,2,3,4,5,6-hexahydro-2,6-methano-benzo[d]azocine

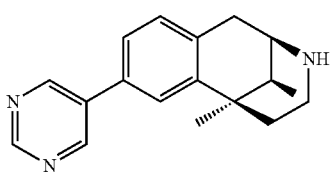 [SMILES: C[C@@H]1[C@H]2Cc3ccc(-c4cncnc4)cc3[C@]1(C)CCN2]

Mass spectrum (ESI$^+$): m/z=280 [M+H]$^+$

(18) 6,11,11-Trimethyl-7-pyridin-3-yl-1,2,3,4,5,6-hexahydro-2,6-methano-benzo[d]azocine

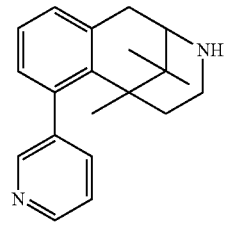 [SMILES: CC12CCNC(Cc3cccc(-c4cccnc4)c31)C2(C)C]

Mass spectrum (ESI$^+$): m/z=293 [M+H]$^+$

(19) 6,11,11-Trimethyl-1,2,3,4,5,6-hexahydro-2,6-methano-benzo[d]azocine-7-carbonitrile

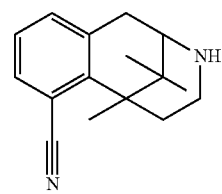 [SMILES: CC12CCNC(Cc3cccc(C#N)c31)C2(C)C]

Mass spectrum (ESI$^+$): m/z=241 [M+H]$^+$

(20) (2R,6R,11S)-6,11-Dimethyl-8-(5-methyl-[1,3,4]oxadiazol-2-yl)-1,2,3,4,5,6-hexahydro-2,6-methano-benzo[d]azocine

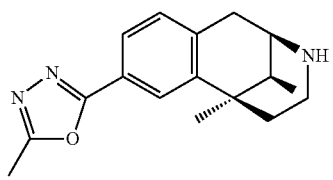 [SMILES: Cc1nnc(-c2ccc3c(c2)[C@]2(C)CCN[C@H](C3)[C@H]2C)o1]

Mass spectrum (ESI$^+$): m/z=284 [M+H]$^+$
The compound is isolated as its trifluoroacetic acid salt.

(21) (2R,6R,11S)-6,11-Dimethyl-8-[1,3,4]oxadiazol-2-yl-1,2,3,4,5,6-hexahydro-2,6-methano-benzo[d]azocine

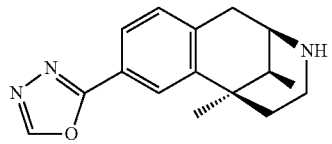 [SMILES: C[C@@H]1[C@H]2Cc3ccc(-c4nnco4)cc3[C@]1(C)CCN2]

Mass spectrum (ESI$^+$): m/z=270 [M+H]$^+$

(22) 1,1,1-Trifluoro-2-[(2R,6S)-6,11,11-trimethyl-1,2,3,4,5,6-hexahydro-2,6-methano-benzo[d]azocin-8-yl]-propan-2-ol

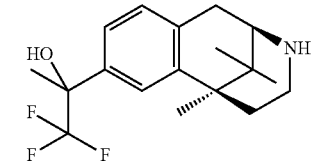 [SMILES: CC(O)(c1ccc2c(c1)[C@]1(C)CCN[C@H](C2)C1(C)C)C(F)(F)F]

Mass spectrum (ESI$^+$): m/z=328 [M+H]$^+$

Example XXI

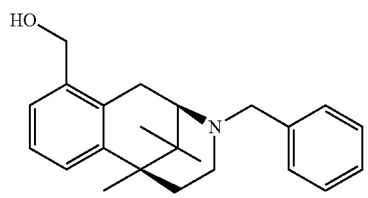 [SMILES: CC1(C)[C@H]2Cc3c(CO)cccc3[C@]1(C)CCN2Cc1ccccc1]

[(2R,6S)-3-Benzyl-6,11,11-trimethyl-1,2,3,4,5,6-hexahydro-2,6-methano-benzo[d]azocin-10-yl]-methanol A solution of (2R,6S)-3-benzyl-6,11,11-trimethyl-1,2,3,4,5,6-hexahydro-2,6-methano-benzo-[d]azocine-10-carboxylic acid ethyl ester (0.96 g) in tetrahydrofuran (2 mL) is added dropwise to LiAlH$_4$ (1.6 mL, 2.4 mol/L in THF) in tetrahydrofuran (1.5 mL). The reaction mixture is stirred at ambient temperature for 90 min. Then, water (4 mL) is added carefully and the resulting mixture is extracted with ethyl acetate. The combined organic extracts are washed with water and brine and dried (MgSO$_4$). The solvent is removed under reduced pressure to give the product.

Yield: 0.62 g (72% of theory)
Mass spectrum (ESI$^+$): m/z=336 [M+H]$^+$

Example XXII

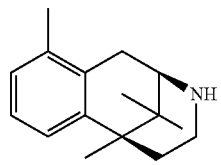 [SMILES: Cc1cccc2c1C[C@H]1NCC[C@]2(C)C1(C)C]

(2R,6S)-6,10,11,11-Tetramethyl-1,2,3,4,5,6-hexahydro-2,6-methano-benzo[d]azocine 10% Palladium on carbon (0.10 g) is added to a solution of [(2R,6S)-3-benzyl-6,11,11-trimethyl-1,2,3,4,5,6-hexahydro-2,6-methano-benzo[d]azocin-10-yl]-methanol (0.60 g) in methanol (10 mL). The mixture is stirred under hydrogen atmosphere (50 psi) at room temperature overnight. Then, another portion of 10% palladium on carbon (0.2 g) and 4 M hydrochloric acid (1 mL) are added and the mixture is further stirred in hydrogen atmosphere for 4 h. After the catalyst is separated by filtration, the filtrate is concentrated under reduced pressure to give the hydrochloric acid salt of the title product.

Yield: 0.50 g (100% of theory)
The following compound is obtained analogously to Example XXII:

(1) 8-Methoxy-3-methyl-2,3,4,5-tetrahydro-1H-2,6-methano-benzo[d]azocine-6-carboxylic acid methyl ester

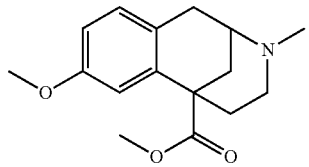

The compound may be obtained from 1-hydroxy-8-methoxy-3-methyl-2,3,4,5-tetrahydro-1H-2,6-methano-benzo[d]azocine-6-carboxylic acid methyl ester employing the procedure described above. Alternatively, the reduction may be conducted in analogy to *J. Org. Chem.* 1987, 52, 5233-5239.

Example XXIII

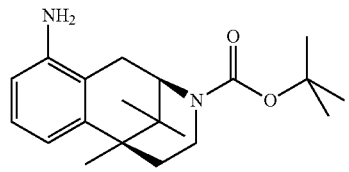 [SMILES: CC(C)(C)OC(=O)N1CC[C@@]2(C)c3cccc(N)c3C[C@@H]1C2(C)C]

(2R,6S)-10-Amino-6,11,11-trimethyl-1,2,5,6-tetrahydro-4H-2,6-methano-benzo[d]azocine-3-carboxylic acid tert-butyl ester A flask charged with a stir bar, (2R,6S)-6,11,11-trimethyl-10-trifluoromethanesulfonyloxy-1,2,5,6-tetrahydro-4H-2,6-methano-benzo[d]azocine-3-carboxylic acid tert-butyl ester (4.0 g), benzhydrylideneamine (3.2 mL), Cs$_2$CO$_3$ (5.6 g), and toluene (80 mL) is flushed with argon for 10 min. Then, 2,2'-bis-diphenylphosphanyl-[1,1']binaphthalenyl (0.35 g) and tris(dibenzylideneacetone)dipalladium (0.18 g) are added and the resulting mixture is stirred at reflux temperature overnight. After cooling to room temperature, the reaction mixture is washed with water and concentrated. The residue is taken up in tetrahydrofuran and 2 M hydrochloric acid is added. The mixture is stirred at ambient temperature for 4 h. The precipitate is separated by filtration and the filtrate is concentrated under reduced pressure. The residue is purified by chromatography on silica gel (cyclohexane/ethyl acetate 1:7) to give the product as a brown oil.

Yield: 0.83 g (29% of theory)
Mass spectrum (ESI$^+$: m/z=331 [M+H]$^+$

The following compounds are obtained analogously to Example XXIII:

(1) 9-Amino-6,11,11-trimethyl-1,2,5,6-tetrahydro-4H-2,6-methano-benzo[d]azocine-3-carboxylic acid tert-butyl ester

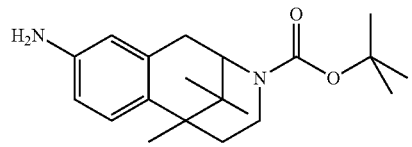 [SMILES: CC(C)(C)OC(=O)N1CCC2(C)c3ccc(N)cc3CC1C2(C)C]

Mass spectrum (ESI$^+$): m/z=331 [M+H]$^+$ (2) 8-Amino-6,11,11-trimethyl-1,2,5,6-tetrahydro-4H-2,6-methano-benzo[d]azocine-3-carboxylic acid tert-butyl ester

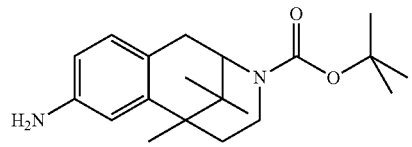 [SMILES: CC(C)(C)OC(=O)N1CCC2(C)c3cc(N)ccc3CC1C2(C)C]

Mass spectrum (ESI$^+$): m/z=331 [M+H]$^+$

Example XXIV

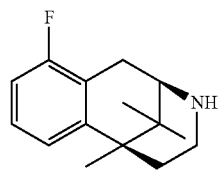 [SMILES: CC1(C)[C@H]2Cc3c(F)cccc3[C@]1(C)CCN2]

(2R,6S)-10-Fluoro-6,11,11-trimethyl-1,2,3,4,5,6-hexahydro-2,6-methano-benzo[d]azocine A solution of nitrosonium tetrafluoroborate (0.25 g) in dioxane (2 mL) is added to a solution of (2R,6S)-10-amino-6,11,11-trimethyl-1,2,5,6-tetrahydro-4H-2,6-methano-benzo[d]azocine-3-carboxylic acid tert-butyl ester (0.10 g) in dioxane (2 mL). The solution is heated to 50° C. and stirred at this temperature overnight. The reaction solution is diluted with methanol and then concentrated under reduced pressure. The residue is purified by HPLC on reversed phase (MeCN/H$_2$O/F$_3$CCO$_2$H) to yield the title product.

Yield: 25 mg (36% of theory)
Mass spectrum (ESI$^+$): m/z=234 [M+H]$^+$

The following compounds are obtained analogously to Example XXIV:

(1) 8-Fluoro-6,11,11-trimethyl-1,2,3,4,5,6-hexahydro-2,6-methano-benzo[d]azocine

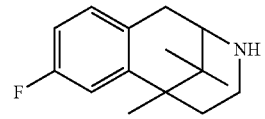

(2) 9-Fluoro-6,11,11-trimethyl-1,2,3,4,5,6-hexahydro-2,6-methano-benzo[d]azocine

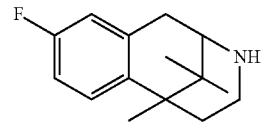 [SMILES: CC12CCNC(Cc3cc(F)ccc31)C2(C)C]

In cases in which the tert-butyloxycarbonyl group is not completely cleaved off after the reaction the crude product is treated with trifluoroacetic acid in dichloromethane.

Example XXV

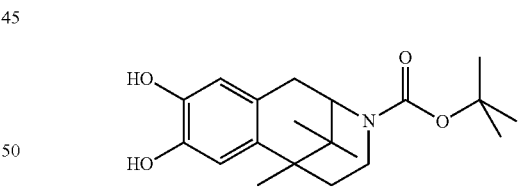

8,9-Dihydroxy-6,11,11-trimethyl-1,2,5,6-tetrahydro-4H-2,6-methano-benzo[d]azocine-3-carboxylic acid tert-butyl ester Di-tert-butyl dicarbonate (0.34 g) is added to a solution of 6,11,11-trimethyl-1,2,3,4,5,6-hexahydro-2,6-methano-benzo[d]azocine-8,9-diol (0.44 g) and triethylamine (0.43 mL) in dichloromethane (5 mL). The solution is stirred at room temperature for 2 h. Then, the solution is washed twice with water and once with brine. After drying (MgSO$_4$), the solvent is removed under reduced pressure to yield the product.

Yield: 0.43 g (80% of theory)
Mass spectrum (ESI$^-$): m/z=346 [M−H]$^-$

Example XXVI

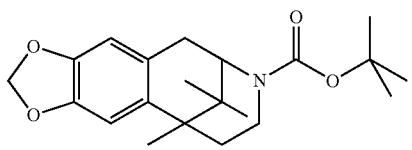 [SMILES: CC(C)(C)OC(=O)N1CCC2(C)c3cc4c(cc3CC1C2(C)C)OCO4]

8,9-Methylenedioxy-6,11,11-trimethyl-1,2,5,6-tetrahydro-4H-2,6-methano-benzo[d]azocine-3-carboxylic acid tert-butyl ester A mixture of 8,9-dihydroxy-6,11,11-trimethyl-1,2,5,6-tetrahydro-4H-2,6-methano-benzo[d]-azocine-3-carboxylic acid tert-butyl ester (0.21 g), $K_2CO_3$ (0.19 g) and diiodomethane (54 μL) in dimethylformamide (5 mL) is heated to 100° C. and stirred at this temperature for 2 h. Then, another portion of diiodomethane (54 μL) and $K_2CO_3$ (0.18 g) is added and the mixture is further stirred at 100° C. for 5 h. After cooling to room temperature, water is added and the resulting mixture is extracted with ethyl acetate. The combined organic extracts are washed with brine and dried ($MgSO_4$). After removal of the solvent, the residue is purified by chromatography on silica gel (cyclohexane/ethyl acetate 1:1).

Yield: 0.20 g (93% of theory)
Mass spectrum (ESI$^+$): m/z=360 [M+H]$^+$

Example XXVII

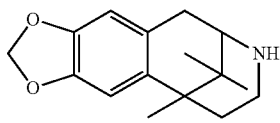 [SMILES: CC12CCNC(Cc3cc4c(cc31)OCO4)C2(C)C]

8,9-Methylenedioxy-6,11,11-trimethyl-1,2,3,4,5,6-hexahydro-2,6-methano-benzo[d]azocine Isopropanolic hydrochloric acid (5 mol/L, 0.55 mL) is added to 8,9-methylenedioxy-6,11,11-trimethyl-1,2,5,6-tetrahydro-4H-2,6-methano-benzo[d]azocine-3-carboxylic acid tert-butyl ester (0.19 g) dissolved in dichloromethane (2 mL). The resulting solution is stirred for 2 h at room temperature. Then, the solution is concentrated under reduced pressure to give the title product as its hydrochloric acid salt.

Yield: 0.15 g (97% of theory)
Mass spectrum (ESI$^+$): m/z=260 [M+H]$^+$

Example XXVIII

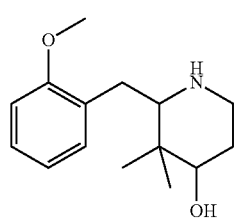 [SMILES: COc1ccccc1CC1NCCC(O)C1(C)C]

2-(2-Methoxy-benzyl)-3,3-dimethyl-piperidin-4-ol

Sodium borohydride (0.31 g) is added to 2-(2-methoxy-benzyl)-3,3-dimethyl-piperidin-4-one (2.00 g, prepared according to *J. Med. Chem.* 2002, 45, 3755-3765 from racemic starting material) dissolved in methanol (20 mL). The solution is stirred for 3 h at room temperature and then 1 M sodium hydroxide solution (40 mL) is added. After stirring for 10 min, the mixture is extracted with dichloromethane. The combined organic extracts are washed with water and dried ($MgSO_4$). The solvent is evaporated to give the title product.

Yield: 2.00 g (99% of theory)
Mass spectrum (ESI$^+$): m/z=250 [M+H]$^+$

Example XXIX

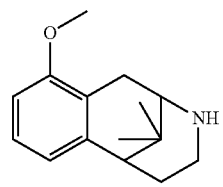 [SMILES: COc1cccc2c1CC1NCCC2C1(C)C]

10-Methoxy-11,11-dimethyl-1,2,3,4,5,6-hexahydro-2,6-methano-benzo[d]azocine

A solution of 2-(2-methoxy-benzyl)-3,3-dimethyl-piperidin-4-ol (0.80 g) in polyphosphoric acid (10 mL) is stirred at 120° C. overnight. After cooling the solution to ca. 80° C., water (300 mL) is added and the mixture is stirred vigorously for another 10 min. Then, the mixture is cooled in an ice bath, more water is added, and the mixture is basified using 10 M aqueous NaOH. The resulting mixture is extracted with ethyl acetate, the combined organic extracts are washed with brine and dried ($MgSO_4$). The solvent is removed under reduced pressure to yield the title product that is used without further purification.

Yield: 0.36 g (49% of theory)

The following compound is obtained analogously to Example XXIX:

(1) (2S,6R)-9-Methoxy-6,11,11-trimethyl-1,2,3,4,5,6-hexahydro-2,6-methano-benzo[d]azocine

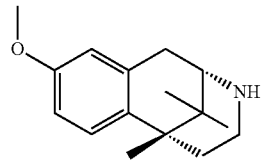 [SMILES: COc1ccc2c(c1)C[C@@H]1NCC[C@@]2(C)C1(C)C]

The racemic product mixture is resolved into its enantiomers by using HPLC on chiral phase. The compound may also be obtained in analogy to the procedure described in *J. Med. Chem.* 1997, 40, 2922-2930.

Example XXX

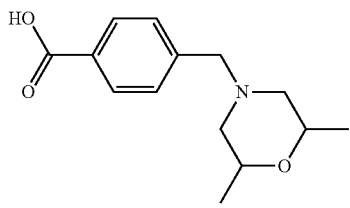 [SMILES: CC1CN(Cc2ccc(C(=O)O)cc2)CC(C)O1]

4-(2,6-Dimethyl-morpholin-4-ylmethyl)-benzoic acid

Acetic acid (0.34 mL), trimethyl orthoformate (0.66 mL), and sodium triacetoxyborohydride (0.53 g) are successively added to 4-formyl-benzoic acid (150 mg) and 2,6-dimethyl-morpholine (115 mg) dissolved in dimethylformamide (3 mL). The solution is stirred at room temperature overnight. Trifluoroacetic acid (50% in water) is added, the solution is stirred for another 2 h and then concentrated under reduced pressure. The residue is purified by HPLC on reversed phase (MeCN/H$_2$O) to give the title compound as its trifluoroacetic acid salt.

Yield: 199 mg (55% of theory)
Mass spectrum (ESI$^+$): m/z=250 [M+H]$^+$

The following compounds are obtained analogously to Example XXX:

(1) 4-(4-Hydroxy-4-methyl-piperidin-1-ylmethyl)-benzoic acid

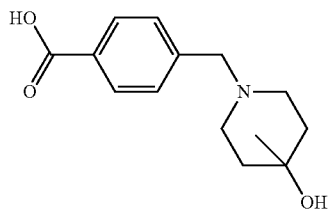

Mass spectrum (ESI$^+$): m/z=250 [M+H]$^+$
The compound is isolated as its trifluoroacetic acid salt

(2) endo-4-(3-Hydroxy-8-aza-bicyclo[3.2.1]oct-8-ylmethyl)-benzoic acid

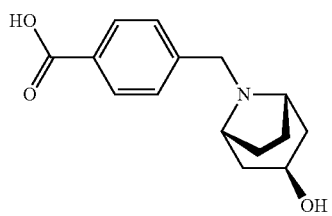

Mass spectrum (ESI$^+$): m/z=262 [M+H]$^+$
The compound is isolated as its trifluoroacetic acid salt

(3) 4-(3-Hydroxy-azetidin-1-ylmethyl)-benzoic acid

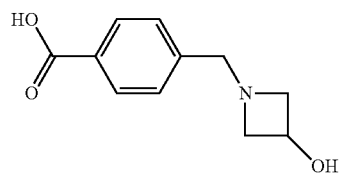 [SMILES: O=C(O)c1ccc(CN2CC(O)C2)cc1]

Mass spectrum (ESI$^+$): m/z=208 [M+H]$^+$
The compound is isolated as its trifluoroacetic acid salt

(4) 4-(3-Hydroxy-pyrrolidin-1-ylmethyl)-benzoic acid

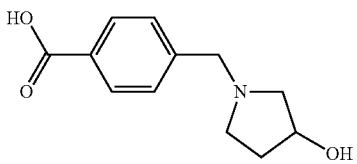 [SMILES: O=C(O)c1ccc(CN2CCC(O)C2)cc1]

Mass spectrum (ESI$^+$): m/z=221 [M+H]$^+$
The compound is isolated as its trifluoroacetic acid salt

(5) 4-(4-Methoxy-piperidin-1-ylmethyl)-benzoic acid

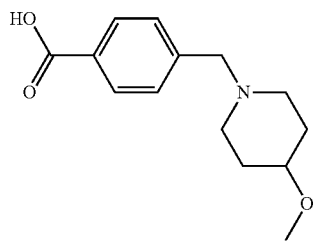 [SMILES: COC1CCN(Cc2ccc(C(=O)O)cc2)CC1]

Mass spectrum (ESI$^+$): m/z=250 [M+H]$^+$
The compound is isolated as its trifluoroacetic acid salt

(6) 4-(4-Hydroxy-piperidin-1-ylmethyl)-benzoic acid

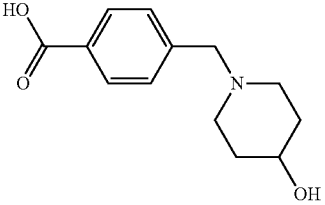 [SMILES: O=C(O)c1ccc(CN2CCC(O)CC2)cc1]

Mass spectrum (ESI$^+$): m/z=236 [M+H]$^+$
The compound is isolated as its trifluoroacetic acid salt

Example XXXI

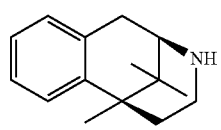

(2R,6S)-6,11,11-Trimethyl-1,2,3,4,5,6-hexahydro-2,6-methano-benzo[d]azocine

10% Pd/C (0.20 g) is added to a solution of (2R,6S)-trifluoro-methanesulfonic acid 3-benzyl-6,11,11-trimethyl-1,2,3,4,5,6-hexahydro-2,6-methano-benzo[d]azocin-10-yl ester (0.50 g) in ethanol (10 mL). The resulting mixture is shaken under hydrogen atmosphere (50 psi) at room temperature overnight. Then, the catalyst is separated by filtration and Pd(OH)$_2$ (0.2 g) is added to the filtrate (the benzyl group was not completely removed after the treatment in the presence of Pd/C). The mixture is shaken for another 16 h in hydrogen atmosphere (50 psi) at room temperature. The catalyst is separated and the filtrate is concentrated under reduced pressure to give the crude product that is used without further purification.

Yield: 0.23 g (98% of theory)

The following compound is obtained analogously to Example XXXI:

(1) 3,5,9-Triaza-tricyclo[6.3.1.0*2,6*]dodeca-2(6),4-diene (racemic mixture of the diastereomer shown)

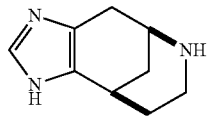 [SMILES: c1nc2c([nH]1)[C@@H]1CCN[C@H](C2)C1]

Example XXXII

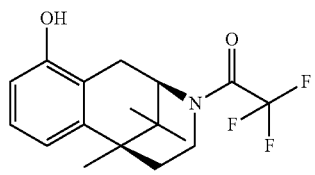 [SMILES: CC1(C)[C@H]2Cc3c(O)cccc3[C@]1(C)CCN2C(=O)C(F)(F)F]

(2R,6S)-2,2,2-Trifluoro-1-(10-hydroxy-6,11,11-trimethyl-1,2,5,6-tetrahydro-4H-2,6-methano-benzo[d]azocin-3-yl)-ethanone Trifluoroacetic anhydride (5.0 mL) is added to a solution of the hydrobromic acid salt of (2R,6S)-6,11,11-trimethyl-1,2,3,4,5,6-hexahydro-2,6-methano-benzo[d]azocin-10-ol (5.0 g) and triethylamine (5.5 mL) in dichloromethane (50 mL) chilled in an ice bath. The resulting solution is stirred at ambient temperature overnight. Then, water is added, the resulting mixture is stirred for an additional 15 min, and the organic phase is separated. The organic phase is washed with water and brine, dried (Na$_2$SO$_4$), and the solvent is evaporated. The residue is purified by chromatography on silica gel (ethyl acetate/cyclohexane 1:4) to give the product as a foam-like solid.

Yield: 3.34 g (64% of theory)

Mass spectrum (ESI$^+$): m/z=328 [M+H]$^+$

The following compounds are obtained analogously to Example XXXII:

(1) (2R,6S)-2,2,2-Trifluoro-1-(6,11,11-trimethyl-1,2,5,6-tetrahydro-4H-2,6-methano-benzo[d]azocin-3-yl)-ethanone

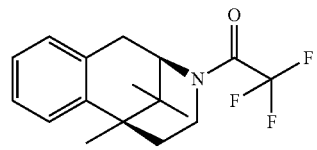 [SMILES: CC1(C)[C@H]2Cc3ccccc3[C@]1(C)CCN2C(=O)C(F)(F)F]

Mass spectrum (ESI$^+$): m/z=312 [M+H]$^+$ (2) (2R,6R,11S)-2,2,2-Trifluoro-1-(8-hydroxy-6,11-dimethyl-1,2,5,6-tetrahydro-4H-2,6-methano-benzo[d]azocin-3-yl)-ethanone

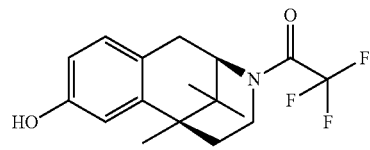 [SMILES: CC1(C)[C@H]2Cc3ccc(O)cc3[C@]1(C)CCN2C(=O)C(F)(F)F]

Mass spectrum (ESI$^+$): m/z=314 [M+H]$^+$ (3) (2R,6R,11R)-2,2,2-Trifluoro-1-(8-hydroxy-6,11-dimethyl-1,2,5,6-tetrahydro-4H-2,6-methano-benzo[d]azocin-3-yl)-ethanone

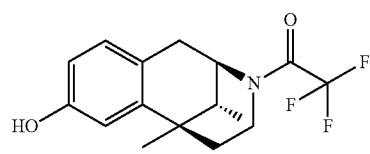 [SMILES: C[C@H]1[C@H]2Cc3ccc(O)cc3[C@]1(C)CCN2C(=O)C(F)(F)F]

Mass spectrum (ESI$^+$): m/z=314 [M+H]$^+$ (4) (2R,6S)-2,2,2-Trifluoro-1-(9-hydroxy-6,11,11-trimethyl-1,2,5,6-tetrahydro-4H-2,6-methano-benzo[d]azocin-3-yl)-ethanone

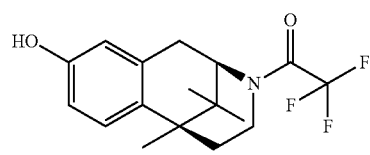 [SMILES: CC1(C)[C@H]2Cc3cc(O)ccc3[C@]1(C)CCN2C(=O)C(F)(F)F]

Example XXXIII

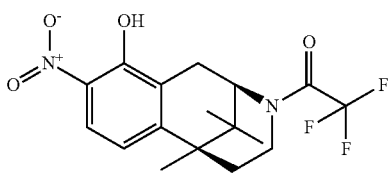 [SMILES: CC1(C)[C@H]2Cc3c(ccc([N+](=O)[O-])c3O)[C@]1(C)CCN2C(=O)C(F)(F)F]

2,2,2-Trifluoro-1-[(2R,6S)-10-hydroxy-6,11,11-trimethyl-9-nitro-1,2,5,6-tetrahydro-4H-2,6-methano-benzo[d]azocin-3-yl]-ethanone Nitric acid (0.4 mL) is slowly added to a solution of 2,2,2-trifluoro-1-[(2R,6S)-10-hydroxy-6,11,11-trimethyl-1,2,5,6-tetrahydro-4H-2,6-methano-benzo[d]azocin-3-yl]-ethanone (2.9 g) in acetic acid (5 mL) chilled in an ice bath. The ice bath is removed and the solution is stirred at ambient temperature overnight. The solution is poured into ice-cold water and the resulting mixture is extracted with ethyl acetate. The combined extracts are washed with brine and dried (Na$_2$SO$_4$). After removal of the solvent under reduced pressure, the residue is purified by chromatography on silica gel (ethyl acetate/cyclohexane 1:9->1:3).

Yield: 1.3 g (39% of theory)

Mass spectrum (ESI$^-$): m/z=371 [M−H]$^-$

The following compounds are obtained analogously to Example XXXIII:

(1) 2,2,2-Trifluoro-1-[(2R,6R,11S)-8-hydroxy-6,11-dimethyl-9-nitro-1,2,5,6-tetrahydro-4H-2,6-methano-benzo[d]azocin-3-yl]-ethanone

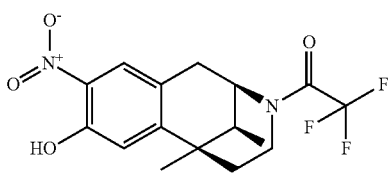 [SMILES: C[C@@H]1[C@H]2Cc3cc([N+](=O)[O-])c(O)cc3[C@]1(C)CCN2C(=O)C(F)(F)F]

Mass spectrum (ESI$^+$): m/z=359 [M+H]$^+$ (2) 2,2,2-Trifluoro-1-[(2R,6R,11S)-8-hydroxy-6,11-dimethyl-7-nitro-1,2,5,6-tetrahydro-4H-2,6-methano-benzo[d]azocin-3-yl]-ethanone

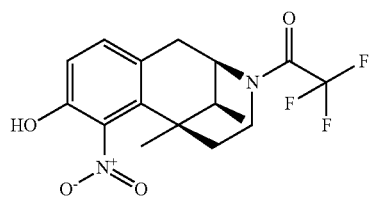 [SMILES: C[C@@H]1[C@H]2Cc3ccc(O)c([N+](=O)[O-])c3[C@]1(C)CCN2C(=O)C(F)(F)F]

Mass spectrum (ESI$^+$): m/z=359 [M+H]$^+$

The compound is obtained in a mixture with compound Example XXXIII(1) that is separated by chromatography as described above.

(3) 2,2,2-Trifluoro-1-[(2R,6S)-9-hydroxy-6,11,11-trimethyl-8-nitro-1,2,5,6-tetrahydro-4H-2,6-methano-benzo[d]azocin-3-yl]-ethanone

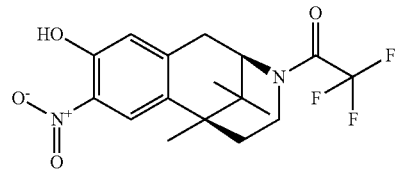 [SMILES: CC1(C)[C@H]2Cc3cc(O)c([N+](=O)[O-])cc3[C@]1(C)CCN2C(=O)C(F)(F)F]

Mass spectrum (ESI$^+$): m/z=373 [M+H]$^+$

The compound is obtained in a mixture with compound Example XXXIII(4) that is separated by chromatography as described above.

(4) 2,2,2-Trifluoro-1-[(2R,6S)-9-hydroxy-6,11,11-trimethyl-10-nitro-1,2,5,6-tetrahydro-4H-2,6-methano-benzo[d]azocin-3-yl]-ethanone

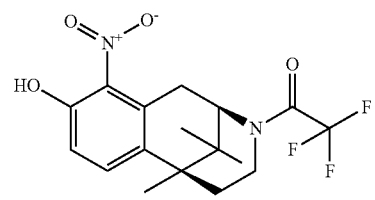 [SMILES: CC1(C)[C@H]2Cc3c(ccc(O)c3[N+](=O)[O-])[C@]1(C)CCN2C(=O)C(F)(F)F]

Mass spectrum (ESI$^+$): m/z=373 [M+H]$^+$

The compound is obtained in a mixture with compound Example XXXIII(3) that is separated by chromatography as described above.

Example XXXIV

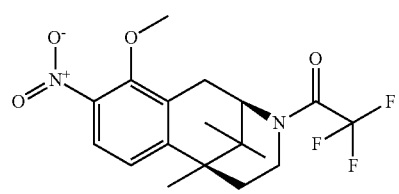 [SMILES: COc1c([N+](=O)[O-])ccc2c1C[C@H]1N(C(=O)C(F)(F)F)CC[C@]2(C)C1(C)C]

(2R,6S)-2,2,2-Trifluoro-1-(10-methoxy-6,11,11-trimethyl-9-nitro-1,2,5,6-tetrahydro-4H-2,6-methano-benzo[d]azocin-3-yl)-ethanone Methyl iodide (80 μL) is added to a mixture of (2R,6S)-2,2,2-trifluoro-1-(10-hydroxy-6,11,11-trimethyl-9-nitro-1,2,5,6-tetrahydro-4H-2,6-methano-benzo[d]azocin-3-yl)-ethanone (0.40 g) and potassium carbonate (0.17 g) in dimethylformamide (5 mL). The mixture is stirred at room temperature overnight, before another portion of methyl iodide (80 μL) and potassium carbonate (0.16 g) are added.

The mixture is stirred for another 6 h at room temperature. Then, water and ethyl acetate are added, the organic phase is separated, and the aqueous phase is extracted with ethyl acetate. The combined organic phases are washed with brine and dried (Na₂SO₄). The solvent is evaporated to give the crude product that is used without further purification.

Yield: 0.41 g (100% of theory)

Mass spectrum (ESI⁺): m/z=387 [M+H]⁺

The following compounds are obtained analogously to Example XXXIV:

(1) (2S,6R)-8-Methoxy-6,9,11,11-tetramethyl-1,2,5,6-tetrahydro-4H-2,6-methano-benzo[d]azocine-3-carboxylic acid tert-butyl ester

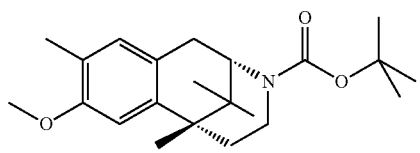 [SMILES: COc1cc2c(cc1C)C[C@@H]1N(C(=O)OC(C)(C)C)CC[C@@]2(C)C1(C)C]

The compound may be obtained by resolution of the racemic mixture by HPLC on chiral phase or by using the enantiomerically pure (2S,6R)-8-hydroxy-6,9,11,11-tetramethyl-1,2,5,6-tetrahydro-4H-2,6-methano-benzo[d]azocine-3-carboxylic acid tert-butyl ester.

(2) (2R,6S)-8-Methoxy-6,9,11,11-tetramethyl-1,2,5,6-tetrahydro-4H-2,6-methano-benzo[d]azocine-3-carboxylic acid tert-butyl ester

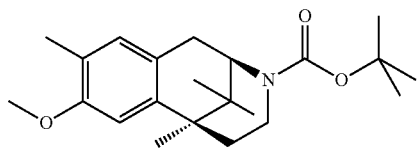 [SMILES: COc1cc2c(cc1C)C[C@H]1N(C(=O)OC(C)(C)C)CC[C@]2(C)C1(C)C]

The compound may be obtained by resolution of the racemic mixture by HPLC on chiral phase or by using the enantiomerically pure (2R,6S)-8-hydroxy-6,9,11,11-tetramethyl-1,2,5,6-tetrahydro-4H-2,6-methano-benzo[d]azocine-3-carboxylic acid tert-butyl ester.

(3) (2S,6R)-9-Methoxy-6,8,11,11-tetramethyl-1,2,5,6-tetrahydro-4H-2,6-methano-benzo[d]azocine-3-carboxylic acid tert-butyl ester

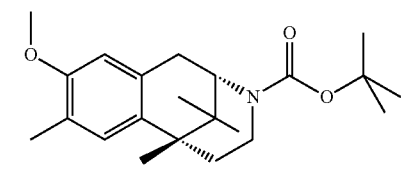 [SMILES: COc1cc2c(cc1C)[C@@]1(C)CCN(C(=O)OC(C)(C)C)[C@@H](C2)C1(C)C]

The compound may be obtained by resolution of the racemic mixture by HPLC on chiral phase or by using the enantiomerically pure (2S,6R)-9-hydroxy-6,8,11,11-tetramethyl-1,2,5,6-tetrahydro-4H-2,6-methano-benzo[d]azocine-3-carboxylic acid tert-butyl ester.

(4) (2R,6S)-9-Methoxy-6,8,11,11-tetramethyl-1,2,5,6-tetrahydro-4H-2,6-methano-benzo[d]azocine-3-carboxylic acid tert-butyl ester

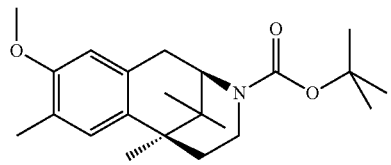 [SMILES: COc1cc2c(cc1C)[C@]1(C)CCN(C(=O)OC(C)(C)C)[C@H](C2)C1(C)C]

The compound may be obtained by resolution of the racemic mixture by HPLC on chiral phase or by using the enantiomerically pure (2R,6S)-9-hydroxy-6,8,11,11-tetramethyl-1,2,5,6-tetrahydro-4H-2,6-methano-benzo[d]azocine-3-carboxylic acid tert-butyl ester.

(5) 8,9-Dimethoxy-6,11,11-trimethyl-1,2,5,6-tetrahydro-4H-2,6-methano-benzo[d]azocine-3-carboxylic acid tert-butyl ester

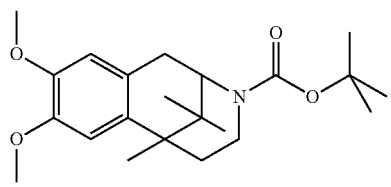 [SMILES: COc1cc2c(cc1OC)C1(C)CCN(C(=O)OC(C)(C)C)C(C2)C1(C)C]

Twice the amount of methyl iodide and potassium carbonate as described in the procedure above are employed to prepare the compound from 8,9-dihydroxy-6,11,11-trimethyl-1,2,5,6-tetrahydro-4H-2,6-methano-benzo[d]azocine-3-carboxylic acid tert-butyl ester.

(6) 9-Hydroxy-8-methoxy-6,11,11-trimethyl-1,2,5,6-tetrahydro-4H-2,6-methano-benzo[d]azocine-3-carboxylic acid tert-butyl ester

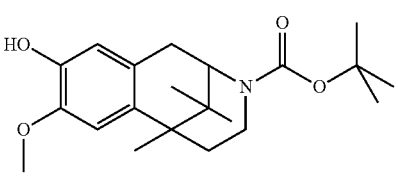 [SMILES: COc1cc2c(cc1O)CC1N(C(=O)OC(C)(C)C)CCC2(C)C1(C)C]

The compound is obtained in a mixture with 8-hydroxy-9-methoxy-6,11,11-trimethyl-1,2,5,6-tetrahydro-4H-2,6-methano-benzo[d]azocine-3-carboxylic acid tert-butyl ester and 8,9-dimethoxy-6,11,11-trimethyl-1,2,5,6-tetrahydro-4H-2,6-methano-benzo[d]azocine-3-carboxylic acid tert-butyl ester from 8,9-dihydroxy-6,11,11-trimethyl-1,2,5,6-tetrahydro-4H-2,6-methano-benzo[d]azocine-3-carboxylic acid tert-butyl ester that may be separated by HPLC on reversed phase.

(7) 8-Hydroxy-9-methoxy-6,11,11-trimethyl-1,2,5,6-tetrahydro-4H-2,6-methano-benzo[d]azocine-3-carboxylic acid tert-butyl ester

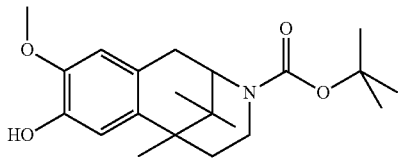 [SMILES: COc1cc2c(cc1O)C1(C)CCN(C(=O)OC(C)(C)C)C(C2)C1(C)C]

The compound is obtained in a mixture with 9-hydroxy-8-methoxy-6,11,11-trimethyl-1,2,5,6-tetrahydro-4H-2,6-methano-benzo[d]azocine-3-carboxylic acid tert-butyl ester and 8,9-dimethoxy-6,11,11-trimethyl-1,2,5,6-tetrahydro-4H-2,6-methano-benzo[d]azocine-3-carboxylic acid tert-butyl ester from 8,9-dihydroxy-6,11,11-trimethyl-1,2,5,6-tetrahydro-4H-2,6-methano-benzo[d]azocine-3-carboxylic acid tert-butyl ester that may be separated by HPLC on reversed phase.

(8) 9-Methoxy-6,11,11-trimethyl-1,2,3,4,5,6-hexahydro-2,6-methano-benzo[d]azocine

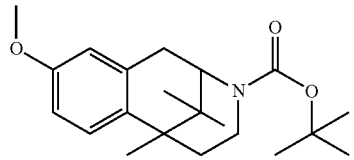 [SMILES: COc1ccc2c(c1)CC1N(C(=O)OC(C)(C)C)CCC2(C)C1(C)C]

(9) (2S,6R)-9-Methoxy-6,11,11-trimethyl-1,2,3,4,5,6-hexahydro-2,6-methano-benzo[d]azocine

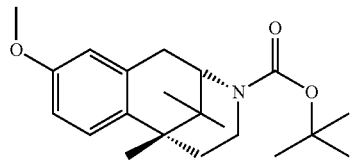

The compound may be obtained from the racemic mixture by HPLC on chiral phase.

(10) 2,2,2-Trifluoro-1-[(2R,6R,11S)-8-methoxy-6,11-dimethyl-9-nitro-1,2,5,6-tetrahydro-4H-2,6-methano-benzo[d]azocin-3-yl]-ethanone

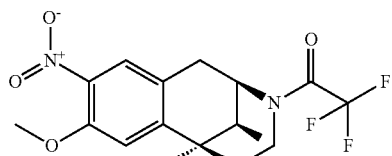

Mass spectrum (ESI$^+$): m/z=373 [M+H]$^+$

(11) 2,2,2-Trifluoro-1-[(2R,6R,11S)-8-methoxy-6,11-dimethyl-7-nitro-1,2,5,6-tetrahydro-4H-2,6-methano-benzo[d]azocin-3-yl]-ethanone

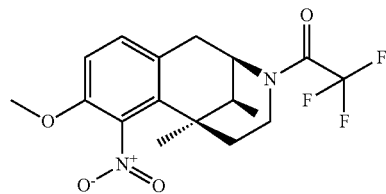 [SMILES: COc1ccc2c(c1[N+](=O)[O-])[C@]1(C)CCN(C(=O)C(F)(F)F)[C@H](C2)[C@H]1C]

Mass spectrum (ESI$^+$): m/z=373 [M+H]$^+$

Example XXXV

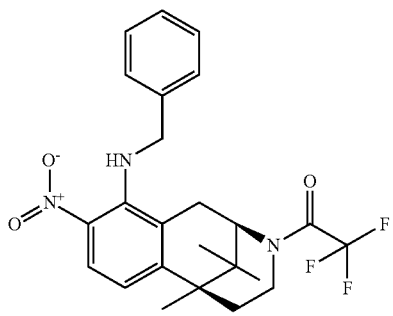 [SMILES: CC1(C)[C@H]2Cc3c(ccc([N+](=O)[O-])c3NCc3ccccc3)[C@]1(C)CCN2C(=O)C(F)(F)F]

1-[(2R,6S)-10-Benzylamino-6,11,11-trimethyl-9-nitro-1,2,5,6-tetrahydro-4H-2,6-methano-benzo[d]azocin-3-yl]-2,2,2-trifluoro-ethanone 2,2,2-Trifluoro-1-[(2R,6S)-10-methoxy-6,11,11-trimethyl-9-nitro-1,2,5,6-tetrahydro-4H-2,6-methano-benzo[d]azocin-3-yl]-ethanone_(0.41 g) is combined with benzylamine (0.7 mL) and the resulting mixture is stirred at 70° C. overnight. After cooling to room temperature, the mixture is purified by HPLC on reversed phase (MeCN/H$_2$O/TFA) to give the product as an oil.

Yield: 0.19 g (38% of theory)
Mass spectrum (ESI$^+$): m/z=462 [M+H]$^+$

The following compound is obtained analogously to Example XXXV:

(1) 1-[(2R,6R,11S)-8-Benzylamino-6,11-dimethyl-9-nitro-1,2,5,6-tetrahydro-4H-2,6-methano-benzo[d]azocin-3-yl]-2,2,2-trifluoro-ethanone

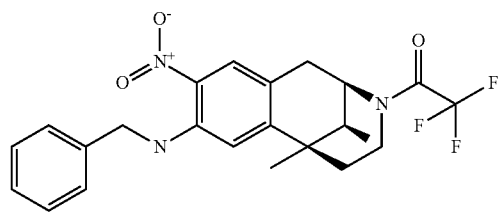 [SMILES: C[C@@H]1[C@H]2Cc3cc([N+](=O)[O-])c(NCc4ccccc4)cc3[C@]1(C)CCN2C(=O)C(F)(F)F]

The reaction mixture is stirred at 170° C. for 5 h.

Example XXXVI

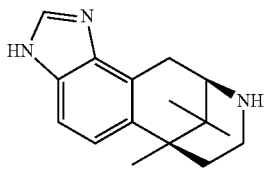 [SMILES: CC1(C)[C@H]2Cc3c(ccc4[nH]cnc34)[C@]1(C)CCN2]

(5R,9S)-4,5,6,7,8,9-hexahydro-9,12,12-trimethyl-5,
9-methano-1H-imidazo[5,4-i][3]benzazocine A mixture of Raney-Ni (0.1 g), 1-[(2R,6S)-10-benzylamino-6,11,11-trimethyl-9-nitro-1,2,5,6-tetrahydro-4H-2,6-methano-benzo[d]azocin-3-yl]-2,2,2-trifluoro-ethanone_ (0.19 g), and formic acid (10 mL) is stirred in hydrogen atmosphere at 50° C. overnight. Then, the catalyst is separated by filtration and the filtrate is concentrated. The remainder is taken up in methanol (10 mL) and treated with 4 M NaOH solution (2 mL) at 50° C. overnight. After cooling to room temperature, the solution is neutralized with 2 M hydrochloric acid and the solvent is removed. The residue is purified by HPLC on reversed phase (MeCN/H$_2$O).

Yield: 35 mg (33% of theory)

The following compound is obtained analogously to Example XXXVI:

(1) (6R,10R,12S)-5,6,7,8,9,10-Hexahydro-10,12-dimethyl-6,10-methano-1H-imidazo[5,4-i][3]benzazocine

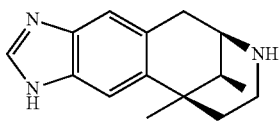 [SMILES: C[C@@H]1[C@H]2Cc3cc4nc[nH]c4cc3[C@]1(C)CCN2]

Mass spectrum (ESI$^+$): m/z=242 [M+H]$^+$

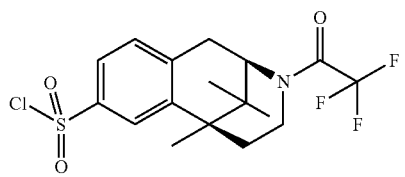

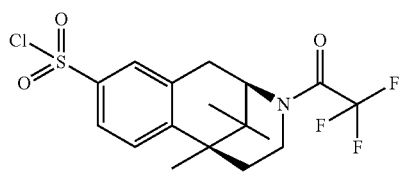

Example XXXVII (2R,6S)-6,11,11-Trimethyl-3-(2,2,2-trifluoro-acetyl)-1,2,3,4,5,6-hexahydro-2,6-methano-benzo[d]azocine-8-sulfonyl chloride and (2R,6S)-6,11,11-trimethyl-3-(2,2,2-trifluoro-acetyl)-1,2,3,4,5,6-hexahydro-2,6-methano-benzo[d]azocine-9-sulfonyl chloride Chlorosulfonic acid (1.15 mL) is slowly added to a solution of 2,2,2-trifluoro-1-[(2R,6S)-6,11,11-trimethyl-1,2,5,6-tetrahydro-4H-2,6-methano-benzo[d]azocin-3-yl]-ethanone (0.90 g) in dichloromethane (10 mL) at room temperature. Then, the solution is stirred at ambient temperature overnight. The solution is poured into ice-cold water and the resulting mixture is extracted with ethyl acetate. The combined organic extracts are washed with brine and dried (MgSO$_4$). The solvent is removed under reduced pressure to give the crude title compounds in a mixture that is used without further purification.

Yield: 1.18 g

Example XXXVIII

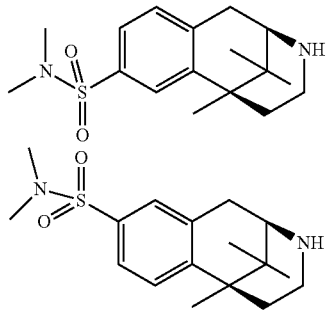

(2R,6S)-6,11,11-Trimethyl-1,2,3,4,5,6-hexahydro-2,6-methano-benzo[d]azocine-8-sulfonic acid dimethylamide and (2R,6S)-6,11,11-trimethyl-1,2,3,4,5,6-hexahydro-2,6-methano-benzo[d]azocine-9-sulfonic acid dimethylamide Dimethylamine (3.3 mL, 2 M in THF) is added to a mixture of (2R,6S)-6,11,11-trimethyl-3-(2,2,2-trifluoro-acetyl)-1,2,3,4,5,6-hexahydro-2,6-methano-benzo[d]azocine-8-sulfonyl chloride and (2R,6S)-6,11,11-trimethyl-3-(2,2,2-trifluoro-acetyl)-1,2,3,4,5,6-hexahydro-2,6-methano-benzo[d]azocine-9-sulfonyl chloride (0.90 g, crude product from Example XXXVII) dissolved in ethanol (5 mL) and chilled in an ice bath. The cooling bath is removed and the solution is stirred at room temperature for 2 h. Then, 4 M NaOH solution (2.2 mL) is added to cleave off the trifluoroacetyl group. After stirring at room temperature for 1 h, the solution is diluted with water and the resulting mixture is extracted with ethyl acetate. The combined extracts are washed with brine and dried (MgSO$_4$). The solvent is removed and the residue is purified by HPLC on reversed phase (MeCN/H$_2$O/NH$_3$) to give the two title compounds separated.

(2R,6S)-6,11,11-Trimethyl-1,2,3,4,5,6-hexahydro-2,6-methano-benzo[d]azocine-8-sulfonic acid dimethylamide:

Yield: 500 mg (71% of theory)

Mass spectrum (ESI$^+$): m/z=323 [M+H]$^+$ (2R,6S)-6,11,11-Trimethyl-1,2,3,4,5,6-hexahydro-2,6-methano-benzo[d]azocine-9-sulfonic acid dimethylamide:
Yield: 50 mg (7% of theory)
Mass spectrum (ESI⁺): m/z=323 [M+H]⁺
The following compounds are obtained analogously to Example XXXVIII:

(1) (2R,6S)-6,11,11-Trimethyl-1,2,3,4,5,6-hexahydro-2,6-methano-benzo[d]azocine-8-sulfonic acid methylamide

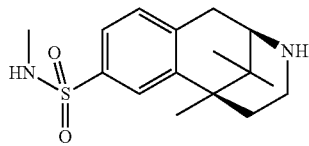 [SMILES: CNS(=O)(=O)c1ccc2c(c1)[C@]1(C)CCN[C@H](C2)C1(C)C]

Mass spectrum (ESI⁺): m/z=309 [M+H]⁺
Methylamine is used as coupling partner.

(2) (2R,6S)-6,11,11-Trimethyl-1,2,3,4,5,6-hexahydro-2,6-methano-benzo[d]azocine-8-sulfonic acid amide

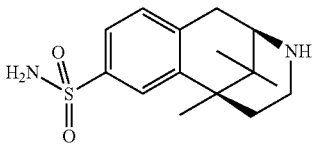 [SMILES: CC1(C)[C@H]2Cc3ccc(S(N)(=O)=O)cc3[C@]1(C)CCN2]

Mass spectrum (ESI⁺): m/z=295 [M+H]⁺
Ammonia is used as coupling partner.

Example XXXIX

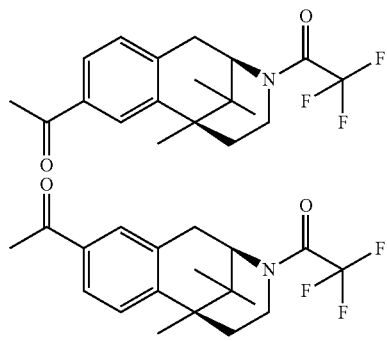

1-[(2R,6S)-8-Acetyl-6,11,11-trimethyl-1,2,5,6-tetrahydro-4H-2,6-methano-benzo[d]azocin-3-yl]-2,2,2-trifluoro-ethanone and 1-[(2R,6S)-9-acetyl-6,11,11-trimethyl-1,2,5,6-tetrahydro-4H-2,6-methano-benzo[d]azocin-3-yl]-2,2,2-trifluoro-ethanone Acetyl chloride (0.25 mL) is added to a suspension of AlCl₃ (1.3 g) in dichloromethane (5 mL) chilled in an ice bath. After stirring the mixture for 5 min, 2,2,2-trifluoro-1-[(2R,6S)-6,11,11-trimethyl-1,2,5,6-tetrahydro-4H-2,6-methano-benzo[d]azocin-3-yl]-ethanone (1.0 g) dissolved in dichloromethane (5 mL) is added dropwise. The mixture is stirred at ambient temperature overnight and then poured into ice-cold half-concentrated hydrochloric acid (20 mL). The resulting mixture is extracted with dichloromethane and the combined organic extracts are washed with water, aqueous NaHCO₃ solution, and brine and dried (MgSO₄). The solvent is removed and the residue is purified by chromatography on silica gel (cyclohexane/ethyl acetate 3:1->1:1) to give the two regioisomeric title compounds in a ca. 3:1 mixture.
Yield: 0.83 g (73% of theory)
Mass spectrum (ESI⁺): m/z=354 [M+H]⁺

Example XL

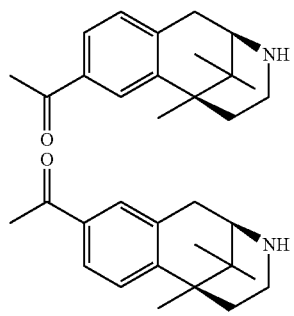

1-[(2R,6S)-6,11,11-Trimethyl-1,2,3,4,5,6-hexahydro-2,6-methano-benzo[d]azocin-8-yl]-ethanone and 1-[(2R,6S)-6,11,11-trimethyl-1,2,3,4,5,6-hexahydro-2,6-methano-benzo[d]azocin-9-yl]-ethanone 4 M NaOH solution (2.5 mL) is added to a ca. 3:1 mixture of 1-[(2R,6S)-8-acetyl-6,11,11-trimethyl-1,2,5,6-tetrahydro-4H-2,6-methano-benzo[d]azocin-3-yl]-2,2,2-trifluoro-ethanone and 1-[(2R,6S)-9-acetyl-6,11,11-trimethyl-1,2,5,6-tetrahydro-4H-2,6-methano-benzo[d]azocin-3-yl]-2,2,2-trifluoro-ethanone (0.83 g) in methanol (10 mL). The resulting solution is stirred at room temperature overnight. Then, the solution is neutralized with 1 M hydrochloric acid and concentrated. The residue is purified by HPLC on reversed phase (acetonitrile/water/NH₃) to give the two title compounds separated.
Yield: 0.35 g of 1-[(2R,6S)-6,11,11-trimethyl-1,2,3,4,5,6-hexahydro-2,6-methano-benzo[d]azocin-8-yl]-ethanone and 0.07 g 1-[(2R,6S)-6,11,11-trimethyl-1,2,3,4,5,6-hexahydro-2,6-methano-benzo[d]azocin-9-yl]-ethanone (combined 71% of theory)
Mass spectrum (ESI⁺): m/z=258 [M+H]⁺
The following compounds are obtained analogously to Example XL:

(1) (2R,6R,11S)-8-Hydroxy-6,11-dimethyl-1,2,3,4,5,6-hexahydro-2,6-methano-benzo[d]azocine-9-carbonitrile

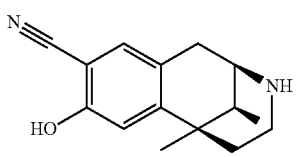 [SMILES: C[C@@H]1[C@H]2Cc3cc(C#N)c(O)cc3[C@]1(C)CCN2]

Mass spectrum (ESI⁺): m/z=243 [M+H]⁺

(2) (2R,6S)-8-Methanesulfonyl-6,11,11-trimethyl-1,2,3,4,5,6-hexahydro-2,6-methano-benzo[d]azocine

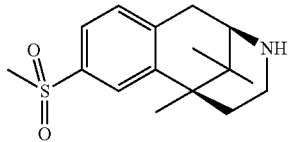 [SMILES: CC1(C)[C@H]2Cc3ccc(S(C)(=O)=O)cc3[C@]1(C)CCN2]

Mass spectrum (ESI$^+$): m/z=294 [M+H]$^+$ (3) (2R,6S)-10-Methanesulfonyl-6,11,11-trimethyl-1,2,3,4,5,6-hexahydro-2,6-methano-benzo[d]azocine

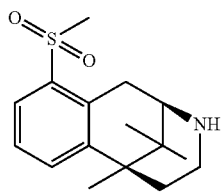 [SMILES: CC1(C)[C@H]2Cc3c(cccc3S(C)(=O)=O)[C@]1(C)CCN2]

Mass spectrum (ESI$^+$): m/z=294 [M+H]$^+$ (4) (6R,10S)-5,6,7,8,9,10-Hexahydro-2,10,12,12-tetramethyl-6,10-methano-1H-imidazo[5,4-i][3]benzazocine

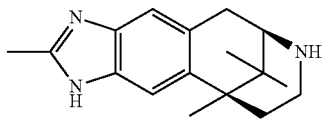 [SMILES: Cc1nc2cc3c(cc2[nH]1)[C@]1(C)CCN[C@H](C3)C1(C)C]

(5) (6R,10S)-5,6,7,8,9,10-Hexahydro-10,12,12-trimethyl-6,10-methano-1H-imidazo[5,4-i][3]benzazocine

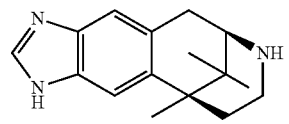 [SMILES: CC1(C)[C@H]2Cc3cc4nc[nH]c4cc3[C@]1(C)CCN2]

(6) (2R,6R,11S)-6,11-Dimethyl-7-nitro-1,2,3,4,5,6-hexahydro-2,6-methano-benzo[d]azocin-8-ol

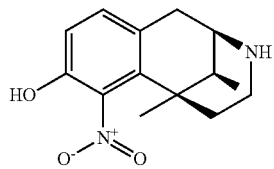

Mass spectrum (ESI$^+$): m/z=227 [M+H]$^+$ (7) (6R,10S)-5,6,7,8,9,10-Hexahydro-10,12,12-trimethyl-6,10-methano-1H-triazolo[5,4-i][3]benzazocine

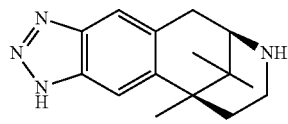 [SMILES: CC1(C)[C@H]2Cc3cc4nn[nH]c4cc3[C@]1(C)CCN2]

Mass spectrum (ESI$^+$): m/z=257 [M+H]$^+$ (8) (6R,10S)-5,6,7,8,9,10-Hexahydro-10,12,12-trimethyl-2-pyrazin-2-yl-6,10-methano-1H-imidazo[5,4-i][3]benzazocine

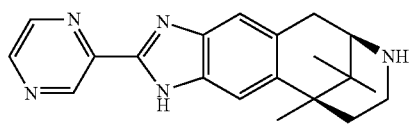 [SMILES: CC1(C)[C@H]2Cc3cc4nc(-c5cnccn5)[nH]c4cc3[C@]1(C)CCN2]

Mass spectrum (ESI$^+$): m/z=334 [M+H]$^+$ (9) (6R,10S)-2-(1-Acetyl-piperidin-4-yl)-5,6,7,8,9,100-hexahydro-10,12,12-trimethyl-6,10-methano-1H-imidazo[5,4-i][3]-benzazocine

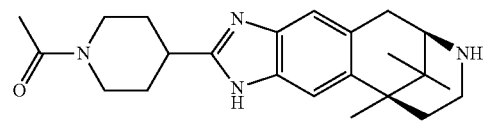 [SMILES: CC(=O)N1CCC(c2nc3cc4c(cc3[nH]2)[C@]2(C)CCN[C@H](C4)C2(C)C)CC1]

(10) (6R,10S)-2-Cyclopropyl-5,6,7,8,9,10-hexahydro-10,12,12-trimethyl-6,10-methano-1H-imidazo[5,4-i][3]benzazocine

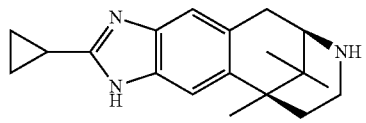 [SMILES: CC1(C)[C@H]2Cc3cc4nc(C5CC5)[nH]c4cc3[C@]1(C)CCN2]

(11) (6R,10S)-5,6,7,8,9,10-Hexahydro-10,12,12-trimethyl-2-(1-methyl-6-oxo-1,6-dihydro-pyridin-3-yl)-6,10-methano-1H-imidazo[5,4-i][3]benzazocine

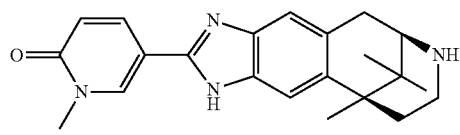 [SMILES: Cn1cc(-c2nc3cc4c(cc3[nH]2)[C@]2(C)CCN[C@H](C4)C2(C)C)ccc1=O]

(12) (R10S)-2-tert-Butyl-5,6,7,8,9,10-hexahydro-10,12,12-trimethyl-6,10-methano-1H-imidazo[5,4-i][3]benzazocine

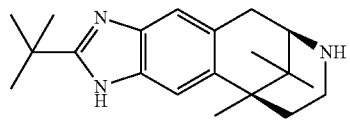 [SMILES: CC(C)(C)c1nc2cc3c(cc2[nH]1)[C@]1(C)CCN[C@H](C3)C1(C)C]

(13) (6R,10S)-5,6,7,8,9,10-Hexahydro-10,12,12-trimethyl-2-pyridin-3-yl-6,10-methano-1H-imidazo[5,4-i][3]benzazocine

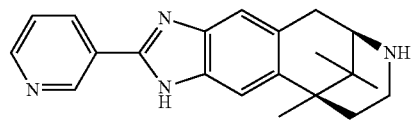

(14) (6R,10S)-5,6,7,8,9,10-Hexahydro-10,12,12-trimethyl-2-[(S)-tetrahydrofuran-2-yl]-6,10-methano-1H-imidazo[5,4-i][3]benzazocine

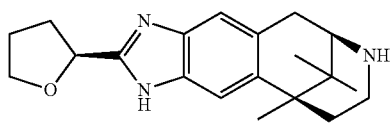 [SMILES: CC1(C)[C@H]2Cc3cc4nc([C@@H]5CCCO5)[nH]c4cc3[C@]1(C)CCN2]

Mass spectrum (ESI$^+$): m/z=326 [M+H]$^+$

(15) (6R,10S)-5,6,7,8,9,10-Hexahydro-10,12,12-trimethyl-2-pyridazin-4-yl-6,10-methano-1H-imidazo[5,4-i][3]benzazocine

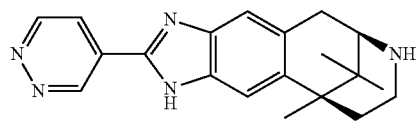 [SMILES: CC1(C)[C@H]2Cc3cc4nc(-c5ccnnc5)[nH]c4cc3[C@]1(C)CCN2]

(16) (6R,10S)-5,6,7,8,9,10-Hexahydro-10,12,12-trimethyl-2-(5-methyl-pyrazin-2-yl)-6,10-methano-1H-imidazo[5,4-i][3]benzazocine

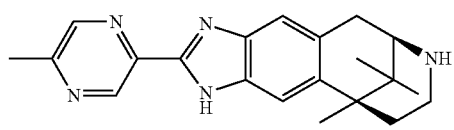 [SMILES: Cc1cnc(-c2nc3cc4c(cc3[nH]2)[C@]2(C)CCN[C@H](C4)C2(C)C)cn1]

Mass spectrum (ESI$^+$): m/z=348 [M+H]$^+$

(17) (6R,10S)-5,6,7,8,9,10-Hexahydro-10,12,12-trimethyl-2-[(R)-tetrahydrofuran-2-yl]-6,10-methano-1H-imidazo[5,4-i][3]benzazocine

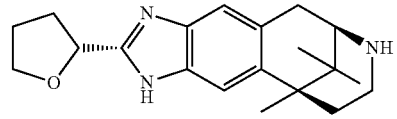

Mass spectrum (ESI$^+$): m/z=326 [M+H]$^+$

(18) (7R,11R,12S)-6,7,8,9,10,11-Hexahydro-2,11,12-trimethyl-6,10-methano-oxazolo[4,5-h][3]benzazocine

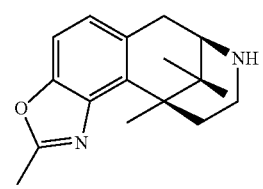

Mass spectrum (ESI$^+$): m/z=257 [M+H]$^+$

(19) (6R,10S)-5,6,7,8,9,10-Hexahydro-2,10,12,12-tetramethyl-6,10-methano-oxazolo[4,5-i][3]benzazocine

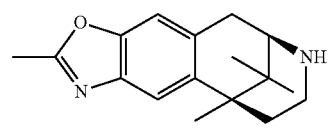 [SMILES: Cc1nc2cc3c(cc2o1)C[C@H]1NCC[C@]3(C)C1(C)C]

(20) (6R,10S)-2-Cyclopropyl-5,6,7,8,9,10-hexahydro-10,12,12-trimethyl-6,10-methano-oxazolo[4,5-i][3]benzazocine

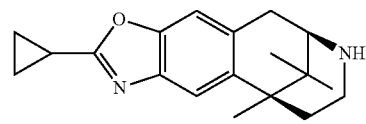 [SMILES: CC1(C)[C@H]2Cc3cc4oc(C5CC5)nc4cc3[C@]1(C)CCN2]

(21) (6R,10R,12S)-5,6,7,8,9,10-Hexahydro-2,10,12-trimethyl-6,10-methano-oxazolo[5,4-i][3]benzazocine

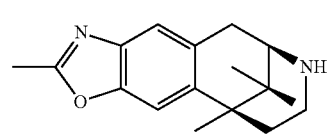

Mass spectrum (ESI$^+$): m/z=257 [M+H]$^+$

(22) (6R,10R,12S)-2-Cyclopropyl-5,6,7,8,9,10-hexahydro-10,12-dimethyl-6,10-methano-oxazolo[5,4-i][3]-benzazocine

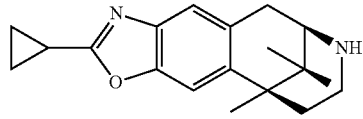

(23) (6R,10S)-2-tert-Butyl-5,6,7,8,9,10-hexahydro-10,12,12-trimethyl-6,10-methano-oxazolo[4,5-i][3]benzazocine

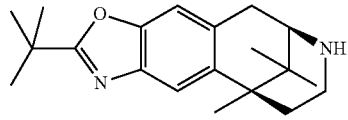 [SMILES: CC(C)(C)c1nc2cc3c(cc2o1)C[C@H]1NCC[C@]3(C)C1(C)C]

(24) (6R,10S)-5,6,7,8,9,10-hexahydro-10,12,12-trimethyl-2-(5-methyl-pyrazin-2-yl)-6,10-methano-oxazolo[4,5-i][3]benzazocine

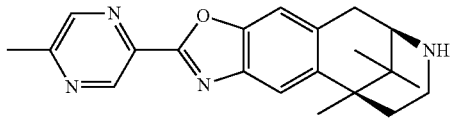 [SMILES: Cc1cnc(-c2nc3cc4c(cc3o2)C[C@H]2NCC[C@]4(C)C2(C)C)cn1]

(25) (6R,10R,12S)-5,6,7,8,9,10-hexahydro-10,12-dimethyl-2-(5-methyl-pyrazin-2-yl)-6,10-methano-oxazolo[5,4-i][3]benzazocine

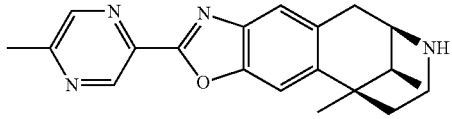 [SMILES: Cc1cnc(-c2nc3cc4c(cc3o2)[C@]2(C)CCN[C@H](C4)[C@H]2C)cn1]

Mass spectrum (ESI+): m/z=335 [M+H]+

(26) (6R,10S)-5,6,7,8,9,10-hexahydro-10,12,12-trimethyl-2-[(R)-tetrahydrofuran-2-yl]-6,10-methano-oxazolo[4,5-i][3]benzazocine

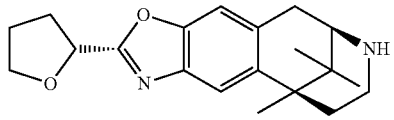

(27) (6R,10S)-5,6,7,8,9,10-hexahydro-10,12,12-trimethyl-2-[(S)-tetrahydrofuran-2-yl]-6,10-methano-oxazolo[4,5-i][3]benzazocine

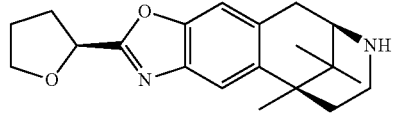

Example XLI

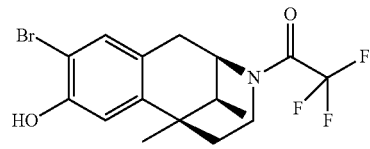 [SMILES: C[C@@H]1[C@H]2Cc3cc(Br)c(O)cc3[C@]1(C)CCN2C(=O)C(F)(F)F]

1-[(2R,6R,11S)-9-Bromo-8-hydroxy-6,11-dimethyl-1,2,5,6-tetrahydro-4H-2,6-methano-benzo[d]azocin-3-yl]-2,2,2-trifluoro-ethanone A solution of 2,2,2-trifluoro-1-[(2R,6R,11S)-8-hydroxy-6,11-dimethyl-1,2,5,6-tetrahydro-4H-2,6-methano-benzo[d]azocin-3-yl]-ethanone (3.0 g) and pyridinium tribromide (3.3 g) in acetic acid (2 mL) is stirred at 80° C. for 2 h. After cooling to room temperature, water is added and the resulting mixture is extracted with ethyl acetate. The combined organic extracts are washed with water, aqueous NaHCO₃ solution, and brine. After drying (Na₂SO₄), the solvent is removed and the residue is purified by chromatography on silica gel (cyclohexane/ethyl acetate 4:1->1:1).

Yield: 2.5 g (67% of theory)
Mass spectrum (ESI+): m/z=392/394 (Br) [M+H]+

The following compound is obtained analogously to Example XLI:

(1) 1-[(2R,6R,11R)-9-Bromo-8-hydroxy-6,11-dimethyl-1,2,5,6-tetrahydro-4H-2,6-methano-benzo[d]azocin-3-yl]-2,2,2-trifluoro-ethanone

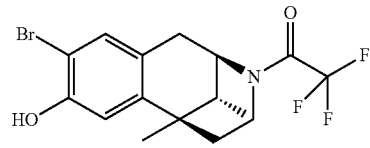 [SMILES: C[C@H]1[C@H]2Cc3cc(Br)c(O)cc3[C@]1(C)CCN2C(=O)C(F)(F)F]

Mass spectrum (ESI+): m/z=392/394 (Br) [M+H]+

Example XLII

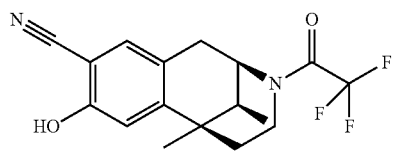 [SMILES: C[C@@H]1[C@H]2Cc3cc(C#N)c(O)cc3[C@]1(C)CCN2C(=O)C(F)(F)F]

(2R,6R,11S)-8-Hydroxy-6,11-dimethyl-3-(2,2,2-trifluoro-acetyl)-1,2,3,4,5,6-hexahydro-2,6-methano-benzo[d]azocine-9-carbonitrile A mixture of 1-[(2R,6R,11S)-9-bromo-8-hydroxy-6,11-dimethyl-1,2,5,6-tetrahydro-4H-2,6-methano-benzo[d]azocin-3-yl]-2,2,2-trifluoro-ethanone (0.50 g) and copper cyanide (0.23 g) in N-methyl-pyrrolidone (2 mL) is stirred in a microwave oven at 180° C. for 1 h. After cooling to room temperature, water is added and the resulting mixture is extracted with ethyl acetate. The combined organic extracts are washed with brine and dried ($Na_2SO_4$). After removing the solvent, the residue is purified by chromatography on silica gel (cyclohexane/ethyl acetate 2:1->1:2).
Yield: 0.20 g (46% of theory)
Mass spectrum (ESI$^+$): m/z=339 [M+H]$^+$ The following compound is obtained analogously to Example XLII:

(1) (2R,6R,11R)-8-Hydroxy-6,11-dimethyl-3-(2,2,2-trifluoro-acetyl)-1,2,3,4,5,6-hexahydro-2,6-methano-benzo[d]azocine-9-carbonitrile

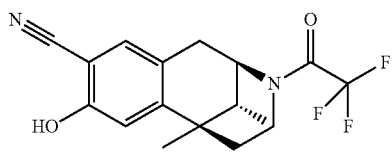 [SMILES: C[C@H]1[C@H]2Cc3cc(C#N)c(O)cc3[C@]1(C)CCN2C(=O)C(F)(F)F]

Mass spectrum (ESI$^+$): m/z=339 [M+H]$^+$

Example XLIII

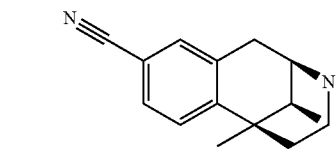 [SMILES: C[C@@H]1[C@H]2Cc3cc(C#N)ccc3[C@]1(C)CCN2]

(2R,6R,11S)-6,11-Dimethyl-1,2,3,4,5,6-hexahydro-2,6-methano-benzo[d]azocine-9-carbonitrile A solution of KF (76 mg) in water (1 mL) followed by polymethylhydrosiloxane (1.0 g) is added to a mixture of (2R,6R,11S)-trifluoro-methanesulfonic acid 9-cyano-6,11-dimethyl-3-(2,2,2-trifluoro-acetyl)-1,2,3,4,5,6-hexahydro-2,6-methano-benzo[d]azocin-8-yl ester (0.30 g) and Pd(OAc)$_2$ (7 mg) in tetrahydrofuran (3 mL). The resulting mixture is stirred at room temperature overnight before 1 M NaOH (20 mL) is added. After stirring vigorously for 1 h, the organic phase is separated and the aqueous phase is extracted with ethyl acetate. The combined organic phases are washed with water and brine and dried ($MgSO_4$). The solvent is removed and the residue is taken up in 4 M NaOH (1 mL) and methanol (3 mL) and stirred at room temperature overnight. Then, the solution is neutralized with 1 M hydrochloric acid, filtered, concentrated and the residue is purified by HPLC on reversed phase (MeCN/water).
Yield: 0.07 g (48% of theory)
Mass spectrum (ESI$^+$): m/z=227 [M+H]$^+$ The following compound is obtained analogously to Example XLIII:

(1) (2R,6R,11R)-6,11-Dimethyl-1,2,3,4,5,6-hexahydro-2,6-methano-benzo[d]azocine-9-carbonitrile

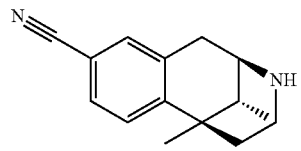 [SMILES: C[C@H]1[C@H]2Cc3cc(C#N)ccc3[C@]1(C)CCN2]

Example XLIV

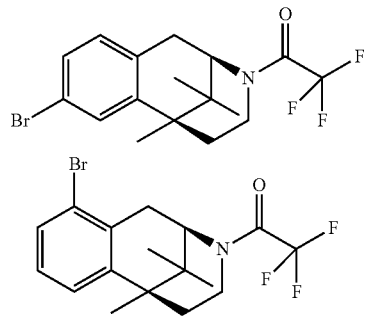

1-[(2R,6S)-8-Bromo-6,11,11-trimethyl-1,2,5,6-tetrahydro-4H-2,6-methano-benzo[d]azocin-3-yl]-2,2,2-trifluoro-ethanone and 1-[(2R,6S)-10-bromo-6,11,11-trimethyl-1,2,5,6-tetrahydro-4H-2,6-methano-benzo[d]azocin-3-yl]-2,2,2-trifluoro-ethanone AlCl$_3$ (147 mg) is added to a solution of 2,2,2-trifluoro-1-[(2R,6S)-6,11,11-trimethyl-1,2,5,6-tetrahydro-4H-2,6-methano-benzo[d]azocin-3-yl]-ethanone (275 mg) in 1,2-dichloroethane (10 mL). The resulting mixture is stirred at ambient temperature for 10 min before bromine (52 µL) is added. The mixture is heated to 50° C. After stirring at 50° C. for 1 h, the mixture is cooled to ambient temperature and diluted with dichloromethane (30 mL) and water (10 mL). The resulting mixture is stirred vigorously for 5 min and then 4 M hydrochloric acid (10 mL) is added. The organic phase is separated and washed with 4 M hydrochloric acid and water and dried (MgSO$_4$). The solvent is removed under reduced pressure to give the two title compounds in a mixture with a further regioisomerically brominated educt.
Yield: 328 mg (95% of theory)
Mass spectrum (ESI$^+$): m/z=390/392 (Br) [M+H]$^+$ Example XLV

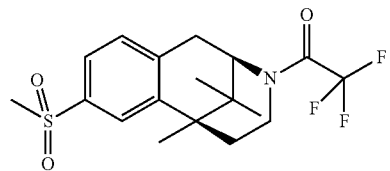

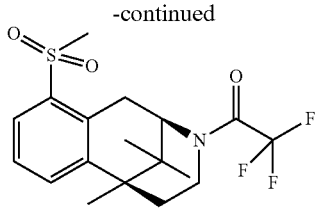

2,2,2-Trifluoro-1-[(2R,6S)-8-methanesulfonyl-6,11,11-trimethyl-1,2,5,6-tetrahydro-4H-2,6-methano-benzo[d]azocin-3-yl]-ethanone and 2,2,2-trifluoro-1-[(2R,6S)-10-methanesulfonyl-6,11,11-trimethyl-1,2,5,6-tetrahydro-4H-2,6-methano-benzo[d]azocin-3-yl]-ethanone MeSO$_2$Na (0.79 g) is added to a mixture of CuI (1.5 g) and 1-[(2R,6S)-8-bromo-6,11,11-trimethyl-1,2,5,6-tetrahydro-4H-2,6-methano-benzo[d]azocin-3-yl]-2,2,2-trifluoro-ethanone/1-[(2R,6S)-10-bromo-6,11,11-trimethyl-1,2,5,6-tetrahydro-4H-2,6-methano-benzo[d]azocin-3-yl]-2,2,2-trifluoro-ethanone (300 mg, crude product from Example XLIV) in dimethylsulfoxide (6 mL). The resulting mixture is heated to 120° C. and stirred at this temperature overnight. After cooling to ambient temperature, the mixture is poured into a solution of concentrated aqueous ammonia (20 mL) and water (80 mL). The resulting mixture is extracted with ethyl acetate and the combined organic extracts are washed with 2 M ammonia solution and brine.

After drying (MgSO$_4$), the solvent is removed under reduced pressure and the residue is purified by HPLC on reversed phase (MeCN/water) to give the two title compounds separated.

2,2,2-Trifluoro-1-[(2R,6S)-8-methanesulfonyl-6,11,11-trimethyl-1,2,5,6-tetrahydro-4H-2,6-methano-benzo[d]azocin-3-yl]-ethanone: Yield: 150 mg (50% of theory)

Mass spectrum (ESI$^+$): m/z=390 [M+H]$^+$ 2,2,2-Trifluoro-1-[(2R,6S)-10-methanesulfonyl-6,11,11-trimethyl-1,2,5,6-tetrahydro-4H-2,6-methano-benzo[d]azocin-3-yl]-ethanone: Yield: 100 mg (33% of theory)

Mass spectrum (ESI$^+$): m/z=390 [M+H]$^+$

Example XLVI

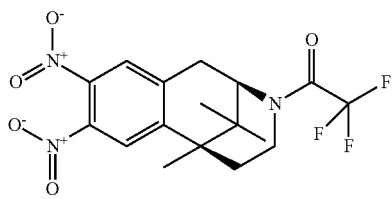 [SMILES: CC1(C)[C@H]2Cc3cc([N+](=O)[O-])c([N+](=O)[O-])cc3[C@]1(C)CCN2C(=O)C(F)(F)F]

2,2,2-Trifluoro-1-[(2R,6S)-6,11,11-trimethyl-8,9-dinitro-1,2,5,6-tetrahydro-4H-2,6-methano-benzo[d]azocin-3-yl]-ethanone Nitric acid (0.16 mL) is added to a solution of trifluoroacetic acid (0.65 mL) in dichloromethane (4 mL) chilled in an ice bath (ca. 0° C.). After stirring for 10 min, 2,2,2-trifluoro-1-[(2R,6S)-6,11,11-trimethyl-1,2,5,6-tetrahydro-4H-2,6-methano-benzo[d]azocin-3-yl]-ethanone (0.50 g) in dichloromethane (5 mL) is added. The resulting solution is stirred in the cooling bath for 2 h and then at ambient temperature overnight. The solution is poured into ice-cold water and the resulting mixture is extracted with dichloromethane. The combined organic extracts are washed with aqueous NaHCO$_3$ solution and dried (MgSO$_4$). The solvent is removed under reduced pressure and the residue is purified by chromatography on silica gel (cyclohexane/ethyl acetate 1:0->9:1).

Yield: 330 mg (51% of theory)

Mass spectrum (ESI$^+$): m/z=402 [M+H]$^+$

Example XLVII

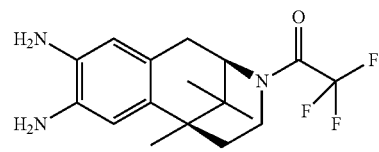 [SMILES: CC1(C)[C@H]2Cc3cc(N)c(N)cc3[C@]1(C)CCN2C(=O)C(F)(F)F]

1-[(2R,6S)-8,9-Diamino-6,1,11-trimethyl-1,2,5,6-tetrahydro-4H-2-methano-benzo[d]azocin-3-yl]-2,2,2-trifluoro-ethanone A mixture of 10% palladium on carbon (300 mg) and (2R,6S)-2,2,2-trifluoro-1-(6,11,11-trimethyl-8,9-dinitro-1,2,5,6-tetrahydro-4H-2,6-methano-benzo[d]azocin-3-yl)-ethanone (330 mg) in methanol (5 mL) is shaken under hydrogen atmosphere at room temperature for 2 h. Then, the catalyst is separated by filtration and the solvent is removed under reduced pressure to give the crude title compound that is used without further purification.

Yield: 260 mg (93% of theory)

Mass spectrum (ESI$^+$): m/z=342 [M+H]$^+$

The following compounds are obtained analogously to Example XLVII:

(1) 1-[(2R,6R,11S)-7-Amino-8-hydroxy-6,11-dimethyl-1,2,5,6-tetrahydro-4H-2,6-methano-benzo[d]azocin-3-yl]-2,2,2-trifluoro-ethanone

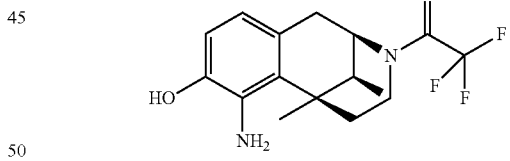

Mass spectrum (ESI$^+$): m/z=329 [M+H]$^+$ (2) 1-[(2R,6S)-8-Amino-9-hydroxy-6,11,11-trimethyl-1,2,5,6-tetrahydro-4H-2,6-methano-benzo[d]azocin-3-yl]-2,2,2-trifluoro-ethanone

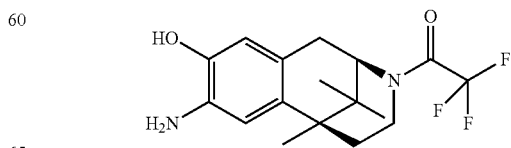

Mass spectrum (ESI$^+$): m/z=343 [M+H]$^+$ (3) 1-[(2R,6R,11S)-9-Amino-8-hydroxy-6,11-dimethyl-1,2,5,6-tetrahydro-4H-2,6-methano-benzo[d]azocin-3-yl]-2,2,2-trifluoro-ethanone

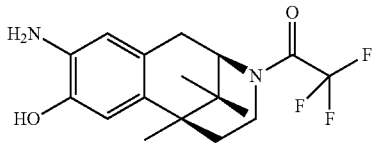

Mass spectrum (ESI⁺): m/z=329 [M+H]⁺

Example XLVIII

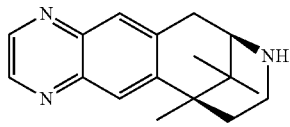 [SMILES: CC1(C)[C@H]2Cc3cc4nccnc4cc3[C@]1(C)CCN2]

(7R,11S)-6,7,8,9,10,11-Hexahydro-11,13,13-trimethyl-7,11-methano-pyrazino[2,3-i][3]benzazocine Glyoxal (40% in water, 95 μL) is added to (2R,6S)-1-(8,9-diamino-6,11,11-trimethyl-1,2,5,6-tetrahydro-4H-2,6-methano-benzo[d]azocin-3-yl)-2,2,2-trifluoro-ethanone (260 mg) dissolved in ethanol (3 mL) and chilled in an ice bath. The cooling bath is removed and the solution is stirred at ambient temperature overnight. Then, the solution is concentrated and the residue is taken up in methanol (1 mL) and treated with 4 M aqueous NaOH solution (0.38 mL). After stirring at ambient temperature overnight, brine is added and the resulting mixture is extracted with ethyl acetate. The combined organic extracts are washed with brine, dried (MgSO₄), and the solvent is removed under reduced pressure to give the crude title compound that is used without further purification.

Yield: 204 mg

Mass spectrum (ESI⁺): m/z=268 [M+H]⁺

The following compounds are obtained analogously to Example XLVIII:

(1) (7R,11S)-6,7,8,9,10,11-Hexahydro-2,3,11,13,13-pentamethyl-7,11-methano-pyrazino[2,3-i][3]benzazocine

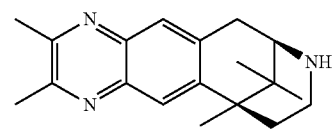 [SMILES: Cc1nc2cc3c(cc2nc1C)[C@]1(C)CCN[C@H](C3)C1(C)C]

Mass spectrum (ESI⁺): m/z=296 [M+H]⁺

The compound is obtained by using diacetyl according to the procedure described above.

(2) (7R,11S)-6,7,8,9,10,11-Hexahydro-3,11,13,13-tetramethyl-7,11-methano-pyrazino[2,3-i][3]benzazocine and (7R,11S)-6,7,8,9,10,11-hexahydro-2,11,13,13-tetramethyl-7,11-methano-pyrazino[2,3-i][3]benzazocine

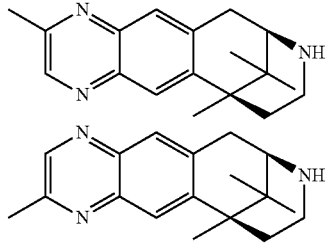

Mass spectrum (ESI⁺): m/z=296 [M+H]⁺

The compounds are obtained as a mixture of each other by using methylglyoxal.

Example IL

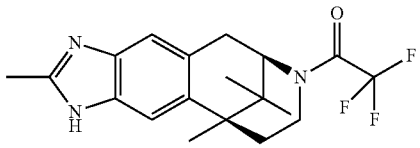 [SMILES: Cc1nc2cc3c(cc2[nH]1)[C@]1(C)CCN(C(=O)C(F)(F)F)[C@H](C3)C1(C)C]

2,2,2-Trifluoro-1-[(6R,10S)-5,6,7,8,9,10-hexahydro-2,10,12,12-tetramethyl-6,10-methano-1H-imidazo[5,4-i][3]benzazocin-7-yl]-ethanone (2R,6S)-1-(8,9-Diamino-6,11,11-trimethyl-1,2,5,6-tetrahydro-4H-2,6-methano-benzo[d]-azocin-3-yl)-2,2,2-trifluoro-ethanone (600 mg) dissolved in glacial acetic acid is stirred at 130° C. for 3 h. After cooling to ambient temperature, the solution is concentrated under reduced pressure and the residue is taken up in ethyl acetate. The organic solution is washed with aqueous K₂CO₃ solution and brine and dried (MgSO₄). The solvent is removed under reduced pressure to give the crude title compound as a foam-like solid.

Yield: 642 mg

Mass spectrum (ESI⁺): m/z=366 [M+H]⁺

The following compound is obtained analogously to Example IL:

(1) 2,2,2-Trifluoro-1-[(6R,10S)-5,6,7,8,9,10-hexahydro-10,12,12-trimethyl-6,10-methano-1H-imidazo[5,4-i][3]benzazocin-7-yl]-ethanone

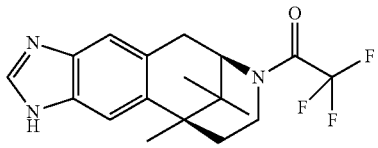 [SMILES: CC1(C)[C@H]2Cc3cc4nc[nH]c4cc3[C@]1(C)CCN2C(=O)C(F)(F)F]

Mass spectrum (ESI⁺): m/z=352 [M+H]⁺

The reaction is carried out with formic acid instead of acetic acid.

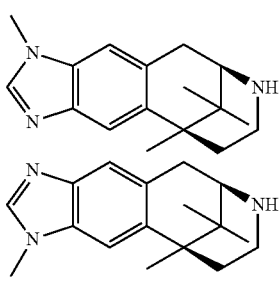

Example L (6R,10S)-5,6,7,8,9,10-Hexahydro-3,10,12,12-tetramethyl-6,10-methano-imidazo[4,5-i][3]benzazocine and (6R,10S)-5,6,7,8,9,10-hexahydro-1,10,12,12-tetramethyl-6,10-methano-imidazo[5,4-i][3]benzazocine Methyl iodide (69 μL) is added to a mixture of 2,2,2-trifluoro-1-[(6R,10S)-5,6,7,8,9,10-hexahydro-10,12,12-trimethyl-6,10-methano-1H-imidazo[5,4-i][3]benzazocin-7-yl]-ethanone (300 mg) and K₂CO₃ (118 mg) in dimethylformamide (2 mL). The resulting mixture is stirred at room temperature overnight. Then, water is added and the mixture is extracted with ethyl acetate. The combined extracts are washed with brine and dried (MgSO₄). The solvent is removed and the residue is taken up in methanol (3 mL) and treated with 4 M aqueous NaOH solution (0.5 mL). The solution is stirred at room temperature overnight and then diluted with ethyl acetate. The resulting solution is washed with water and brine and dried (MgSO₄). The solvent is removed under reduced pressure to give the crude title compounds as a mixture.

Yield: 90 mg (39% of theory)

The following compounds are obtained analogously to Example L:

(1) (6R,10S)-5,6,7,8,9,10-hexahydro-1,2,10,12,12-pentamethyl-6,10-methano-imidazo[5,4-i][3]benzazocine

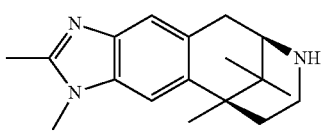 [SMILES: Cc1nc2cc3c(cc2n1C)[C@]1(C)CCN[C@H](C3)C1(C)C]

Mass spectrum (ESI⁺): m/z=284 [M+H]⁺

(2) (6R,10S)-5,6,7,8,9,10-hexahydro-2,3,10,12,12-pentamethyl-6,10-methano-imidazo[4,5-i][3]benzazocine

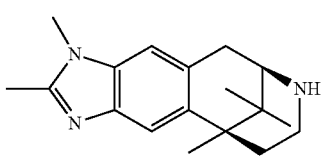 [SMILES: Cc1nc2cc3c(cc2n1C)C[C@H]1NCC[C@]3(C)C1(C)C]

Mass spectrum (ESI⁺): m/z=284 [M+H]⁺

The two isomeric compounds (1) and (2) were obtained from the same starting compound and separated by HPLC on reversed phase.

(3) Mixture of (6R,10S)-5,6,7,8,9,10-hexahydro-1,10,12,12-tetramethyl-6,10-methano-triazolo[5,4-i][3]benzazocine and (6R,10S)-5,6,7,8,9,10-hexahydro-3,10,12,12-tetramethyl-6,10-methano-triazolo[4,5-i][3]benzazocine

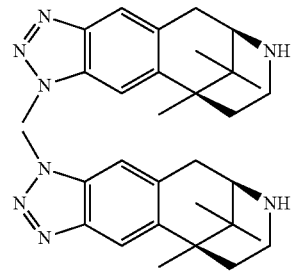

The compounds are obtained from compound Example LIX after carrying out the reactions described above.

Example LI

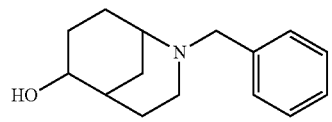 [SMILES: OC1CCC2CC1CCN2Cc1ccccc1]

2-Benzyl-2-aza-bicyclo[3.3.1]nonan-6-ol

Diisobutylaluminumhydride (1.5 mol/L in toluene, 21 mL) is added to a solution of acetic acid 2-benzyl-3-oxo-2-aza-bicyclo[3.3.1]non-6-yl ester (1.50 g, for synthesis see *J. Chem. Soc., Perkin Trans. 1* 1999, 1157-1162) in toluene (30 mL) cooled to −70° C. The cooling bath is removed and the solution is stirred at ambient temperature overnight. Then, another portion of diisobutylaluminumhydride (1.5 mol/L in toluene, 20 mL) is added and the solution is stirred for additional 4 h at room temperature. Then, the solution is poured into ice-cold water and the resulting mixture is extracted with ethyl acetate. The aqueous phase is acidified using 4 M hydrochloric acid and extracted one more time with ethyl acetate. The combined organic extracts are dried (Na₂SO₄) and the solvent is removed. The residue is purified by chromatography on silica gel (dichloromethane/methanol 1:0->2:1).

Yield: 440 mg (36% of theory)

Mass spectrum (ESI⁺): m/z=232 [M+H]⁺

Example LII

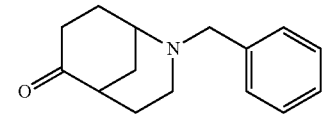 [SMILES: O=C1CCC2CC1CCN2Cc1ccccc1]

2-Benzyl-2-aza-bicyclo[3.3.1]nonan-6-one

Dess-Martin periodinane (1.30 g) is added to a solution of 2-benzyl-2-aza-bicyclo[3.3.1]-nonan-6-ol (0.60 g) in dichloromethane (15 mL) chilled in an ice bath. The cooling bath is removed and the solution is stirred at ambient temperature for 1 h. Then, the solution is diluted with dichloromethane and washed with a mixture of aqueous $Na_2S_2O_3$ solution and aqueous $NaHCO_3$ solution. The solution is dried ($Na_2SO_4$) and the solvent is removed. The residue is purified by chromatography on silica gel (dichloromethane/methanol 1:0->2:1).

Yield: 250 mg (42% of theory)
Mass spectrum (ESI$^+$): m/z=230 [M+H]$^+$

Example LIII

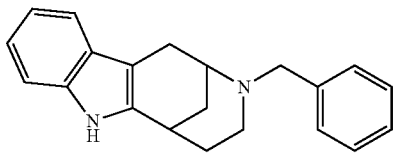 [SMILES: c1ccc(CN2CCC3CC2Cc2c3[nH]c3ccccc23)cc1]

3-Benzyl-2,3,4,5,6,7-hexahydro-2,6-methano-1H-azocino[5,4-b]indole

A solution of 2-benzyl-2-aza-bicyclo[3.3.1]nonan-6-one in acetic acid (0.24 g) is added to a solution of PhNHNH$_2$*HCl (173 mg) in acetic acid (4 mL) heated at reflux temperature. After stirring at this temperature for 2 h, the solution is cooled to room temperature and aqueous $K_2CO_3$ solution is added. The resulting mixture is extracted with ethyl acetate, the combined organic extracts are dried ($Na_2SO_4$), and the solvent is removed. The residue is purified by HPLC on reversed phase (MeCN/water).

Yield: 160 mg (49% of theory)

Example LIV

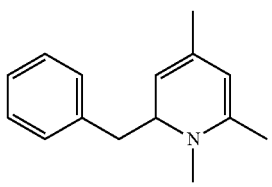 [SMILES: CC1=CC(Cc2ccccc2)N(C)C(C)=C1]

2-Benzyl-1,4,6-trimethyl-1,2-dihydro-pyridine

PhCH$_2$MgCl (1 M in Et$_2$O, 180 mL) is added dropwise to a solution of 1,2,4-trimethyl-pyridinium iodide (24.3 g) in Et$_2$O(90 mL) chilled in an ice bath. After stirring in the ice bath for 2 h, the solution is poured into a mixture of 72% aqueous HClO$_4$ (40 mL) and crushed ice (ca. 900 mL). The resulting mixture is stirred for 1 h and the precipitate formed is separated by filtration. The precipitate is washed with methanol and dried to afford the HClO$_4$ salt of the title compound.

Yield: 22.6 g (74% of theory)
Mass spectrum (ESI$^+$): m/z=214 [M+H]$^+$

Example LV

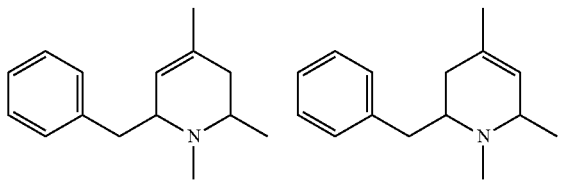

6-Benzyl-1,2,4-trimethyl-1,2,3,6-tetrahydro-pyridine and 2-benzyl-1,4,6-trimethyl-1,2,3,6-tetrahydro-pyridine NaBH$_4$ (3.8 g) is added portionwise to a solution of 2-benzyl-1,4,6-trimethyl-1,2-dihydro-pyridine (22.6 g) in MeOH (65 mL) and NaOH (1 M in water, 200 mL). The resulting mixture is stirred at room temperature for 20 min and then at 60° C. for 30 min. After cooling to ambient temperature, the mixture is diluted with water (150 mL) and extracted with Et$_2$O(3×150 mL). The combined organic extracts are dried (Na$_2$SO$_4$) and the solvent is removed to give a mixture of the two title compounds that is used without further purification for the next reaction step.

Yield: 11.7 g (76% of theory)
Mass spectrum (ESI$^+$): m/z=216 [M+H]$^+$

Example LVI

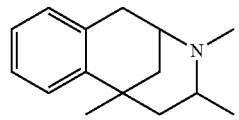 [SMILES: CC1CC2(C)CC(Cc3ccccc32)N1C]

3,4,6-Trimethyl-1,2,3,4,5,6-hexahydro-2,6-methano-benzo[d]azocine

A mixture of 6-benzyl-1,2,4-trimethyl-1,2,3,6-tetrahydropyridine and 2-benzyl-1,4,6-trimethyl-1,2,3,6-tetrahydropyridine (from Example LV, 11.7 g) is combined with 48% HBr in water (30 mL) and 33% HBr in acetic acid (20 mL). The mixture is heated to reflux temperature and stirred at this temperature for 4 d. After cooling to ambient temperature, aqueous ammonia (32%, 45 mL) is carefully added and the resulting mixture is extracted with Et$_2$O (3×50 mL). The combined organic extracts are extracted with 2 M hydrochloric acid (3×50 mL), the combined aqueous extracts are basified using 32% aqueous ammonia (20 mL), and the basic aqueous phase is extracted with Et$_2$O (3×50 mL). The combined organic extracts are dried (MgSO$_4$), the solvent is removed, and the residue is purified by chromatography on silica gel (EtOAc/MeOH/NH$_3$95:5.0.5->75:25:2.5). The title compound obtained thereafter is dissolved in iPrOH and treated with HCl in iPrOH to precipitate the HCl salt of the title compound from the iPrOH solution.

Yield: 1.7 g (15% of theory)
Mass spectrum (ESI$^+$): m/z=216 [M+H]$^+$

Example LVII

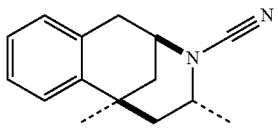

4,6-Dimethyl-1,2,5,6-tetrahydro-4H-2,6-methano-
benzo[d]azocine-3-carbonitrile (one diastereomer,
relative configurations of the substituents given in
the structure drawn above are confirmed by NMR
experiments)

3,4,6-Trimethyl-1,2,3,4,5,6-hexahydro-2,6-methano-benzo[d]azocine (from Example LVI, 1.7 g) dissolved in $CH_2Cl_2$ (40 mL) is added to a solution of BrCN (1.17 g) in $CH_2Cl_2$ (10 mL) chilled in an ice bath. The cooling bath is removed and the mixture is stirred at ambient temperature for 1 h and at 45° C. for 2 h. After cooling to ambient temperature, the solution is washed with water, 2 M hydrochloric acid, and 10% aqueous $K_2CO_3$ solution. The solution is dried ($MgSO_4$), the solvent is removed, and the residue is triturated with little acetone to give the title compound.

Yield: 0.98 g (54% of theory)
Mass spectrum (ESI⁺): m/z=227 [M+H]⁺

The following compound is obtained in analogy to Example LVII:

(1) 5,6-Dimethyl-1,2,5,6-tetrahydro-4H-2,6-
methano-benzo[d]azocine-3-carbonitrile (racemic
mixture of diastereomer shown)

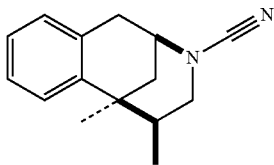

Mass spectrum (ESI⁺): m/z=227 [M+H]⁺

The starting compound, 3,5,6-trimethyl-1,2,3,4,5,6-hexahydro-2,6-methano-benzo[d]azocine, may be obtained as described in *J. Med. Chem.* 1971, 14, 565-68.

Example LVIII

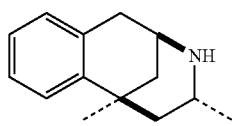

3,4,6-Trimethyl-1,2,3,4,5,6-hexahydro-2,6-methano-
benzo[d]azocine (racemic mixture of diastereomer
shown)

A mixture of 4,6-dimethyl-1,2,5,6-tetrahydro-4H-2,6-methano-benzo[d]azocine-3-carbonitrile (one diastereomer, 925 mg), water (30 mL), and 4 M hydrochloric acid (30 mL) is stirred at reflux temperature for 9 h. After cooling to ambient temperature, the solution is basified using concentrated aqueous ammonia solution and the resulting mixture is extracted with EtOAc (2×50 mL). The combined organic extracts are washed with brine and dried ($MgSO_4$). Removal of the solvent under reduced pressure affords the title compound.

Yield: 439 mg (53% of theory)
Mass spectrum (ESI⁺): m/z=202 [M+H]⁺

The following compound is obtained in analogy to Example LVIII:

(1) 5,6-Dimethyl-1,2,3,4,5,6-hexahydro-2,6-
methano-benzo[d]azocine (racemic mixture of diastereomer shown)

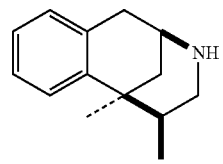

Mass spectrum (ESI⁺): m/z=202 [M+H]⁺

Example LIX

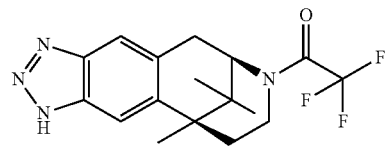 [SMILES: CC1(C)[C@H]2Cc3cc4nn[nH]c4cc3[C@]1(C)CCN2C(=O)C(F)(F)F]

2,2,2-Trifluoro-1-[(6R,10S)-5,6,7,8,9,10-hexahydro-
10,12,12-trimethyl-6,10-methano-1H-triazolo[5,4-i]
[3]benzazocin-7-yl]-ethanone A solution of $NaNO_2$ (330 mg) in water (2 mL) is slowly added to a flask charged with a stir bar, 1-[(2R,6S)-8,9-di-amino-6,11,11-trimethyl-1,2,5,6-tetrahydro-4H-2,6-methano-benzo[d]azocin-3-yl]-2,2,2-trifluoro-ethanone (650 mg), and acetic acid (15 mL) and chilled in an ice bath. The resulting mixture is stirred in the cooling bath for 2 h and at ambient temperature for 1 h. Then, the solution is poured into ice-cold water and the precipitate formed is separated by filtration and dried to afford the title compound that is used without further purification.

Yield: 610 mg (91% of theory)
Mass spectrum (ESI⁺): m/z=353 [M+H]⁺

Example LX

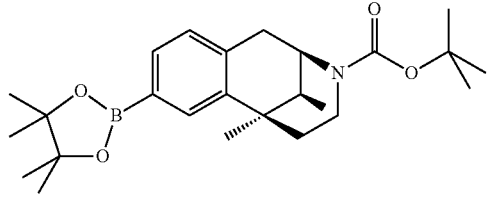 [SMILES: C[C@@H]1[C@H]2Cc3ccc(B4OC(C)(C)C(C)(C)O4)cc3[C@]1(C)CCN2C(=O)OC(C)(C)C]

(2R,6R,11S)-6,11-Dimethyl-8-(4,4,5,5-tetramethyl-[1,3,2]dioxaborolan-2-yl)-1,2,5,6-tetrahydro-4H-2,6-methano-benzo[d]azocine-3-carboxylic acid tert-butyl ester A flask charged with a stir bar, (2R,6R,11S)-6,11-dimethyl-8-trifluoromethanesulfonyloxy-1,2,5,6-tetrahydro-4H-2,6-methano-benzo[d]azocine-3-carboxylic acid tert-butyl ester (9.90 g), bis(pinacolato)diboron (6.15 g), 1,1'-bis(diphenylphosphino)ferrocene (0.73 g), and dioxane (50 mL) is flushed with argon for 15 min. Then, 1,1'-bis(diphenylphosphino)-ferrocene-palladium dichloride dichloromethane complex (1.08 g) is added and the mixture is heated to 80° C. After stirring at 80° C. for 2 d and cooling to ambient temperature, the mixture is diluted with tBuOMe (150 mL) and washed with water (3×100 mL) and brine (1×100 mL). The organic phase is dried (MgSO$_4$) and the solvent is removed under reduced pressure. The residue is purified by chromatography on silica gel (cyclohexane/ethyl acetate 9:1->2:3) to give the title compound as a colorless oil.

Yield: 6.90 g (73% of theory)

Mass spectrum (ESI$^+$: m/z=428 [M+H]+

Example LXI

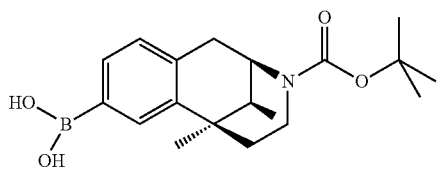 [SMILES: C[C@@H]1[C@H]2Cc3ccc(B(O)O)cc3[C@]1(C)CCN2C(=O)OC(C)(C)C]

(2R,6R,11S)-6,11-Dimethyl-8-borono-1,2,5,6-tetrahydro-4H-2,6-methano-benzo[d]azocine-3-carboxylic acid tert-butyl ester A solution of (2R,6R,11S)-6,11-dimethyl-8-(4,4,5,5-tetramethyl-[1,3,2]dioxaborolan-2-yl)-1,2,5,6-tetrahydro-4H-2,6-methano-benzo[d]azocine-3-carboxylic acid tert-butyl ester (2.50 g) and NaIO$_4$ (5.00 g) in 1 M aqueous NH$_4$OAc solution (34 mL) and acetone (60 mL) is stirred at room temperature overnight. Then, the solution is concentrated, water is added to the residue, and the resulting mixture is extracted with ethyl acetate. The combined organic extracts are washed with water and brine and dried (Na$_2$SO$_4$). The solvent is removed under reduced pressure to give the title compound as a colorless, foam-like solid.

Yield: 1.83 g (91% of theory)

Mass spectrum (ESI$^-$): m/z=390 [M+HCOO]$^-$

Example LXII

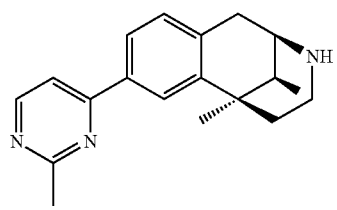 [SMILES: Cc1nccc(-c2ccc3c(c2)[C@]2(C)CCN[C@H](C3)[C@H]2C)n1]

(2R,6R,11S)-6,11-Dimethyl-8-(2-methyl-pyrimidin-4-yl)-1,2,3,4,5,6-hexahydro-2,6-methano-benzo[d]azocine Pd(OAc)$_2$ (3.3 mg) is added to a mixture of (2R,6R,11S)-6,11-dimethyl-8-borono-1,2,5,6-tetrahydro-4H-2,6-methano-benzo[d]azocine-3-carboxylic acid tert-butyl ester (0.30 g), 4-chloro-2-methyl-pyrimidine (93 mg), K$_3$PO$_4$ (0.31 g), and 2-dicyclohexylphosphino-2',6'-dimethoxy-1,1'-biphenyl (11.5 mg) in n-butanol (2 mL) under argon atmosphere. The resulting mixture is heated to 100° C. and stirred at this temperature overnight. After cooling to room temperature, ethyl acetate is added, the resulting mixture is filtered, and the filtrate is concentrated under reduced pressure. The residue is taken up in CH$_2$Cl$_2$ (3 mL) and treated with F$_3$CCO$_2$H (0.5 mL) for 1 h. Then, the solution is concentrated and the residue is purified by HPLC on reversed phase (MeCN/H$_2$O/NH$_3$) to afford the title compound.

Yield: 0.10 g (48% of theory)

Mass spectrum (ESI$^+$): m/z=294 [M+H]$^+$

The following compound is obtained in analogy to Example LXII:

(1) (2R,6R,11S)-6,11-Dimethyl-8-pyrimidin-4-yl-1,2,3,4,5,6-hexahydro-2,6-methano-benzo[d]azocine

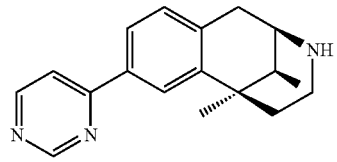 [SMILES: C[C@@H]1[C@H]2Cc3ccc(-c4ccncn4)cc3[C@]1(C)CCN2]

Mass spectrum (ESI$^+$): m/z=280 [M+H]$^+$

Example LXIII

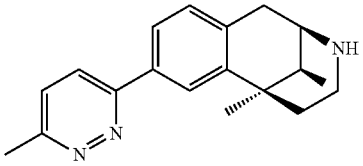 [SMILES: Cc1ccc(-c2ccc3c(c2)[C@]2(C)CCN[C@H](C3)[C@H]2C)nn1]

(2R,6R,11S)-6,11-Dimethyl-8-(6-methyl-pyridazin-3-yl)-1,2,3,4,5,6-hexahydro-2,6-methano-benzo[d]azocine 2 M Aqueous Na$_2$CO$_3$ solution (1.13 mL) is added to a mixture of (2R,6R,11S)-6,11-dimethyl-8-(4,4,5,5-tetramethyl-[1,3,2]dioxaborolan-2-yl)-1,2,5,6-tetrahydro-4H-2,6-methano-benzo[d]azocine-3-carboxylic acid tert-butyl ester (483 mg) and 3-chloro-6-methyl-pyridazine (218 mg) in dimethylformamide (2 mL). The resulting mixture is flushed with argon and then 1,1'-bis(diphenylphosphino)ferrocene-palladium dichloride dichloromethane complex (73 mg) is added. The mixture is heated to 100° C. and stirred at this temperature overnight. After cooling to room temperature, water is added and the resulting mixture is extracted with ethyl acetate. The combined organic extracts are washed with water and brine and dried (MgSO$_4$). The solvent is removed under reduced pressure and the residue is taken up in CH$_2$Cl$_2$ (3 mL) and treated with F$_3$CCOO$_2$H (0.5 mL) for 1 h. Then, the solution is concentrated and the residue is purified by HPLC on reversed phase (MeCN/H$_2$O/NH$_3$) to afford the title compound.

Yield: 225 mg (68% of theory)

Mass spectrum (ESI$^+$): m/z=294 [M+H]$^+$

The following compounds are obtained in analogy to Example LXIII:

(1) (2R,6R,11S)-6,11-Dimethyl-8-(1-methyl-2-oxo-1,2-dihydro-pyridin-4-yl)-1,2,3,4,5,6-hexahydro-2,6-methano-benzo[d]azocine

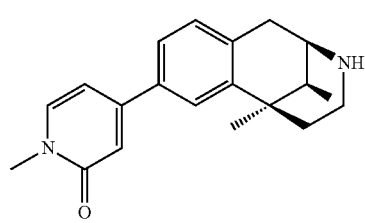 [SMILES: C[C@@H]1[C@H]2Cc3ccc(-c4ccn(C)c(=O)c4)cc3[C@]1(C)CCN2]

Mass spectrum (ESI⁺): m/z=309 [M+H]⁺
Trifluoro-methanesulfonic acid 1-methyl-2-oxo-1,2-dihydro-pyridin-4-yl ester or 4-bromo-1-methyl-1H-pyridin-2-one are used as the coupling partner (2) 5-[(2R,6R,11S)-6,11-Dimethyl-1,2,3,4,5,6-hexahydro-2,6-methano-benzo[d]azocin-8-yl]-1-methyl-1H-pyridin-2-one

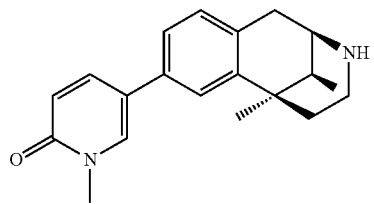 [SMILES: C[C@@H]1[C@H]2Cc3ccc(-c4ccc(=O)n(C)c4)cc3[C@]1(C)CCN2]

(3) 6-[(2R,6R,11S)-6,11-Dimethyl-1,2,3,4,5,6-hexahydro-2,6-methano-benzo[d]azocin-8-yl]-2-methyl-2H-pyridazin-3-one

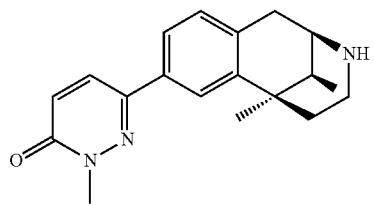 [SMILES: C[C@@H]1[C@H]2Cc3ccc(-c4ccc(=O)n(C)n4)cc3[C@]1(C)CCN2]

6-Chloro-2-methyl-2H-pyridazin-3-one is used as the coupling partner.

(4) (2R,6R,11S)-6,11-Dimethyl-8-(2-methyl-pyrimidin-5-yl)-1,2,3,4,5,6-hexahydro-2,6-methano-benzo[d]azocine

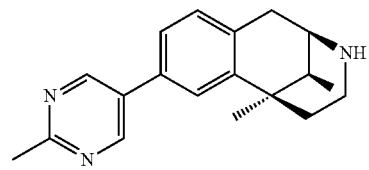 [SMILES: Cc1ncc(-c2ccc3c(c2)[C@]2(C)CCN[C@H](C3)[C@H]2C)cn1]

Mass spectrum (ESI⁺): m/z=294 [M+H]⁺
5-Bromo-2-methyl-pyrimidine is used as the coupling partner.

Example LXIV

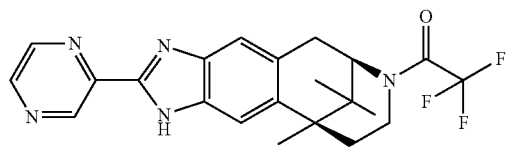 [SMILES: CC1(C)[C@H]2Cc3cc4nc(-c5cnccn5)[nH]c4cc3[C@]1(C)CCN2C(=O)C(F)(F)F]

2,2,2-Trifluoro-1-[(6R,10S)-5,6,7,8,9,10-hexahydro-10,12,12-trimethyl-2-pyrazin-2-yl-6,10-methano-1H-imidazo[5,4-i][3]benzazocin-7-yl]-ethanone A solution of pyrazine-2-carboxylic acid (152 mg), 2-(1H-benzotriazol-1-yl)-1,1,3,3-tetramethyluronium tetrafluoroborate (397 mg), and triethylamine (0.5 mL) in dimethylformamide (5 mL) is stirred at room temperature for 30 min, before 1-[(2R,6S)-8,9-diamino-6,11,11-trimethyl-1,2,5,6-tetrahydro-4H-2,6-methano-benzo[d]azocin-3-yl]-2,2,2-trifluoro-ethanone (300 mg) is added. The solution is stirred at room temperature overnight. Then, the solution is diluted with EtOAc and washed with water and 2 M aqueous K₂CO₃ solution and dried (MgSO₄). The solvent is removed under reduced pressure and the residue is taken up in acetic acid (5 mL). The resulting solution is heated at 80° C. overnight. Then, the solvent is removed under reduced pressure and the residue is evaporated twice with toluene to give the crude title compound that is used without further purification.

Yield: 380 mg (quantitative)
Mass spectrum (ESI⁺): m/z=430 [M+H]⁺
The following compounds are obtained in analogy to Example LXIV:

(1) 1-[(6R,10S)-2-(1-Acetyl-piperidin-4-yl)-5,6,7,8,9,10-hexahydro-10,12,12-trimethyl-6,10-methano-1H-imidazo[5,4-i][3]benzazocin-7-yl]-2,2,2-trifluoro-ethanone

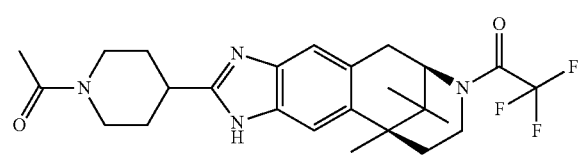 [SMILES: CC(=O)N1CCC(c2nc3cc4c(cc3[nH]2)[C@]2(C)CCN(C(=O)C(F)(F)F)[C@H](C4)C2(C)C)CC1]

Mass spectrum (ESI⁺): m/z=477 [M+H]⁺

(2) 1-[(6R,10S)-2-Cyclopropyl-5,6,7,8,9,10-hexahydro-10,12,12-trimethyl-6,10-methano-1H-imidazo[5,4-i][3]benzazocin-7-yl]-2,2,2-trifluoro-ethanone

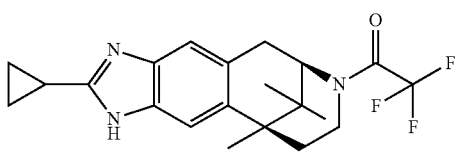 [SMILES: CC1(C)[C@H]2Cc3cc4nc(C5CC5)[nH]c4cc3[C@]1(C)CCN2C(=O)C(F)(F)F]

(3) 2,2,2-Trifluoro-1-[(6R,10S)-5,6,7,8,9,10-hexahydro-10,12,12-trimethyl-2-(1-methyl-6-oxo-1,6-dihydro-pyridin-3-yl-6,10-methano-1H-imidazo[5,4-i][3]benzazocin-7-yl]-ethanone

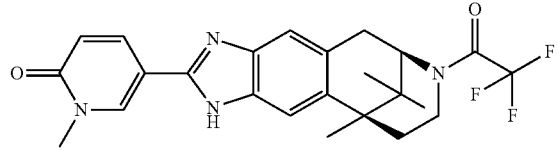 [SMILES: Cn1cc(-c2nc3cc4c(cc3[nH]2)[C@]2(C)CCN(C(=O)C(F)(F)F)[C@H](C4)C2(C)C)ccc1=O]

(4) 1-[(6R,10S)-2-tert-Butyl-5,6,7,8,9,10-hexahydro-10,12,12-trimethyl-6,100-methano-1H-imidazo[5,4-i][3]benzazocin-7-yl]-2,2,2-trifluoro-ethanone

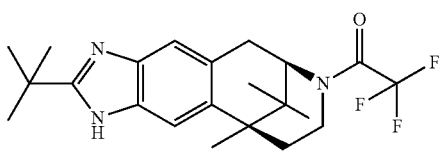 [SMILES: CC(C)(C)c1nc2cc3c(cc2[nH]1)[C@]1(C)CCN(C(=O)C(F)(F)F)[C@H](C3)C1(C)C]

(5) 2,2,2-Trifluoro-1-[(6R,10S)-5,6,7,8,9,10-hexahydro-10,12,12-trimethyl-2-pyridin-3-yl-6,10-methano-1H-imidazo[5,4-i][3]benzazocin-7-yl]-ethanone

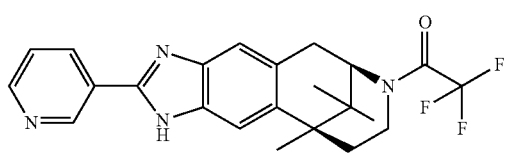 [SMILES: CC1(C)[C@H]2Cc3cc4nc(-c5cccnc5)[nH]c4cc3[C@]1(C)CCN2C(=O)C(F)(F)F]

(6) 2,2,2-Trifluoro-1-{(6R,10S)-5,6,7,8,9,10-hexahydro-10,12,12-trimethyl-2-[(S)-tetrahydrofuran-2-yl]-6,10-methano-1H-imidazo[5,4-i][3]benzazocin-7-yl}-ethanone

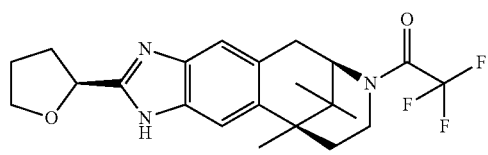 [SMILES: CC1(C)[C@H]2Cc3cc4nc([C@@H]5CCCO5)[nH]c4cc3[C@]1(C)CCN2C(=O)C(F)(F)F]

(7) 2,2,2-Trifluoro-1-[(6R,10S)-5,6,7,8,9,10-hexahydro-10,12,12-trimethyl-2-pyridazin-4-yl-6,10-methano-1H-imidazo[5,4-i][3]-benzazocin-7-yl]-ethanone

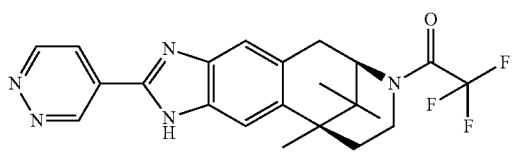 [SMILES: CC1(C)[C@H]2Cc3cc4nc(-c5ccnnc5)[nH]c4cc3[C@]1(C)CCN2C(=O)C(F)(F)F]

(8) 2,2,2-Trifluoro-1-[(6R,10S)-5,6,7,8,9,10-hexahydro-10,12,12-trimethyl-2-(5-methyl-pyrazin-2-yl)-6,10-methano-1H-imidazo[5,4-i][3]benzazocin-7-yl]-ethanone

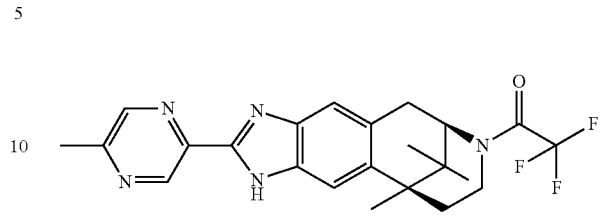

(9) 2,2,2-Trifluoro-1-{(6R,10S)-5,6,7,8,9,10-hexahydro-10,12,12-trimethyl-2-[(R)-tetrahydrofuran-2-yl]-6,10-methano-1H-imidazo[5,4-i][3]benzazocin-7-yl}-ethanone

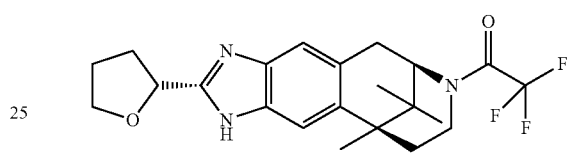

Mass spectrum (ESI⁺): m/z=422 [M+H]⁺

Example LXV

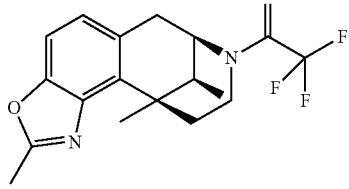

2,2,2-Trifluoro-1-[(7R,11R,12S)-6,7,8,9,10,11-hexahydro-2,11,12-trimethyl-7,11-methano-1H-oxazolo[4,5-h][3]benzazocin-8-yl]-ethanone 1-[(2R,6R,11S)-7-Amino-8-hydroxy-6,11-dimethyl-1,2,5,6-tetrahydro-4H-2,6-methano-benzo[d]azocin-3-yl]-2,2,2-trifluoro-ethanone (200 mg) taken up in trimethyl orthoacetate (1 mL) is heated at 100° C. for 3 h. After cooling to ambient temperature, the mixture is concentrated and the residue is triturated with little methanol and dried to give the title compound.

Yield: 100 mg (47% of theory)
Mass spectrum (ESI⁺): m/z=353 [M+H]⁺
The following compounds are obtained in analogy to Example LXV:

(1) 2,2,2-Trifluoro-1-[(6R,10S)-5,6,7,8,9,10-hexahydro-2,10,12,12-tetramethyl-6,10-methano-oxazolo[4,5-i][3]benzazocin-7-yl]-ethanone

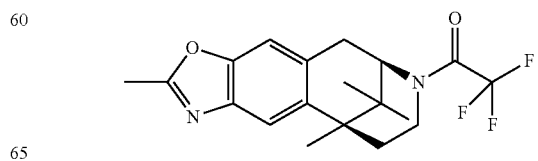

Mass spectrum (ESI⁺): m/z=367 [M+H]⁺

(2) 2,2,2-Trifluoro-1-[(6R,10R,12S)-5,6,7,8,9,10-hexahydro-2,10,12-trimethyl-6,10-methano-oxazolo[5,4-i][3]benzazocin-7-yl]-ethanone

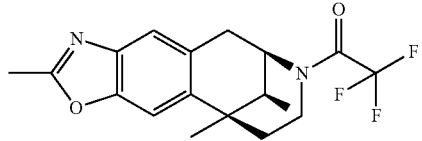 [SMILES: Cc1nc2cc3c(cc2o1)[C@]1(C)CCN(C(=O)C(F)(F)F)[C@H](C3)[C@H]1C]

Mass spectrum (ESI+): m/z=353 [M+H]+

Example LXVI

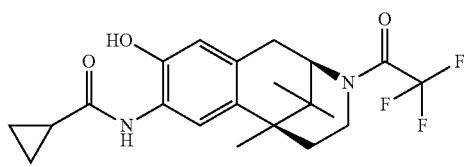 [SMILES: CC1(C)[C@H]2Cc3cc(O)c(NC(=O)C4CC4)cc3[C@]1(C)CCN2C(=O)C(F)(F)F]

Cyclopropanecarboxylic acid [(2R,6S)-9-hydroxy-6,11,11-trimethyl-3-(2,2,2-trifluoro-acetyl)-1,2,3,4,5,6-hexahydro-2,6-methano-benzo[d]azocin-8-yl]-amide Cyclopropylcarbonyl chloride (0.13 mL) is added to a solution of 1-[(2R,6S)-8-amino-9-hydroxy-6,11,11-trimethyl-1,2,5,6-tetrahydro-4H-2,6-methano-benzo[d]azocin-3-yl]-2,2,2-trifluoro-ethanone (0.50 g) and triethylamine (0.25 mL) in dichloromethane (3 mL). After stirring the solution at room temperature overnight, concentrated aqueous ammonia solution (1 mL) and methanol (2 mL) are added and the resulting mixture is stirred for additional 2 h. Then, the solution is concentrated and water is added to the residue. The resulting mixture is extracted with ethyl acetate and the combined organic extracts are washed with brine and dried (MgSO4). The solvent is removed under reduced pressure to give the crude title compound that is used without further purification.

Yield: 0.62 g (quantitative)

The following compounds are obtained in analogy to Example LXVI:

(1) Cyclopropanecarboxylic acid [(2R,6R,11S)-9-hydroxy-6,11-dimethyl-3-(2,2,2-trifluoro-acetyl)-1,2,3,4,5,6-hexahydro-2,6-methano-benzo[d]azocin-8-yl]-amide

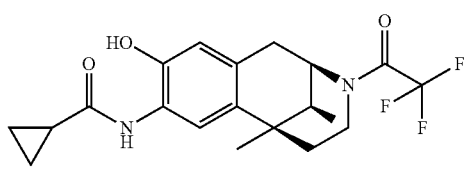 [SMILES: C[C@@H]1[C@H]2Cc3cc(O)c(NC(=O)C4CC4)cc3[C@]1(C)CCN2C(=O)C(F)(F)F]

(2) Cyclopropanecarboxylic acid [(2R,6R,11S)-8-hydroxy-6,11-dimethyl-3-(2,2,2-trifluoro-acetyl)-1,2,3,4,5,6-hexahydro-2,6-methano-benzo[d]azocin-9-yl]-amide

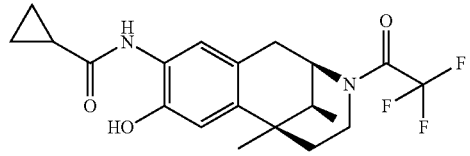 [SMILES: C[C@@H]1[C@H]2Cc3cc(NC(=O)C4CC4)c(O)cc3[C@]1(C)CCN2C(=O)C(F)(F)F]

Mass spectrum (ESI+): m/z=397 [M+H]+

(3) N-[(2R,6S)-9-Hydroxy-6,11,11-trimethyl-3-(2,2,2-trifluoro-acetyl)-1,2,3,4,5,6-hexahydro-2,6-methano-benzo[d]azocin-8-yl]-2,2-dimethyl-propionamide

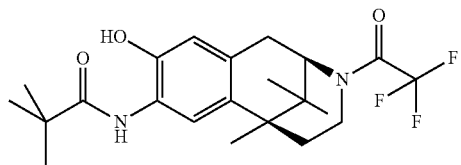 [SMILES: CC(C)(C)C(=O)Nc1cc2c(cc1O)C[C@H]1N(C(=O)C(F)(F)F)CC[C@]2(C)C1(C)C]

(4) 5-Methyl-pyrazine-2-carboxylic acid [(2R,6S)-9-hydroxy-6,11,11-trimethyl-3-(2,2,2-trifluoro-acetyl)-1,2,3,4,5,6-hexahydro-2,6-methano-benzo[d]azocin-8-yl]-amide

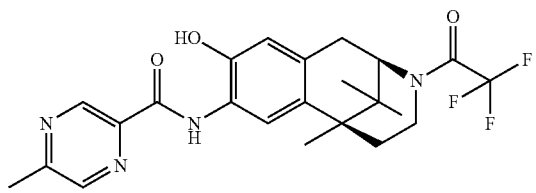 [SMILES: Cc1cnc(C(=O)Nc2cc3c(cc2O)C[C@H]2N(C(=O)C(F)(F)F)CC[C@]3(C)C2(C)C)cn1]

Mass spectrum (ESI+): m/z=463 [M+H]+

Alternatively, the compound is obtained from 5-methyl-pyrazine-2-carboxylic acid using 2-(1H-benzotriazol-1-yl)-1,1,3,3-tetramethyluronium tetrafluoroborate and ethyldiisopropylamine in dimethylformamide as described in Procedure A.

(5) 5-Methyl-pyrazine-2-carboxylic acid [(2R,6R,11S)-8-hydroxy-6,11-dimethyl-3-(2,2,2-trifluoro-acetyl)-1,2,3,4,5,6-hexahydro-2,6-methano-benzo[d]azocin-9-yl]-amide

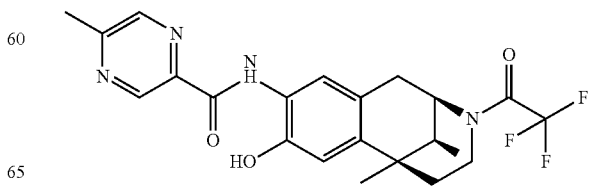

Mass spectrum (ESI⁺): m/z=449 [M+H]⁺

Alternatively, the compound is obtained from 5-methyl-pyrazine-2-carboxylic acid using 2-(1H-benzotriazol-1-yl)-1,1,3,3-tetramethyluronium tetrafluoroborate and ethyldiisopropylamine in dimethylformamide as described in Procedure A.

(6) (R)-Tetrahydro-furan-2-carboxylic acid [(2R,6S)-9-hydroxy-6,11,11-trimethyl-3-(2,2,2-trifluoro-acetyl)-1,2,3,4,5,6-hexahydro-2,6-methano-benzo[d]azocin-8-yl]-amide

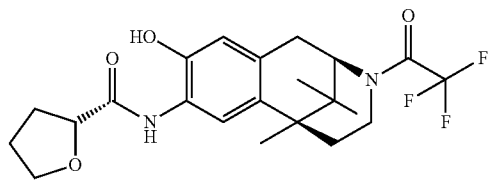

Preferably, the compound is obtained from (R)-tetrahydro-furan-2-carboxylic acid using 2-(1H-benzotriazol-1-yl)-1,1,3,3-tetramethyluronium tetrafluoroborate and ethyldiisopropylamine in dimethylformamide as described in Procedure A.

(7) (S)-Tetrahydro-furan-2-carboxylic acid [(2R,6S)-9-hydroxy-6,11,11-trimethyl-3-(2,2,2-trifluoro-acetyl)-1,2,3,4,5,6-hexahydro-2,6-methano-benzo[d]azocin-8-yl]-amide

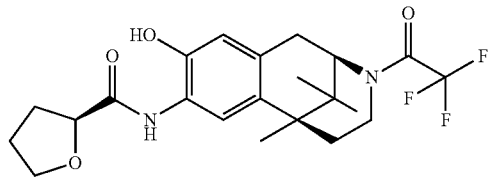 [SMILES: CC1(C)[C@H]2Cc3cc(O)c(NC(=O)[C@@H]4CCCO4)cc3[C@]1(C)CCN2C(=O)C(F)(F)F]

Preferably, the compound is obtained from (S)-tetrahydro-furan-2-carboxylic acid using 2-(1H-benzotriazol-1-yl)-1,1,3,3-tetramethyluronium tetrafluoroborate and ethyldiisopropylamine in dimethylformamide as described in Procedure A.

Example LXVII

1-[(6R,10S)-2-Cyclopropyl-5,6,7,8,9,10-hexahydro-10,12,12-trimethyl-6,10-methano-oxazolo[4,5-i][3]benzazocin-7-yl]-2,2,2-trifluoro-ethanone

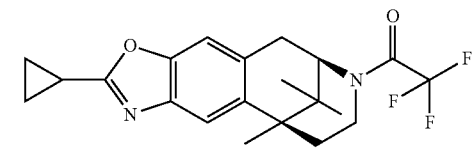 [SMILES: CC1(C)[C@H]2Cc3cc4oc(C5CC5)nc4cc3[C@]1(C)CCN2C(=O)C(F)(F)F]

A solution of cyclopropanecarboxylic acid [(2R,6S)-9-hydroxy-6,11,11-trimethyl-3-(2,2,2-trifluoro-acetyl)-1,2,3,4,5,6-hexahydro-2,6-methano-benzo[d]azocin-8-yl]-amide (0.62 g) and pyridinium p-toluenesulfonate (76 mg) in xylene (6 mL) is stirred at reflux temperature for 5 h. After cooling to room temperature, the solution is concentrated, ethyl acetate is added to the residue, and the resulting mixture is washed with water and brine. The organic solution is dried (MgSO₄) and the solvent is evaporated to afford the title compound.

Yield: 0.52 g (89% of theory)

The following compounds are obtained in analogy to Example LXVII:

(1) 1-[(6R,10R,12S)-2-Cyclopropyl-5,6,7,8,9,10-hexahydro-10,12-dimethyl-6,10-methano-oxazolo[4,5-i][3]benzazocin-7-yl]-2,2,2-trifluoro-ethanone

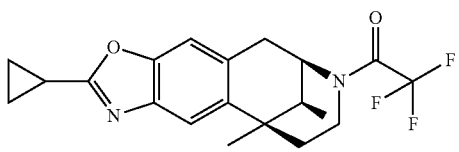 [SMILES: C[C@@H]1[C@H]2Cc3cc4oc(C5CC5)nc4cc3[C@]1(C)CCN2C(=O)C(F)(F)F]

(2) 1-[(6R,10R,12S)-2-Cyclopropyl-5,6,7,8,9,10-hexahydro-10,12-dimethyl-6,10-methano-oxazolo[5,4-i][3]benzazocin-7-yl]-2,2,2-trifluoro-ethanone

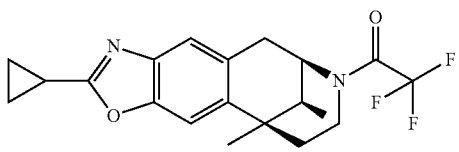 [SMILES: C[C@@H]1[C@H]2Cc3cc4nc(C5CC5)oc4cc3[C@]1(C)CCN2C(=O)C(F)(F)F]

Mass spectrum (ESI⁺): m/z=379 [M+H]⁺

(3) 1-[(6R,10S)-2-tert-Butyl-5,6,7,8,9,10-hexahydro-10,12,12-trimethyl-6,10-methano-oxazolo[4,5-i][3]benzazocin-7-yl]-2,2,2-trifluoro-ethanone

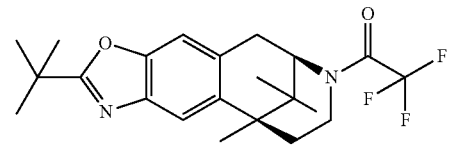 [SMILES: CC(C)(C)c1nc2cc3c(cc2o1)C[C@H]1N(C(=O)C(F)(F)F)CC[C@]3(C)C1(C)C]

(4) 2,2,2-Trifluoro-1-[(6R,10S)-5,6,7,8,9,10-hexahydro-10,12,12-trimethyl-2-(5-methyl-pyrazin-2-yl)-6,1-methano-oxazolo[4,5-i][3]benzazocin-7-yl]-ethanone

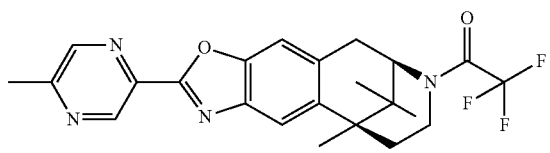 [SMILES: Cc1cnc(-c2nc3cc4c(cc3o2)C[C@H]2N(C(=O)C(F)(F)F)CC[C@]4(C)C2(C)C)cn1]

(5) 2,2,2-Trifluoro-1-[(6R,10R,12S)-5,6,7,8,9,10-hexahydro-10,12-dimethyl-2-(5-methyl-pyrazin-2-yl)-6,1-methano-oxazolo[5,4-i][3]benzazocin-7-yl]-ethanone

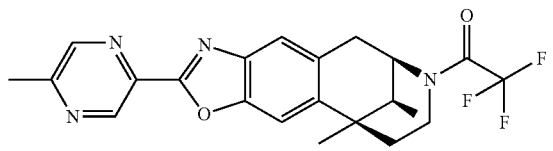 [SMILES: Cc1cnc(-c2nc3cc4c(cc3o2)[C@]2(C)CCN(C(=O)C(F)(F)F)[C@H](C4)[C@H]2C)cn1]

(6) 2,2,2-Trifluoro-1-[(6R,10S)-5,6,7,8,9,10-hexahydro-10,12,12-trimethyl-2-[(R)-tetrahydrofuran-2-yl]-6,10-methano-oxazolo[4,5-i][3]benzazocin-7-yl]-ethanone

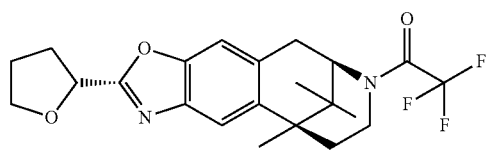

(7) 2,2,2-Trifluoro-1-[(6R,10S)-5,6,7,8,9,10-hexahydro-10,12,12-trimethyl-2-[(S)-tetrahydrofuran-2-yl]-6,10-methano-oxazolo[4,5-i][3]benzazocin-7-yl]-ethanone

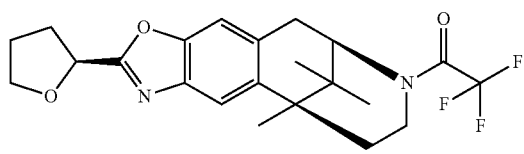 [SMILES: CC1(C)[C@H]2Cc3cc4oc([C@@H]5CCCO5)nc4cc3[C@]1(C)CCN2C(=O)C(F)(F)F]

Example LXVIII

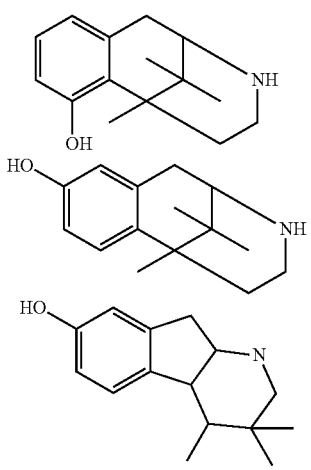

6,11,11-Trimethyl-1,2,3,4,5,6-hexahydro-2,6-methano-benzo[d]azocin-7-ol, 6,11,11-trimethyl-1,2,3,4,5,6-hexahydro-2,6-methano-benzo[d]azocin-9-ol, and 3,3,4-trimethyl-2,3,4,4a,9,9a-hexahydro-1H-indeno[2,1-b]pyridin-7-ol 2-(3-Methoxy-benzyl)-3,3-dimethyl-4-methylene-piperidine-1-carbaldehyde (for preparation see *J. Med. Chem.* 1997, 40, 2928-2939; 47.5 g) is combined with 48% HBr in water (300 mL). The mixture is heated to reflux temperature and stirred at this temperature for 24 h. After cooling to ambient temperature, the precipitate is separated by filtration, washed with water, and triturated with acetone. Then, the precipitate is taken up in a mixture of 1 N aqueous NaOH solution and $CH_2Cl_2$. The $CH_2Cl_2$ phase is separated, dried ($Na_2SO_4$), and concentrated. The residue is recrystallized from EtOAc to afford 6,11,11-trimethyl-1,2,3,4,5,6-hexahydro-2,6-methano-benzo[d]azocin-9-ol. The filtrate of the reaction mixture is combined with the water and acetone phases (from washing and triturating the precipitate) and basified using concentrated aqueous ammonia solution. The resulting mixture is extracted with $CH_2Cl_2$, the combined organic extracts are dried ($MgSO_4$), and the solvent is evaporated. The residue is purified by chromatography on silica gel (EtOAc/MeOH/$NH_4OH$ 90:10:1->70:30:3) to afford 6,11,11-trimethyl-1,2,3,4,5,6-hexahydro-2,6-methano-benzo[d]azocin-7-ol and 3,3,4-trimethyl-2,3,4,4a,9,9a-hexahydro-1H-indeno[2,1-b]pyridin-7-ol separated.

6,11,11-Trimethyl-1,2,3,4,5,6-hexahydro-2,6-methano-benzo[d]azocin-7-ol

Yield: 5.2 g (13% of theory)
Mass spectrum (ESI$^+$): m/z=232 [M+H]$^+$ 6,11,11-Trimethyl-1,2,3,4,5,6-hexahydro-2,6-methano-benzo[d]azocin-9-ol Yield: 9.3 g (23% of theory)
Mass spectrum (ESI$^+$): m/z=232 [M+H]$^+$ 3,3,4-Trimethyl-2,3,4,4a,9,9a-hexahydro-1H-indeno[2,1-b]pyridin-7-ol Yield: 4.2 g (10% of theory)
Mass spectrum (ESI$^+$): m/z=232 [M+H]$^+$ Example LXIX

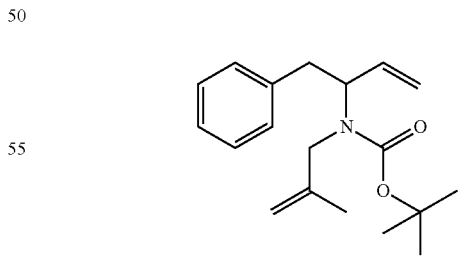

(1-Benzyl-allyl)-(2-methyl-allyl)-carbamic acid tert-butyl ester

NaH (60% in mineral oil, 0.15 g) is added to a solution of (1-benzyl-allyl)-carbamic acid tert-butyl ester (for preparation see e.g. *Eur. J. Org. Chem.* 2002, 1, 139-144; 0.86 g) in N-methylpyrrolidinone (5 mL). The resulting mixture is stirred at room temperature for 30 min, before 3-bromo-2-methyl-propene (0.38 mL) is added. After stirring for 5 h, brine is added and the resulting mixture is extracted with ethyl acetate. The combined organic extracts are dried (Na$_2$SO$_4$), the solvent is evaporated, and the residue is purified by chromatography on silica gel (cyclohexane/ethyl acetate 1:0->1:1).

Yield: 0.79 g (75% of theory)

Mass spectrum (ESI$^+$): m/z=302 [M+H]$^+$

The following compound is obtained in analogy to Example LXIX:

(1) (1-Benzyl-allyl)-(4-methyl-pent-4-enyl)-carbamic acid tert-butyl ester

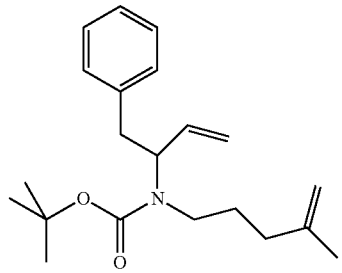 [SMILES: C=CC(Cc1ccccc1)N(CCCC(=C)C)C(=O)OC(C)(C)C]

Mass spectrum (ESI$^+$): m/z=330 [M+H]$^+$

Methanesulfonic acid 4-methyl-pent-4-enyl ester, prepared from 4-methyl-pent-4-en-1-ol and mesyl chloride in the presence of NEt$_3$ in dichloromethane, is used as the electrophile.

Example LXX

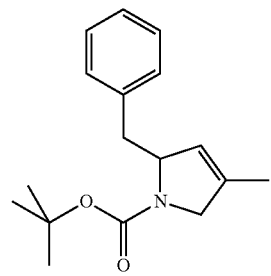 [SMILES: CC1=CC(Cc2ccccc2)N(C(=O)OC(C)(C)C)C1]

2-Benzyl-4-methyl-2,5-dihydro-pyrrole-1-carboxylic acid tert-butyl ester

[(1,3-Bis(2,4,6-trimethylphenyl)-2-imidazolidinylidene]-(phenylmethylene)-(tricyclohexylphosphine)-ruthenium (28 mg) is added to a solution of (1-benzyl-allyl)-(2-methyl-allyl)-carbamic acid tert-butyl ester (0.79 g) in toluene (50 mL) under argon atmosphere at room temperature. The resulting mixture is heated to 60° C. and stirred at this temperature for 3 h. After cooling to room temperature, the solvent is evaporated and the residue is purified by chromatography on silica gel (cyclohexane/ethyl acetate 1:0->1:1).

Yield: 0.40 g (56% of theory)

Mass spectrum (ESI$^+$): m/z=274 [M+H]$^+$

The following compound is obtained in analogy to Example LXX:

(1) 7-Benzyl-5-methyl-2,3,4,7-tetrahydro-azepine-1-carboxylic acid tert-butyl ester

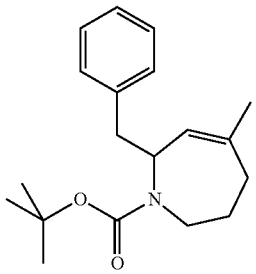 [SMILES: CC1=CC(Cc2ccccc2)N(C(=O)OC(C)(C)C)CCC1]

Mass spectrum (ESI$^+$): m/z=302 [M+H]$^+$

Example LXXI

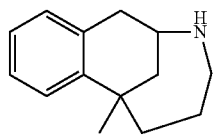

1-Methyl-10-aza-tricyclo[7.4.1.0*2,7*]tetradeca-2,4,6-triene

Trifluoromethanesulfonic acid (2.5 mL) is added to a solution of 7-benzyl-5-methyl-2,3,4,7-tetrahydro-azepine-1-carboxylic acid tert-butyl ester (0.30 g) in dichloromethane (5 mL) chilled in an ice bath. The ice bath is removed and the solution is stirred at room temperature for 5 h. Then, ice-cold water and aqueous K$_2$CO$_3$ solution are added and the resulting mixture is extracted with ethyl acetate. The combined extracts are dried (Na$_2$SO$_4$), the solvent is evaporated, and the residue is purified by chromatography on silica gel (dichloromethane/methanol 99:1->9:1).

Yield: 0.10 g (50% of theory)

Example LXXII

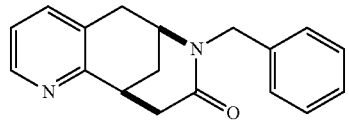 [SMILES: O=C1C[C@@H]2C[C@@H](Cc3cccnc32)N1Cc1ccccc1]

7-Benzyl-6,7,9,10-tetrahydro-5H-6,10-methano-pyrido[3,2-d]azocin-8-one (racemic mixture of diastereomer shown)

A flask charged with a stir bar, 2-benzyl-2-aza-bicyclo[3.3.1]nonane-3,6-dione (for preparation see *J. Chem. Soc., Perkin Trans.* 1, 1999, 1157-1162; 0.80 g), NaAuCl$_4$.2 H$_2$O (30 mg), propargylamine (0.45 mL), and ethanol (5 mL) is heated at 100° C. with microwave irradiation for 10 min. After cooling to room temperature, the mixture is filtered and the filtrate is concentrated. The residue is purified by chromatography on silica gel (cyclohexane/ethyl acetate/methanol 6:4:1).

Yield: 0.52 g (56% of theory)

Example LXXIII

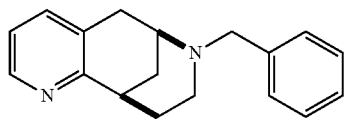 [SMILES: c1ccc(CN2CC[C@@H]3C[C@H]2Cc2cccnc23)cc1]

7-Benzyl-5,6,7,8,9,10-hexahydro-6,10-methano-pyrido[3,2-d]azocine (racemic mixture of diastereomer shown)

LiAlH$_4$ (1 M in THF, 4.5 mL) is added dropwise to a solution of 7-benzyl-6,7,9,10-tetrahydro-5H-6,10-methanopyrido[3,2-d]azocin-8-one (0.55 g) in THF (3 mL) chilled in an ice bath. The cooling bath is removed and the mixture is stirred at room temperature for 2 h. Ice-cold water and 4 M hydrochloric acid (4 mL) are added and the mixture is stirred for another 15 min. Then, the mixture is basified using 4 M aqueous NaOH solution and the mixture is extracted with ethyl acetate. The combined organic extracts are dried (Na$_2$SO$_4$), the solvent is evaporated, and the residue is purified by chromatography on silica gel (cyclohexane/ethyl acetate/methanol 4:1:0->1:1:1).

Yield: 0.16 g (32% of theory)

The following compounds are obtained in analogy to Example LXXIII:

(1) 9-Benzyl-3,5,9-triaza-tricyclo[6.3.1.0*2,6*]dodeca-2(6),4-diene (racemic mixture of diastereomer shown)

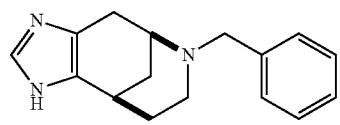 [SMILES: c1ccc(CN2CC[C@@H]3C[C@H]2Cc2nc[nH]c23)cc1]

Mass spectrum (ESI$^+$): m/z=254 [M+H]$^+$ (2) 9-Benzyl-4-methyl-3,5,9-triaza-tricyclo[6.3.1.0*2,6*]dodeca-2(6),4-diene (racemic mixture of diastereomer shown)

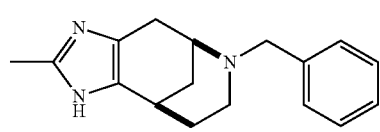 [SMILES: Cc1nc2c([nH]1)[C@@H]1CCN(Cc3ccccc3)[C@H](C2)C1]

Mass spectrum (ESI$^+$): m/z=268 [M+H]$^+$

Example LXXIV

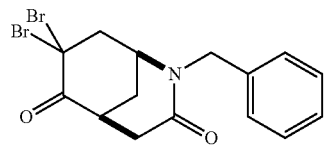 [SMILES: O=C1C[C@@H]2C[C@@H](CC(Br)(Br)C2=O)N1Cc1ccccc1]

2-Benzyl-7,7-dibromo-2-aza-bicyclo[3.3.1]nonane-3,6-dione (racemic mixture of diastereomer shown)

A solution of bromine (1.2 mL) in acetic acid (5 mL) is added to a solution of 2-benzyl-2-aza-bicyclo[3.3.1]nonane-3,6-dione (for preparation see *J. Chem. Soc., Perkin Trans.* 1, 1999, 1157-1162; 3.05 g) in acetic acid (40 mL). The resulting solution is stirred at room temperature for 2 h. Then, the solution is poured into ice-cold water and the resulting mixture is extracted with ethyl acetate. The combined organic extracts are dried (Na$_2$SO$_4$) and the solvent is evaporated to afford the title compound as a solid.

Yield: 4.69 g (88% of theory)

Mass spectrum (ESI$^+$): m/z=400/402/404 (2 Br) [M+H]$^+$

Example LXXV

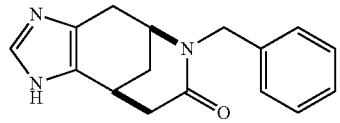 [SMILES: O=C1C[C@@H]2C[C@@H](Cc3nc[nH]c32)N1Cc1ccccc1]

9-Benzyl-3,5,9-triaza-tricyclo[6.3.1.0*2,6*]dodeca-2(6),4-dien-10-one (racemic mixture of diastereomer shown)

A mixture of 2-benzyl-7,7-dibromo-2-aza-bicyclo[3.3.1]nonane-3,6-dione (one diastereomer, 2.50 g), paraforamaldehyde (0.19 g), and ca. 7 M ammonia in methanol (25 mL) is stirred at room temperature overnight. Then, the solution is concentrated and the residue is purified by chromatography on silica gel (CH$_2$Cl$_2$/MeOH 99:1->9:1).

Yield: 0.85 g (ca. 85% pure, 44% of theory)

Mass spectrum (ESI$^+$): m/z=268 [M+H]$^+$

The following compound is obtained in analogy to Example LXXV:

(1) 9-Benzyl-4-methyl-3,5,9-triaza-tricyclo[6.3.1.0*2,6*]dodeca-2(6),4-dien-10-one (racemic mixture of diastereomer shown)

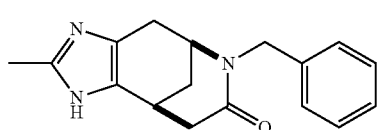

Acetaldehyde instead of paraformaldehyde is used.

Example LXXVI

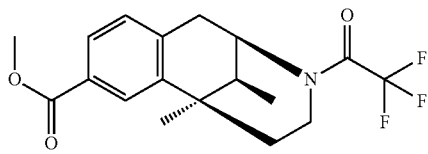 [SMILES: COC(=O)c1ccc2c(c1)[C@]1(C)CCN(C(=O)C(F)(F)F)[C@H](C2)[C@H]1C]

(2R,6R,11S)-6,11-Dimethyl-3-(2,2,2-trifluoro-acetyl)-1,2,3,4,5,6-hexahydro-2,6-methano-benzo[d]azocine-8-carboxylic acid methyl ester 2,2,6,6-Tetramethylpiperidine (5.4 mL), 1,3-bis(diphenylphosphino)propane (1.30 g), and Pd(OAc)$_2$ (0.78 g) are added in turn to a flask charged with trifluoromethanesulfonic acid (2R,6R,11S)-6,11-dimethyl-3-(2,2,2-trifluoro-acetyl)-1,2,3,4,5,6-hexahydro-2,6-methano-benzo[d]azocin-8-yl ester (7.0 g), dimethylformamide (30 mL), and methanol (30 mL) in argon atmosphere. The reaction flask is put under CO pressure (7 bar) and shaken at 70° C. for 17 h. After cooling to ambient temperature, water is added and the resulting mixture is extracted with Et$_2$O. The combined organic extracts are washed with water and brine and dried (MgSO$_4$). The solvent is evaporated to give the title compound as an oil that crystallizes while standing.

Yield: 5.2 g (93% of theory)

Mass spectrum (ESI$^+$): m/z=356 [M+H]$^+$

Example LXXVII

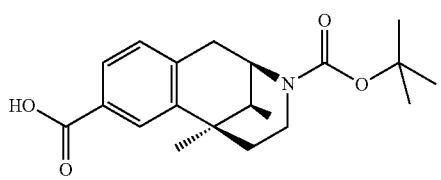 [SMILES: C[C@@H]1[C@H]2Cc3ccc(C(=O)O)cc3[C@]1(C)CCN2C(=O)OC(C)(C)C]

(2R,6R,11S)-6,11-Dimethyl-1,2,5,6-tetrahydro-4H-2,6-methano-benzo[d]azocine-3,8-dicarboxylic acid 3-tert-butyl ester 4 M aqueous NaOH solution (18.5 mL) is added to a solution of (2R,6R,11S)-6,11-dimethyl-3-(2,2,2-trifluoro-acetyl)-1,2,3,4,5,6-hexahydro-2,6-methano-benzo[d]azocine-8-carboxylic acid methyl ester (5.2 g) in methanol (40 mL). The solution is stirred at room temperature overnight. After neutralization of the solution with MeCOOH, NEt$_3$ (10 mL) and THF (20 mL) are added and the solution is cooled in an ice bath. Then, di-tertbutyl dicarbonate (4.0 g) is added, the cooling bath is removed, and the solution is stirred at ambient temperature overnight. 1 M aqueous HCl solution (30 mL) is added and the resulting mixture is extracted with ethyl acetate. The combined organic extracts are washed with brine and dried (MgSO$_4$).

The solvent is evaporated to give the title compound.

Yield: 5.3 g (quantitative)

Mass spectrum (ESI$^+$): m/z=346 [M+H]$^+$

Example LXXVIII

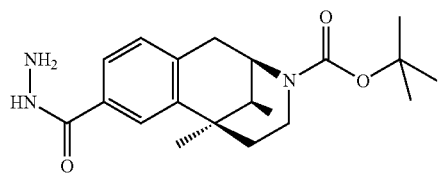 [SMILES: C[C@@H]1[C@H]2Cc3ccc(C(=O)NN)cc3[C@]1(C)CCN2C(=O)OC(C)(C)C]

(2R,6R,11S)-8-Hydrazinocarbonyl-6,11-dimethyl-1,2,5,6-tetrahydro-4H-2,6-methano-benzo[d]azocine-3-carboxylic acid tert-butyl ester NEt$_3$ (1.7 mL) and 2-(1H-benzotriazol-1-yl)-1,1,3,3-tetramethyluronium tetrafluoroborate (3.9 g) are added in turn to a solution of (2R,6R,11S)-6,11-dimethyl-1,2,5,6-tetrahydro-4H-2,6-methano-benzo[d]azocine-3,8-dicarboxylic acid 3-tertbutyl ester (4.2 g) in dimethylformamide (10 mL). The resulting solution is stirred at ambient temperature for 30 min, before hydrazine hydrate (3 mL) is added. The solution is stirred further at room temperature for 1 h and then water (30 mL) is added. The resulting mixture is extracted with ethyl acetate and the combined organic extracts are washed with 1 M aqueous NaOH solution, water, and brine. After drying (MgSO$_4$), the solvent is evaporated and the residue is purified by chromatography on silica gel (cyclohexane/EtOAc 1:4->0:1) to give the title compound.

Yield: 2.8 g (64% of theory)

Mass spectrum (ESI$^-$): m/z=358 [M–H]$^-$

Example LXXIX

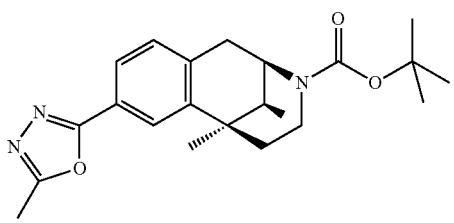 [SMILES: Cc1nnc(-c2ccc3c(c2)[C@]2(C)CCN(C(=O)OC(C)(C)C)[C@H](C3)[C@H]2C)o1]

(2R,6R,11S)-6,11-Dimethyl-8-(5-methyl-[1,3,4]oxadiazol-2-yl)-1,2,5,6-tetrahydro-4H-2,6-methano-benzo[d]azocine-3-carboxylic acid tert-butyl ester (2R,6R,11S)-8-Hydrazinocarbonyl-6,11-dimethyl-1,2,5,6-tetrahydro-4H-2,6-methano-benzo[d]azocine-3-carboxylic acid tert-butyl ester (0.50 g) in (EtO)$_3$CMe (2 mL) is heated in a microwave oven at 120° C. for 30 min. After cooling to room temperature, the mixture is concentrated under reduced pressure and the residue is purified by HPLC on reversed phase (MeCN/H$_2$O/NH$_4$OH) to give the title compound.

Yield: 93 mg (17% of theory)

Mass spectrum (ESI$^+$): m/z=384 [M+H]$^+$

The following compound is obtained in analogy to Example LXXIX:

(1) (2R,6R,11S)-6,11-Dimethyl-8-[1,3,4]oxadiazol-2-yl-1,2,5,6-tetrahydro-4H-2,6-methano-benzo[d]azocine-3-carboxylic acid tert-butyl ester

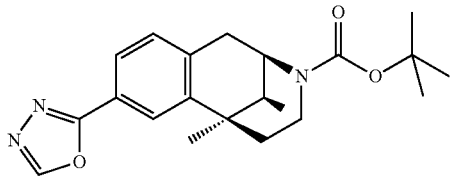 [SMILES: C[C@@H]1[C@H]2Cc3ccc(-c4nnco4)cc3[C@]1(C)CCN2C(=O)OC(C)(C)C]

Mass spectrum (ESI+): m/z=370 [M+H]+

The reaction is conducted at 145° C. with (EtO)₃CH.

Example LXXX

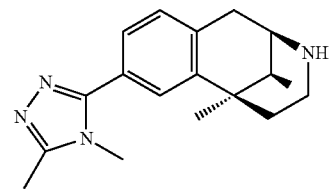 [SMILES: Cc1nnc(-c2ccc3c(c2)[C@]2(C)CCN[C@H](C3)[C@H]2C)n1C]

(2R,6R,11S)-8-(4,5-Dimethyl-4H-[1,2,4]triazol-3-yl)-6,11-dimethyl-1,2,3,4,5,6-hexahydro-2,6-methano-benzo[d]azocine Oxalylic chloride (0.12 mL) is added to a solution N-methylacetamide (102 mg) and 2,6-lutidine (0.33 mL) in dichloromethane (5 mL) chilled in an ice bath. After stirring the solution for 15 min, (2R,6R,11S)-8-hydrazinocarbonyl-6,11-dimethyl-1,2,5,6-tetrahydro-4H-2,6-methano-benzo[d]azocine-3-carboxylic acid tert-butyl ester (0.50 g) is added and the cooling bath is removed. The resulting solution is stirred at ambient temperature for 1 h and then neutralized with aqueous NaHCO₃ solution. The resulting mixture is extracted with dichloromethane, the combined organic extracts are dried (MgSO₄), and the solvent is evaporated. The residue is taken up in acetic acid (3 mL) and stirred at 120° C. for 2.5 h. After cooling to room temperature, the mixture is concentrated under reduced pressure and the residue is taken up in trifluoroacetic acid (1 mL) and dichloromethane (5 mL) to cleave off the tert-butoxycarbonyl group. The solution is stirred at room temperature overnight and then concentrated. The residue is dissolved in little methanol/acetonitrile, neutralized with aqueous ammonia, and purified by HPLC on reversed phase (MeCN/H₂O/NH₄OH) to give the title compound.

Yield: 50 mg (12% of theory)

Mass spectrum (ESI+): m/z=297 [M+H]+

Example LXXXI

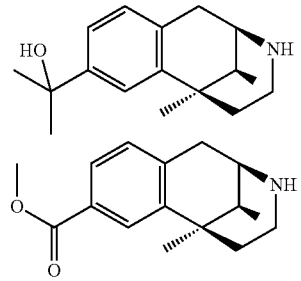

2-[(2R,6R,11S)-6,11-Dimethyl-1,2,3,4,5,6-hexahydro-2,6-methano-benzo[d]azocin-8-yl]-propan-2-ol and (2R,6R,11S)-6,11-dimethyl-1,2,3,4,5,6-hexahydro-2,6-methano-benzo[d]azocine-8-carboxylic acid methyl ester MeMgBr (1.4 mol/L in tetrahydrofuran/toluene, 2.0 mL) is added to a solution of (2R,6R,11S)-6,11-dimethyl-3-(2,2,2-trifluoro-acetyl)-1,2,3,4,5,6-hexahydro-2,6-methano-benzo[d]azocine-8-carboxylic acid methyl ester (0.20 g) in tetrahydrofuran (5 mL) chilled in an ice bath. The solution is stirred with cooling for 2 h, before aqueous NH₄Cl solution is added carefully. The resulting mixture is extracted with ethyl acetate and the combined organic extracts are washed with brine and dried (MgSO₄). The solvent is evaporated to yield a mixture of the title compounds (ca. 4:1 in favor of 2-[(2R,6R,11S)-6,11-dimethyl-1,2,3,4,5,6-hexahydro-2,6-methano-benzo[d]azocin-8-yl]-propan-2-ol).

Yield: 0.15 g

Mass spectrum (ESI+): m/z=260 [M+H] for both compounds determined with analytical HPLC-MS

Example LXXXII

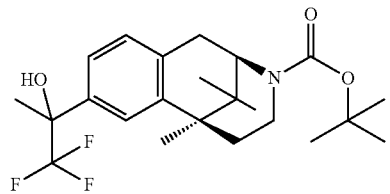 [SMILES: CC(C)(C)OC(=O)N1CC[C@@]2(C)c3cc(C(C)(O)C(F)(F)F)ccc3C[C@@H]1C2(C)C]

(2R,6S)-6,11,11-Trimethyl-8-(2,2,2-trifluoro-1-hydroxy-1-methyl-ethyl)-1,2,5,6-tetrahydro-4H-2,6-methano-benzo[d]azocine-3-carboxylic acid tert-butyl ester Me₃SiCF₃ (2 M in tetrahydrofuran, 0.42 mL) is added dropwise to a mixture of (2R,6S)-8-acetyl-6,11,11-trimethyl-1,2,5,6-tetrahydro-4H-2,6-methano-benzo[d]azocine-3-carboxylic acid tert-butyl ester (0.30 g) and CsF (13 mg) in tetrahydrofuran (3 mL) cooled to ca. −5° C. The mixture is stirred at −5° C. for 1.5 h. Then, 1 M aqueous HCl solution (70 mL) is added and the mixture is stirred for 1 h. The mixture is basified using aqueous K₂CO₃ solution and then extracted with ethyl acetate. The combined organic extracts are washed with brine and dried (MgSO₄). The solvent is evaporated to give the crude title compound that is submitted for cleaving the protective group without further purification.

Yield: 0.36 g (crude)

Example LXXXIII

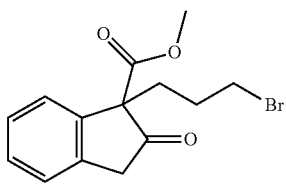 [SMILES: COC(=O)C1(CCCBr)C(=O)Cc2ccccc21]

1-(3-Bromo-propyl)-2-oxo-indan-1-carboxylic acid methyl ester

A solution of 2-oxo-indan-1-carboxylic acid methyl ester (3.8 g) and NaOH (1 M in water, 20 mL) in ethanol (30 mL) is added dropwise to a solution of 1,3-dibromopropane (10 mL) in ethanol (20 mL) at room temperature. The solution is warmed to 40° C. and stirred at this temperature for 2 d. Then, the solution is concentrated under reduced pressure and ethyl acetate is added to the residue. The resulting mixture is washed with water and brine and dried (MgSO₄). After removing the solvent, the residue is purified by chromatography on silica gel (cyclohexane/ethyl acetate 20:1->9:1) to give the title compound as an oil.

Yield: 2.1 g (33% of theory)

Mass spectrum (ESI⁺): m/z=311/313 (Br) [M+H]⁺

Example LXXXIV

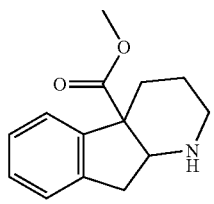 [SMILES: COC(=O)C12CCCNC1Cc1ccccc12]

1,2,3,4,9,9a-Hexahydro-indeno[2,1-b]pyridine-4-a-carboxylic acid methyl ester

NaN₃ (0.44 g) is added to a solution of 1-(3-bromo-propyl)-2-oxo-indan-1-carboxylic acid methyl ester (2.06 g) in dimethylformamide (10 mL) at room temperature. The solution is stirred at room temperature for 4 h and then tBuOMe and ethyl acetate are added. The resulting mixture is washed with water and brine and dried (MgSO₄). Most of the organic solvent is evaporated and tetrahydrofuran (10 mL), acetic acid (0.5 mL), and finally 10% Pd/C (150 mg) are added to the residue. The resulting mixture is shaken in hydrogen atmosphere (1 bar) at room temperature for 14 h. Then, the mixture is filtered, the filtrate is concentrated, and the residue is taken up in tBuOMe. The organic phase is washed with aqueous Na₂CO₃ solution and brine and dried (MgSO₄). Then, the solvent is evaporated and the residue is dissolved in methanol (10 mL). To the solution is added acetic acid (0.5 mL) and 10% Pd/C (50 mg) and the resulting mixture is shaken under hydrogen atmosphere (1 bar) at room temperature for 6 h. Then, the mixture is filtered and the filtrate is concentrated under reduced pressure to give the crude title compound that is used without further purification.

Yield: 0.44 g (crude)

Preparation of the End Compounds:

Procedure A (Described for Example 1, Table 3)

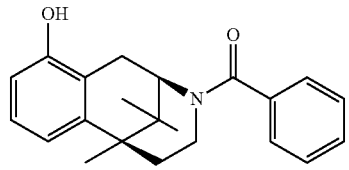 [SMILES: CC1(C)[C@H]2Cc3c(O)cccc3[C@]1(C)CCN2C(=O)c1ccccc1]

[(2R,6S)-10-Hydroxy-6,11,11-trimethyl-1,2,5,6-tetrahydro-4H-2,6-methano-benzo[d]azocin-3-yl]-phenyl-methanone 2-(1H-Benzotriazol-1-yl)-1,1,3,3-tetramethyluronium tetrafluoroborate (155 mg; alternatively, N,N,N',N'-tetramethyl-O-(7-azabenzotriazol-1-yl)uronium hexafluorophosphate may be used) is added to a solution of benzoic acid (60 mg) and ethyldiisopropylamine (0.25 mL) in dichloromethane (1 mL; DMF may be used as well). The resulting solution is stirred at ambient temperature for 15 min before it is cooled in an ice bath. (2R,6S)-6,11,11-Trimethyl-1,2,3,4,5,6-hexahydro-2,6-methano-benzo[d]azocin-10-ol (0.10 g) is added and the solution is warmed to room temperature and stirred overnight. The mixture is concentrated under reduced pressure and the residue is purified by HPLC on reversed phase (H₂O/MeCN) to give the product as a beige solid.

Yield: 55 mg (51% of theory)

Mass spectrum (ESI⁺): m/z=336 [M+H]⁺

Procedure B (Described for Example 151, Table 3)

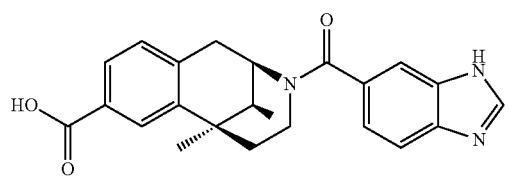 [SMILES: C[C@@H]1[C@H]2Cc3ccc(C(=O)O)cc3[C@]1(C)CCN2C(=O)c1ccc2nc[nH]c2c1]

(2R,6R,11S)-3-(3H-Benzoimidazole-5-carbonyl)-6,11-dimethyl-1,2,3,4,5,6-hexahydro-2,6-methano-benzo[d]azocine-8-carboxylic acid Aqueous 4 M NaOH solution (1 mL) is added to a solution of (2R,6R,11S)-3-(3H-benzoimidazole-5-carbonyl)-6,11-dimethyl-1,2,3,4,5,6-hexahydro-2,6-methano-benzo[d]azocine-8-carboxylic acid ethyl ester (0.60 g) in ethanol (3 mL). The resulting solution is stirred at ambient temperature for 3 h. Then, the solution is slightly acidified (pH ca. 5) using 1 M hydrochloric acid and the resulting solution is extracted with ethyl acetate. The combined organic extracts are washed with brine and dried (MgSO$_4$). The solvent is evaporated under reduced pressure to give the product as a white solid.

Yield: 0.38 g (68% of theory)
Mass spectrum (ESI$^+$): m/z=390 [M+H]$^+$
Procedure C (Described for Example 155, Table 3)

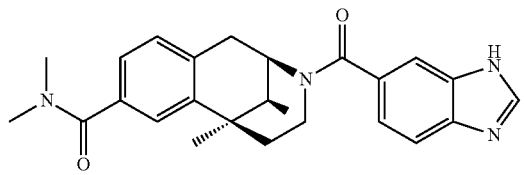 [SMILES: C[C@@H]1[C@H]2Cc3ccc(C(=O)N(C)C)cc3[C@]1(C)CCN2C(=O)c1ccc2nc[nH]c2c1]

(2R,6R,11S)-3-(3H-Benzoimidazole-5-carbonyl)-6,
11-dimethyl-1,2,3,4,5,6-hexahydro-2,6-methano-
benzo[d]azocine-8-carboxylic acid dimethylamide 2-(1H-Benzotriazol-1-yl)-1,1,3,3-tetramethyluronium tetrafluoroborate (90 mg) is added to a solution of (2R,6R,11S)-3-(3H-benzoimidazole-5-carbonyl)-6,11-dimethyl-1,2,3,4,5,6-hexahydro-2,6-methano-benzo[d]azocine-8-carboxylic acid benzoic acid (0.10 g) and ethyldiisopropylamin (53 µL) in dimethylformamide (2 mL). The resulting solution is stirred at ambient temperature for 20 min before dimethylamine (40% in H$_2$O, 60 µL) is added. The solution is stirred overnight. The mixture is concentrated under reduced pressure and the residue is purified by HPLC on reversed phase (H$_2$O/MeCN/NH$_3$) to give the product as a solid.

Yield: 55 mg (51% of theory)
Mass spectrum (ESI$^+$): m/z=417 [M+H]$^+$
Procedure D (Described for Example 172, Table 3)

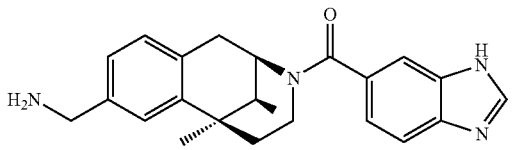 [SMILES: C[C@@H]1[C@H]2Cc3ccc(CN)cc3[C@]1(C)CCN2C(=O)c1ccc2nc[nH]c2c1]

[(2R,6R,11S)-8-Aminomethyl-6,11-dimethyl-1,2,5,
6-tetrahydro-4H-2,6-methano-benzo[d]azocin-3-yl]-
(3H-benzoimidazol-5-yl)-methanone A solution of (2R,6R,11S)-3-(3H-benzoimidazole-5-carbonyl)-6,11-dimethyl-1,2,3,4,5,6-hexahydro-2,6-methano-benzo[d]azocine-8-carbonitrile (50 mg) in 1 M ammonia in methanol (5 mL) is treated with Raney Ni (50 mg) under hydrogen atmosphere at 50° C. for 3 h. Then, the catalyst is separated by filtration and the filtrate is concentrated under reduced pressure.

The residue is purified by HPLC on reversed phase (H$_2$O/MeCN) to give the product as a white foam-like solid.

Yield: 20 mg (33% of theory)
Mass spectrum (ESI$^+$): m/z=375 [M+H]$^+$
Procedure E (Described for Example 174, Table 3)

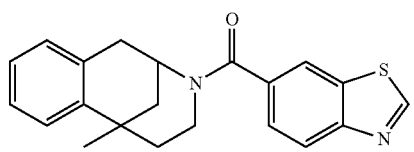 [SMILES: CC12CCN(C(=O)c3ccc4ncsc4c3)C(Cc3ccccc31)C2]

Benzothiazol-6-yl-(6-methyl-1,2,5,6-tetrahydro-4H-
2,6-methano-benzo[d]azocin-3-yl)-methanone Palladiumdiacetate (10 mg), triethylamine (0.25 mL), formic acid (93 µL), and triphenylphosphine (16 mg) are added in turn to a solution of trifluoro-methanesulfonic acid 3-(benzothiazole-6-carbonyl)-6-methyl-1,2,3,4,5,6-hexahydro-2,6-methano-benzo[d]azocin-8-yl ester (0.30 g) in dimethylformamide (1 mL) under argon atmosphere. The resulting mixture is stirred at 60° C. for 20 h. After cooling to room temperature, brine is added and the resulting mixture is extracted three times with ethyl acetate. The combined organic extracts are washed with brine and dried (Na$_2$SO$_4$). The solvent is evaporated under reduced pressure and the residue is purified by HPLC on reversed phase (H$_2$O/MeCN).

Yield: 46 mg (22% of theory)
Mass spectrum (ESI$^+$): m/z=349 [M+H]$^+$
Procedure F (Described for Example 175, Table 3)

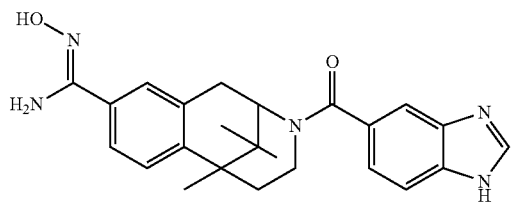 [SMILES: CC12CCN(C(=O)c3ccc4[nH]cnc4c3)C(Cc3cc(/C(N)=N/O)ccc31)C2(C)C]

3-(1H-Benzoimidazole-5-carbonyl)-N-hydroxy-6,11,
11-trimethyl-1,2,3,4,5,6-hexahydro-2,6-methano-
benzo[d]azocine-9-carboxamidine A solution of 3-(1H-benzoimidazole-5-carbonyl)-6,11,11-trimethyl-1,2,3,4,5,6-hexahydro-2,6-methano-benzo[d]azocine-9-carbonitrile (0.30 g) and hydroxylamine (50% in water, 0.5 ml) in ethanol (5 mL) is stirred at reflux temperature for 2 h. After cooling to room temperature, the mixture is concentrated under reduced pressure to give the title compound as a white foam-like solid.

Yield: 0.32 g (98% of theory)
Mass spectrum (ESI$^+$): m/z=418 [M+H]$^+$
Procedure G (Described for Example 176, Table 3)

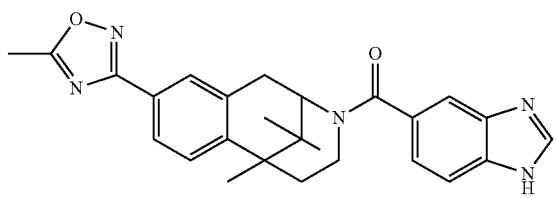 [SMILES: Cc1nc(-c2ccc3c(c2)CC2N(C(=O)c4ccc5[nH]cnc5c4)CCC3(C)C2(C)C)no1]

(1H-Benzoimidazol-5-yl)-[6,11,11-trimethyl-9-(5-
methyl-[1,2,4]oxadiazol-3-yl)-1,2,5,6-tetrahydro-
4H-2,6-methano-benzo[d]azocin-3-yl]-methanone Acetic anhydride (0.1 mL) is added to a solution of 3-(1H-benzoimidazole-5-carbonyl)-N-hydroxy-6,11,11-trimethyl-1,2,3,4,5,6-hexahydro-2,6-methano-benzo[d]azocine-9-carboxamidine (0.15 g) in 2,4,6-trimethylpyridine (2 mL). The resulting solution is stirred at ambient temperature for 1 h and then at 120° C. for 3 h. After cooling to room temperature, the mixture is concentrated under reduced pressure and the residue is taken up in methanol (10 mL). Concentrated aqueous ammonia solution (1 mL) is added and the solution is stirred at ambient temperature for 1 h. The solution is concentrated under reduced pressure and the residue is purified by HPLC on reversed phase (water/MeCN) to give the title compound as a white foam-like solid.

Yield: 0.15 g (95% of theory)

Mass spectrum (ESI⁺): m/z=442 [M+H]⁺

Procedure H (described for Example 177, Table 3)

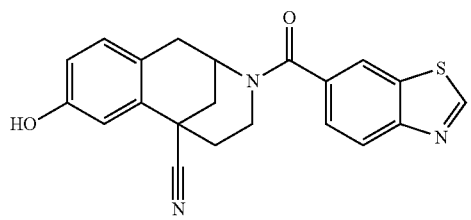 [SMILES: N#CC12CCN(C(=O)c3ccc4ncsc4c3)C(Cc3ccc(O)cc31)C2]

3-(Benzothiazole-6-carbonyl)-8-hydroxy-2,3,4,5-tetrahydro-1H-2,6-methano-benzo[d]azocine-6-carbonitrile Trifluoroacetic anhydride (43 µL) is added to a solution of 3-(benzothiazole-6-carbonyl)-8-hydroxy-2,3,4,5-tetrahydro-1H-2,6-methano-benzo[d]azocine-6-carboxylic acid amide (40 mg) and ethyldiisopropylamine (50 µL) in dichloromethane (0.5 mL) chilled in an ice bath. The ice bath is removed and the solution is stirred at ambient temperature for 4 h. Then, another portion of trifluoroacetic anhydride (43 µL) and ethyldiisopropylamine (50 µL) are added and the solution is stirred overnight. Methanol (1 mL) is added and the solution is stirred for another 10 min. The solution is concentrated under reduced pressure and the residue is purified by HPLC on reversed phase (water/MeCN) to give the title compound.

Yield: 18 mg (47% of theory)

Mass spectrum (ESI⁺): m/z=476 [M+H]⁺

Procedure I (Described for Example 178, Table 3)

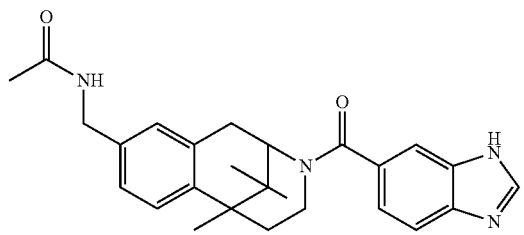 [SMILES: CC(=O)NCc1ccc2c(c1)CC1N(C(=O)c3ccc4nc[nH]c4c3)CCC2(C)C1(C)C]

N-[3-(3H-Benzoimidazole-5-carbonyl)-6,11,11-trimethyl-1,2,3,4,5,6-hexahydro-2,6-methano-benzo[d]azocin-9-ylmethyl]-acetamide Triethylamine (38 µL) and acetic anhydride (26 µL) are added to a suspension of (9-aminomethyl-6,11,11-trimethyl-1,2,5,6-tetrahydro-4H-2,6-methano-benzo[d]azocin-3-yl)-(3H-benzoimidazol-5-yl)-methanone (0.10 g) in acetonitrile (2 mL). The resulting mixture is stirred at ambient temperature for 1 h. Then, methanol (1 mL) and concentrated aqueous ammonia solution (0.5 mL) are added and the resulting solution is stirred for another 30 min. The solution is concentrated under reduced pressure and the residue is purified by HPLC on reversed phase (water/MeCN) to give the title compound as a white foam-like solid.

Yield: 73 mg (66% of theory)

Mass spectrum (ESI⁺): m/z=431 [M+H]⁺

Procedure J (Described for Example 180, Table 3)

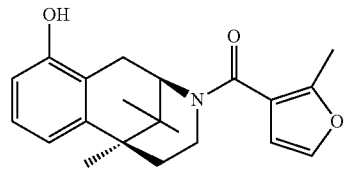 [SMILES: Cc1occc1C(=O)N1CC[C@@]2(C)c3cccc(O)c3C[C@@H]1C2(C)C]

[(2R,6S)-10-Hydroxy-6,11,11-trimethyl-1,2,5,6-tetrahydro-4H-2,6-methano-benzo[d]azocin-3-yl]-(2-methyl-furan-3-yl)-methanone Boron tribromide (2 mL) is added to a solution of [(2R,6S)-10-methoxy-6,11,11-trimethyl-1,2,5,6-tetrahydro-4H-2,6-methano-benzo[d]azocin-3-yl]-(2-methyl-furan-3-yl)-methanone (0.22 g) in dichloromethane (10 mL). The resulting solution is stirred at ambient temperature for 2 h. Then, water is added and the mixture is stirred for another 10 min. The organic phase is separated and the aqueous phase is extracted with dichloromethane. The combined organic phases are washed with brine and dried (Na₂SO₄). The solvent is evaporated to give the title compound.

Yield: 0.20 g (96% of theory)

Mass spectrum (ESI⁺): m/z=340 [M+H]⁺

Procedure K (Described for Example 181, Table 3)

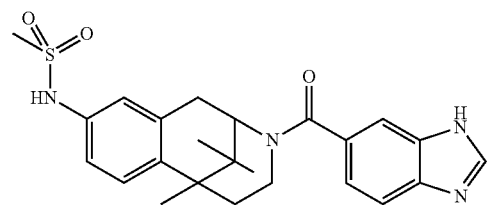 [SMILES: CC12CCN(C(=O)c3ccc4nc[nH]c4c3)C(Cc3cc(NS(C)(=O)=O)ccc31)C2(C)C]

N-[3-(3H-Benzoimidazole-5-carbonyl)-6,11,11-trimethyl-1,2,3,4,5,6-hexahydro-2,6-methano-benzo[d]azocin-9-yl]-methanesulfonamide Triethylamine (38 µL) and methanesulfonyl chloride (21 µL) are added to a suspension of N-[3-(3H-benzoimidazole-5-carbonyl)-6,11,11-trimethyl-1,2,3,4,5,6-hexahydro-2,6-methano-benzo[d]azocin-9-yl]-methanesulfonamide (50 mg) in acetonitrile (1 mL). After 1 h the reaction is complete delivering the title product additionally sulfonylated at one imidazole nitrogen. Methanol (1 mL) and concentrated aqueous ammonia solution (0.5 mL) are added and the mixture is stirred at room temperature overnight and then at 45° C. for another 4 h. The reaction mixture is concentrated under reduced pressure and the residue is purified by HPLC on reversed phase (water/MeCN/NH₃) to give the title compound as a white foam-like solid.

Yield: 20 mg (33% of theory)
Mass spectrum (ESI⁺): m/z=453 [M+H]⁺
Procedure L (Described for Example 183, Table 3)

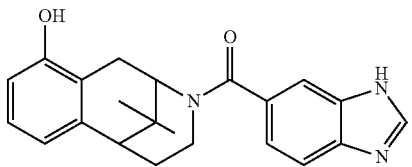 [SMILES: CC1(C)C2CCN(C(=O)c3ccc4nc[nH]c4c3)C1Cc1c(O)cccc12]

(3H-Benzoimidazol-5-yl)-(10-hydroxy-11,11-dimethyl-1,2,5,6-tetrahydro-4H-2,6-methano-benzo[d]azocin-3-yl)-methanone A solution of (3H-benzoimidazol-5-yl)-(10-methoxy-11,11-dimethyl-1,2,5,6-tetrahydro-4H-2,6-methano-benzo[d]azocin-3-yl)-methanone (0.10 g) in hydrobromic acid (2 mL, 48% in water) is stirred at 80° C. for 24 h. After cooling to ambient temperature, the solution is concentrated under reduced pressure and the residue is purified by HPLC on reversed phase (MeCN/H₂O/NH₃).

Yield: 0.03 g (30% of theory)
Mass spectrum (ESI⁺): m/z=362 [M+H]⁺
Procedure M (Described for Example 83, Table 3)

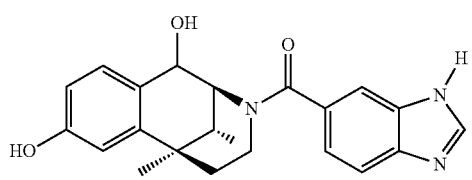 [SMILES: C[C@H]1[C@H]2C(O)c3ccc(O)cc3[C@]1(C)CCN2C(=O)c1ccc2nc[nH]c2c1]

(3H-Benzoimidazol-5-yl)-[(2S,6R,11R)-1,8-dihydroxy-6,11-dimethyl-1,2,5,6-tetrahydro-4H-2,6-methano-benzo[d]azocin-3-yl]-methanone Sodium borohydride (50 mg) is added to a solution of (2S,6R,11R)-3-(3H-benzoimidazole-5-carbonyl)-8-hydroxy-6,11-dimethyl-3,4,5,6-tetrahydro-2H-2,6-methano-benzo[d]azocin-1-one (50 g) in ethanol (3 mL). The resulting mixture is stirred at ambient temperature overnight. Then, the solution is cooled in an ice bath and 1 M hydrochloric acid (0.5 mL) is added. After stirring for 5 min, the resulting mixture is concentrated and the residue is purified by HPLC on reversed phase (MeCN/H₂O/NH₃).

Yield: 15 mg (30% of theory)
Mass spectrum (ESI⁺): m/z=378 [M+H]⁺
Procedure N (Described for Example 228, Table 3)

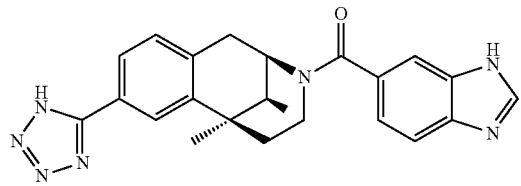 [SMILES: C[C@@H]1[C@H]2Cc3ccc(-c4nnn[nH]4)cc3[C@]1(C)CCN2C(=O)c1ccc2nc[nH]c2c1]

(3H-Benzoimidazol-5-yl)-[(2R,6R,11S)-6,11-dimethyl-8-(1H-tetrazol-5-yl)-1,2,5,6-tetrahydro-4H-2,6-methano-benzo[d]azocin-3-yl]-methanone A mixture of sodium azide (105 mg), NH₄Cl (87 mg), and (2R,6R,11S)-3-(3H-benzoimidazole-5-carbonyl)-6,11-dimethyl-1,2,3,4,5,6-hexahydro-2,6-methano-benzo[d]azocine-8-carbonitrile (0.30 g) in dimethylformamide (3 mL) is stirred at 100° C. overnight. Then, another portion of NaN₃ (50 mg) and NH₄Cl (40 mg) is added and the mixture is stirred at 110° C. for additional 14 h. After cooling to ambient temperature, the mixture is diluted with water and MeCN and purified by HPLC on reversed phase (MeCN/H₂O/NH₃).

Yield: 0.24 g (72% of theory)
Mass spectrum (ESI⁺): m/z=414 [M+H]⁺
Procedure O (Described for Example 229, Table 3)

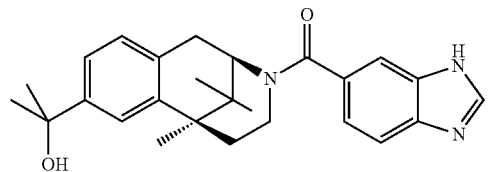 [SMILES: CC(C)(O)c1ccc2c(c1)[C@]1(C)CCN(C(=O)c3ccc4nc[nH]c4c3)[C@H](C2)C1(C)C]

(3H-Benzoimidazol-5-yl)-[(2R,6S)-8-(1-hydroxy-1-methyl-ethyl)-6,11,11-trimethyl-1,2,5,6-tetrahydro-4H-2,6-methano-benzo[d]azocin-3-yl]-methanone A solution of 1-[(2R,6S)-3-(3H-benzoimidazole-5-carbonyl)-6,11,11-trimethyl-1,2,3,4,5,6-hexahydro-2,6-methano-benzo[d]azocin-8-yl]-ethanone (0.10 g) in tetrahydrofuran (1 mL) is added to a solution of MeMgI (3 mol/L in Et₂O, 0.25 mL) in tetrahydrofuran (1 mL) chilled in an ice bath (ca. 0° C.). Then, the cooling bath is removed and the solution is stirred at room temperature. After 5 h of stirring, more MeMgI (3 mol/L in Et₂O, 0.25 mL) is added and the solution is stirred at 50° C. for 4 h. After cooling in an ice bath, aqueous NH₄Cl solution is added and the resulting mixture is extracted with ethyl acetate. The combined organic extracts are dried (MgSO₄) and the solvent is removed under reduced pressure. The residue is purified by HPLC on reversed phase (MeCN/H₂O).

Yield: 26 mg (25% of theory)
Mass spectrum (ESI⁺): m/z=418 [M+H]⁺
Procedure P (Described for Example 232, Table 3)

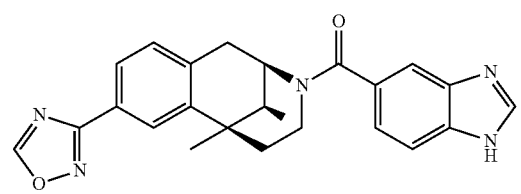 [SMILES: C[C@@H]1[C@H]2Cc3ccc(-c4ncon4)cc3[C@]1(C)CCN2C(=O)c1ccc2[nH]cnc2c1]

(1H-Benzoimidazol-5-yl)-[(2R,6R,11S)-6,11-dimethyl-8-[1,2,4]oxadiazol-3-yl-1,2,5,6-tetrahydro-4H-2,6-methano-benzo[d]azocin-3-yl]-methanone A mixture of triethyl orthoformate (4 mL) and (2R,6R,11S)-3-(1H-benzoimidazole-5-carbonyl)-N-hydroxy-6,11-dimethyl-1,2,3,4,5,6-hexahydro-2,6-methano-benzo[d]azocine-8-carboxamidine (0.25 g) is stirred at 100° C. for 6 h.

After cooling to room temperature, the mixture is concentrated and the residue is purified by HPLC on reversed phase (water/MeCN/NH$_3$) to give the title compound as a white solid.

Yield: 0.15 g (59% of theory)
Mass spectrum (ESI$^+$): m/z=414 [M+H]$^+$
Procedure Q (Described for Example 267, Table 3)

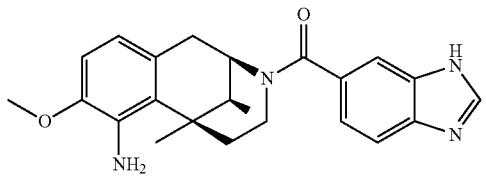 [SMILES: COc1ccc2c(c1N)[C@]1(C)CCN(C(=O)c3ccc4nc[nH]c4c3)[C@H](C2)[C@H]1C]

[(2R,6R,11S)-7-Amino-8-methoxy-6,11-dimethyl-1,2,5,6-tetrahydro-4H-2,6-methano-benzo[d]azocin-3-yl]-(3H-benzoimidazol-5-yl)-methanone A mixture of 10% palladium on carbon (1.0 g) and (3H-benzoimidazol-5-yl)-[(2R,6R,11S)-8-methoxy-6,11-dimethyl-7-nitro-1,2,5,6-tetrahydro-4H-2,6-methano-benzo[d]azocin-3-yl]-methanone (1.50 g) in methanol (20 mL) is shaken under hydrogen atmosphere at room temperature for 1 d. Then, the mixture is filtered and the filtrate is concentrated under reduced pressure to give the title compound as a foam-like solid.

Yield: 1.25 g (90% of theory)
Mass spectrum (ESI$^+$): m/z=391 [M+H]$^+$
Procedure R (Described for Example 270, Table 3)

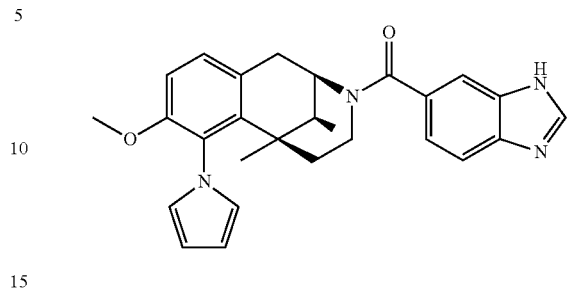

(3H-Benzoimidazol-5-yl)-[(2R,6R,11S)-8-methoxy-6,11-dimethyl-7-pyrrol-1-yl-1,2,5,6-tetrahydro-4H-2,6-methano-benzo[d]azocin-3-yl]-methanone A solution of [(2R,6R,11S)-7-amino-8-methoxy-6,11-dimethyl-1,2,5,6-tetrahydro-4H-2,6-methano-benzo[d]azocin-3-yl]-(3H-benzoimidazol-5-yl)-methanone (150 mg) and 2,5-dimethoxy-tetrahydrofuran (50 µL) in acetic acid (2 mL) is stirred at 110° C. for 3 h. After cooling to ambient temperature, the solution is diluted with water and extracted with ethyl acetate. The combined organic extracts are washed with brine and dried (MgSO$_4$). Then, the solvent is removed to afford the title compound as a foam-like solid.

Yield: 73 mg (43% of theory)
Mass spectrum (ESI$^+$): m/z=441 [M+H]$^+$

TABLE 3

| Example No. | Chemical Name/Structure/Remarks | Prepared in analogy to Procedure | Characterization |
|---|---|---|---|
| 1 | [(2R,6S)-10-Hydroxy-6,11,11-trimethyl-1,2,5,6-tetrahydro-4H-2,6-methano-benzo[d]azocin-3-yl]-phenyl-methanone | A | Mass spectrum (ESI$^+$): m/z =336 [M + H]$^+$ |
| 2 | (2-Chloro-phenyl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 370/372 (Cl) [M + H]$^+$ |

TABLE 3-continued

| Example No. | Chemical Name/Structure/Remarks | Prepared in analogy to Procedure | Characterization |
|---|---|---|---|
| 3 | 4-[(2R,6S)-10-Hydroxy-6,11,11-trimethyl-1,2,5,6-tetrahydro-4H-2,6-methano-benzo[d]azocine-3-carbonyl]benzamide | A | Mass spectrum (ESI$^+$): m/z = 379 [M + H]$^+$ |
| 4 | (3H-Benzoimidazol-5-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 376 [M + H]$^+$ |
| 5 | [(2R,6S)-10-Hydroxy-6,11,11-trimethyl-1,2,5,6-tetrahydro-4H-2,6-methano-benzo[d]azocin-3-yl]-o-tolyl-methanone | A | Mass spectrum (ESI$^+$): m/z = 350 [M + H]$^+$ |
| 6 | [(2R,6S)-10-Hydroxy-6,11,11-trimethyl-1,2,5,6-tetrahydro-4H-2,6-methano-benzo[d]azocin-3-yl]-(2-methoxy-phenyl)-methanone | A | Mass spectrum (ESI$^+$): m/z = 366 [M + H]$^+$ |
| 7 | [(2R,6S)-10-Hydroxy-6,11,11-trimethyl-1,2,5,6-tetrahydro-4H-2,6-methano-benzo[d]azocin-3-yl]-m-tolyl-methanone | A | Mass spectrum (ESI$^+$): m/z = 350 [M + H]$^+$ |

TABLE 3-continued

| Example No. | Chemical Name/Structure/Remarks | Prepared in analogy to Procedure | Characterization |
|---|---|---|---|
| 8 | 2-[(2R,6S)-10-Hydroxy-6,11,11-trimethyl-1,2,5,6-tetrahydro-4H-2,6-methano-benzo[d]azocine-3-carbonyl]-benzonitrile | A | Mass spectrum (ESI$^+$): m/z = 361 [M + H]$^+$ |
| 9 | N-{3-[(2R,6S)-10-Hydroxy-6,11,11-trimethyl-1,2,5,6-tetrahydro-4H-2,6-methano-benzo[d]azocine-3-carbonyl]-phenyl}-acetamide | A | Mass spectrum (ESI$^+$): m/z = 393 [M + H]$^+$ |
| 10 | 3-[(2R,6S)-10-Hydroxy-6,11,11-trimethyl-1,2,5,6-tetrahydro-4H-2,6-methano-benzo[d]azocine-3-carbonyl]-benzonitrile | A | Mass spectrum (ESI$^+$): m/z = 361 [M + H]$^+$ |
| 11 | [(2R,6S)-10-Hydroxy-6,11,11-trimethyl-1,2,5,6-tetrahydro-4H-2,6-methano-benzo[d]azocin-3-yl]-(3-methoxy-phenyl)-methanone | A | Mass spectrum (ESI$^+$): m/z = 366 [M + H]$^+$ |
| 12 | [(2R,6S)-10-Hydroxy-6,11,11-trimethyl-1,2,5,6-tetrahydro-4H-2,6-methano-benzo[d]azocin-3-yl]-p-tolyl-methanone | A | Mass spectrum (ESI$^+$): m/z = 350 [M + H]$^+$ |

TABLE 3-continued

| Example No. | Chemical Name/Structure/Remarks | Prepared in analogy to Procedure | Characterization |
|---|---|---|---|
| 13 | 4-[(2R,6S)-10-Hydroxy-6,11,11-trimethyl-1,2,5,6-tetrahydro-4H-2(6-methano-benzo[d]azocine-3-carbonyl]-benzonitrile | A | Mass spectrum (ESI$^+$): m/z = 361 [M + H]$^+$ |
| 14 | [(2R,6S)-10-Hydroxy-6,11,11-trimethyl-1,2,5,6-tetrahydro-4H-2,6-methano-benzo[d]azocin-3-yl]-(4-methoxy-phenyl)-methanone | A | Mass spectrum (ESI$^+$): m/z = 366 [M + H]$^+$ |
| 15 | N-{4-[(2R,6S)-10-Hydroxy-6,11,11-trimethyl-1,2,5,6-tetrahydro-4H-2,6-methano-benzo[d]azocine-3-carbonyl]-phenyl}-acetamide | A | Mass spectrum (ESI$^+$): m/z = 393 [M + H]$^+$ |
| 16 | [(2R,6S)-10-Hydroxy-6,11,11-trimethyl-1,2,5,6-tetrahydro-4H-2,6-methano-benzo[d]azocin-3-yl]-[4-(2,2,2-trifluoro-1-hydroxy-1-methyl-ethyl)-phenyl]-methanone | A | Mass spectrum (ESI$^+$): m/z = 448 [M + H]$^+$ |
| 17 | [(2R,6S)-10-Hydroxy-6,11,11-trimethyl-1,2,5,6-tetrahydro-4H-2,6-methano-benzo[d]azocin-3-yl]-(2-methyl-3H-benzoimidazol-5-yl)-methanone | A | Mass spectrum (ESI$^+$): m/z = 390 [M + H]$^+$ |

TABLE 3-continued

| Example No. | Chemical Name/Structure/Remarks | Prepared in analogy to Procedure | Characterization |
|---|---|---|---|
| 18 | (1H-Benzoimidazol-4-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 376 [M + H]$^+$ |
| 19 | [(2R,6S)-10-Hydroxy-6,11,11-trimethyl-1,2,5,6-tetrahydro-4H-2,6-methano-benzo[d]azocin-3-yl]-(1-methyl-1H-benzoimidazol-5-yl)-methanone | A | Mass spectrum (ESI$^+$): m/z = 390 [M + H]$^+$ |
| 20 | (2,3-Dihydro-benzo[1,4]dioxin-6-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 394 [M + H]$^+$ |
| 21 | (3H-Benzotriazol-5-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 377 [M + H]$^+$ |
| 22 | [(2R,6S)-10-Hydroxy-6,11,11-trimethyl-1,2,5,6-tetrahydro-4H-2,6-methano-benzo[d]azocin-3-yl]-(4-piperidin-1-ylmethyl-phenyl)-methanone | A | Mass spectrum (ESI$^+$): m/z = 433 [M + H]$^+$ |

TABLE 3-continued

| Example No. | Chemical Name/Structure/Remarks | Prepared in analogy to Procedure | Characterization |
|---|---|---|---|
| 23 | [(2R,6S)-10-Hydroxy-6,11,11-trimethyl-1,2,5,6-tetrahydro-4H-2,6-methano-benzo[d]azocin-3-yl]-[4-(4-methyl-piperazin-1-ylmethyl)-phenyl]-methanone 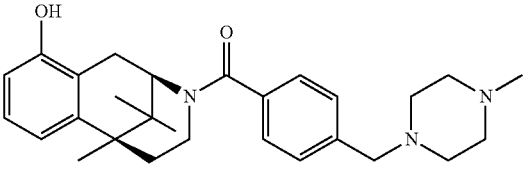 [SMILES: CN1CCN(Cc2ccc(C(=O)N3CC[C@@]4(C)c5cccc(O)c5C[C@@H]3C4(C)C)cc2)CC1] | A | Mass spectrum (ESI$^+$): m/z = 448 [M + H]$^+$ |
| 24 | [(2R,6S)-10-Hydroxy-6,11,11-trimethyl-1,2,5,6-tetrahydro-4H-2,6-methano-benzo[d]azocin-3-yl]-(4-morpholin-4-ylmethyl-phenyl)-methanone 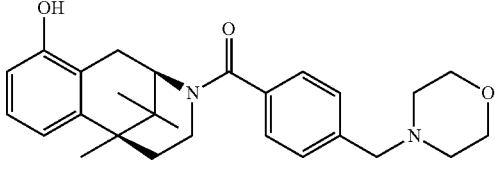 [SMILES: CC1(C)[C@H]2Cc3c(O)cccc3[C@]1(C)CCN2C(=O)c1ccc(CN2CCOCC2)cc1] | A | Mass spectrum (ESI$^+$): m/z = 435 [M + H]$^+$ |
| 25 | [(2R,6S)-10-Hydroxy-6,11,11-trimethyl-1,2,5,6-tetrahydro-4H-2,6-methano-benzo[d]azocin-3-yl]-(4-morpholin-4-yl-phenyl)-methanone 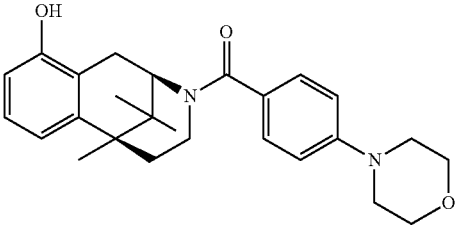 [SMILES: CC1(C)[C@H]2Cc3c(O)cccc3[C@]1(C)CCN2C(=O)c1ccc(N2CCOCC2)cc1] | A | Mass spectrum (ESI$^+$): m/z = 421 [M + H]$^+$ |
| 26 | [(2R,6S)-10-Hydroxy-6,11,11-trimethyl-1,2,5,6-tetrahydro-4H-2,6-methano-benzo[d]azocin-3-yl]-(4-piperazin-1-yl-phenyl)-methanone 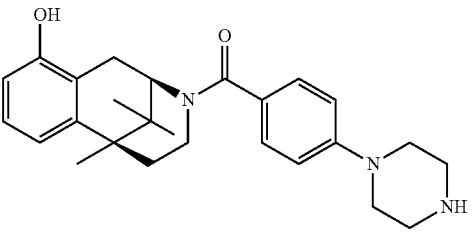 [SMILES: CC1(C)[C@H]2Cc3c(O)cccc3[C@]1(C)CCN2C(=O)c1ccc(N2CCNCC2)cc1]<br><br>The coupling product is obtained from 4-(4-carboxy-phenyl)-piperazine-1-carboxylic acid tert-butyl ester using procedure A. The tertbutyl ester is cleaved afterwards using the conditions described in Example XXVII. | A | Mass spectrum (ESI$^+$): m/z = 420 [M + H]$^+$ |

TABLE 3-continued

| Example No. | Chemical Name/Structure/Remarks | Prepared in analogy to Procedure | Characterization |
|---|---|---|---|
| 27 | N-{2-Fluoro-4-[(2R,6S)-10-hydroxy-6,11,11-trimethyl-1,2,5,6-tetrahydro-4H-2,6-methano-benzo[d]azocine-3-carbonyl]-phenyl}-acetamide | A | Mass spectrum (ESI$^+$): m/z = 411 [M + H]$^+$ |
| 28 | 1-{4-[(2R,6S)-10-Hydroxy-6,11,11-trimethyl-1,2,5,6-tetrahydro-4H-2,6-methano-benzo[d]azocine-3-carbonyl]-phenyl}-ethanone | A | Mass spectrum (ESI$^+$): m/z = 378 [M + H]$^+$ |
| 29 | 5-[(2R,6S)-10-Hydroxy-6,11,11-trimethyl-1,2,5,6-tetrahydro-4H-2,6-methano-benzo[d]azocine-3-carbonyl]-1-methyl-1,3-dihydro-benzoimidazol-2-one | A | Mass spectrum (ESI$^+$): m/z = 406 [M + H]$^+$ |
| 30 | 3-[(2R,6S)-10-Hydroxy-6,11,11-trimethyl-1,2,5,6-tetrahydro-4H-2,6-methano-benzo[d]azocine-3-carbonyl]-benzoic acid methyl ester | A | Mass spectrum (ESI$^+$): m/z = 394 [M + H]$^+$ |
| 31 | [(2R,6S)-10-Hydroxy-6,11,11-trimethyl-1,2,5,6-tetrahydro-4H-2,6-methano-benzo[d]azocin-3-yl]-(1H-indol-6-yl)-methanone | A | Mass spectrum (ESI$^+$): m/z = 375 [M + H]$^+$ |

TABLE 3-continued

| Example No. | Chemical Name/Structure/Remarks | Prepared in analogy to Procedure | Characterization |
|---|---|---|---|
| 32 | [3-Ethynyl-4-(pyrrolidine-1-carbonyl)-phenyl]-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 457 [M + H]$^+$ |
| 33 | 6-[(2R,6S)-10-Hydroxy-6,11,11-trimethyl 1,2,5,6-tetrahydro-4H-2,6-methano-benzo[d]azocine-3-carbonyl]-1,3-dihydro-indol-2-one | A | Mass spectrum (ESI$^+$): m/z = 391 [M + H]$^+$ |
| 34 | 7-[(2R,6S)-10-Hydroxy-6,11,11-trimethyl-1,2,5,6-tetrahydro-4H-2,6-methano-benzo[d]azocine-3-carbonyl]-2-methyl-3H-quinazolin-4-one | A | Mass spectrum (ESI$^+$): m/z = 418 [M + H]$^+$ |
| 35 | [(2R,6S)-10-Hydroxy-6,11,11-trimethyl-1,2,5,6-tetrahydro-4H-2,6-methano-benzo[d]azocin-3-yl]-[3-methyl-4-(pyrrolidine-1-carbonyl)-phenyl]-methanone | A | Mass spectrum (ESI$^+$): m/z = 447 [M + H]$^+$ |

TABLE 3-continued

| Example No. | Chemical Name/Structure/Remarks | Prepared in analogy to Procedure | Characterization |
|---|---|---|---|
| 36 | 4-[(2R,6S)-10-Hydroxy-6,11,11-trimethyl-1,2,5,6-tetrahydro-4H-2,6-methano-benzo[d]azocine-3-carbonyl]-N-methyl-benzamide | A | Mass spectrum (ESI$^+$): m/z = 393 [M + H]$^+$ |
| 37 | 4-[(2R,6S)-10-Hydroxy-6,11,11-trimethyl-1,2,5,6-tetrahydro-4H-2,6-methano-benzo[d]azocine-3-carbonyl]-N,N-dimethyl-benzamide | A | Mass spectrum (ESI$^+$): m/z = 407 [M + H]$^+$ |
| 38 | 3-[(2R,6S)-10-Hydroxy-6,11,11-trimethyl-1,2,5,6-tetrahydro-4H-2,6-methano-benzo[d]azocine-3-carbonyl]-N,N-dimethyl-benzamide | A | Mass spectrum (ESI$^+$): m/z = 407 [M + H]$^+$ |
| 39 | 3-[(2R,6S)-10-Hydroxy-6,11,11-trimethyl-1,2,5,6-tetrahydro-4H-2,6-methano-benzo[d]azocine-3-carbonyl]-N-methyl-benzamide | A | Mass spectrum (ESI$^+$): m/z = 393 [M + H]$^+$ |
| 40 | [(2R,6S)-10-Hydroxy-6,11,11-trimethyl-1,2,5,6-tetrahydro-4H-2,6-methano-benzo[d]azocin-3-yl]-[3-((R)-2-methoxymethyl-pyrrolidine-1-carbonyl)-phenyl]-methanone | A | Mass spectrum (ESI$^+$): m/z = 477 [M + H]$^+$ |

TABLE 3-continued

| Example No. | Chemical Name/Structure/Remarks | Prepared in analogy to Procedure | Characterization |
| --- | --- | --- | --- |
| 41 | 3-[(2R,6S)-10-Hydroxy-6,11,11-trimethyl-1,2,5,6-tetrahydro-4H-2,6-methano-benzo[d]azocine-3-carbonyl]-benzamide | A | Mass spectrum (ESI$^+$): m/z = 379 [M + H]$^+$ |
| 42 | 3-Chloro-5-[(2R,6S)-10-hydroxy-6,11,11-trimethyl-1,2,5,6-tetrahydro-4H-2,6-methano-benzo[d]azocine-3-carbonyl]-benzoic acid methyl ester | A | Mass spectrum (ESI$^+$): m/z = 428/430 (Cl) [M + H]$^+$ |
| 43 | 3-Fluoro-5-[(2R,6S)-10-hydroxy-6,11,11-trimethyl-1,2,5,6-tetrahydro-4H-2,6-methano-benzo[d]azocine-3-carbonyl]-benzoic acid methyl ester | A | Mass spectrum (ESI$^+$): m/z = 412 [M + H]$^+$ |
| 44 | 6-[(2R,6S)-10-Hydroxy-6,11,11-trimethyl-1,2,5,6-tetrahydro-4H-2,6-methano-benzo[d]azocine-3-carbonyl]-3,4-dihydro-1H-quinoxalin-2-one | A | Mass spectrum (ESI$^+$): m/z = 406 [M + H]$^+$ |
| 45 | Benzothiazol-5-yl-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 393 [M + H]$^+$ |

TABLE 3-continued

| Example No. | Chemical Name/Structure/Remarks | Prepared in analogy to Procedure | Characterization |
|---|---|---|---|
| 46 | Benzothiazol-6-yl-[(2R,6S)-10-hydroxy-6,11,11-trimethyl-1,2,5,6-tetrahydro-4H-2,6-methano-benzo[d]azocin-3-yl]-methanone | A | Mass spectrum (ESI+): m/z = 393 [M + H]+ |
| 47 | 8-[(2R,6S)-10-Hydroxy-6,11,11-trimethyl-1,2,5,6-tetrahydro-4H-2,6-methano-benzo[d]azocine-3-carbonyl]-3,4-dihydro-1H-benzo[e][1,4]diazepine-2,5-dione | A | Mass spectrum (ESI+): m/z = 434 [M + H]+ |
| 48 | [(2R,6S)-10-Hydroxy-6,11,11-trimethyl-1,2,5,6-tetrahydro-4H-2,6-methano-benzo[d]azocin-3-yl]-(4-methylamino-phenyl)-methanone | A | Mass spectrum (ESI+): m/z = 365 [M + H]+ |
| 49 | [(2R,6S)-10-Hydroxy-6,11,11-trimethyl-1,2,5,6-tetrahydro-4H-2,6-methano-benzo[d]azocin-3-yl]-(1H-indol-5-yl)-methanone | A | Mass spectrum (ESI+): m/z = 375 [M + H]+ |
| 50 | 4-[(2R,6S)-10-Hydroxy-6,11,11-trimethyl-1,2,5,6-tetrahydro-4H-2,6-methano-benzo[d]azocine-3-carbonyl]-benzoic acid methyl ester | A | Mass spectrum (ESI+): m/z = 394 [M + H]+ |

TABLE 3-continued

| Example No. | Chemical Name/Structure/Remarks | Prepared in analogy to Procedure | Characterization |
|---|---|---|---|
| 51 | (3H-Benzoimidazol-5-yl)-(8-hydroxy-6-methyl-1,2,5,6-tetrahydro-4H-2,6-methano-benzo[d]azocin-3-yl)-methanone | A | Mass spectrum (ESI+): m/z = 348 [M + H]+ |
| 52 | (3H-Benzoimidazol-5-yl)-[(2R,6R,11S)-8-hydroxy-6,11-dimethyl-1,2,5,6-tetrahydro-4H-2,6-methano-benzo[d]azocin-3-yl]-methanone | A | Mass spectrum (ESI+): m/z = 362 [M + H]+ |
| 53 | (3H-Benzoimidazol-5-yl)-[(2S,6S,11R)-8-hydroxy-6,11-dimethyl-1,2,5,6-tetrahydro-4H-2,6-methano-benzo[d]azocin-3-yl]-methanone | A | Mass spectrum (ESI+): m/z = 362 [M + H]+ |
| 54 | (3H-Benzoimidazol-5-yl)-(8-hydroxy-6,11-dimethyl-1,2,5,6-tetrahydro-4H-2,6-methano-benzo[d]azocin-3-yl)-methanone | A | Mass spectrum (ESI+): m/z = 362 [M + H]+ |
| 55 | (3H-Benzoimidazol-5-yl)-(8-hydroxy-1,2,5,6-tetrahydro-4H-2,6-methano-benzo[d]azocin-3-yl)-methanone | A | Mass spectrum (ESI+): m/z = 334 [M + H]+ |
| 56 | (3H-Benzoimidazol-5-yl)-(6,8-dihydroxy-11,11-dimethyl-1,2,5,6-tetrahydro-4H-4,6-methano-benzo[d]azocin-3-yl)-methanone | A | Mass spectrum (ESI+): m/z = 378 [M + H]+ |

TABLE 3-continued

| Example No. | Chemical Name/Structure/Remarks | Prepared in analogy to Procedure | Characterization |
|---|---|---|---|
| 57 | (3H-Benzoimidazol-5-yl)-(6-hydroxy-11,11-dimethyl-1,2,5,6-tetrahydro-4H-2,6-methano-benzo[d]azocin-3-yl)-methanone | A | Mass spectrum (ESI$^+$): m/z = 362 [M + H]$^+$ |
| 58 | (3H-Benzoimidazol-5-yl)-(8-hydroxy-6,11,11-trimethyl-1,2,5,6-tetrahydro-4H-2,6-methano-benzo[d]azocin-3-yl)-methanone | A | Mass spectrum (ESI$^+$): m/z = 376 [M + H]$^+$ |
| 59 | (3H-Benzoimidazol-5-yl)-(9-hydroxy-6,11,11-trimethyl-1,2,5,6-tetrahydro-4H-2,6-methano-benzo[d]azocin-3-yl)-methanone | A | Mass spectrum (ESI$^+$): m/z = 376 [M + H]$^+$ |
| 60 | (3H-Benzoimidazol-5-yl)-(1,2,5,6-tetrahydro-4H-2,6-methano-benzo[d]azocin-3-yl)-methanone | A | Mass spectrum (ESI$^+$): m/z = 318 [M + H]$^+$ |
| 61 | (3H-Benzoimidazol-5-yl)-[(2S,6R)-8-methoxy-6,9,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 404 [M + H]$^+$ |

TABLE 3-continued

| Example No. | Chemical Name/Structure/Remarks | Prepared in analogy to Procedure | Characterization |
|---|---|---|---|
| 62 | (3H-Benzoimidazol-5-yl)-[(2R,6S)-8-methoxy-6,9,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 404 [M + H]$^+$ |
| 63 | (3H-Benzoimidazol-5-yl)-[(2R,6S)-9-methoxy-6,8,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 404 [M + H]$^+$ |
| 64 | (3H-Benzoimidazol-5-yl)-[(2S,6R)-9-methoxy-6,8,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 404 [M + H]$^+$ |

TABLE 3-continued

| Example No. | Chemical Name/Structure/Remarks | Prepared in analogy to Procedure | Characterization |
|---|---|---|---|
| 65 | (3H-Benzoimidazol-5-yl)-[(2R,6S)-8-hydroxy-6,9,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 390 [M + H]$^+$ |
| 66 | (3H-Benzoimidazol-5-yl)-[(2S,6R)-8-hydroxy-6,9,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 390 [M + H]$^+$ |
| 67 | (3H-Benzoimidazol-5-yl)-[(2R,6S)-9-hydroxy-6,8,11,11-tetramethyl-1,2,5,6-tetrahydro-4H-2,6-methano-benzo[d]azocin-a 3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 390 [M + H]$^+$ |
| 68 | (3H-Benzoimidazol-5-yl)-[(2S,6R)-9-hydroxy-6,8,11,11-tetramethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 390 [M + H]$^+$ |

TABLE 3-continued

| Example No. | Chemical Name/Structure/Remarks | Prepared in analogy to Procedure | Characterization |
| --- | --- | --- | --- |
| 69 | (3H-Benzoimidazol-5-yl)-(6,8,11,11-tetramethyl-1,2,5,6-tetrahydro-4H-2,6-methano-benzo[d]azocin-3-yl)-methanone | A | Mass spectrum (ESI$^+$): m/z = 374 [M + H]$^+$ |
| 70 | (3H-Benzoimidazol-5-yl)-(8-fluoro-6,11,11-trimethyl-1,2,5,6-tetrahydro-4H-2,6-methano-benzo[d]azocin-3-yl)-methanone | A | Mass spectrum (ESI$^+$): m/z = 378 [M + H]$^+$ |
| 71 | (3H-Benzoimidazol-5-yl)-(9-hydroxy-8-methoxy-6,11,11-trimethyl-1,2,5,6-tetrahydro-4H-2,6-methano-benzo[d]azocin-3-yl)-methanone | A | Mass spectrum (ESI$^+$): m/z = 406 [M + H]$^+$ |
| 72 | (3H-Benzoimidazol-5-yl)-(8,9-dimethoxy-6,11,11-trimethyl-1,2,5,6-tetrahydro-4H-2,6-methano-benzo[d]azocin-3-yl)-methanone | A | Mass spectrum (ESI$^+$): m/z = 420 [M + H]$^+$ |
| 73 | (3H-Benzoimidazol-5-yl)-(8-hydroxy-9-methoxy-6,11,11-trimethyl-1,2,5,6-tetrahydro-4H-2,6-methano-benzo[d]azocin-3-yl)-methanone | A | Mass spectrum (ESI$^+$): m/z = 406 [M + H]$^+$ |
| 74 | (3H-Benzoimidazol-5-yl)-[(2R,6S)-9-methoxy-6,11,11-trimethyl-1,2,5,6-tetrahydro-4H-2,6-methano-benzo[d]azocin-3-yl]-methanone | A | Mass spectrum (ESI$^+$): m/z = 390 [M + H]$^+$ |

TABLE 3-continued

| Example No. | Chemical Name/Structure/Remarks | Prepared in analogy to Procedure | Characterization |
|---|---|---|---|
| 75 | (3H-Benzoimidazol-5-yl)-(8-chloro-6,11,11-trimethyl-1,2,5,6-tetrahydro-4H-2,6-methano-benzo[d]azocin-3-yl)-methanone | A | Mass spectrum (ESI$^+$): m/z = 394/396 (Cl) [M + H]$^+$ |
| 76 | (3H-Benzoimidazol-5-yl)-[(2R,6S)-10-methoxy-6,11,11-trimethyl-1,2,5,6-tetrahydro-4H-2,6-methano-benzo[d]azocin-3-yl]-methanone | A | Mass spectrum (ESI$^+$): m/z = 390 [M + H]$^+$ |
| 77 | (3H-Benzoimidazol-5-yl)-(6,11-dimethyl-1,2,5,6-tetrahydro-4H-2,6-methano-benzo[d]azocin-3-yl)-methanone<br><br>compound is a racemic mixture of the pure diastereomer shown | A | Mass spectrum (ESI$^+$): m/z = 346 [M + H]$^+$ |
| 78 | (3H-Benzoimidazol-5-yl)-(7-hydroxy-6,11,11-trimethyl-1,2,5,6-tetrahydro-4H-2,6-methano-benzo[d]azocin-3-yl)-methanone | A | Mass spectrum (ESI$^+$): m/z = 376 [M + H]$^+$ |
| 79 | (3H-Benzoimidazol-5-yl)-[(2S,6R)-8-hydroxy-6,11,11-trimethyl-1,2,5,6-tetrahydro-4H-2,6-methano-benzo[d]azocin-3-yl]-methanone | A | Mass spectrum (ESI$^+$): m/z = 376 [M + H]$^+$ |

TABLE 3-continued

| Example No. | Chemical Name/Structure/Remarks | Prepared in analogy to Procedure | Characterization |
|---|---|---|---|
| 80 | (3H-Benzoimidazol-5-yl)-[(2R,6S)-8-hydroxy-6,11,11-trimethyl-1,2,5,6-tetrahydro-4H-2,6-methano-benzo[d]azocin-3-yl]-methanone | A | Mass spectrum (ESI$^+$): m/z = 376 [M + H]$^+$ |
| 81 | [(2R,6S)-10-Hydroxy-6,11,11-trimethyl-1,2,5,6-tetrahydro-4H-2,6-methano-benzo[d]azocin-3-yl]-(3-methyl-3H-benzoimidazol-5-yl)-methanone | A | Mass spectrum (ESI$^+$): m/z = 390 [M + H]$^+$ |
| 82 | (3H-Benzoimidazol-5-yl)-[(2R,6S)-6,11,11-trimethyl-1,2,5,6-tetrahydro-4H-2,6-methano-benzo[d]azocin-3-yl]-methanone<br><br>The compound is obtained after resolution of the racemic mixture using HPLC on chiral phase or using the enantiomerically pure starting material that in turn is obtained by resolution of the racemic mixture using HPLC on chiral phase. | A | Mass spectrum (ESI$^+$): m/z = 360 [M + H]$^+$ |
| 83 | (3H-Benzoimidazol-5-yl)-[(2S,6R,11R)-1,8-dihydroxy-6,11-dimethyl-1,2,5,6-tetrahydro-4H-2,6-methano-benzo[d]azocin-3-yl]-methanone | M | Mass spectrum (ESI$^+$): m/z = 378 [M + H]$^+$ |
| 84 | (2R,6R,11S)-3-(3H-Benzoimidazole-5-carbonyl)-6,11-dimethyl-1,2,3,4,5,6-hexahydro-2,6-methano-benzo[d]azocine-8-carbonitrile | A | Mass spectrum (ESI$^+$): m/z = 371 [M + H]$^+$ |

TABLE 3-continued

| Example No. | Chemical Name/Structure/Remarks | Prepared in analogy to Procedure | Characterization |
|---|---|---|---|
| 85 | (3H-Benzoimidazol-5-yl)-(6,11-diethyl-8-hydroxy-1,2,5,6-tetrahydro-4H-2,6-methano-benzo[d]azocin-3-yl)-methanone<br><br>compound is a racemic mixture of the diastereomer shown | A | Mass spectrum (ESI+): m/z = 390 [M + H]+ |
| 86 | (3H-Benzoimidazol-5-yl)-(6,11-diethyl-8-hydroxy-1,2,5,6-tetrahydro-4H-2,6-methano-benzo[d]azocin-3-yl)-methanone<br><br>compound is a racemic mixture of the diastereomer shown | A | Mass spectrum (ESI+): m/z = 390 [M + H]+ |
| 87 | (3H-Benzoimidazol-5-yl)-(6-ethyl-8-hydroxy-11-methyl-1,2,5,6-tetrahydro-4H-2,6-methano-benzo[d]azocin-3-yl)-methanone<br><br>compound is a racemic mixture of the diastereomer shown | A | Mass spectrum (ESI+): m/z = 376 [M + H]+ |
| 88 | (3H-Benzoimidazol-5-yl)-(8-hydroxy-6-propyl-1,2,5,6-tetrahydro-4H-2,6-methano-benzo[d]azocin-3-yl)-methanone | A | Mass spectrum (ESI+): m/z = 376 [M + H]+ |
| 89 | (3H-Benzoimidazol-5-yl)-(6-ethyl-8-hydroxy-11,11-dimethyl-1,2,5,6-tetrahydro-4H-2,6-methano-benzo[d]azocin-3-yl)-methanone | A | Mass spectrum (ESI+): m/z = 390 [M + H]+ |

TABLE 3-continued

| Example No. | Chemical Name/Structure/Remarks | Prepared in analogy to Procedure | Characterization |
|---|---|---|---|
| 90 | (3H-Benzoimidazol-5-yl)-(6-ethyl-8-hydroxy-1,2,5,6-tetrahydro-4H-2,6-methano-benzo[d]azocin-3-yl)-methanone | A | Mass spectrum (ESI$^+$): m/z = 362 [M + H]$^+$ |
| 91 | (2R,6R,11S)-3-(3H-Benzoimidazole-5-carbonyl)-6,11-dimethyl-1,2,3,4,5,6-hexahydro-2,6-methano-benzo[d]azocine-8-carboxylic acid ethyl ester | A | Mass spectrum (ESI$^+$): m/z = 418 [M + H]$^+$ |
| 92 | Benzothiazol-6-yl-(8-hydroxy-6-methyl-1,2,5,6-tetrahydro-4H-2,6-methano-benzo[d]azocin-3-yl)-methanone | A | Mass spectrum (ESI$^+$): m/z = 365 [M + H]$^+$ |
| 93 | (2R,6S)-3-(3H-Benzoimidazole-5-carbonyl)-6,11,11-trimethyl-1,2,3,4,5,6-hexahydro-2,6-methano-benzo[d]azocine-10-carbonitrile | A | Mass spectrum (ESI$^+$): m/z = 385 [M + H]$^+$ |

| Example No. | Chemical Name/Structure/Remarks | Prepared in analogy to Procedure | Characterization |
|---|---|---|---|
| 94 | 3-(Benzothiazole-6-carbonyl)-8-hydroxy-2,3,4,5-tetrahydro-1H-2,6-methano-benzo[d]azocine-6-carboxylic acid methyl ester<br><br>The compound may also be obtained from 8-acetoxy-2,3,4,5-tetrahydro-1H-2,6-methano-benzo[d]azocine-6-carboxylic acid methyl ester and treating the amide coupling product with $K_2CO_3$ in methanol to remove the acetyl group from the phenolic oxygen. | A | Mass spectrum (ESI$^+$): m/z = 409 [M + H]$^+$ |
| 95 | (2R,6S)-3-(1H-Benzoimidazole-5-carbonyl)-6,11,11-trimethyl-1,2,3,4,5,6-hexahydro-2,6-methano-benzo[d]azocine-10-carboxylic acid ethyl ester | A | Mass spectrum (ESI$^+$): m/z = 432 [M + H]$^+$ |
| 96 | 3-(1H-Benzoimidazole-5-carbonyl)-6,11,11-trimethyl-1,2,3,4,5,6-hexahydro-2,6-methano-benzo[d]azocine-9-carbonitrile | A | Mass spectrum (ESI$^+$): m/z = 385 [M + H]$^+$ |
| 97 | 3-(1H-Benzoimidazole-5-carbonyl)-6,11,11-trimethyl-1,2,3,4,5,6-hexahydro-2,6-methano-benzo[d]azocine-9-carboxylic acid ethyl ester | A | Mass spectrum (ESI$^+$): m/z = 432 [M + H]$^+$ |

TABLE 3-continued

| Example No. | Chemical Name/Structure/Remarks | Prepared in analogy to Procedure | Characterization |
|---|---|---|---|
| 98 | (3H-Benzoimidazol-5-yl)-(1-methyl-11-aza-tricyclo[8.3.1.0*2,7*]tetradeca-2,4,6-trien-11-yl)-methanone | A | Mass spectrum (ESI$^+$): m/z = 346 [M + H]$^+$ |
| 99 | (3H-Benzoimidazol-5-yl)-(4-methoxy-9-aza-tricyclo[6.3.1.0*2,7*]dodeca-2,4,6-trien-9-yl)-methanone | A | Mass spectrum (ESI$^+$): m/z = 334 [M + H]$^+$ |
| 100 | (3H-Benzoimidazol-5-yl)-(4-hydroxy-9-aza-tricyclo[6.3.1.0*2,7*]dodeca-2,4,6-trien-9-yl)-methanone | A | Mass spectrum (ESI$^+$): m/z = 320 [M + H]$^+$ |
| 101 | [(2R,6S)-4-10-Hydroxy-6,11,11-trimethyl-1,2,5,6-tetrahydro-4H-2,6-methano-benzo[d]azocine-3-carbonyl]-benzoic acid<br><br>The compound is synthesized using terephthalic acid mono-tert-butyl ester as the coupling partner in analogy to the procedure A. Subsequently, the tert-butyl ester function is cleaved using trifluoroacetic acid in dichloromethane. | A | Mass spectrum (ESI$^+$): m/z = 380 [M + H]$^+$ |

TABLE 3-continued

| Example No. | Chemical Name/Structure/Remarks | Prepared in analogy to Procedure | Characterization |
| --- | --- | --- | --- |
| 102 | (3H-Benzoimidazol-5-yl)-[(2R,6S)-6,11,11-trimethyl-9-phenyl-1,2,5,6-tetrahydro-4H-2,6-methano-benzo[d]azocin-3-yl]-methanone | A | Mass spectrum (ESI$^+$): m/z = 436 [M + H]$^+$ |
| 103 | (3H-Benzoimidazol-5-yl)-(6-methoxy-11,11-dimethyl-1,2,5,6-tetrahydro-4H-2,6-methano-benzo[d]azocin-3-yl)-methanone | A | Mass spectrum (ESI$^+$): m/z = 376 [M + H]$^+$ |
| 104 | [(2R,6S)-10-Methoxy-6,11,11-trimethyl-1,2,5,6-tetrahydro-4H-2,6-methano-benzo[d]azocin-3-yl]-(2-methyl-furan-3-yl)-methanone | A | Mass spectrum (ESI$^+$): m/z = 354 [M + H]$^+$ |
| 105 | (8-Hydroxy-6,11-dimethyl-1,2,5,6-tetrahydro-4H-2,6-methano-benzo[d]azocin-3-yl)-phenyl-methanone | A | Mass spectrum (ESI$^+$): m/z = 322 [M + H]$^+$ |
| 106 | (8-Hydroxy-6,11-dimethyl-1,2,5,6-tetrahydro-4H-2,6-methano-benzo[d]azocin-3-yl)-o-tolyl-methanone | A | Mass spectrum (ESI$^+$): m/z = 336 [M + H]$^+$ |

TABLE 3-continued

| Example No. | Chemical Name/Structure/Remarks | Prepared in analogy to Procedure | Characterization |
|---|---|---|---|
| 107 | [(2R,6R,11R)-8-Methoxy-6,11-dimethyl-1,2,5,6-tetrahydro-4H-2,6-methano-benzo[d]azocin-3-yl]-pyridin-3-yl-methanone | A | Mass spectrum (ESI$^+$): m/z = 337 [M + H]$^+$ |
| 108 | [(2R,6R,11R)-8-Methoxy-6,11-dimethyl-1,2,5,6-tetrahydro-4H-2,6-methano-benzo[d]azocin-3-yl]-(2-nitro-phenyl)-methanone | A | Mass spectrum (ESI$^+$): m/z = 381 [M + H]$^+$ |
| 109 | [(2R,6R,11R)-8-Methoxy-6,11-dimethyl-1,2,5,6-tetrahydro-4H-2,6-methano-benzo[d]azocin-3-yl]-o-tolyl-methanone | A | Mass spectrum (ESI$^+$): m/z = 350 [M + H]$^+$ |
| 110 | Furan-2-yl-[(2R,6R,11R)-8-methoxy-6,11-dimethyl-1,2,5,6-tetrahydro-4H-2,6-methano-benzo[d]azocin-3-yl]-methanone | A | Mass spectrum (ESI$^+$): m/z = 326 [M + H]$^+$ |
| 111 | [(2R,6R,11R)-8-Methoxy-6,11-dimethyl-1,2,5,6-tetrahydro-4H-2,6-methano-benzo[d]azocin-3-yl]-(3-methyl-furan-2-yl)-methanone | A | Mass spectrum (ESI$^+$): m/z = 340 [M + H]$^+$ |
| 112 | [(2R,6R,11R)-8-Hydroxy-6,11-dimethyl-1,2,5,6-tetrahydro-4H-2,6-methano-benzo[d]azocin-3-yl]-(3-methyl-furan-2-yl)-methanone | A | Mass spectrum (ESI$^+$): m/z = 326 [M + H]$^+$ |

TABLE 3-continued

| Example No. | Chemical Name/Structure/Remarks | Prepared in analogy to Procedure | Characterization |
|---|---|---|---|
| 113 | Furan-2-yl-[(2R,6R,11R)-8-hydroxy-6,11-dimethyl-1,2,5,6-tetrahydro-4H-2,6-methano-benzo[d]azocin-3-yl]-methanone | A | Mass spectrum (ESI$^+$): m/z = 312 [M + H]$^+$ |
| 114 | [(2R,6R,11R)-8-Hydroxy-6,11-dimethyl-1,2,5,6-tetrahydro-4H-2,6-methano-benzo[d]azocin-3-yl]pyridin-3-yl-methanone | A | Mass spectrum (ESI$^+$): m/z = 323 [M + H]$^+$ |
| 115 | [(2R,6R,11R)-8-Hydroxy-6,11-dimethyl-1,2,5,6-tetrahydro-4H-2,6-methano-benzo[d]azocin-3-yl]-(2-nitro-phenyl)-methanone | A | Mass spectrum (ESI$^+$): m/z = 367 [M + H]$^+$ |
| 116 | [(2R,6S)-10-Hydroxy-6,11,11-trimethyl-1,2,5,6-tetrahydro-4H-2,6-methano-benzo[d]azocin-3-yl]-(1H-indol-2-yl)-methanone | A | Mass spectrum (ESI$^+$): m/z = 375 [M + H]$^+$ |
| 117 | (4-Aminomethyl-phenyl)-[(2R,6S)-10-hydroxy-6,11,11-trimethyl-1,2,5,6-tetrahydro-4H-2,6-methano-benzo[d]azocin-3-yl]-methanone<br><br>The acid coupling partner is 4-(tert-butoxycarbonylamino-methyl)-benzoic acid that is liberated from the tert-butoxycarbonyl residue after the amide formation by treatment with trifluoroacetic acid in dichloromethane | A | Mass spectrum (ESI$^+$): m/z = 365 [M + H]$^+$ |

TABLE 3-continued

| Example No. | Chemical Name/Structure/Remarks | Prepared in analogy to Procedure | Characterization |
|---|---|---|---|
| 118 | [(2R,6S)-10-Hydroxy-6,11,11-trimethyl-1,2,5,6-tetrahydro-4H-2,6-methano-benzo[d]azocin-3-yl]-(1H-indol-3-yl)-methanone | A | Mass spectrum (ESI$^+$): m/z = 375 [M + H]$^+$ |
| 119 | (4-Diethylaminomethyl-phenyl)-[(2R,6S)-10-hydroxy-6,11,11-trimethyl-1,2,5,6-tetrahydro-4H-2,6-methano-benzo[d]azocin-3-yl]-methanone<br><br>The compound is isolated as the trifluoroacetic acid salt | A | Mass spectrum (ESI$^+$): m/z = 421 [M + H]$^+$ |
| 120 | [(2R,6S)-10-Hydroxy-6,11,11-trimethyl-1,2,5,6-tetrahydro-4H-2,6-methano-benzo[d]azocin-3-yl]-(4-pyrrolidin-1-ylmethyl-phenyl)-methanone<br><br>The compound is isolated as the trifluoroacetic acid salt | A | Mass spectrum (ESI$^+$): m/z = 419 [M + H]$^+$ |
| 121 | (3,5-Dimethyl-isoxazo-4-yl-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 355 [M + H]$^+$ |

TABLE 3-continued

| Example No. | Chemical Name/Structure/Remarks | Prepared in analogy to Procedure | Characterization |
|---|---|---|---|
| 122 | 1-{4-[(2R,6S)-10-Hydroxy-6,11,11-trimethyl-1,2,5,6-tetrahydro-4H-2,6-methano-benzo[d]azocine-3-carbonyl]-2-methoxy-benzyl}-pyrrolidin-2-one | A | Mass spectrum (ESI$^+$): m/z = 463 [M + H]$^+$ |
| 123 | [(2R,6S)-10-Hydroxy-6,11,11-trimethyl-1,2,5,6-tetrahydro-4H-2,6-methano-benzo[d]azocin-3-yl]-(4-imidazol-1-ylmethyl-phenyl)-methanone<br><br>The compound is isolated as the trifluoroacetic acid salt. | A | Mass spectrum (ESI$^+$): m/z = 416 [M + H]$^+$ |
| 124 | (1,5-Dimethyl-1H-pyrazol-3-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 354 [M + H]$^+$ |
| 125 | N-{4-[(2R,6S)-10-Hydroxy-6,11,11-trimethyl-1,2,5,6-tetrahydro-4H-2,6-methano-benzo[d]azocine-3-carbonyl]-benzyl}-benzamide | A | Mass spectrum (ESI$^+$): m/z = 469 [M + H]$^+$ |

TABLE 3-continued

| Example No. | Chemical Name/Structure/Remarks | Prepared in analogy to Procedure | Characterization |
|---|---|---|---|
| 126 | [(2R,6S)-10-Hydroxy-6,11,11-trimethyl-1,2,5,6-tetrahydro-4H-2,6-methano-benzo[d]azocin-3-yl]-pyridin-4-yl-methanone | A | Mass spectrum (ESI$^+$): m/z = 337 [M + H]$^+$ |
| 127 | [(2R,6S)-10-Hydroxy-6,11,11-trimethyl-1,2,5,6-tetrahydro-4H-2,6-methano-benzo[d]azocin-3-yl]-pyridin-3-yl-methanone | A | Mass spectrum (ESI$^+$): m/z = 337 [M + H]$^+$ |
| 128 | [(2R,6S)-10-Hydroxy-6,11,11-trimethyl-1,2,5,6-tetrahydro-4H-2,6-methano-benzo[d]azocin-3-yl]-pyridin-2-yl-methanone | A | Mass spectrum (ESI$^+$): m/z = 337 [M + H]$^+$ |
| 129 | [(2R,6S)-10-Hydroxy-6,11,11-trimethyl-1,2,5,6-tetrahydro-4H-2,6-methano-benzo[d]azocin-3-yl]-pyrimidin-4-yl-methanone | A | Mass spectrum (ESI$^+$): m/z = 338 [M + H]$^+$ |
| 130 | 1-{4-[(2R,6S)-10-Hydroxy-6,11,11-trimethyl-1,2,5,6-tetrahydro-4H-2,6-methano-benzo[d]azocine-3-carbonyl]-benzyl}-pyrrolidin-2-one | A | Mass spectrum (ESI$^+$): m/z = 432 [M + H]$^+$ |

TABLE 3-continued

| Example No. | Chemical Name/Structure/Remarks | Prepared in analogy to Procedure | Characterization |
|---|---|---|---|
| 131 | [(2R,6S)-10-Hydroxy-6,11,11-trimethyl-1,2,5,6-tetrahydro-4H-2,6-methano-benzo[d]azocin-3-yl]-(4-[1,2,4]triazol-1-ylmethyl-phenyl)-methanone | A | Mass spectrum (ESI$^+$): m/z = 417 [M + H]$^+$ |
| 132 | N-{4-[(2R,6S)-10-Hydroxy-6,11,11-trimethyl-1,2,5,6-tetrahydro-4H-2,6-methano-benzo[d]azocine-3-carbonyl]-benzyl}-acetamide | A | Mass spectrum (ESI$^+$): m/z = 407 [M + H]$^+$ |
| 133 | [(2R,6S)-10-Hydroxy-6,11,11-trimethyl-1,2,5,6-tetrahydro-4H-2,6-methano-benzo[d]azocin-3-yl]-[4-(pyrrolidine-1-carbonyl)-phenyl]-methanone | A | Mass spectrum (ESI$^+$): m/z = 433 [M + H]$^+$ |
| 134 | [(2R,6S)-10-Hydroxy-6,11,11-trimethyl-1,2,5,6-tetrahydro-4H-2,6-methano-benzo[d]azocin-3-yl]-[4-(morpholine-4-carbonyl)-phenyl]-methanone | A | Mass spectrum (ESI$^+$): m/z = 449 [M + H]$^+$ |

TABLE 3-continued

| Example No. | Chemical Name/Structure/Remarks | Prepared in analogy to Procedure | Characterization |
|---|---|---|---|
| 135 | 4-[(2R,6S)-10-Hydroxy-6,11,11-trimethyl-1,2,5,6-tetrahydro-4H-2,6-methano-benzo[d]azocine-3-carbonyl]-N-phenyl-benzamide | A | Mass spectrum (ESI$^+$): m/z = 455 [M + H]$^+$ |
| 136 | [(2R,6S)-10-Hydroxy-6,11,11-trimethyl-1,2,5,6-tetrahydro-4H-2,6-methano-benzo[d]azocin-3-yl]-[4-(4-methyl-piperazine-1-carbonyl)-phenyl]-methanone<br><br>The compound is isolated as the trifluoroacetic acid salt. | A | Mass spectrum (ESI$^+$): m/z = 462 [M + H]$^+$ |
| 137 | N-Benzyl-4-[(2R,6S)-10-hydroxy-6,11,11-trimethyl-1,2,5,6-tetrahydro-4H-2,6-methano-benzo[d]azocine-3-carbonyl]-benzamide | A | Mass spectrum (ESI$^+$): m/z = 469 [M + H]$^+$ |
| 138 | N-Ethyl-4-[(2R,6S)-10-hydroxy-6,11,11-trimethyl-1,2,5,6-tetrahydro-4H-2,6-methano-benzo[d]azocine-3-carbonyl]-benzamide | A | Mass spectrum (ESI$^+$): m/z = 407 [M + H]$^+$ |

TABLE 3-continued

| Example No. | Chemical Name/Structure/Remarks | Prepared in analogy to Procedure | Characterization |
|---|---|---|---|
| 139 | (3H-Benzoimidazol-5-yl)-[(2R,6S)-6,10,11,11-tetramethyl-1,2,5,6-tetrahydro-4H-2,6-methano-benzo[d]azocin-3-yl]-methanone | A | Mass spectrum (ESI$^+$): m/z = 374 [M + H]$^+$ |
| 140 | (3H-Benzoimidazol-5-yl)-[(2R,6S)-10-fluoro-6,11,11-trimethyl-1,2,5,6-tetrahydro-4H-2,6-methano-benzo[d]azocin-3-yl]-methanone | A | Mass spectrum (ESI$^+$): m/z = 378 [M + H]$^+$ |
| 141 | (9-Amino-6,11,11-trimethyl-1,2,5,6-tetrahydro-4H-2,6-methano-benzo[d]azocin-3-yl)-(3H-benzoimidazol-5-yl)-methanone | A | Mass spectrum (ESI$^+$): m/z = 375 [M + H]$^+$ |
| 142 | N-Ethyl-4-[(2R,6S)-10-hydroxy-6,11,11-trimethyl-1,2,5,6-tetrahydro-4H-2,6-methano-benzo[d]azocine-3-carbonyl]-benzamide<br><br>The compound is isolated as its trifluoroacetic acid salt | A | Mass spectrum (ESI$^+$): m/z = 449 [M + H]$^+$ |
| 143 | (8,9-Methylenedioxy-6,11,11-trimethyl-1,2,5,6-tetrahydro-4H-2,6-methano-benzo[d]azocin-3-yl)-(3H-benzoimidazol-5-yl)-methanone | A | Mass spectrum (ESI$^+$): m/z = 404 [M + H]$^+$ |

TABLE 3-continued

| Example No. | Chemical Name/Structure/Remarks | Prepared in analogy to Procedure | Characterization |
|---|---|---|---|
| 144 | (3-Chloro-pyridin-4-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 371/373 (Cl) [M + H]$^+$ |
| 145 | (3H-Benzoimidazol-5-yl)-(9-fluoro-6,11,11-trimethyl-1,2,5,6-tetrahydro-4H-2,6-methano-benzo[d]azocin-3-yl)-methanone | A | Mass spectrum (ESI$^+$): m/z = 378 [M + H]$^+$ |
| 146 | (3H-Benzoimidazol-5-yl)-(10-methoxy-11,11-dimethyl-1,2,5,6-tetrahydro-4H-2,6-methano-benzo[d]azocin-3-yl)-methanone | A | Mass spectrum (ESI$^+$): m/z = 376 [M + H]$^+$ |
| 147 | (3H-Benzoimidazol-5-yl)-[(2S,6R)-9-methoxy-6,11,11-trimethyl-1,2,5,6-tetrahydro-4H-2,6-methano-benzo[d]azocin-3-yl]-methanone | A | Mass spectrum (ESI$^+$): m/z = 390 [M + H]$^+$ |
| 148 | (3H-Benzoimidazol-5-yl)-(6-phenyl-1,2,5,6-tetrahydro-4H-2,6-methano-benzo[d]azocin-3-yl)-methanone<br><br>The starting material, 6-phenyl-1,2,3,4,5,6-hexahydro-2,6-methano-benzo[d]azocine, is obtained as described in *J. Org. Chem.* 1966, 31, 1905-11. | A | Mass spectrum (ESI$^+$): m/z = 394 [M + H]$^+$ |

TABLE 3-continued

| Example No. | Chemical Name/Structure/Remarks | Prepared in analogy to Procedure | Characterization |
|---|---|---|---|
| 149 | (3H-Benzoimidazol-5-yl)-(8-hydroxy-6-phenyl-1,2,5,6-tetrahydro-4H-2,6-methano-benzo[d]azocin-3-yl)-methanone | A | Mass spectrum (ESI$^+$): m/z = 410 [M + H]$^+$ |
| | The starting material, 6-phenyl-1,2,3,4,5,6-hexahydro-2,6-methano-benzo[d]azocin-8-ol, is obtained as described in *J. Med. Chem.* 1969, 12, 845-847. | | |
| 150 | (3H-Benzoimidazol-5-yl)-(8-hydroxy-11,11-dimethyl-6-phenyl-1,2,5,6-tetrahydro-4H-2,6-methano-benzo[d]azocin-3-yl)-methanone | A | Mass spectrum (ESI$^+$): m/z = 438 [M + H]$^+$ |
| 151 | (2R,6R,11S)-3-(3H-Benzoimidazole-5-carbonyl)-6,11-dimethyl-1,2,3,4,5,6-hexahydro-2,6-methano-benzo[d]azocine-8-carboxylic acid | B | Mass spectrum (ESI$^+$): m/z = 390 [M + H]$^+$ |
| 152 | (2R,6S)-3-(3H-Benzoimidazole-5-carbonyl)-6,11,11-trimethyl-1,2,3,4,5,6-hexahydro-2,6-methano-benzo[d]azocine-10-carboxylic acid | B | Mass spectrum (ESI$^+$): m/z = 404 [M + H]$^+$ |

TABLE 3-continued

| Example No. | Chemical Name/Structure/Remarks | Prepared in analogy to Procedure | Characterization |
|---|---|---|---|
| 153 | 3-(Benzothiazole-6-carbonyl)-8-hydroxy-2,3,4,5-tetrahydro-1H-2,6-methano-benzo[d]azocine-6-carboxylic acid | B | Mass spectrum (ESI$^+$): m/z = 395 [M + H]$^+$ |
| 154 | 3-(3H-Benzoimidazole-5-carbonyl)-6,11,11-trimethyl-1,2,3,4,5,6-hexahydro-2,6-methano-benzo[d]azocine-9-carboxylic acid | B | Mass spectrum (ESI$^+$): m/z = 404 [M + H]$^+$ |
| 155 | (2R,6R,11S)-3-(3H-Benzoimidazole-5-carbonyl)-6,11-dimethyl-1,2,3,4,5,6-hexahydro-2,6-methano-benzo[d]azocine-8-carboxylic acid dimethylamide | C | Mass spectrum (ESI$^+$): m/z = 417 [M + H]$^+$ |
| 156 | (2R,6R,11S)-3-(3H-Benzoimidazole-5-carbonyl)-6,11-dimethyl-1,2,3,4,5,6-hexahydro-2,6-methano-benzo[d]azocine-8 carboxylic acid methylamide<br><br>Aminomethane is used as coupling partner. | C | Mass spectrum (ESI$^+$): m/z = 403 [M + H]$^+$ |
| 157 | (2R,6R,11S)-3-(3H-Benzoimidazole-5-carbonyl)-6,11-dimethyl-1,2,3,4,5,6-hexahydro-2,6-methano-benzo[d]azocine-8-carboxylic acid amide<br><br>Ammonia is used as coupling partner. | C | Mass spectrum (ESI$^+$): m/z = 389 [M + H]$^+$ |

TABLE 3-continued

| Example No. | Chemical Name/Structure/Remarks | Prepared in analogy to Procedure | Characterization |
|---|---|---|---|
| 158 | (2R,6S)-3-(3H-Benzoimidazole-5-carbonyl)-6,11,11-trimethyl-1,2,3,4,5,6-hexahydro-2,6-methano-benzo[d]azocine-10-carboxylic acid dimethylamide | C | Mass spectrum (ESI$^+$): m/z = 431 [M + H]$^+$ |
| 159 | (2R,6S)-3-(3H-Benzoimidazole-5-carbonyl)-6,11,11-trimethyl-1,2,3,4,5,6-hexahydro-2,6-methano-benzo[d]azocine-10-carboxylic acid methylamide<br><br>Aminomethane is used as coupling partner. | C | Mass spectrum (ESI$^+$): m/z = 417 [M + H]$^+$ |
| 160 | (2R,6S)-3-(3H-Benzoimidazole-5-carbonyl)-6,11,11-trimethyl-1,2,3,4,5,6-hexahydro-2,6-methano-benzo[d]azocine-10-carboxylic acid amide<br><br>Ammonia is used as coupling partner. | C | Mass spectrum (ESI$^+$): m/z = 403 [M + H]$^+$ |
| 161 | 3-(3H-Benzoimidazole-5-carbonyl)-6,11,11-trimethyl-1,2,3,4,5,6-hexahydro-2,6-methano-benzo[d]azocine-9-carboxylic acid dimethylamide | C | Mass spectrum (ESI$^+$): m/z = 431 [M + H]$^+$ |

TABLE 3-continued

| Example No. | Chemical Name/Structure/Remarks | Prepared in analogy to Procedure | Characterization |
|---|---|---|---|
| 162 | 3-(3H-Benzoimidazole-5-carbonyl)-6,11,11-trimethyl-1,2,3,4,5,6-hexahydro-2,6-methano-benzo[d]azocine-9-carboxylic acid methylamide<br><br>Aminomethane is used as coupling partner. | C | Mass spectrum (ESI$^+$): m/z = 417 [M + H]$^+$ |
| 163 | 3-(3H-Benzoimidazole-5-carbonyl)-6,11,11-trimethyl-1,2,3,4,5,6-hexahydro-2,6-methano-benzo[d]azocine-9-carboxylic acid amide<br><br>Ammonia is used as coupling partner. | C | Mass spectrum (ESI$^+$): m/z = 403 [M + H]$^+$ |
| 164 | 3-(Benzothiazole-6-carbonyl)-8-hydroxy-2,3,4,5-tetrahydro-1H-2,6-methano-benzo[d]azocine-6-carboxylic acid dimethylamide | C | Mass spectrum (ESI$^+$): m/z = 422 [M + H]$^+$ |
| 165 | 3-(Benzothiazole-6-carbonyl)-8-hydroxy-2,3,4,5-tetrahydro-1H-2,6-methano-benzo[d]azocine-6-carboxylic acid methylamide<br><br>Aminomethane is used as coupling partner. | C | Mass spectrum (ESI$^+$): m/z = 408 [M + H]$^+$ |

TABLE 3-continued

| Example No. | Chemical Name/Structure/Remarks | Prepared in analogy to Procedure | Characterization |
| --- | --- | --- | --- |
| 166 | 3-(Benzothiazole-6-carbonyl)-8-hydroxy-2,3,4,5-tetrahydro-1H-2,6-methano-benzo[d]azocine-6-carboxylic acid amide<br><br>Ammonia is used as coupling partner. | C | Mass spectrum (ESI$^+$): m/z = 394 [M + H]$^+$ |
| 167 | 4-[(2R,6S)-10-Hydroxy-6,11,11-trimethyl-1,2,5,6-tetrahydro-4H-2,6-methano-benzo[d]azocine-3-carbonyl]-N-methyl-N-propyl-benzamide<br><br>The compound is synthesized from 4-[(2R,6S)-10-hydroxy-6,11,11-trimethyl-1,2,5,6-tetrahydro-4H-2,6-methano-benzo[d]azocine-3-carbonyl]-benzoic acid and methylpropylamine as described in the procedure C. | C | Mass spectrum (ESI$^+$): m/z = 435 [M + H]$^+$ |
| 168 | N,N-Diethyl-4-[(2R,6S)-10-hydroxy-6,11,11-trimethyl-1,2,5,6-tetrahydro-4H-2,6-methano-benzo[d]azocine-3-carbonyl]-benzamide<br><br>The compound is synthesized from 4-[(2R,6S)-10-hydroxy-6,11,11-trimethyl-1,2,5,6-tetrahydro-4H-2,6-methano-benzo[d]azocine-3-carbonyl]-benzoic acid and dimethylamine as described in the procedure C. | C | Mass spectrum (ESI$^+$): m/z = 435 [M + H]$^+$ |

TABLE 3-continued

| Example No. | Chemical Name/Structure/Remarks | Prepared in analogy to Procedure | Characterization |
|---|---|---|---|
| 169 | [(2R,6S)-10-Hydroxy-6,11,11-trimethyl-1,2,5,6-tetrahydro-4H-2,6-methano-benzo[d]azocin-3-yl]-[4-(piperidine-1-carbonyl)-phenyl]-methanone<br><br>The compound is synthesized from 4-[(2R,6S)-10-hydroxy-6,11,11-trimethyl-1,2,5,6-tetrahydro-4H-2,6-methano-benzo[d]azocine-3-carbonyl]-benzoic acid and piperidine as described in the procedure C. | C | Mass spectrum (ESI$^+$): m/z = 447 [M + H]$^+$ |
| 170 | N-Benzyl-4-[(2R,6S)-10-hydroxy-6,11,11-trimethyl-1,2,5,6-tetrahydro-4H-2,6-methano-benzo[d]azocine-3-carbonyl]-N-methyl-benzamide<br><br>The compound is synthesized from 4-[(2R,6S)-10-hydroxy-6,11,11-trimethyl-1,2,5,6-tetrahydro-4H-2,6-methano-benzo[d]azocine-3-carbonyl]-benzoic acid and benzylmethylamine as described in the procedure C. | C | Mass spectrum (ESI$^+$): m/z = 483 [M + H]$^+$ |
| 171 | 4-[(2R,6S)-10-Hydroxy-6,11,11-trimethyl-1,2,5,6-tetrahydro-4H-2,6-methano-benzo[d]azocine-3-carbonyl]-N-propyl-benzamide<br><br>The compound is synthesized from 4-[(2R,6S)-10-hydroxy-6,11,11-trimethyl-1,2,5,6-tetrahydro-4H-2,6-methano-benzo[d]azocine-3-carbonyl]-benzoic acid and n-propylamine as described in the procedure C. | C | Mass spectrum (ESI$^+$): m/z = 421 [M + H]$^+$ |

TABLE 3-continued

| Example No. | Chemical Name/Structure/Remarks | Prepared in analogy to Procedure | Characterization |
|---|---|---|---|
| 172 | [(2R,6R,11S)-8-Aminomethyl-6,11-dimethyl-1,2,5,6-tetrahydro-4H-2,6-methano-benzo[d]azocin-3-yl]-(3H-benzoimidazol-5-yl)-methanone 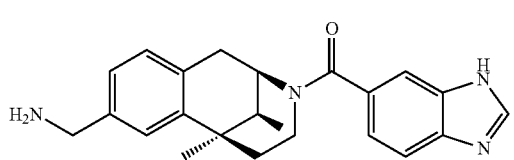 [SMILES: C[C@@H]1[C@H]2Cc3ccc(CN)cc3[C@]1(C)CCN2C(=O)c1ccc2nc[nH]c2c1] | D | Mass spectrum (ESI$^+$): m/z = 375 [M + H]$^+$ |
| 173 | (9-Aminomethyl-6,11,11-trimethyl-1,2,5,6-tetrahydro-4H-2,6-methano-benzo[d]azocin-3-yl)-(3H-benzoimidazol-5-yl)-methanone 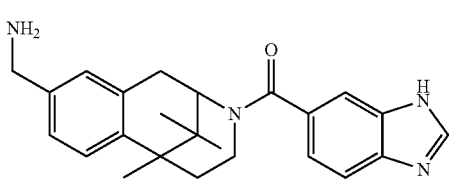 [SMILES: CC12CCN(C(=O)c3ccc4nc[nH]c4c3)C(Cc3cc(CN)ccc31)C2(C)C] | D | Mass spectrum (ESI$^+$): m/z = 389 [M + H]$^+$ |
| 174 | Benzothiazol-6-yl-(6-methyl-1,2,5,6-tetrahydro-4H-2,6-methano-benzo[d]azocin-3-yl)-methanone 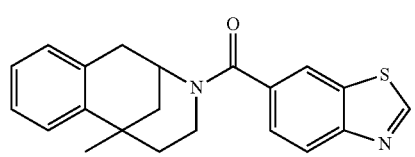 [SMILES: CC12CCN(C(=O)c3ccc4ncsc4c3)C(Cc3ccccc31)C2] | E | Mass spectrum (ESI$^+$): m/z = 349 [M + H]$^+$ |
| 175 | 3-(1H-Benzoimidazole-5-carbonyl)-N-hydroxy-6,11,11-trimethyl-1,2,3,4,5,6-hexahydro-2,6-methano-benzo[d]azocine-9-carboxamidine 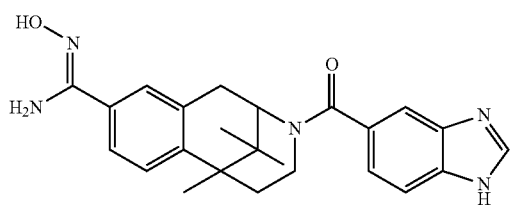 [SMILES: CC12CCN(C(=O)c3ccc4[nH]cnc4c3)C(Cc3cc(/C(N)=N/O)ccc31)C2(C)C] | F | Mass spectrum (ESI$^+$): m/z = 418 [M + H]$^+$ |
| 176 | (1H-Benzoimidazol-5-yl)-[6,11,11-trimethyl-9-(5-methyl-[1,2,4]oxadiazol-3-yl)-1,2,5,6-tetrahydro-4H-2,6-methano-benzo[d]azocin-3-yl]-methanone 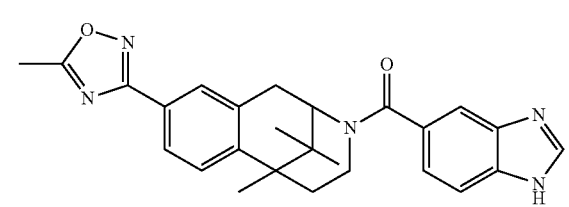 [SMILES: Cc1nc(-c2ccc3c(c2)CC2N(C(=O)c4ccc5[nH]cnc5c4)CCC3(C)C2(C)C)no1] | G | Mass spectrum (ESI$^+$): m/z = 442 [M + H]$^+$ |

TABLE 3-continued

| Example No. | Chemical Name/Structure/Remarks | Prepared in analogy to Procedure | Characterization |
|---|---|---|---|
| 177 | 3-(Benzothiazole-6-carbonyl)-8-hydroxy-2,3,4,5-tetrahydro-1H-2,6-methano-benzo[d]azocine-6-carbonitrile | H | Mass spectrum (ESI$^+$): m/z = 476 [M + H]$^+$ |
| 178 | N-[3-(3H-Benzoimidazole-5-carbonyl)-6,11,11-trimethyl-1,2,3,4,5,6-hexahydro-2,6-methano-benzo[d]azocin-9-ylmethyl]-acetamide | I | Mass spectrum (ESI$^+$): m/z = 431 [M + H]$^+$ |
| 179 | N-[3-(3H-Benzoimidazole-5-carbonyl)-6,11,11-trimethyl-1,2,3,4,5,6-hexahydro-2,6-methano-benzo[d]azocin-9-yl]-acetamide | I | Mass spectrum (ESI$^+$): m/z = 417 [M + H]$^+$ |
| 180 | [(2R,6S)-10-Hydroxy-6,11,11-trimethyl-1,2,5,6-tetrahydro-4H-2,6-methano-benzo[d]azocin-3-yl]-(2-methyl-furan-3-yl)-methanone | J | Mass spectrum (ESI$^+$): m/z = 340 [M + H]$^+$ |
| 181 | N-[3-(3H-Benzoimidazole-5-carbonyl)-6,11,11-trimethyl-1,2,3,4,5,6-hexahydro-2,6-methano-benzo[d]azocin-9-yl]-methanesulfonamide | K | Mass spectrum (ESI$^+$): m/z = 453 [M + H]$^+$ |

TABLE 3-continued

| Example No. | Chemical Name/Structure/Remarks | Prepared in analogy to Procedure | Characterization |
|---|---|---|---|
| 182 | 4-[(2R,6S)-10-Hydroxy-6,11,11-trimethyl-1,2,5,6-tetrahydro-4H-2,6-methano-benzo[d]azocine-3-carbonyl]-benzoic acid<br><br>The compound is synthesized from coupling with 4-tert-butoxycarbonylbenzoic acid according to procedure A and subsequent cleavage of the tertbutyl ester with trifluoroacetic acid in dichloromethane | A | Mass spectrum (ESI$^+$): m/z = 380 [M + H]$^+$ |
| 183 | (3H-Benzoimidazol-5-yl)-(10-hydroxy-11,11-dimethyl-1,2,5,6-tetrahydro-4H-2,6-methano-benzo[d]azocin-3-yl)-methanone | L | Mass spectrum (ESI$^+$): m/z = 362 [M + H]$^+$ |
| 184 | [4-(2,6-Dimethyl-morpholin-4-ylmethyl)-phenyl]-[(2R,6S)-10-hydroxy-6,11,11-trimethyl-1,2,5,6-tetrahydro-4H-2,6-methano-benzo[d]azocin-3-yl]-methanone<br><br>The compound is isolated as its trifluoroacetic acid salt | A | Mass spectrum (ESI$^+$): m/z = 463 [M + H]$^+$ |
| 185 | [4-(4-Hydroxy-4-methyl-piperidin-1-ylmethyl)-phenyl]-[(2R,6S)-10-hydroxy-6,11,11-trimethyl-1,2,5,6-tetrahydro-4H-2,6 methano-benzo[d]azocin-3-yl]-methanone<br><br>The compound is isolated as its trifluoroacetic acid salt | A | Mass spectrum (ESI$^+$): m/z = 463 [M + H]$^+$ |

TABLE 3-continued

| Example No. | Chemical Name/Structure/Remarks | Prepared in analogy to Procedure | Characterization |
|---|---|---|---|
| 186 | [4-(endo-3-Hydroxy-8-aza-bicyclo[3.2.1]oct-8-ylmethyl)-phenyl]-[(2R,6S)-10-hydroxy-6,11,11-trimethyl-1,2,5,6-tetrahydro-4H-2,6-methano-benzo[d]azocin-3-yl]-methanone<br><br>The compound is isolated as its trifluoroacetic acid salt | A | Mass spectrum (ESI$^+$): m/z = 475 [M + H]$^+$ |
| 187 | [4-(3-Hydroxy-azetidin-1-ylmethyl)-phenyl]-[(2R,6S)-10-hydroxy-6,11,11-trimethyl-1,2,5,6-tetrahydro-4H-2,6-methano-benzo[d]azocin-3-yl]-methanone<br><br>The compound is isolated as its trifluoroacetic acid salt | A | Mass spectrum (ESI$^+$): m/z = 421 [M + H]$^+$ |
| 188 | [4-(3-Hydroxy-pyrrolidin-1-ylmethyl)-phenyl]-[(2R,6S)-10-hydroxy-6,11,11-trimethyl-1,2,5,6-tetrahydro-4H-2,6-methano-benzo[d]azocin-3-yl]-methanone<br><br>The compound is isolated as its trifluoroacetic acid salt | A | Mass spectrum (ESI$^+$): m/z = 435 [M + H]$^+$ |
| 189 | [(2R,6S)-10-Hydroxy-6,11,11-trimethyl-1,2,5,6-tetrahydro-4H-2,6-methano-benzo[d]azocin-3-yl]-[4-(4-methoxy-piperidin-1-ylmethyl)-phenyl]-methanone<br><br>The compound is isolated as its trifluoroacetic acid salt | A | Mass spectrum (ESI$^+$): m/z = 463 [M + H]$^+$ |

TABLE 3-continued

| Example No. | Chemical Name/Structure/Remarks | Prepared in analogy to Procedure | Characterization |
|---|---|---|---|
| 190 | [4-(4-Hydroxy-piperidin-1-ylmethyl)-phenyl]-[(2R,6S)-10-hydroxy-6,11,11-trimethyl-1,2,5,6-tetrahydro-4H-2,6-methano-benzo[d]azocin-3-yl]-methanone<br><br>The compound is isolated as its trifluoroacetic acid salt | A | Mass spectrum (ESI$^+$): m/z = 449 [M + H]$^+$ |
| 191 | (3H-Benzoimidazol-5-yl)-[(5R,9S)-4,5,6,7,8,9-hexahydro-2,10,12,12-trimethyl-5,9-methano-1H-imidazo[5,4-j][3]benzazocin-6-yl]-methanone<br><br>The compound is isolated as its trifluoroacetic acid salt | A | Mass spectrum (ESI$^+$): m/z = 400 [M + H]$^+$ |
| 192 | [(2R,6S)-10-Hydroxy-6,11,11-trimethyl-1,2,5,6-tetrahydro-4H-2,6-methano-benzo[d]azocin-3-yl]-(1H-indazol-3-yl)-methanone | A | Mass spectrum (ESI$^+$): m/z = 376 [M + H]$^+$ |
| 193 | (5-Fluoro-1H-indol-3-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 393 [M + H]$^+$ |

TABLE 3-continued

| Example No. | Chemical Name/Structure/Remarks | Prepared in analogy to Procedure | Characterization |
|---|---|---|---|
| 194 | [(2R,6S)-10-Hydroxy-6,11,11-trimethyl-1,2,5,6-tetrahydro-4H-2,6-methano-benzo[d]azocin-3-yl]-(1-methyl-1H-indazol-3-yl)-methanone | A | Mass spectrum (ESI$^+$): m/z = 390 [M + H]$^+$ |
| 195 | [(2R,6S)-10-Hydroxy-6,11,11-trimethyl-1,2,5,6-tetrahydro-4H-2,6-methano-benzo[d]azocin-3-yl]-(4-methoxy-1H-indol-3-yl)-methanone | A | Mass spectrum (ESI$^+$): m/z = 405 [M + H]$^+$ |
| 196 | (5-Chloro-1H-indol-3-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 409/411 (Cl) [M + H]$^+$ |
| 197 | [(2R,6S)-10-Hydroxy-6,11,11-trimethyl-1,2,5,6-tetrahydro-4H-2,6-methano-benzo[d]azocin-3-yl]-(2-methyl-1H-indol-3-yl)-methanone | A | Mass spectrum (ESI$^+$): m/z = 389 [M + H]$^+$ |
| 198 | Benzofuran-3-yl-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 376 [M + H]$^+$ |

TABLE 3-continued

| Example No. | Chemical Name/Structure/Remarks | Prepared in analogy to Procedure | Characterization |
|---|---|---|---|
| 199 | [(2R,6S)-10-Hydroxy-6,11,11-trimethyl-1,2,5,6-tetrahydro-4H-2,6-methano-benzo[d]azocin-3-yl]-(1-methyl-1H-indol-3-yl)-methanone | A | Mass spectrum (ESI⁺): m/z = 389 (Cl) [M + H]⁺ |
| 200 | (3H-Benzoimidazol-5-yl)-(6-ethyl-8-hydroxy-11-methyl-1,2,5,6-tetrahydro-4H-2,6-methano-benzo[d]azocin-3-yl)-methanone<br><br>compound is a racemic mixture of the diastereomer shown | A | Mass spectrum (ESI⁺): m/z = 390 [M + H]⁺ |
| 201 | (2R,6S)-3-(3H-Benzoimidazole-5-carbonyl)-6,11,11-trimethyl-1,2,3,4,5,6-hexahydro-2,6-methano-benzo[d]azocine-8-sulfonic acid dimethylamide | A | Mass spectrum (ESI⁺): m/z = 467 [M + H]⁺ |
| 202 | (2R,6S)-3-(3H-Benzoimidazole-5-carbonyl)-6,11,11-trimethyl-1,2,3,4,5,6-hexahydro-2,6-methano-benzo[d]azocine-8-sulfonic acid methylamide | A | Mass spectrum (ESI⁺): m/z = 453 [M + H]⁺ |
| 203 | (2R,6S)-3-(3H-Benzoimidazole-5-carbonyl)-6,11,11-trimethyl-1,2,3,4,5,6-hexahydro-2,6-methano-benzo[d]azocine-8-sulfonic acid amide | A | Mass spectrum (ESI⁺): m/z = 439 [M + H]⁺ |

TABLE 3-continued

| Example No. | Chemical Name/Structure/Remarks | Prepared in analogy to Procedure | Characterization |
|---|---|---|---|
| 204 | 1-[(2R,6S)-3-(3H-Benzoimidazole-5-carbonyl)-6,11,11-trimethyl-1,2,3,4,5,6-hexahydro-2,6-methano-benzo[d]azocin-8-yl]-ethanone | A | Mass spectrum (ESI$^+$): m/z = 402 [M + H]$^+$ |
| 205 | 1-[(2R,6S)-3-(3H-Benzoimidazole-5-carbonyl)-6,11,11-trimethyl-1,2,3,4,5,6-hexahydro-2,6-methano-benzo[d]azocin-9-a yl]-ethanone | A | Mass spectrum (ESI$^+$): m/z = 402 [M + H]$^+$ |
| 206 | (2R,6S)-3-(3H-Benzoimidazole-5-carbonyl)-6,11,11-trimethyl-1,2,3,4,5,6-hexahydro-2,6-methano-benzo[d]azocine-9-carbonitrile | A | Mass spectrum (ESI$^+$): m/z = 385 [M + H]$^+$ |
| 207 | 4-[(2R,6S)-4-(10-Hydroxy-6,11,11-trimethyl 1,2,5,6-tetrahydro-4H-2,6-methano-benzo[d]azocine-3-carbonyl)-benzyl]-morpholin-3-one<br><br>the coupling partner, 4-(3-oxo-morpholin-4-ylmethyl)-benzoic acid, is obtained from 3-oxo-morpholine and 4-bromomethylbenzoic acid using NaH as base and NMP as solvent followed by hydrolysis with KOH in MeOH | A | Mass spectrum (ESI$^+$): m/z = 449 [M + H]$^+$ |
| 208 | 4-[(2R,6S)-10-Hydroxy-6,11,11-trimethyl-1,2,5,6-tetrahydro-4H-2,6-methano-benzo[d]azocine-3-carbonyl]-N-methyl-N-phenyl-benzamide | A | Mass spectrum (ESI$^+$): m/z = 469 [M + H]$^+$ |

TABLE 3-continued

| Example No. | Chemical Name/Structure/Remarks | Prepared in analogy to Procedure | Characterization |
|---|---|---|---|
| 209 | (3H-Benzoimidazol-5-yl)-[(2R,6S)-9-(1-hydroxy-ethyl)-6,11,11-trimethyl-1,2,5,6-tetrahydro-4H-2,6-methano-benzo[d]azocin-3-yl]-methanone | M | Mass spectrum (ESI$^+$): m/z = 404 [M + H]$^+$ |
| 210 | [(2R,6S)-10-Hydroxy-6,11,11-trimethyl-1,2,5,6-tetrahydro-4H-2,6-methano-benzo[d]azocin-3-yl]-(6-methyl-3H-benzoimidazol-5-yl)-methanone | A | Mass spectrum (ESI$^+$): m/z = 390 [M + H]$^+$ |
| 211 | (3H-Benzoimidazol-5-yl)-[(2R,6S)-8-(1-hydroxy-ethyl)-6,11,11-trimethyl-1,2,5,6-tetrahydro-4H-2,6-methano-benzo[d]azocin-3-yl]-methanone | M | Mass spectrum (ESI$^+$): m/z = 404 [M + H]$^+$ |
| 212 | 3-(3H-Benzoimidazole-5-carbonyl)-8-hydroxy-2,3,4,5-tetrahydro-1H-2,6-methano-benzo[d]azocine-6-carboxylic acid methyl ester | A | Mass spectrum (ESI$^+$): m/z = 392 [M + H]$^+$ |
| 213 | 3-(3H-Benzoimidazole-5-carbonyl)-8-hydroxy-2,3,4,5-tetrahydro-1H-2,6-methano-benzo[d]azocine-6-carboxylic acid | B | Mass spectrum (ESI$^+$): m/z = 378 [M + H]$^+$ |

TABLE 3-continued

| Example No. | Chemical Name/Structure/Remarks | Prepared in analogy to Procedure | Characterization |
|---|---|---|---|
| 214 | 3-(3H-Benzoimidazole-5-carbonyl)-8-hydroxy-2,3,4,5-tetrahydro-1H-2,6-methano-benzo[d]azocine-6-carboxylic acid amide | A | Mass spectrum (ESI$^+$): m/z = 377 [M + H]$^+$ |
| 215 | (2,5-Dimethyl-2H-pyrazol-3-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 354 [M + H]$^+$ |
| 216 | [(2R,6S)-10-Hydroxy-6,11,11-trimethyl-1,2,5,6-tetrahydro-4H-2,6-methano-benzo[d]azocin-3-yl]-(2-phenyl-2H-pyrazol-3-yl)-methanone | A | Mass spectrum (ESI$^+$): m/z = 402 [M + H]$^+$ |
| 217 | Benzo[b]thiophen-3-yl-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 392 [M + H]$^+$ |

TABLE 3-continued

| Example No. | Chemical Name/Structure/Remarks | Prepared in analogy to Procedure | Characterization |
|---|---|---|---|
| 218 | [(2R,6S)-10-Hydroxy-6,11,11-trimethyl-1,2,5,6-tetrahydro-4H-2,6-methano-benzo[d]azocin-3-yl]-(3-phenyl-3H-imidazol-4-yl)-methanone | A | Mass spectrum (ESI$^+$): m/z = 402 [M + H]$^+$ |
| 219 | [(2R,6S)-10-Hydroxy-6,11,11-trimethyl-1,2,5,6-tetrahydro-4H-2,6-methano-benzo[d]azocin-3-yl]-(4,5,6,7-tetrahydro-1H-indazol-3-yl)-methanone | A | Mass spectrum (ESI$^+$): m/z = 380 [M + H]$^+$ |
| 220 | [(2R,6S)-10-Hydroxy-6,11,11-trimethyl-1,2,5,6-tetrahydro-4H-2,6-methano-benzo[d]azocin-3-yl]-(1,4,5,6-tetrahydro-cyclopentapyrazol-3-yl)-methanone | A | Mass spectrum (ESI$^+$): m/z = 366 [M + H]$^+$ |
| 221 | [(2R,6S)-10-Hydroxy-6,11,11-trimethyl-1,2,5,6-tetrahydro-4H-2,6-methano-benzo[d]azocin-3-yl]-(5-phenyl-2H-pyrazol-3-yl)-methanone | A | Mass spectrum (ESI$^+$): m/z = 402 [M + H]$^+$ |

TABLE 3-continued

| Example No. | Chemical Name/Structure/Remarks | Prepared in analogy to Procedure | Characterization |
|---|---|---|---|
| 222 | (1-Ethyl-1H-indol-3-yl)-[(2R,6S)-10-hydroxy-6,11,11-trimethyl-1,2,5,6-tetrahydro-4H-2,6-methano-benzo[d]azocin-3-yl]-methanone | A | Mass spectrum (ESI$^+$): m/z = 403 [M + H]$^+$ |
| 223 | (2R,6R,11S)-3-(3H-Benzoimidazole-5-carbonyl)-8-hydroxy-6,11-dimethyl-1,2,3,4,5,6-hexahydro-2,6-methano-benzo[d]azocine-9-carbonitrile | A | Mass spectrum (ESI$^+$): m/z = 387 [M + H]$^+$ |
| 224 | (3H-Benzoimidazol-5-yl)-[(6R,10R,12S)-5,6,7,8,9,10-hexahydro-10,12-dimethyl-6,10-methano-1H-imidazo[5,4-i][3]benzazocin-7-yl]-methanone | A | Mass spectrum (ESI$^+$): m/z = 386 [M + H]$^+$ |
| 225 | [(2R,6S)-10-Hydroxy-6,11,11-trimethyl-1,2,5,6-tetrahydro-4H-2,6-methano-benzo[d]azocin-3-yl]-(7-methyl-1H-benzoimidazol-5-yl)-methanone | A | Mass spectrum (ESI$^+$): m/z = 390 [M + H]$^+$ |
| 226 | 3-(3H-Benzoimidazole-5-carbonyl)-8-hydroxy-2,3,4,5-tetrahydro-1H-2,6-methano-benzo[d]azocine-6-carbonitrile | H | Mass spectrum (ESI$^+$): m/z = 359 [M + H]$^+$ |

TABLE 3-continued

| Example No. | Chemical Name/Structure/Remarks | Prepared in analogy to Procedure | Characterization |
|---|---|---|---|
| 227 | (2R,6R,11S)-3-(3H-Benzoimidazole-5-carbonyl)-6,11-dimethyl-1,2,3,4,5,6-hexahydro-2,6-methano-benzo[d]azocine-9-carbonitrile | A | Mass spectrum (ESI$^+$): m/z = 387 [M + H]$^+$ |
| 228 | (2R,6R,11S)-(3H-Benzoimidazol-5-yl)-[6,11-dimethyl-8-(1H-tetrazol-5-yl)-1,2,5,6-tetrahydro-4H-2,6-methano-benzo[d]azocin-3-yl]-methanone | N | Mass spectrum (ESI$^+$): m/z = 414 [M + H]$^+$ |
| 229 | (3H-Benzoimidazol-5-yl)-[(2R,6S)-8-(1-hydroxy-1-methyl-ethyl)-6,11,11-trimethyl-1,2,5,6-tetrahydro-4H-2,6-methano-benzo[d]azocin-3-yl]-methanone | O | Mass spectrum (ESI$^+$): m/z = 418 [M + H]$^+$ |
| 230 | (2R,6R,11S)-3-(3H-Benzoimidazole-5-carbonyl)-N-hydroxy-6,11-dimethyl-1,2,3,4,5,6-hexahydro-2,6-methano-benzo[d]azocine-8-carboxamidine | F | Mass spectrum (ESI$^+$): m/z = 404 [M + H]$^+$ |
| 231 | (3H-Benzoimidazol-5-yl)-[(2R,6R,11S)-6,11-dimethyl-8-(5-methyl-[1,2,4]oxadiazol-3-yl)-1,2,5,6-tetrahydro-4H-2,6-methano-benzo[d]azocin-3-yl]-methanone | G | Mass spectrum (ESI$^+$): m/z = 428 [M + H]$^+$ |

TABLE 3-continued

| Example No. | Chemical Name/Structure/Remarks | Prepared in analogy to Procedure | Characterization |
|---|---|---|---|
| 232 | (3H-Benzoimidazol-5-yl)-[(2R,6R,11S)-6,11-dimethyl-8-[1,2,4]oxadiazol-3-yl-1,2,5,6-tetrahydro-4H-2,6-methano-benzo[d]azocin-3-yl]-methanone | P | Mass spectrum (ESI$^+$): m/z = 414 [M + H]$^+$ |
| 233 | (3H-Benzoimidazol-5-yl)-[(2R,6S)-8-methanesulfonyl-6,11,11-trimethyl-1,2,5,6-tetrahydro-4H-2,6-methano-benzo[d]azocin-3-yl]-methanone | A | Mass spectrum (ESI$^+$): m/z = 438 [M + H]$^+$ |
| 234 | (3H-Benzoimidazol-5-yl)-[(2R,6S)-10-methanesulfonyl-6,11,11-trimethyl-1,2,5,6-tetrahydro-4H-2,6-methano-benzo[d]azocin-3-yl]-methanone | A | Mass spectrum (ESI$^+$): m/z = 438 [M + H]$^+$ |
| 235 | (3H-Benzoimidazol-5-yl)-[(7R,11S)-6,7,8,9,10,11-hexahydro-11,13,13-trimethyl-6,10-methano-pyrazino[2,3-i][3]benzazocin-8-yl]-methanone | A | Mass spectrum (ESI$^+$): m/z = 412 [M + H]$^+$ |
| 236 | (2R,6R,11R)-3-(3H-Benzoimidazole-5-carbonyl)-6,11-dimethyl-1,2,3,4,5,6,8,9-octahydro-2,6-methano-benzo[d]azocine-9-carbonitrile | A | Mass spectrum (ESI$^+$): m/z = 371 [M + H]$^+$ |

TABLE 3-continued

| Example No. | Chemical Name/Structure/Remarks | Prepared in analogy to Procedure | Characterization |
|---|---|---|---|
| 237 | (2R,6S)-3-(3H-Benzoimidazole-5-carbonyl)-6,11,11-trimethyl-1,2,3,4,5,6-hexahydro-2,6-methano-benzo[d]azocine-9-sulfonic acid dimethylamide | A | Mass spectrum (ESI$^+$): m/z = 467 [M + H]$^+$ |
| 238 | (3H-Benzoimidazol-5-yl)-[(6R,10S)-5,6,7,8,9,10-hexahydro-2,10,12,12-tetramethyl-6,10-methano-1H-imidazo[5,4-i][3]benzazocin-7-yl]-methanone | A | Mass spectrum (ESI$^+$): m/z = 414 [M + H]$^+$ |
| 239 | (3H-Benzoimidazol-5-yl)-[(6R,10S)-5,6,7,8,9,10-hexahydro-10,12,12-trimethyl-6,10-methano-1H-imidazo[5,4-i][3]benzazocin-7-yl]-methanone | A | Mass spectrum (ESI$^+$): m/z = 400 [M + H]$^+$ |
| 240 | (3H-Benzoimidazol-5-yl)-[(6R,10S)-5,6,7,8,9,10-hexahydro-3,10,12,12-tetramethyl-6,10-methano-imidazo[4,5-i][3]benzazocin-7-yl]-methanone<br><br>the mixture of Example L was used as starting material; the compound was separated from compound Example 241 by HPLC on reversed phase | A | Mass spectrum (ESI$^+$): m/z = 414 [M + H]$^+$ |
| 241 | (3H-Benzoimidazol-5-yl)-[(6R,10S)-5,6,7,8,9,10-hexahydro-1,10,12,12-tetramethyl-6,10-methano-imidazo[5,4-i][3]benzazocin-7-yl]-methanone<br><br>the mixture of Example L was used as starting material; the compound was separated from compound Example 240 by HPLC on reversed phase | A | Mass spectrum (ESI$^+$): m/z = 414 [M + H]$^+$ |

TABLE 3-continued

| Example No. | Chemical Name/Structure/Remarks | Prepared in analogy to Procedure | Characterization |
|---|---|---|---|
| 242 | (3H-Benzoimidazol-5-yl)-[(6R,10S)-5,6,7,8,9,10-hexahydro-1,2,10,12,12-pentamethyl-6,10-methano-imidazo[5,4-i][3]benzazocin-7-yl]-methanone | A | Mass spectrum (ESI+): m/z = 428 [M + H]+ |
| 243 | (3H-Benzoimidazol-5-yl)-[(6R,10S)-5,6,7,8,9,10-hexahydro-2,3,10,12,12-pentamethyl-6,10-methano-imidazo[4,5-i][3]benzazocin-7-yl]-methanone | A | Mass spectrum (ESI+): m/z = 428 [M + H]+ |
| 244 | (3H-Benzoimidazol-5-yl)-[(7R,11S)-6,7,8,9,10,11-hexahydro-2,3,11,13,13-pentamethyl-7,11-methano-pyrazino[2,3-i][3]benzazocin-8-yl]-methanone | A | Mass spectrum (ESI+): m/z = 440 [M + H]+ |
| 245 | (3H-Benzoimidazol-5-yl)-(2,3,4,5,6,7-hexahydro-2,6-methano-azocino[5,4-b]indol-3-yl)-methanone | A | Mass spectrum (ESI+): m/z = 357 [M + H]+ |
| 246 | (3H-Benzoimidazol-5-yl)-[(2S,6S,11S)-8-hydroxy-6,11-dimethyl-1,2,5,6-tetrahydro-4H-2,6-methano-benzo[d]azocin-3-yl)-methanone | A | Mass spectrum (ESI+): m/z = 362 [M + H]+ |
| 247 | (3H-Benzoimidazol-5-yl)-[(2R,6R,11R)-8-hydroxy-6,11-dimethyl-1,2,5,6-tetrahydro-4H-2,6-methano-benzo[d]azocin-3-yl)-methanone | A | Mass spectrum (ESI+): m/z = 362 [M + H]+ |

TABLE 3-continued

| Example No. | Chemical Name/Structure/Remarks | Prepared in analogy to Procedure | Characterization |
| --- | --- | --- | --- |
| 248 | [(2R,6S)-10-Hydroxy-6,11,11-trimethyl-1,2,5,6-tetrahydro-4H-2,6-methano-benzo[d]azocin-3-yl)-(5-methyl-1H-indol-3-yl)-methanone | A | Mass spectrum (ESI$^+$): m/z = 389 [M + H]$^+$ |
| 249 | (3H-Benzoimidazol-5-yl)-[(2R,6R,11S)-6,11-dimethyl-8-phenyl-1,2,5,6-tetrahydro-4H-2,6-methano-benzo[d]azocin-3-yl)-methanone | A | Mass spectrum (ESI$^+$): m/z = 422 [M + H]$^+$ |
| 250 | (3H-Benzoimidazol-5-yl)-[(2R,6R,11S)-6,11-dimethyl-8-pyridin-3-yl-1,2,5,6-tetrahydro-4H-2,6-methano-benzo[d]azocin-3-yl]-methanone | A | Mass spectrum (ESI$^+$): m/z = 423 [M + H]$^+$ |
| 251 | (3H-Benzoimidazol-5-yl)-[(2R,6R,11S)-6,11-dimethyl-8-pyridin-4-yl-1,2,5,6-tetrahydro-4H-2,6-methano-benzo[d]azocin-3-yl]-methanone | A | Mass spectrum (ESI$^+$): m/z = 423 [M + H]$^+$ |
| 252 | (3H-Benzoimidazol-5-yl)-[(2R,6R,11S)-6,11-dimethyl-8-pyrimidin-5-yl-1,2,5,6-tetrahydro-4H-2,6-methano-benzo[d]azocin-3-yl]-methanone | A | Mass spectrum (ESI$^+$): m/z = 424 [M + H]$^+$ |

TABLE 3-continued

| Example No. | Chemical Name/Structure/Remarks | Prepared in analogy to Procedure | Characterization |
|---|---|---|---|
| 253 | (3H-Benzoimidazol-5-yl)-(4,6-dimethyl 1,2,5,6-tetrahydro-4H-2,6-methano-benzo[d]azocin-3-yl)-methanone<br><br>racemic mixture of diastereomer shown | A | Mass spectrum (ESI$^+$): m/z = 346 [M + H]$^+$ |
| 254 | (3H-Benzoimidazol-5-yl)-[(7R,11S)-6,7,8,9,10,11-hexahydro-3,11,13,13-tetramethyl-7,11-methano-pyrazino[2,3-i][3]benzazocin-8-yl]-methanone<br><br>the compound is obtained in a mixture with compound Example 255 | A | Mass spectrum (ESI$^+$): m/z = 426 [M + H]$^+$ |
| 255 | (3H-Benzoimidazol-5-yl)-[(7R,11S)-6,7,8,9,10,11-hexahydro-2,11,13,13-tetramethyl-7,11-methano-pyrazino[2,3-i][3]benzazocin-8-yl]-methanone<br><br>the compound is obtained in a mixture with compound Example 254 | A | Mass spectrum (ESI$^+$): m/z = 426 [M + H]$^+$ |
| 256 | (1-Methyl-1H-indol-3-yl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 373 [M + H]$^+$ |
| 257 | (3H-Benzoimidazol-5-yl)-[(6R,10S)-5,6,7,8,9,10-hexahydro-1,10,12,12-tetramethyl-6,10-methano-triazolo[5,4-i][3]benzazocin-7-yl]-methanone<br><br>the compound is obtained in a mixture with compound Example 258 which was separated by HPLC on chiral phase | A | Mass spectrum (ESI$^+$): m/z = 415 [M + H]$^+$ |

TABLE 3-continued

| Example No. | Chemical Name/Structure/Remarks | Prepared in analogy to Procedure | Characterization |
|---|---|---|---|
| 258 | (3H-Benzoimidazol-5-yl)-[(6R,10S)-5,6,7,8,9,10-hexahydro-3,10,12,12-tetramethyl-6,10-methano-triazolo[4,5-i][3]benzazocin-7-yl]-methanone<br><br>the compound is obtained in a mixture with compound Example 257 which was separated by HPLC on chiral phase | A | Mass spectrum (ESI⁺): m/z = 415 [M + H]⁺ |
| 259 | (1H-Indol-3-yl)-[(2R,6S)-6,11,11-trimethyl-1,2,5,6-tetrahydro-4H-2,6-methano-benzo[d]azocin-3-yl]-methanone | A | Mass spectrum (ESI⁺): m/z = 359 [M + H]⁺ |
| 260 | [(2R,6S)-10-Hydroxy-6,11,11-trimethyl-1,2,5,6-tetrahydro-4H-2,6-methano-benzo[d]azocin-3-yl]-[3-(2,2,2-trifluoro-1-hydroxy-1-methyl-ethyl)-phenyl]-methanone | A | Mass spectrum (ESI⁺): m/z = 448 [M + H]⁺ |
| 261 | (3H-Benzoimidazol-5-yl)-[(2R,6R,11S)-8-methoxy-6,11-dimethyl-7-nitro-1,2,5,6-tetrahydro-4H-2,6-methano-benzo[d]azocin-3-yl]-methanone | A | Mass spectrum (ESI⁺): m/z = 421 [M + H]⁺ |
| 262 | (3H-Benzoimidazol-5-yl)-[(2R,6R,11S)-6,11-dimethyl-8-(2-methyl-pyrimidin-4-yl)-1,2,5,6-tetrahydro-4H-2,6-methano-benzo[d]azocin-3-yl]-methanone | A | Mass spectrum (ESI⁺): m/z = 438 [M + H]⁺ |

TABLE 3-continued

| Example No. | Chemical Name/Structure/Remarks | Prepared in analogy to Procedure | Characterization |
|---|---|---|---|
| 263 | (3H-Benzoimidazol-5-yl)-[(2R,6R,11S)-6,11-dimethyl-8-(6-methyl-pyridazin-3-yl)-1,2,5,6-tetrahydro-4H-2,6-methano-benzo[d]azocin-3-yl]-methanone | A | Mass spectrum (ESI$^+$): m/z = 438 [M + H]$^+$ |
| 264 | (3H-Benzoimidazol-5-yl)-[(2R,6R,11S)-6,11-dimethyl-8-pyrimidin-4-yl-1,2,5,6-tetrahydro-4H-2,6-methano-benzo[d]azocin-3-yl]-methanone | A | Mass spectrum (ESI$^+$): m/z = 424 [M + H]$^+$ |
| 265 | (3H-Benzoimidazol-5-yl)-[(6R,10S)-5,6,7,8,9,10-hexahydro-10,12,12-trimethyl-6,10-methano-1H-triazolo[5,4-i][3]benzazocin-7-yl]-methanone | A | Mass spectrum (ESI$^+$): m/z = 401 [M + H]$^+$ |
| 266 | (3H-Benzoimidazol-5-yl)-[(6R,10S)-5,6,7,8,9,10-hexahydro-10,12,12-trimethyl-2-pyrazin-2-yl-6,10-methano-imidazo[5,4-i][3]benzazocin-7-yl]-methanone | A | Mass spectrum (ESI$^+$): m/z = 478 [M + H]$^+$ |
| 267 | (3H-Benzoimidazol-5-yl)-[(2R,6R,11S)-7-amino-8-methoxy-6,11-dimethyl-1,2,5,6-tetrahydro-4H-2,6-methano-benzo[d]azocin-3-yl]-methanone | Q | Mass spectrum (ESI$^+$): m/z = 391 [M + H]$^+$ |

TABLE 3-continued

| Example No. | Chemical Name/Structure/Remarks | Prepared in analogy to Procedure | Characterization |
|---|---|---|---|
| 268 | N-[(2R,6R,11S)-3-(3H-Benzoimidazole-5-carbonyl)-8-methoxy-6,11-dimethyl-1,2,3,4,5,6-hexahydro-2,6-methano-benzo[d]azocin-7-yl]-methanesulfonamide | K | Mass spectrum (ESI$^+$): m/z = 469 [M + H]$^+$ |
| 269 | [(6R,10S)-2-(1-Acetyl-piperidin-4-yl)-5,6,7,8,9,10-hexahydro-10,12,12-trimethyl-6,10-methano-imidazo[5,4-i][3]benzazocin-7-yl]-(3H-benzoimidazol-5-yl)-methanone | A | Mass spectrum (ESI$^+$): m/z = 525 [M + H]$^+$ |
| 270 | (3H-Benzoimidazol-5-yl)-[(2R,6R,11S)-8-methoxy-6,11-dimethyl-7-pyrrol-1-yl-1,2,5,6-tetrahydro-4H-2,6-methano-benzo[d]azocin-3-yl]-methanone | R | Mass spectrum (ESI$^+$): m/z = 441 [M + H]$^+$ |
| 271 | (3H-Benzoimidazol-5-yl)-[(6R,10S)-2-cyclopropyl-5,6,7,8,9,10-hexahydro-10,12,12-trimethyl-6,10-methano-imidazo[5,4-i][3]benzazocin-7-yl]-methanone | A | Mass spectrum (ESI$^+$): m/z = 440 [M + H]$^+$ |
| 272 | (3H-Benzoimidazol-5-yl)-[(6R,10S)-5,6,7,8,9,10-hexahydro-10,12,12-trimethyl-2-(1-methyl-6-oxo-1,6-dihydro-pyridin-3-yl)-6,10-methano-imidazo[5,4-i][3]benzazocin-7-yl]-methanone | A | Mass spectrum (ESI$^+$): m/z = 507 [M + H]$^+$ |

TABLE 3-continued

| Example No. | Chemical Name/Structure/Remarks | Prepared in analogy to Procedure | Characterization |
|---|---|---|---|
| 273 | (3H-Benzoimidazol-5-yl)-[(6R,10S)-2-tert-butyl-5,6,7,8,9,10-hexahydro-10,12,12-trimethyl-6,10-methano-imidazo[5,4-i][3]benzazocin-7-yl]-methanone | A | Mass spectrum (ESI$^+$): m/z = 456 [M + H]$^+$ |
| 274 | (3H-Benzoimidazol-5-yl)-[(6R,10S)-5,6,7,8,9,10-hexahydro-10,12,12-trimethyl-2-pyridin-3-yl-6,10-methano-imidazo[5,4-i][3]benzazocin-7-yl]-methanone | A | Mass spectrum (ESI$^+$): m/z = 477 [M + H]$^+$ |
| 275 | (3H-Benzoimidazol-5-yl)-[(6R,10S)-5,6,7,8,9,10-hexahydro-10,12,12-trimethyl-2-[(S)-tetrahydrofuran-2-yl]-6,10-methano-imidazo[5,4-i][3]benzazocin-7-yl]-methanone | A | Mass spectrum (ESI$^+$): m/z = 470 [M + H]$^+$ |
| 276 | (3H-Benzoimidazol-5-yl)-[(6R,10S)-5,6,7,8,9,10-hexahydro-10,12,12-trimethyl-2-pyridazin-4-yl-6,10-methano-imidazo[5,4-i][3]benzazocin-7-yl]-methanone | A | Mass spectrum (ESI$^+$): m/z = 478 [M + H]$^+$ |
| 277 | the compound was isolated as its F$_3$CO$_2$H salt (3H-Benzoimidazol-5-yl)-[(6R,10S)-5,6,7,8,9,10-hexahydro-10,12,12-trimethyl-2-(5-methyl-pyrazin-2-yl)-6,10-methano-imidazo[5,4-i][3]benzazocin-7-yl]-methanone | A | Mass spectrum (ESI$^+$): m/z = 492 [M + H]$^+$ |
| 278 | Quinoxalin-6-yl-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 372 [M + H]$^+$ |

TABLE 3-continued

| Example No. | Chemical Name/Structure/Remarks | Prepared in analogy to Procedure | Characterization |
|---|---|---|---|
| 279 | (3H-Benzoimidazol-5-yl)-[(2R,6R,11S)-6,11-dimethyl-8-(1-methyl-2-oxo-1,2-dihydro-pyridin-4-yl)-1,2,5,6-tetrahydro-4H-2,6-methano-benzo[d]azocin-3-yl]-methanone | A | Mass spectrum (ESI$^+$): m/z = 453 [M + H]$^+$ |
| 280 | (4-Nitro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 365 [M + H]$^+$ |
| 281 | (4-Amino-2,3,5,6-tetrafluoro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 407 [M + H]$^+$ |
| 282 | Naphthalen-2-yl-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 370 [M + H]$^+$ |
| 283 | (4-Amino-3,5-dichloro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 403/405/407 (2Cl) [M + H]$^+$ |

TABLE 3-continued

| Example No. | Chemical Name/Structure/Remarks | Prepared in analogy to Procedure | Characterization |
|---|---|---|---|
| 284 | Naphthalen-1-yl-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 370 [M + H]$^+$ |
| 285 | (1H-Indazol-6-yl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 360 [M + H]$^+$ |
| 286 | (4-Amino-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 335 [M + H]$^+$ |
| 287 | (3H-Benzoimidazol-5-yl)-[(6R,10S)-5,6,7,8,9,10-hexahydro-10,12,12-trimethyl-2-[(R)-tetrahydrofuran-2-yl]-6,10-methano-imidazo[5,4-i][3]benzazocin-7-yl]-methanone | A | Mass spectrum (ESI$^+$): m/z = 470 [M + H]$^+$ |
| 288 | 6-[(2R,6S)-6,11,11-Trimethyl-1,2,5,6-tetrahydro-4H-2,6-methano-benzo[d]azocine-3-carbonyl)-indan-1-one | A | Mass spectrum (ESI$^+$): m/z = 374 [M + H]$^+$ |

TABLE 3-continued

| Example No. | Chemical Name/Structure/Remarks | Prepared in analogy to Procedure | Characterization |
|---|---|---|---|
| 289 | 5-[(2R,6R,11S)-3-(3H-Benzoimidazole-5-carbonyl)-6,11-dimethyl-1,2,3,4,5,6-hexahydro-2,6-methano-benzo[d]azocin-8-yl]-1-methyl-1H-pyridin-2-one | A | Mass spectrum (ESI$^+$): m/z = 453 [M + H]$^+$ |
| 290 | 6-[(2R,6R,11S)-3-(3H-Benzoimidazole-5-carbonyl)-6,11-dimethyl-1,2,3,4,5,6-hexahydro-2,6-methano-benzo[d]azocin-8-yl]-2-methyl-2H-pyridazin-3-one | A | Mass spectrum (ESI$^+$): m/z = 454 [M + H]$^+$ |
| 291 | (3-Hydroxy-indan-5-yl)-[(2R,6S)-6,11,11-trimethyl-1,2,5,6-tetrahydro-4H-2,6-methano-benzo[d]azocin-3-yl]-methanone | M | Mass spectrum (ESI$^+$): m/z = 376 [M + H]$^+$ |
| 292 | (3-Hydroxy-3-methyl-indan-5-yl)-[(2R,6S)-6,11,11-trimethyl-1,2,5,6-tetrahydro-4H-2,6-methano-benzo[d]azocin-3-yl]-methanone | O | Mass spectrum (ESI$^+$): m/z = 390 [M + H]$^+$ |
| 293 | (1H-Indazol-5-yl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 360 [M + H]$^+$ |

TABLE 3-continued

| Example No. | Chemical Name/Structure/Remarks | Prepared in analogy to Procedure | Characterization |
|---|---|---|---|
| 294 | (3H-Benzoimidazol-5-yl)-(5,6-dimethyl-1,2,5,6-tetrahydro-4H-2,6-methano-benzo[d]azocin-3-yl)-methanone<br><br>(racemic mixture of diastereomer shown) | A | Mass spectrum (ESI$^+$): m/z = 346 [M + H]$^+$ |
| 295 | (4-Amino-3-chloro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 369/371 (Cl) [M + H]$^+$ |
| 296 | (4-Amino-3-fluoro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 353 [M + H]$^+$ |
| 297 | (3,4,5-Trifluoro-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 374 [M + H]$^+$ |
| 298 | 5-[(2R,6S)-6,11,11-Trimethyl-1,2,5,6-tetrahydro-4H-2,6-methano-benzo[d]azocine-3-carbonyl]-1,3-dihydro indol-2-one | A | Mass spectrum (ESI$^+$): m/z = 375 [M + H]$^+$ |

TABLE 3-continued

| Example No. | Chemical Name/Structure/Remarks | Prepared in analogy to Procedure | Characterization |
| --- | --- | --- | --- |
| 299 | 1-{4-[[(2R,6S)-6,11,11-Trimethyl-1,2,5,6-tetrahydro-4H-2,6-methano-benzo[d]azocine-3-carbonyl]-phenyl}-ethanone | A | Mass spectrum (ESI+): m/z = 362 [M + H]+ |
| 300 | (3H-Benzoimidazol-5-yl)-[(7R,11R,12S)-6,7,8,9,10,11-hexahydro-2,11,12-trimethyl-6,10-methano-oxazolo[4,5-h][3]benzazocin-8-yl]-methanone | A | Mass spectrum (ESI+): m/z = 401 [M + H]+ |
| 301 | (3H-Benzoimidazol-5-yl)-[(6R,10S)-5,6,7,8,9,10-hexahydro-2,10,12,12-tetramethyl-6,10-methano-oxazolo[4,5-i][3]benzazocin-7-yl]-methanone | A | Mass spectrum (ESI+): m/z = 415 [M + H]+ |
| 302 | (3H-Benzoimidazol-5-yl)-[(6R,10S)-2-cyclopropyl-5,6,7,8,9,10-hexahydro-10,12,12-trimethyl-6,10-methano-oxazolo[4,5-i][3]benzazocin-7-yl]-methanone | A | Mass spectrum (ESI+): m/z = 441 [M + H]+ |
| 303 | (6-Hydroxy-pyridin-3-yl)-[(2R,6S)-6,11,11-trimethyl-1,2,5,6-tetrahydro-4H-2,6-methano-benzo[d]azocin-3-yl)-methanone | A | Mass spectrum (ESI+): m/z = 337 [M + H]+ |

TABLE 3-continued

| Example No. | Chemical Name/Structure/Remarks | Prepared in analogy to Procedure | Characterization |
|---|---|---|---|
| 304 | (6-Amino-pyridin-3-yl)-[(2R,6S)-6,11,11-trimethyl-1,2,5,6-tetrahydro-4H-2,6-methano-benzo[d]azocin-3-yl)-methanone | A | Mass spectrum (ESI$^+$): m/z = 336 [M + H]$^+$ |
| 305 | (3H-Benzoimidazol-5-yl)-[(6R,10R,12S)-5,6,7,8,9,10-hexahydro-2,10,12-trimethyl-6,10-methano-oxazolo[5,4-i][3]benzazocin 7-yl]-methanone | A | Mass spectrum (ESI$^+$): m/z = 401 [M + H]$^+$ |
| 306 | [4-(1-Hydroxy-1-methyl-ethyl)-phenyl]-[(2R,6S)-6,11,11-trimethyl-1,2,5,6-tetrahydro-4H-2,6-methano-benzo[d]azocin-3-yl]-methanone | O | Mass spectrum (ESI$^+$): m/z = 378 [M + H]$^+$ |
| 307 | 1-{3-[(2R,6S)-6,11,11-Trimethyl-1,2,5,6-tetrahydro-4H-2,6-methano-benzo[d]azocine-3-carbonyl]-phenyl}-ethanone | A | Mass spectrum (ESI$^+$): m/z = 362 [M + H]$^+$ |
| 308 | 3,3-Dimethyl-5-[(2R,6S)-6,11,11-trimethyl-1,2,5,6-tetrahydro-4H-2,6-methano-benzo[d]azocine-3-carbonyl]-1,3-dihydro-indol-2-one | A | Mass spectrum (ESI$^+$): m/z = 403 [M + H]$^+$ |

TABLE 3-continued

| Example No. | Chemical Name/Structure/Remarks | Prepared in analogy to Procedure | Characterization |
|---|---|---|---|
| 309 | (1H-Benzoimidazol-5-yl)-(6,11,11-trimethyl-7-pyridin-3-yl-1,2,5,6-tetrahydro-4H-2,6-methano-benzo[d]azocin-3-yl)-methanone | A | Mass spectrum (ESI$^+$): m/z = 437 [M + H]$^+$ |
| 310 | [3-(1-Hydroxy-ethyl)-phenyl]-[(2R,6S)-6,11,11-trimethyl-1,2,5,6-tetrahydro-4H-2,6-methano-benzo[d]azocin-3-yl]-methanone | M | Mass spectrum (ESI$^+$): m/z = 364 [M + H]$^+$ |
| 311 | (3H-Benzoimidazol-5-yl)-[(6R,10R,12S)-2-cyclopropyl-5,6,7,8,9,10-hexahydro-10,12-dimethyl-6,10-methano-oxazolo[5,4-i][3]benzazocin-7-yl]-methanone | A | Mass spectrum (ESI$^+$): m/z = 427 [M + H]$^+$ |
| 312 | (3H-Benzoimidazol-5-yl)-[(6R,10S)-2-tert-butyl-5,6,7,8,9,10-hexahydro-10,12,12-trimethyl-6,10-methano-oxazolo[4,5-i][3]benzazocin-7-yl]-methanone | A | Mass spectrum (ESI$^+$): m/z = 457 [M + H]$^+$ |
| 313 | (3H-Benzoimidazol-5-yl)-[(6R,10S)-5,6,7,8,9,10-hexahydro-10,12,12-trimethyl-2-(5-methyl-pyrazin-2-yl)-6,10-methano-oxazolo[4,5-i][3]benzazocin-7-yl]-methanone | A | Mass spectrum (ESI$^+$): m/z = 493 [M + H]$^+$ |

TABLE 3-continued

| Example No. | Chemical Name/Structure/Remarks | Prepared in analogy to Procedure | Characterization |
|---|---|---|---|
| 314 | [3-(1-Hydroxy-ethyl)-phenyl]-[(2R,6S)-6,11,11-trimethyl-1,2,5,6-tetrahydro-4H-2,6-methano-benzo[d]azocin-3-yl]-methanone | M | Mass spectrum (ESI$^+$): m/z = 364 [M + H]$^+$ |
| 315 | (3H-Benzoimidazol-5-yl)-[(2R,6R,11S)-6,11-dimethyl-8-(2-methyl-pyrimidin-5-yl)-1,2,5,6-tetrahydro-4H-2,6-methano-benzo[d]azocin-3-yl]-methanone | A | Mass spectrum (ESI$^+$): m/z = 438 [M + H]$^+$ |
| 316 | 3-(1H-Benzoimidazole-5-carbonyl)-6,11,11-trimethyl-1,2,3,4,5,6-hexahydro-2,6-methano-benzo[d]azocine-7-carbonitrile | A | Mass spectrum (ESI$^+$): m/z = 437 [M + H]$^+$ |
| 317 | [3-(1-Hydroxy-1-methyl-ethyl)-phenyl]-[(2R,6S)-6,11,11-trimethyl-1,2,5,6-tetrahydro-4H-2,6-methano-benzo[d]azocin-3-yl]-methanone | O | Mass spectrum (ESI$^+$): m/z = 378 [M + H]$^+$ |
| 318 | (4-Hydroxy-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 336 [M + H]$^+$ |

TABLE 3-continued

| Example No. | Chemical Name/Structure/Remarks | Prepared in analogy to Procedure | Characterization |
|---|---|---|---|
| 319 | (3-Hydroxy-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 336 [M + H]$^+$ |
| 320 | (3,5-Dichloro-4-hydroxy-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 404/406/408 (2Cl) [M + H]$^+$ |
| 321 | (3H-Benzoimidazol-5-yl)-(5-methoxy-3,3a,8,8a-tetrahydro-2H-1-aza-cyclopenta[a]inden-1-yl)-methanone<br><br>The starting material, 5-methoxy-1,2,3,3a,8,8a-hexahydro-1-aza-cyclopenta[a]indene, is obtained as described in WO 9200961 | A | Mass spectrum (ESI$^+$): m/z = 334 [M + H]$^+$ |
| 322 | (3H-Benzoimidazol-5-yl)-(5-hydroxy-3,3a,8,8a-tetrahydro-2H-1-aza-cyclopenta[a]inden-1-yl)-methanone | J or as described in Example XIII | Mass spectrum (ESI$^+$): m/z = 320 [M + H]$^+$ |
| 323 | (3H-Benzoimidazol-5-yl)-(1-methyl-10-aza-tricyclo[7.2.1.0*2,7*]dodeca-2,4,6-trien-10-yl)-methanone | A | Mass spectrum (ESI$^+$): m/z = 318 [M + H]$^+$ |

TABLE 3-continued

| Example No. | Chemical Name/Structure/Remarks | Prepared in analogy to Procedure | Characterization |
|---|---|---|---|
| 324 | (3H-Benzoimidazol-5-yl)-(1-methyl-10-aza-tricyclo[7.4.1.0*2,7*]tetradeca-2,4,6-trien-10-yl)-methanone | A | Mass spectrum (ESI$^+$): m/z = 346 [M + H]$^+$ |
| 325 | (3H-Benzoimidazol-5-yl)-(5,8,9,10-tetrahydro-6H-6,10-methano-pyrido[3,2-d]azocin-7-yl)-methanone | A | Mass spectrum (ESI$^+$): m/z = 319 [M + H]$^+$ |
| 326 | racemic mixture of the diastereomer shown (3H-Benzoimidazol-5-yl)-(3,5,9-triaza-tricyclo[6.3.1.0*2,6*]dodeca-2(6),3-dien-9-yl)-methanone | A | Mass spectrum (ESI$^+$): m/z = 308 [M + H]$^+$ |
| 327 | racemic mixture of the diastereomer shown (1H-Indol-3-yl)-(3,5,9-triaza-tricyclo[6.3.1.0*2,6*]dodeca-2(6),3-dien-9-yl)-methanone | A | Mass spectrum (ESI$^+$): m/z = 307 [M + H]$^+$ |
| 328 | racemic mixture of the diastereomer shown (3H-Benzoimidazol-5-yl)-(4-methyl-3,5,9-triaza-tricyclo[6.3.1.0*2,6*]dodeca-2(6),3-dien-9-yl)-methanone | A | Mass spectrum (ESI$^+$): m/z = 322 [M + H]$^+$ |
| 329 | racemic mixture of the diastereomer shown (1H-Indol-3-yl)-(4-methyl-3,5,9-triaza-tricyclo[6.3.1.0*2,6*]dodeca-2(6),3-dien-9-yl)-methanone racemic mixture of the diastereomer shown | A | Mass spectrum (ESI$^+$): m/z = 321 [M + H]$^+$ |

TABLE 3-continued

| Example No. | Chemical Name/Structure/Remarks | Prepared in analogy to Procedure | Characterization |
|---|---|---|---|
| 330 | (3H-Benzoimidazol-5-yl)-(7-hydroxy-3,3,4-trimethyl-2,3,4,4a,9,9a-hexahydro-indeno[2,1-b]pyridin-1-yl)-methanone | A | Mass spectrum (ESI$^+$): m/z = 376 [M + H]$^+$ |
| 331 | (3,5-Difluoro-4-methoxy-phenyl)-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 386 [M + H]$^+$ |
| 332 | (3H-Benzoimidazol-5-yl)-[(2R,6R,11S)-6,11-dimethyl-8-(5-methyl-[1,3,4]oxadiazol-2-yl)-1,2,5,6-tetrahydro-4H-2,6-methano-benzo[d]azocin-3-yl]-methanone | A | Mass spectrum (ESI$^+$): m/z = 428 [M + H]$^+$ |
| 333 | (3H-Benzoimidazol-5-yl)-[(6R,10R,12S)-5,6,7,8,9,10-hexahydro-10,12-dimethyl-2-(5-methyl-pyrazin-2-yl)-6,10-methano-oxazolo[5,4-i][3]benzazocin-7-yl]-methanone | A | Mass spectrum (ESI$^+$): m/z = 479 [M + H]$^+$ |
| 334 | (3H-Benzoimidazol-5-yl)-[(2R,6R,11S)-6,11 dimethyl-8-[1,3,4]oxadiazol-2-yl-1,2,5,6-tetrahydro-4H-2,6-methano-benzo[d]azocin 3-yl]-methanone | A | Mass spectrum (ESI$^+$): m/z = 414 [M + H]$^+$ |

TABLE 3-continued

| Example No. | Chemical Name/Structure/Remarks | Prepared in analogy to Procedure | Characterization |
|---|---|---|---|
| 335 | (3,5-Difluoro-4-hydroxy-phenyl)-[(2R,6S)-6,11,11-trimethyl-1,2,5,6-tetrahydro-4H-2,6-methano-benzo[d]azocin-3-yl]-methanone | J | Mass spectrum (ESI$^+$): m/z = 372 [M + H]$^+$ |
| 336 | (3H-Benzoimidazol-5-yl)-[(2R,6R,11S)-8-(4,5-dimethyl-4H-[1,2,4]triazol-3-yl)-6,11-dimethyl-1,2,5,6-tetrahydro-4H-2,6-methano-benzo[d]azocin-3-yl]-methanone | A | Mass spectrum (ESI$^+$): m/z = 441 [M + H]$^+$ |
| 337 | (3H-Benzoimidazol-5-yl)-[(6R,10S)-5,6,7,8,9,10-hexahydro-10,12,12-trimethyl-2-[(R)-tetrahydrofuran-2-yl)-6,10-methano-oxazolo[4,5-i][3]benzazocin-7-yl]-methanone | A | Mass spectrum (ESI$^+$): m/z = 471 [M + H]$^+$ |
| 338 | (3H-Benzoimidazol-5-yl)-[(6R,10S)-5,6,7,8,9,10-hexahydro-10,12,12-trimethyl-2-[(S)-tetrahydrofuran-2-yl)-6,10-methano-oxazolo[4,5-i][3]benzazocin-7-yl]-methanone | A | Mass spectrum (ESI$^+$): m/z = 471 [M + H]$^+$ |
| 339 | [4-(2,2,2-Trifluoro-1-hydroxy-1-trifluoromethyl-ethyl)-phenyl]-[(2R,6S)-6,11,11-trimethyl-1,2,5,6-tetrahydro-4H-2,6-methano-benzo[d]azocin-3-yl]-methanone | A | Mass spectrum (ESI$^+$): m/z = 486 [M + H]$^+$ |

TABLE 3-continued

| Example No. | Chemical Name/Structure/Remarks | Prepared in analogy to Procedure | Characterization |
|---|---|---|---|
| 340 | (3H-Benzoimidazol-5-yl)-[(2R,6R,11S)-8-(1-hydroxy-1-methyl-ethyl)-6,11-dimethyl-1,2,5,6-tetrahydro-4H-2,6-methano-benzo[d]azocin-3-yl]-methanone<br><br>the compound is separated from compound Example 341 by HPLC on reversed phase | A | Mass spectrum (ESI$^+$): m/z = 404 [M + H]$^+$ |
| 341 | (2R,6R,11S)-3-(3H-Benzoimidazole-5-carbonyl)-6,11-dimethyl-1,2,3,4,5,6-hexahydro-2,6-methano-benzo[d]azocine-8-carboxylic acid methyl ester<br><br>the compound is separated from compound Example 340 by HPLC on reversed phase | A | Mass spectrum (ESI$^+$): m/z = 404 [M + H]$^+$ |
| 342 | 4-[(2R,6S)-6,11,11-Trimethyl-1,2,5,6-tetrahydro-4H-2,6-methano-benzo[d]azocine-3-carbonyl]-benzenesulfonamide | A | Mass spectrum (ESI$^+$): m/z = 399 [M + H]$^+$ |
| 343 | 3-[(2R,6S)-6,11,11-Trimethyl-1,2,5,6-tetrahydro-4H-2,6-methano-benzo[d]azocine-3-carbonyl]-benzenesulfonamide | A | Mass spectrum (ESI$^+$): m/z = 399 [M + H]$^+$ |
| 344 | (3H-Benzoimidazol-5-yl)-[(2R,6S)-6,11,11-trimethyl-8-(2,2,2-trifluoro-1-hydroxy-1-methyl-ethyl)-1,2,5,6-tetrahydro-4H-2,6-methano-benzo[d]azocin-3-yl]-methanone | A | Mass spectrum (ESI$^+$): m/z = 404 [M + H]$^+$ |

TABLE 3-continued

| Example No. | Chemical Name/Structure/Remarks | Prepared in analogy to Procedure | Characterization |
|---|---|---|---|
| 345 | 1-(3H-Benzoimidazole-5-carbonyl)-1,2,3,4,9,9a-hexahydro-indeno[2,1-b]pyridine-4a-carboxylic acid methyl ester 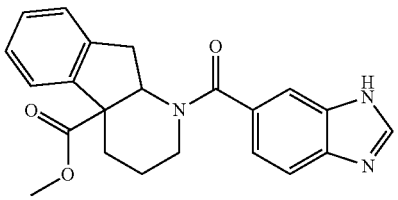 [SMILES: COC(=O)C12CCCN(C(=O)c3ccc4nc[nH]c4c3)C1Cc1ccccc12] | A | Mass spectrum (ESI$^+$): m/z = 376 [M + H]$^+$ |

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of Active Substance
Composition:
1 tablet contains:

| | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

Example B

Tablets Containing 150 mg of Active Substance
Composition:
1 tablet contains:

| | |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

Example C

Hard Gelatine Capsules Containing 150 mg of Active Substance
Composition:
1 capsule contains:

| | |
|---|---:|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

Example D

Suppositories Containing 150 mg of Active Substance
Composition:
1 suppository contains:

| | |
|---|---:|
| 7active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

Example E

Ampoules Containing 10 mg Active Substance
Composition:

| | |
|---|---|
| active substance | 10.0 mg |
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

Example F

Ampoules Containing 50 Ma of Active Substance
Composition:

| | |
|---|---|
| active substance | 50.0 mg |
| 0.01N hydrochloric acid | q.s. |
| double-distilled water | ad 10.0 mL |

Preparation:

The active substance is dissolved in the necessary amount of 0.01 N HCl, made isotonic with common salt, filtered sterile and transferred into 10 mL ampoules.

The invention claimed is:
1. A compound of formula I

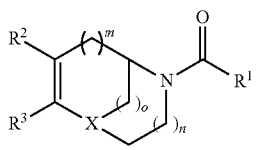

wherein
  $R^1$ denotes heteroaryl,
    selected from the group consisting of indolyl, benzofuranyl, benzothiophenyl, quinolinyl, and isoquinolinyl, wherein 1 to 3 CH of said heteroaryl are optionally replaced by N,
    wherein the above-mentioned heteroaryl rings are optionally substituted with one $R^4$, one to four identical or different $R^5$ and/or one $R^6$, and
    all heteroaryl rings are attached to the carbonyl group via a carbon atom,
  $R^2$ and $R^3$ together with the double bond to which they are attached denote
    a benzo ring optionally substituted with $R^7$, $R^8$ and $R^9$, or
    a pyrido ring optionally substituted with $R^7$, $R^8$ and $R^9$,
  $R^4$ denotes fluorine, chlorine, bromine, iodine,
    $C_{1-6}$-alkyl, $C_{2-6}$-alkenyl, $C_{2-6}$-alkynyl, hydroxy, $C_{1-4}$-alkyloxy,
    nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl,
    $C_{1-3}$-alkyl-carbonylamino, (het)aryl-carbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonylamino)carbonylamino, (het)arylsulfonylamino, (het)aryl-$C_{1-3}$-alkyl-sulfonylamino,
    N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonyl-amino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino,
    oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl,
    cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl,
    carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl,
    carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy,
    hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-

($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl,
$C_{1-3}$-alkylcarbonylamino-$C_{1-3}$-alkyl, arylcarbonylamino-$C_{1-3}$-alkyl,
hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy,
$C_{1-3}$-alkylsulfanyl, $C_{1-3}$-alkysulfinyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethylsulfinyl, trifluoromethylsulfonyl,
aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl,
difluoromethyl, trifluoromethyl, difluoromethoxy, trifluoromethoxy,
2,2,2-trifluoro-1-hydroxyethyl, 2,2,2-trifluoro-1-hydroxy-1-methylethyl, 2,2,2-trifluoro-1-hydroxy-1-(trifluoromethyl)ethyl,
$C_{3-6}$-cycloalkyl, $C_{3-6}$-cycloalkyloxy,
$C_{3-6}$-cycloalkyl-$C_{1-3}$-alkyl, $C_{3-6}$-cycloalkyl-$C_{1-3}$-alkyloxy,
(het)aryl, (het)aryloxy, (het)aryl-$C_{1-3}$-alkyl, (het)aryl-$C_{1-3}$-alkyloxy, (het)aryloxy-$C_{1-3}$-alkyl, or
tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy,
wherein the above-mentioned pyrrolidin-1-yl and piperidin-1-yl moieties are optionally substituted with one or two groups selected from methyl, ethyl, methoxymethyl, hydroxy or methoxy, and,
wherein the above-mentioned piperazin-1-yl and morpholin-4-yl moieties are optionally substituted with one or two groups selected from methyl, ethyl or methoxymethyl, and
wherein the above-mentioned (het)aryl is phenyl, naphthyl, pyrrolyl, furanyl, thienyl, tetrazolyl, pyridyl, indolyl, benzofuranyl, benzothiophenyl, quinolinyl, isoquinolinyl, or
pyrrolyl, furanyl, thienyl, pyridyl in which 1 or 2 CH are replaced by N, or
indolyl, benzofuranyl, benzothiophenyl, quinolinyl, isoquinolinyl in which 1 to 3 CH are replaced by N, or
1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydrobenzo[1,4]dioxinyl, 3,4-dihydro-3-oxo-2H-benzo[1,4]oxazinyl,
and wherein the above-mentioned (het)aryl groups are optionally substituted with one or two $R^{10}$ which may be identical or different,
$R^5$ and $R^6$, which may be identical or different, denote halogen, $C_{1-3}$-alkyl, $C_{2-3}$-alkynyl, trifluormethyl, hydroxy, $C_{1-3}$-alkyloxy, cyano, or
$R^5$ together with $R^6$, if bound to adjacent carbon atoms, may additionally be methylenedioxy, difluoromethylenedioxy, ethylenedioxy, $C_{3-5}$-alkylene,
$R^7$ denotes fluorine, chlorine, bromine, iodine,
$C_{1-4}$-alkyl, hydroxy, $C_{1-4}$-alkyloxy,
nitro, amino, $C_{1-4}$-alkylamino, di-($C_{1-4}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkyl)-pi-perazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-4}$-alkyl)-piperazin-1-yl, 3-oxo-4-($C_{1-4}$-alkyl)-piperazin-1-yl,
$C_{1-4}$-alkyl-carbonylamino, (het)aryl-carbonylamino, (het)aryl-$C_{1-4}$-alkyl-carbonylamino, $C_{1-}$-alkyloxycarbonylamino, aminocarbonylamino, $C_{1-4}$-alkyl-aminocarbonylamino, di-($C_{1-4}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-4}$-alkyl)-piperazin-1-yl-carbonylamino, $C_{1-4}$-alkyl-sulfonylamino, aminosulfonylamino, $C_{1-4}$-alkylamino-sulfonylamino, di-($C_{1-4}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-4}$-alkyl)-piperazin-1-yl-sulfonylamino, ($C_{1-4}$-alkyloxy-carbonylamino)carbonylamino, (het)arylsulfonylamino, (het)aryl-$C_{1-4}$-alkyl-sulfonylamino,
N—($C_{1-4}$-alkyl)-$C_{1-4}$-alkyl-carbonylamino, N—($C_{1-4}$-alkyl)-(het)arylcarbonylamino, N—($C_{1-4}$-alkyl)-(het)aryl-$C_{1-4}$-alkyl-carbonylamino, N—($C_{1-4}$-alkyl)-$C_{1-4}$-alkyloxy-carbonyl-amino, N-(aminocarbonyl)-$C_{1-4}$-alkylamino, N—($C_{1-4}$-alkyl-aminocarbonyl)-$C_{1-4}$-alkylamino, N-[di-($C_{1-4}$-alkyl)aminocarbonyl]-$C_{1-4}$-alkylamino, N—($C_{1-4}$-alkyl)-$C_{1-4}$-alkyl-sulfonylamino, N—($C_{1-4}$-alkyl)-(het)arylsulfonylamino, N—($C_{1-4}$-alkyl)-(het)aryl-$C_{1-4}$-alkyl-sulfonylamino,
oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl,
cyano, (hydroxyimino)aminomethyl, ($C_{1-4}$-alkyloxyimino)aminomethyl, carboxy, $C_{1-4}$-alkyloxy-carbonyl, aminocarbonyl, $C_{1-4}$-alkyl-aminocarbonyl, di-($C_{1-4}$-alkyl)-amino-carbonyl, pyrrolidin-1-ylcarbonyl, piperidin-1-yl-carbonyl, morpholin-4-yl-carbonyl, piperazin-1-yl-carbonyl, 4-($C_{1-4}$-alkyl)-piperazin-1-yl-carbonyl,
$C_{1-4}$-alkyl-carbonyl, (het)aryl-carbonyl,
carboxy-$C_{1-4}$-alkyl, $C_{1-4}$-alkyloxy-carbonyl-$C_{1-4}$-alkyl, cyano-$C_{1-4}$-alkyl, aminocarbonyl-$C_{1-4}$-alkyl, $C_{1-4}$-alkyl-aminocarbonyl-$C_{1-4}$-alkyl, di-($C_{1-4}$-alkyl)-aminocarbonyl-$C_{1-4}$-alkyl, pyrrolidin-1-yl-carbonyl-$C_{1-4}$-alkyl, piperidin-1-yl-carbonyl-$C_{1-4}$-alkyl, morpholin-4-yl-carbonyl-$C_{1-4}$-alkyl, piperazin-1-yl-carbonyl-$C_{1-4}$-alkyl, 4-($C_{1-4}$-alkyl)-piperazin-1-yl-carbonyl-$C_{1-4}$-alkyl,
carboxy-$C_{1-4}$-alkyloxy, $C_{1-4}$-alkyloxy-carbonyl-$C_{1-4}$-alkyloxy, cyano-$C_{1-4}$-alkyloxy, amino-carbonyl-$C_{1-4}$-alkyloxy, $C_{1-4}$-alkyl-aminocarbonyl-$C_{1-4}$-alkyloxy, di-($C_{1-4}$-alkyl)-amino-carbonyl-$C_{1-4}$-alkyloxy, pyrrolidin-1-yl-carbonyl-$C_{1-4}$-alkyl-oxy, piperidin-1-yl-carbonyl-$C_{1-4}$-alkyloxy, morpholin-4-yl-carbonyl-$C_{1-4}$-alkyl-oxy, piperazin-1-yl-carbonyl-$C_{1-4}$-alkyloxy, 4-($C_{1-4}$-alkyl)-piperazin-1-yl-carbonyl-$C_{1-4}$-alkyloxy,
hydroxy-$C_{1-4}$-alkyl, $C_{1-4}$-alkyloxy-$C_{1-4}$-alkyl, amino-$C_{1-4}$-alkyl, $C_{1-4}$-alkylamino-$C_{1-4}$-alkyl, di-($C_{1-4}$-alkyl)-amino-$C_{1-4}$-alkyl, pyrrolidin-1-yl-$C_{1-4}$-alkyl, $C_{1-4}$-alkylcarbonyl-amino-$C_{1-4}$-alkyl, N—($C_{1-4}$-alkyl)-$C_{1-4}$-alkylcarbonyl-amino-$C_{1-4}$-alkyl, 2-oxo-pyrrolidin-1-yl-$C_{1-4}$-alkyl, piperidin-1-yl-$C_{1-4}$-alkyl, 2-oxo-piperidin-1-yl-$C_{1-4}$-alkyl, morpholin-4-yl-$C_{1-4}$-alkyl, 3-oxo-morpholin-4-yl-$C_{1-4}$-alkyl, piperazin-1-yl-$C_{1-4}$-alkyl, 2-oxo-piperazin-1-yl-$C_{1-4}$-alkyl, 3-oxo-piperazin-1-yl-$C_{1-4}$-alkyl, 4-($C_{1-4}$-alkyl)-piperazin-1-yl-$C_{1-4}$-alkyl, 2-oxo-4-($C_{1-4}$-alkyl)-piperazin-1-yl-$C_{1-4}$-alkyl, 3-oxo-4-($C_{1-4}$-alkyl)-piperazin-1-yl-$C_{1-4}$-alkyl,
hydroxy-$C_{1-4}$-alkyloxy, $C_{1-4}$-alkyloxy-$C_{1-4}$-alkyloxy, $C_{1-4}$-alkylsulfanyl-$C_{1-4}$-alkyloxy, $C_{1-4}$-alkylsulfinyl-$C_{1-4}$-alkyloxy, $C_{1-4}$-alkylsulfonyl-$C_{1-4}$-alkyloxy, amino-$C_{1-4}$-alkyloxy, $C_{1-4}$-alkylamino-$C_{1-4}$-alkyloxy, di-($C_{1-4}$-alkyl)-amino-$C_{1-4}$-alkyloxy, pyrrolidin-1-yl-$C_{1-4}$-alkyloxy, 2-oxo-pyrrolidin-1-yl-$C_{1-4}$-alkyloxy, piperidin-1-yl-$C_{1-4}$-alkyloxy, 2-oxo-piperidin-1-yl-$C_{1-4}$-alkyloxy, morpholin-4-yl-$C_{1-4}$-alkyloxy, 3-oxo-morpholin-4-yl-$C_{1-4}$-alkyloxy, piperazin-1-yl-$C_{1-4}$-alkyloxy, 2-oxo-piperazin-1-yl-$C_{1-4}$-alkyloxy, 3-oxo-piperazin-1-yl-$C_{1-4}$-alkyloxy, 4-($C_{1-4}$-alkyl)-piperazin-1-yl-$C_{1-4}$-alkyloxy, 2-oxo-4-($C_{1-4}$-alkyl)-piperazin-1-yl-$C_{1-4}$-alkyloxy, 3-oxo-4-($C_{1-4}$-alkyl)-piperazin-1-yl-$C_{1-4}$-alkyloxy,
$C_{1-4}$-alkylsulfanyl, $C_{1-4}$-alkysulfinyl, $C_{1-4}$-alkylsulfonyl, $C_{1-4}$-alkylsulfonyloxy, (het)arylsulfonyl, (het)arylsulfonyloxy, trifluoromethylsulfanyl, trifluoromethylsulfinyl, trifluoromethylsulfonyl, $C_{3-6}$-cycloalkylsulfanyl, $C_{3-6}$-cycloalkylsulfinyl, $C_{3-6}$-cycloalkylsulfonyl, $C_{3-6}$-cycloalkyl-$C_{1-3}$-alkylsulfanyl, $C_{3-6}$-cycloalkyl-$C_{1-3}$-alkylsulfinyl, $C_{3-6}$-cycloalkyl-$C_{1-3}$-alkylsulfonyl,
aminosulfonyl, $C_{1-4}$-alkyl-aminosulfonyl, di-($C_{1-4}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-4}$-alkyl)-piperazin-1-yl-sulfonyl,
difluoromethyl, trifluoromethyl, difluoromethoxy, trifluoromethoxy,
2,2,2-trifluoro-1-hydroxyethyl, 2,2,2-trifluoro-1-hydroxy-1-methylethyl, 2,2,2-trifluoro-1-hydroxy-1-(trifluoromethyl)ethyl,
$C_{3-6}$-cycloalkyl, $C_{3-6}$-cycloalkyloxy,
hydroxy-$C_{4-6}$-cycloalkyl, $C_{1-3}$-alkyloxy-$C_{3-6}$-cycloalkyl,
$C_{3-6}$-cycloalkyl-$C_{1-3}$-alkyl, $C_{3-6}$-cycloalkyl-$C_{1-3}$-alkyloxy,
(het)aryl, (het)aryloxy, (het)aryl-$C_{1-3}$-alkyl, (het)aryl-$C_{1-3}$-alkyloxy, (het)aryloxy-$C_{1-3}$-alkyl, or
tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy,
wherein the above-mentioned (het)aryl is defined as described for $R^4$ hereinbefore,
$R^8$ and $R^9$, which may be identical or different, are halogen, $C_{1-3}$-alkyl, trifluormethyl, hydroxy, $C_{1-3}$-alkyloxy, cyano, or
$R^8$ together with $R^9$, if bound to adjacent carbon atoms, may additionally be methylenedioxy, difluoromethylenedioxy, ethylenedioxy, $C_{3-5}$-alkylene,
$R^{10}$ is $R^{10'}$ or $R^{10''}$ and
$R^{10'}$ denotes halogen, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, or trifluoromethoxy,
$R^{10''}$ denotes pyrrolyl, furanyl, thienyl, pyridyl, wherein in any of these groups 1 or 2 CH optionally are replaced by N atoms, or
indolyl, benzofuranyl, benzothiophenyl, quinolinyl, isoquinolinyl, wherein in any of these groups 1 to 3 CH optionally are replaced by N atoms, or
phenyl, naphthyl, tetrazolyl, 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, or 3,4-dihydro-3-oxo-2H-benzo[1,4]oxazinyl,
and wherein any of the groups mentioned hereinbefore under $R^{10''}$ optionally are substituted independently with one or two groups selected from halogen, $C_{1-3}$-alkyl, difluoromethyl, trifluoromethyl, cyano, nitro, amino, acetylamino, methylsulfonylamino, carboxy, $C_{1-4}$-alkyl-oxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, and trifluoromethoxy,
X denotes CH,
m, n, o are each 1,
and wherein the bicyclic core structure of formula I is optionally substituted independently with $R^{11}$ to $R^{14}$, wherein
$R^{11}$ denotes fluorine, $C_{1-4}$-alkyl, (het)aryl, hydroxy, $C_{1-4}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, wherein (het)aryl is as described for $R^4$ hereinbefore, $R^{12}$ denotes fluorine or $C_{1-4}$-alkyl, and $R^{13}$ and $R^{14}$, which may be identical or different, denote $C_{1-4}$-alkyl, and wherein the above-mentioned alkyl or alkylene moieties are branched or unbranched, or a tautomer thereof, stereoisomer thereof, mixture thereof, or a salt thereof.

2. A compound according to claim 1, wherein $R^1$ denotes heteroaryl, selected from the group consisting of indolyl, benzofuranyl, benzothiophenyl, quinolinyl, or isoquinolinyl, wherein 1 to 3 CH of said heteroaryls are optionally replaced by N, and each of said heteroaryls are independently substituted with one $R^4$, one to four identical or different $R^5$, and/or one $R^6$, $R^2$ and $R^3$, together with the double bond to which they are attached, denote a benzo or pyrido ring optionally both independently substituted with $R^7$, $R^8$ and $R^9$, $R^4$ denotes fluorine, chlorine, bromine, $C_{1-4}$-alkyl, hydroxyl, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, (het)arylsulfonylamino, (het)aryl-$C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-(het)aryl-$C_{1-3}$-alkyl-carbonylamino, N—($C_{1-3}$-alkyl)-$C_{1-3}$-alkyloxy-carbonyl-amino, N—(aminocarbonyl)-$C_{1-3}$-alkylamino, N—($C_{1-3}$-alkyl-aminocarbonyl)-$C_{1-3}$-alkylamino, N—[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxyethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yl-oxy, tetrahydropyran-3-yl-oxy, tetrahydropyran-4-yl-oxy, tetra-hydrofuranyl-$C_{1-3}$-alkyloxy, tetrahydropyranyl-$C_{1-3}$-alkyloxy, wherein the above-mentioned (het)aryl groups are phenyl, naphthyl, or pyrrolyl, furanyl, thienyl, pyridyl, indolyl, benzofuranyl, benzothiophenyl, quinolinyl, isoquinolinyl, or pyrrolyl, furanyl, thienyl, pyridyl wherein 1 or 2 CH are replaced by N, or indolyl, benzofuranyl, benzothiophenyl, quinolinyl, isoquinolinyl wherein 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro -2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, or 3,4-dihydro-3-oxo-2H-benzo[1,4]oxazinyl, and wherein any of the groups mentioned for the (het)aryl groups are optionally substituted with one or two $R^{10}$ which may be identical or different, $R^5$ and $R^6$ are independently selected from among fluorine, chlorine, bromine, $C_{1-3}$-alkyl, $C_{2-3}$-alkynyl, trifluoromethyl, hydroxy, $C_{1-3}$-alkyloxy, and cyano, or if $R^5$ and $R^6$ are bound to adjacent carbon atoms they together may additionally denote methylenedioxy, difluoromethylenedioxy, ethylenedioxy or $C_{3-5}$-alkylene, $R^7$ denotes fluorine, chlorine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, 3-oxo-piperazin -1-yl, 4-($C_{1-4}$-alkylcarbonyl)-piperazin-1-yl, $C_{1-3}$-alkyl-carbonylamino, (het)aryl-carbonylamino, $C_{1-3}$-alkyloxy-carbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, $C_{1-3}$-alkyl-sulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, (het)arylsulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-$C_{1-3}$-alkyloxy-carbonylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, cyano, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-amino-carbonyl, pyrrolidin-1-yl-carbonyl, piperidin-1-yl-carbonyl, morpholin-4-yl-carbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, ami-nocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-4}$-alkyl, $C_{1-3}$-alkyloxy-$C_{1-4}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, $C_{1-4}$-alkylcarbonyl-amino-$C_{1-3}$-alkyl, N—($C_{1-3}$-alkyl)-$C_{1-4}$-alkyl-carbonyl-amino-$C_{1-3}$-alkyl, 2-oxo-piperidin-1-yl-$C_{1-3}$-alkyl, 3-oxo-morpholin-4-yl-$C_{1-3}$-alkyl, hydroxy-$C_{1-4}$-alkyloxy, $C_{1-4}$-alkyloxy-$C_{1-4}$-alkyloxy, $C_{1-3}$-alkylsulfinyl-$C_{1-3}$-alkyloxy, $C_{1-3}$-alkylsulfonyl-$C_{1-3}$-alkyloxy, di-($C_{1-3}$-alkyl)-amino-$C_{1-3}$-alkyloxy, 2-oxo-pyrrolidin -1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, $C_{1-4}$-alkylsulfanyl, $C_{1-4}$-alkysulfinyl, $C_{1-4}$-alkylsulfonyl, (het)arylsulfonyl, $C_{3-6}$-cycloalkylsulfanyl, $C_{3-6}$-cycloalkylsulfinyl, $C_{3-6}$-cycloalkylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl $C_{1-3}$-alkoxy, (het)aryl, (het)aryloxy, (het)aryl-$C_{1-3}$-alkyl, (het)aryl-$C_{1-3}$-alkyloxy, (het)aryloxy-$C_{1-3}$ -alkyl, or tetrahydrofuran-3-yl-oxy, tetrahydropyran-3-yl-oxy, tetrahydropyran-4-yl-oxy, tetra-hydrofuranyl-$C_{1-3}$-alkyloxy, or tetrahydropyranyl-$C_{1-3}$-alkyloxy, wherein the above-mentioned (het)aryl groups are defined as described hereinbefore under $R^4$, $R^8$ and $R^9$, which may be identical or different, denote fluorine, chlorine, bromine, $C_{1-3}$-alkyl, trifluoromethyl, hydroxy, $C_{1-3}$-alkyloxy or cyano, or if $R^8$ and $R^9$ are bound to adjacent carbon atoms they together may additionally denote methylenedioxy, difluoromethylenedioxy, ethylenedioxy, $C_{3-5}$-alkylene, $R^{10}$ denotes fluorine, chlorine, bromine, $C_{1-3}$-alkyl, difluoromethyl, trifluoromethyl, cyano, nitro, amino, acetylamino, methylsulfonylamino, carboxy, $C_{1-4}$-alkyloxy-carbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, phenyl, hydroxy, $C_{1-3}$-alkyloxy, difluorome -thoxy, or trifluoromethoxy, $R^{11}$ denotes fluorine, $C_{1-3}$-alkyl, phenyl, hydroxy, $C_{1-3}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, $R^{12}$ denotes fluorine, hydrogen or $C_{1-3}$-alkyl; and $R^{13}$ and $R^{14}$, which may be identical or different, denote $C_{1-3}$-alkyl, or a tautomer, stereoisomer, mixture thereof or salt thereof.

3. A compound according to claim 1, wherein $R^1$ denotes indolyl, quinolinyl, or isoquinolinyl, wherein any of these groups optionally are independently substituted with one $R^4$, one to four identical or different $R^5$, and/or one $R^6$, $R^2$ and $R^3$, together with the double bond to which they are attached, denote a benzo or pyrido ring, optionally both independently substituted with $R^7$, $R^8$ and $R^9$, $R^4$ denotes fluorine, chlorine, bromine, $C_{1-4}$-alkyl, hydroxy, $C_{1-4}$-alkyloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkyl-carbonyl)-piperazin-1-yl, 4-($C_{3-6}$-cycloalkylcarbonyl)-piperazin-1-yl, 4-($C_{1-4}$-alkyloxy-carbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, cyano, carboxy, $C_{1-3}$-alkyloxy-carbonyl, aminocarbonyl, $C_{1-3}$-alkyl-aminocarbonyl, di-($C_{1-3}$alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, N—($C_{1-3}$-alkyl)-(het)arylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, aminosulfonyl, (het)aryl, (het)aryl-$C_{1-3}$-alkyl, or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups optionally are substituted with $R^{10}$ $R^5$ and $R^6$ are independently selected from among fluorine, chlorine, bromine, $C_{1-3}$-alkyl, $C_{2-3}$-alkynyl, trifluoromethyl, hydroxy, $C_{1-3}$-alkyloxy, and cyano, or if $R^5$ and $R^6$ are bound to adjacent carbon atoms they together may additionally denote methylenedioxy, difluoromethylenedioxy, ethylenedioxy, or $C_{3-5}$-alkylene, $R^7$ denotes fluorine, chlorine, $C_{1-4}$-alkyl, hydroxy, $C_{1-4}$-alkyloxy, nitro, amino, $C_{1-3}$-alkylamino, 2-oxo-pyrrolidin-1-yl, 2-oxo-piperidin-1-yl, morpholin-4-yl, 3-oxo-morpholin-4-yl, $C_{1-3}$-alkyl-carbonylamino, (het)aryl-carbonylamino, $C_{1-3}$-alkyl-sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl)-$C_{1-3}$-alkyl-sulfonylamino, N—($C_{1-3}$-alkyl)-(het)arylsulfonylamino, cyano, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, $C_{1-3}$-alkyl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-3}$-alkyl, $C_{1-3}$-alkyloxy-$C_{1-3}$-alkyl, $C_{1-4}$-alkylcarbonyl-amino-$C_{1-3}$-alkyl, N—($C_{1-3}$-alkyl)-$C_{1-4}$-alkylcarbonyl-amino-$C_{1-3}$-alkyl, 2-oxo-pyrrolidin-1-yl-$C_{1-3}$-alkyl, 2-oxo-piperid-in-1-yl-$C_{1-3}$-alkyl, 3-oxo-morpholin-4-yl-$C_{1-3}$-alkyl, hydroxy-$C_{1-3}$-alkyloxy, $C_{1-3}$-alkyloxy-$C_{1-3}$-alkyloxy, $C_{1-4}$-alkylsulfanyl, $C_{1-4}$-alkysulfinyl, $C_{1-4}$-alkylsulfonyl, $C_{3-6}$-cycloalkylsulfanyl, $C_{3-6}$-cycloalkylsulfinyl, $C_{3-6}$-cycloalkylsulfonyl, aminosulfonyl, $C_{1-3}$-alkyl-aminosulfonyl, di-($C_{1-3}$-alkyl)-aminosulfonyl, trifluoromethyl, difluoromethoxy, trifluoromethoxy, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl or (het)aryloxy, wherein the above-mentioned (het)aryl groups for $R^7$ denote phenyl, furanyl, thienyl, oxazolyl, thiazolyl, isoxazolyl, imidazolyl, pyrazolyl, oxadiazolyl, triazolyl, tetrazolyl, pyridinyl, pyrimidinyl, pyrazinyl, pyridazinyl, or triazinyl, wherein any of these groups are optionally mono-or disubstituted with $R^{10}$, $R^8$ and $R^9$, which may be identical or different, denote fluorine, chlorine, bromine, $C_{1-3}$-alkyl, trifluoromethyl, hydroxy, $C_{1-3}$-alkyloxy, or cyano, or if $R^8$ and $R^9$ are bound to adjacent carbon atoms they together may additionally denote methylenedioxy, difluoromethylenedioxy, ethylenedioxy, $C_{3-5}$-alkylene, $R^{10}$ denotes fluorine, chlorine, methyl, difluoromethyl, trifluoromethyl, cyano, hydroxy, methoxy, difluoromethoxy, or trifluoromethoxy, R$^{11}$ denotes fluorine, C$_{1-3}$-alkyl, hydroxyl, or C$_{1-3}$-alkyloxy, R$^{12}$ denotes fluorine, or C$_{1-3}$-alkyl, R$^{13}$ and R$^{14}$, which may be identical or different, denote C$_{1-3}$-alkyl, or a tautomer, stereoisomer, mixture thereof or salt thereof.

4. A compound according to claim 1, wherein

R$^1$ denotes, benzofuranyl, indolyl, benzothiophenyl, quinolinyl, or isoquinolinyl, wherein any of these groups optionally are independently substituted with one R$^4$ and and/or one to four different or identical R$^5$, R$^2$ and R$^3$, together with the double bond to which they are attached, denote a benzo or pyrido ring, optionally both independently substituted with R$^7$, R$^8$ and R$^9$, R$^4$ denotes fluorine, chlorine, C$_{1-4}$-alkyl, hydroxy, C$_{1-4}$-alkyloxy, amino, C$_{1-3}$-alkylamino, di-(C$_{1-3}$-alkyl)amino, pyrrolidin-1-yl, piperidin-1-yl, morpholin-4-yl, C$_{1-3}$-alkyl-carbonylamino, aminocarbonyl, C$_{1-3}$-alkyl-aminocarbonyl, di-(C$_{1-3}$-alkyl)-aminocarbonyl, (N-methyl)-benzylaminocarbonyl, (N-methyl)-phenylaminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, hydroxy-C$_{1-3}$-alkyl, C$_{1-3}$-alkyloxy-C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, morpholin-4-yl-C$_{1-3}$-alkyl, (2-methyl-morpholin-4-yl)-C$_{1-3}$-alkyl, (2,6-dimethyl-morpholin-4-yl)-C$_{1-3}$-alkyl, 3-oxo-morpholin-4-yl-methyl, pyrrolidin-1-yl-C$_{1-3}$-alkyl, 2-oxo-pyrrolidin-1-yl-C$_{1-3}$-alkyl, C$_{1-3}$-alkylcarbonylamino-C$_{1-3}$-alkyl, phenylcarbonylamino-C$_{1-3}$-alkyl, imidazolyl-C$_{1-3}$-alkyl, triazolyl-C$_{1-3}$-alkyl, trifluoromethyl, difluoromethoxy, trifluoromethoxy, 2,2,2-trifluoro-1-hydroxyethyl, 2,2,2-trifluoro-1-hydroxy-1-methylethyl, or 2,2,2-trifluoro-1-hydroxy-1-trifluoromethyl-ethyl, or aminosulfonyl R$^5$ and R$^6$ are independently selected from among fluorine, chlorine, bromine, C$_{1-3}$-alkyl, C$_{2-3}$-alkynyl, trifluoromethyl, hydroxy, C$_{1-3}$-alkyloxy, and cyano, or if R$^5$ and R$^6$ are bound to adjacent carbon atoms they together may additionally denote methylenedioxy, difluoromethylenedioxy, ethylenedioxy, or C$_{3-5}$-alkylene, R$^7$ denotes fluorine, chlorine, C$_{1-3}$-alkyl, hydroxy, C$_{1-3}$-alkyloxy, amino, C$_{1-3}$-alkyl -carbonylamino, C$_{1-3}$-alkyl-sulfonylamino, cyano, (hydroxyimino)aminomethyl, carboxy, C$_{1-3}$-alkyloxy-carbonyl, aminocarbonyl, C$_{1-3}$-alkyl-aminocarbonyl, di-(C$_{1-3}$-alkyl)-aminocarbonyl, hydroxy-C$_{1-3}$-alkyl, trifluoromethyl-hydroxy-C$_{1-3}$-alkyl, C$_{1-3}$-alkyloxy-C$_{1-3}$-alkyl, C$_{1-3}$-alkyl -carbonyl-amino-C$_{1-3}$-alkyl, hydroxy-C$_{1-3}$-alkyloxy, C$_{1-3}$-alkyloxy-C$_{1-3}$-alkyloxy, trifluoromethyl, difluoromethoxy, trifluoromethoxy, C$_{1-3}$-alkylcarbonyl, C$_{1-4}$-alkylsulfonyl, C$_{3-6}$-cycloalkylsulfonyl, aminosulfonyl, C$_{1-3}$-alkyl-aminosulfonyl, or di-(C$_{1-3}$-alkyl)-aminosulfonyl, or a (het)aryl group selected from phenyl, pyrrol-1-yl, 4-methyl-4H-[1,2,4] triazol-3-yl, oxadiazolyl, pyridinyl, 1,2-dihydro-1-methyl-2-oxo-pyridinyl, pyrimidinyl, pyridazinyl, and 2,3-dihydro-2-methyl-3-oxo-pyridazinyl, each of them being optionally mono-substituted with R$^{10}$;

R$^8$ and R$^9$, which may be identical or different, denote fluorine, chlorine, bromine, C$_{1-3}$-alkyl, trifluoromethyl, hydroxy, C$_{1-3}$-alkyloxy, or cyano, or if R$^8$ and R$^9$ are bound to adjacent carbon atoms they together may additionally denote methylenedioxy, difluoromethylenedioxy, ethylenedioxy, C$_{3-5}$-alkylene, R$^{10}$ denotes fluorine, chlorine, methyl, difluoromethyl, trifluoromethyl, cyano, hydroxy, methoxy, difluoromethoxy, or trifluoromethoxy, R$^{11}$ denotes fluorine, C$_{1-3}$-alkyl, hydroxyl, or C$_{1-3}$-alkyloxy, R$^{12}$ denotes fluorine, or C$_{1-3}$-alkyl, R$^{13}$ and R$^{14}$, which may be identical or different, denote C$_{1-3}$-alkyl, or a tautomer, stereoisomer, mixture thereof or salt thereof.

5. The compound according to claim 1, wherein

R$^1$ benzofuranyl or indolyl, wherein any of these groups optionally are independently substituted with one R$^4$ and and/or one to four different or identical R$^5$ R$^2$ and R$^3$, together with the double bond to which they are attached, denote a benzo or pyrido ring, both optionally independently substituted with R$^7$, R$^8$ and R$^9$, R$^4$ denotes fluorine, chlorine, bromine, C$_{1-4}$-alkyl, hydroxy, C$_{1-4}$-alkyloxy, amino, C$_{1-3}$-alkylamino, di-(C$_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-(C$_{1-3}$-alkyl)-piperazin-1-yl, 4-(C$_{1-4}$-alkyl -carbonyl)-piperazin-1-yl, 4-(C$_{3-6}$-cycloalkylcarbonyl)-piperazin-1-yl, 4-(C$_{1-4}$-alkyloxy -carbonyl)-piperazin-1-yl, 4-(C$_{1-4}$-alkylsulfonyl)-piperazin-1-yl, 2-oxo-4-(C$_{1-3}$-alkyl) -piperazin-1-yl, 3-oxo-4-(C$_{1-3}$-alkyl)-piperazin-1-yl, C$_{1-3}$-alkyl-carbonylamino, (het)arylcarbonylamino, (het)aryl-C$_{1-3}$-alkyl-carbonylamino, C$_{1-3}$ -alkyloxy-carbonylamino, aminocarbonylamino, C$_{1-3}$-alkyl-aminocarbonylamino, di-(C$_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-(C$_{1-3}$-alkyl)-piperazin-1-yl -carbonylamino, cyano, carboxy, C$_{1-3}$-alkyloxy-carbonyl, aminocarbonyl, C$_{1-3}$-alkyl-aminocarbonyl, di-(C$_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl -carbonyl, piperazin-1-yl-carbonyl, 4-(C$_{1-3}$-alkyl)-piperazin-1-yl-carbonyl, N—(C$_{1-3}$-alkyl) -(het)arylaminocarbonyl, N—(C$_{1-3}$-alkyl)-(het)aryl-C$_{1-3}$-alkylaminocarbonyl, C$_{1-3}$-alkyl-carbonyl, (het)aryl-carbonyl, hydroxy-C$_{1-3}$-alkyl, C$_{1-3}$-alkyloxy-C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, pyrrolidin-1-yl-C$_{1-3}$-alkyl, 2-oxo-pyrrolidin-1-yl-C$_{1-3}$-alkyl, morpholin-4-yl-C$_{1-3}$-alkyl, (methyl-morpholin-4-yl)-C$_{1-3}$-alkyl, (dimethyl-morpholin-4-yl)-C$_{1-3}$ -alkyl, 3-oxo-morpholin-4-yl-C$_{1-3}$-alkyl, C$_{1-3}$-alkylcarbonylamino-C$_{1-3}$-alkyl, (het)arylcarbonylamino-C$_{1-3}$-alkyl, hydroxy-C$_{1-3}$-alkyloxy, C$_{1-3}$-alkyloxy-C$_{1-3}$-alkyloxy, trifluoromethyl, difluoromethoxy, trifluoromethoxy, 2,2,2-trifluoro-l-hydroxyethyl, 2,2,2-trifluoro-1-hydroxy-1-methylethyl, 2,2,2-trifluoro-1-hydroxy-1-(trifluoromethyl)ethyl, aminosulfonyl, (het)aryl, (het)aryl-C$_{1-3}$-alkyl, or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups optionally are substituted with $R^{10}$, $R^5$ and $R^6$ are independently selected from fluorine, chlorine, methyl, ethyl, ethynyl, trifluoromethyl, hydroxy, methoxy, and ethoxy, or if $R^5$ and $R^6$ are bound to adjacent carbon atoms they together may additionally denote methylenedioxy, ethylene-1,2-dioxy, propylene, or butylene, $R^7$ denotes fluorine, chlorine, $C_{1-4}$-alkyl, hydroxy, $C_{1-4}$-alkyloxy, nitro, amino, $C_{1-3}$-alkylamino, 2-oxo-pyrrolidin-1-yl, 2-oxo-piperidin-1-yl, morpholin-4-yl, 3-oxo-morpholin-4-yl, $C_{1-3}$-alkyl-carbonylamino, (het)aryl-carbonylamino, $C_{1-3}$-alkyl-sulfonylamino, N—($C_{1-3}$-alkyl) -$C_{1-3}$-alkyl-carbonylamino, N—($C_{1-3}$-alkyl)-(het)arylcarbonylamino, N—($C_{1-3}$-alkyl)-$C_{1-3}$-alkyl-sulfonylamino, N—($C_{1-3}$-alkyl)-(het)arylsulfonylamino, cyano, (hydroxyimino)aminomethyl, ($C_{1-3}$-alkyloxyimino)aminomethyl, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, $C_{1-3}$-alkyl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, hydroxy-$C_{1-3}$-alkyl, $C_{1-3}$-alkyloxy-$C_{1-3}$-alkyl, $C_{1-4}$-alkylcarbonyl-amino-$C_{1-3}$-alkyl, N—($C_{1-3}$-alkyl) -$C_{1-4}$-alkylcarbonyl-amino-$C_{1-3}$-alkyl, 2-oxo-pyrrolidin-1-yl-$C_{1-3}$-alkyl, 2-oxo-piperid-in-1-yl-$C_{1-3}$-alkyl, 3-oxo-morpholin-4-yl-$C_{1-3}$-alkyl, hydroxy-$C_{1-3}$-alkyloxy, $C_{1-3}$-alkyloxy-$C_{1-3}$-alkyloxy, $C_{1-4}$-alkylsulfanyl, $C_{1-4}$-alkysulfinyl, $C_{1-4}$-alkylsulfonyl, $C_{3-6}$-cycloalkylsulfanyl, $C_{3-6}$-cycloalkylsulfinyl, $C_{3-6}$-cycloalkylsulfonyl, aminosulfonyl, $C_{1-3}$-alkyl-aminosulfonyl, di-($C_{1-3}$-alkyl)-aminosulfonyl, trifluoromethyl, difluoromethoxy, trifluoromethoxy, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl or (het)aryloxy, wherein the above-mentioned (het)aryl groups for $R^7$ denote phenyl, furanyl, thienyl, oxazolyl, thiazolyl, isoxazolyl, imidazolyl, pyrazolyl, oxadiazolyl, triazolyl, tetrazolyl, pyridinyl, pyrimidinyl, pyrazinyl, pyridazinyl, or triazinyl, wherein any of these groups are optionally mono- or disubstituted with $R^{10}$, $R^8$ and $R^9$ independently denote fluorine, chlorine, methyl, ethyl, isopropyl, trifluoromethyl, hydroxy, methoxy, ethoxy, or cyano, or if $R^8$ and $R^9$ are bound to adjacent carbon atoms they together may additionally denote methylenedioxy, ethylene-1,2-dioxy, propylene, butylene or $R^{10}$ denotes fluorine, chlorine, methyl, difluoromethyl, trifluoromethyl, cyano, hydroxy, methoxy, difluoromethoxy, or trifluoromethoxy, $R^{11}$ denotes fluorine, $C_{1-3}$-alkyl, hydroxyl, or $C_{1-3}$-alkyloxy, $R^{12}$ denotes fluorine, or $C_{1-3}$-alkyl, $R^{13}$ and $R^{14}$, which may be identical or different, denote $C_{1-3}$-alkyl, or a tautomer, stereoisomer, mixture thereof or salt thereof.

6. A physiologically acceptable salt of the compound according to claim 1 with an inorganic or organic acid or base.

7. A pharmaceutical composition containing a compound according to claim 1, or a physiologically acceptable salt with an inorganic or organic acid or base, optionally together with one or more inert carriers and/or diluents.

8. A method of inhibiting, 11β-hydroxysteroid dehydrogenase (HSD) 1 comprising administering to a patient in need thereof a compound of formula I wherein $R^1$ denotes heteroaryl selected from the group consisting of indolyl, benzofuranyl, benzothiophenyl, quinolinyl, and isoquinolinyl, wherein 1 to 3 CH of said heteroaryls are optionally replaced by N, wherein the above-mentioned heteroaryl rings are optionally substituted with one $R^4$, one to four identical or different $R^5$, and/or one $R^6$, and all heteroaryl rings are attached to the carbonyl group via a carbon atom, $R^2$ and $R^3$ together with the double bond to which they are attached denote a benzo ring optionally substituted with $R^7$, $R^8$ and $R^9$, or a pyrido ring optionally substituted with $R^7$, $R^8$ and $R^9$, $R^4$ denotes fluorine, chlorine, bromine, iodine, $C_{1-6}$-alkyl, $C_{2-6}$-alkenyl, $C_{2-6}$-alkynyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)aryl-carbonylamino, (het)aryl-$C_{1-3}$-alkyl-carbonylamino, $C_{1-3}$-alkyloxycarbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl) -piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy -carbonylamino) carbonylamino, (het)arylsulfonylamino, (het)aryl-$C_{1-3}$-alkyl- sulfonylamino, N—($C_{1-3}$-alkyl)-$C_{1-3}$-alkyl-carbonylamino, N—($C_{1-3}$-alkyl)-(het)arylcarbonylamino, N—($C_{1-3}$-alkyl) -(het)aryl-$C_{1-3}$-alkyl-carbonylamino, N—($C_{1-3}$-alkyl)-$C_{1-3}$-alkyloxy-carbonyl-amino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulfonylamino, N—($C_{1-3}$-alkyl)-(het)arylsulfonylamino, N—($C_{1-3}$-alkyl)-(het)aryl-$C_{1-3}$-alkyl-sulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl, cyano, carboxy, $C_{1-3}$-alkyloxy-carbonyl, aminocarbonyl, $C_{1-3}$-alkyl-aminocarbonyl, di -($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl -carbonyl, (het)arylaminocarbonyl, N—($C_{1-3}$-alkyl)-(het)arylaminocarbonyl, (het)aryl-$C_{1-3}$-alkylaminocarbonyl, N—($C_{1-3}$-alkyl)-(het)aryl-$C_{1-3}$-alkylaminocarbonyl, $C_{1-3}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, ami-nocarbonyl-$C_{1-3}$ -alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl) -piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl) -aminocarbonyl-$C_{1-3}$-alkyloxy, pyrrolidin-1 -yl-carbonyl-$C_{1-3}$-alkyl-oxy, piperidin-1-yl -carbonyl-$C_{1-3}$-alkyloxy, morpholin-4-yl-carbonyl-$C_{1-3}$-alkyl-oxy, piperazin-1-yl -carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl -$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo -piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl) -piperazin-1 -yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy, wherein the above-mentioned pyrrolidin-1-yl and piperidin-1-yl moieties are optionally substituted with one or two groups selected from methyl, ethyl, methoxymethyl, hydroxy or methoxy, and, wherein the above-mentioned piperazin-1-yl and morpholin-4-yl moieties are optionally substituted with one or two groups selected from methyl, ethyl or methoxymethyl, and wherein the above-mentioned (het)aryl is phenyl, naphthyl, pyrrolyl, furanyl, thienyl, tetrazolyl, pyridyl, indolyl, benzofuranyl, benzothiophenyl, quinolinyl, isoquinolinyl, or pyrrolyl, furanyl, thienyl, pyridyl in which 1 or 2 CH are replaced by N, or indolyl, benzofuranyl, benzothiophenyl, quinolinyl, isoquinolinyl in which 1 to 3 CH are replaced by N, or 1,2-dihydro-2-oxo-pyridinyl, 1,4-dihydro-4-oxo-pyridinyl, 2,3-dihydro-3-oxo -pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro -2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo -benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo -quinazolinyl, 1,4-dihydro-4-oxo-quinazolinyl, 1,2,3,4-tetrahydro-2,4-dioxo -quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro -benzo[1,4]dioxinyl, 3,4-dihydro-3-oxo-2H-benzo[1,4]oxazinyl, and wherein the above-mentioned (het)aryl groups are optionally substituted with one or two $R^{10}$ which may be identical or different, $R^5$ and $R^6$, which may be identical or different, denote halogen, $C_{1-3}$-alkyl, $C_{2-3}$-alkynyl, trifluormethyl, hydroxy, $C_{1-3}$-alkyloxy, cyano, or $R^5$ together with $R^6$, if bound to adjacent carbon atoms, may additionally be methylenedioxy, difluoromethylenedioxy, ethylenedioxy, $C_{3-5}$-alkylene, or $R^7$ denotes fluorine, chlorine, bromine, iodine,
- $C_{1-4}$-alkyl, hydroxy, $C_{1-4}$-alkyloxy,
- nitro, amino, $C_{1-4}$-alkylamino, di-($C_{1-4}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkyl)-pi-perazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-4}$-alkyl)-piperazin-1-yl, 3-oxo-4-($C_{1-4}$-alkyl)-piperazin-1-yl,
- $C_{1-4}$-alkyl-carbonylamino, (het)aryl-carbonylamino, (het)aryl-$C_{1-4}$-alkyl-carbonylamino, $C_{1}$-alkyloxy-carbonylamino, aminocarbonylamino, $C_{1-4}$-alkyl-aminocarbonylamino, di -($C_{1-4}$-alkyl)aminocarbonylamino, pyrrolidin-1-yl-carbonylamino, piperidin-1-yl-carbo-nylamino, morpholin-4-yl-carbonylamino, piperazin-1-yl-carbonylamino, 4-($C_{1-4}$-alkyl) -piperazin-1-yl-carbonylamino, $C_{1-4}$-alkyl-sulfonylamino, aminosulfonylamino, $C_{1-4}$-alkylamino-sulfonylamino, di-($C_{1-4}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-4}$-alkyl)-piperazin-1-yl-sulfonylamino, ($C_{1-4}$-alkyloxy -carbonylamino) carbonylamino, (het)arylsulfonylamino, (het)aryl-$C_{1-4}$-alkyl -sulfonylamino,
- N—($C_{1-4}$-alkyl)-$C_{1-4}$-alkyl-carbonylamino, N—($C_{1-4}$-alkyl)-(het)arylcarbonylamino, N—($C_{1-4}$-alkyl)-(het)aryl-$C_{1-4}$-alkyl-carbonylamino, N—($C_{1-4}$-alkyl)-$C_{1-4}$-alkyloxy-carbonyl -amino, N-(aminocarbonyl)-$C_{1-4}$-alkylamino, N—($C_{1-4}$-alkyl-aminocarbonyl)-$C_{1-4}$-alkylamino, N-[di-($C_{1-4}$-alkyl)aminocarbonyl]-$C_{1-4}$-alkylamino, N—($C_{1-4}$-alkyl)-$C_{1-4}$-alkyl-sulfonylamino, N—($C_{1-4}$-alkyl)-(het)arylsulfonylamino, N—($C_{1-4}$-alkyl)-(het)aryl-$C_{1-4}$-alkyl-sulfonylamino,
- oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl,
- cyano, (hydroxyimino)aminomethyl, ($C_{1-4}$-alkyloxyimino)aminomethyl, carboxy, $C_{1-4}$-alkyloxy-carbonyl, aminocarbonyl, $C_{1-4}$-alkyl-aminocarbonyl, di-($C_{1-4}$-alkyl)-amino -carbonyl, pyrrolidin-1-yl-carbonyl, piperidin-1-yl-carbonyl, morpholin-4-yl-carbonyl, piperazin-1-yl-carbonyl, 4-($C_{1-4}$-alkyl)-piperazin-1-yl-carbonyl,
- $C_{1-4}$-alkyl-carbonyl, (het)aryl-carbonyl,
- carboxy-$C_{1-4}$-alkyl, $C_{1-4}$-alkyloxy-carbonyl-$C_{1-4}$-alkyl, cyano-$C_{1-4}$-alkyl, aminocarbonyl -$C_{1-4}$-alkyl, $C_{1-4}$-alkyl-aminocarbonyl-$C_{1-4}$-alkyl, di-($C_{1-4}$-alkyl)-aminocarbonyl-$C_{1-4}$-alkyl, pyrrolidin-1-yl-carbonyl-$C_{1-4}$-alkyl, piperidin-1-yl-carbonyl-$C_{1-4}$-alkyl, morpholin-4-yl-carbonyl-$C_{1-4}$-alkyl, piperazin-1-yl-carbonyl-$C_{1-4}$-alkyl, 4-($C_{1-4}$-alkyl) -piperazin-1-yl-carbonyl-$C_{1-4}$-alkyl,
- carboxy-$C_{1-4}$-alkyloxy, $C_{1-4}$-alkyloxy-carbonyl-$C_{1-4}$-alkyloxy, cyano-$C_{1-4}$-alkyloxy, amino-carbonyl-$C_{1-4}$-alkyloxy, $C_{1-4}$-alkyl-aminocarbonyl-$C_{1-4}$-alkyloxy, di-($C_{1-4}$-alkyl) -amino-carbonyl-$C_{1-4}$-alkyloxy, pyrrolidin-1 -yl-carbonyl-$C_{1-4}$-alkyl-oxy, piperidin-1-yl -carbonyl-$C_{1-4}$-alkyloxy, morpholin-4-yl-carbonyl-$C_{1-4}$-alkyl-oxy, piperazin-1-yl -carbonyl-$C_{1-4}$-alkyloxy, 4-($C_{1-4}$-alkyl)-piperazin-1 -yl-carbonyl-$C_{1-4}$-alkyloxy,
- hydroxy-$C_{1-4}$-alkyl, $C_{1-4}$-alkyloxy-$C_{1-4}$-alkyl, amino-$C_{1-4}$-alkyl, $C_{1-4}$-alkylamino-$C_{1-4}$-alkyl, di-($C_{1-4}$-alkyl)-amino-$C_{1-4}$-alkyl, pyrrolidin-1-yl-$C_{1-4}$-alkyl, $C_{1-4}$-alkylcarbonyl -amino-$C_{1-4}$-alkyl, N—($C_{1-4}$-alkyl)-$C_{1-4}$-alkylcarbonyl-amino-$C_{1-4}$-alkyl,
- 2-oxo-pyrrolidin-1 -yl-$C_{1-4}$-alkyl, piperidin-1 -yl-$C_{1-4}$-alkyl, 2-oxo-piperidin-1-yl-$C_{1-4}$-alkyl, morpholin-4-yl-$C_{1-4}$-alkyl, 3-oxo-morpholin-4-yl-$C_{1-4}$-alkyl, piperazin-1-yl-$C_{1-4}$-alkyl, 2-oxo-piperazin-1-yl-$C_{1-4}$-alkyl, 3-oxo-piperazin-1-yl-$C_{1-4}$-alkyl, 4-($C_{1-4}$-alkyl) -piperazin-1-yl-$C_{1-4}$-alkyl, 2-oxo-4-($C_{1-4}$-alkyl)-piperazin-1-yl-$C_{1-4}$-alkyl, 3-oxo-4-($C_{1-4}$-alkyl)-piperazin-1-yl-$C_{1-4}$-alkyl,
- hydroxy-$C_{1-4}$-alkyloxy, $C_{1-4}$-alkyloxy-$C_{1-4}$-alkyloxy, $C_{1-4}$-alkylsulfanyl-$C_{1-4}$-alkyloxy, $C_{1-4}$-alkylsulfinyl-$C_{1-4}$-alkyloxy, $C_{1-4}$-alkylsulfonyl-$C_{1-4}$-alkyloxy, amino-$C_{1-4}$-alkyloxy, $C_{1-4}$-alkylamino-$C_{1-4}$-alkyloxy, di-($C_{1-4}$-alkyl)-amino-$C_{1-4}$-alkyloxy, pyrrolidin-1-yl-$C_{1-4}$-alkyloxy, 2-oxo-pyrrolidin-1-yl-$C_{1-4}$-alkyloxy, piperidin-1-yl-$C_{1-4}$-alkyloxy, 2-oxo -piperidin-1-yl-$C_{1-4}$-alkyloxy, morpholin-4-yl-$C_{1-4}$-alkyloxy, 3 -oxo-morpholin-4-yl-$C_{1-4}$-alkyloxy, piperazin-1-yl-$C_{1-4}$-alkyloxy, 2-oxo-piperazin-1-yl-$C_{1-4}$-alkyloxy, 3-oxo -piperazin-1-yl-$C_{1-4}$-alkyloxy, 4-($C_{1-4}$-alkyl)-piperazin-1-yl-$C_{1-4}$-alkyloxy, 2-oxo-4-($C_{1-4}$-alkyl)-piperazin-1 -yl-$C_{1-4}$-alkyloxy, 3 -oxo-4-($C_{1-4}$-alkyl)-piperazin-1 -yl-$C_{1-4}$-alkyloxy,
- $C_{1-4}$-alkylsulfanyl, $C_{1-4}$-alkysulfinyl, $C_{1-4}$-alkylsulfonyl, $C_{1-4}$-alkylsulfonyloxy, (het)arylsulfonyl, (het)arylsulfonyloxy, trifluoromethylsulfanyl, trifluoromethylsulfinyl, trifluoromethylsulfonyl, $C_{3-6}$-cycloalkylsulfanyl, $C_{3-6}$-cycloalkylsulfinyl, $C_{3-6}$-cycloalkylsulfonyl $C_{3-6}$-cycloalkyl-$C_{1-3}$-alkylsulfanyl, $C_{3-6}$-cycloalkyl-$C_{1-3}$-alkylsulfinyl, $C_{3-6}$-cycloalkyl-$C_{1-3}$-alkylsulfonyl,
- aminosulfonyl, $C_{1-4}$-alkyl-aminosulfonyl, di-($C_{1-4}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-4}$-alkyl)-piperazin-1-yl-sulfonyl,
- difluoromethyl, trifluoromethyl, difluoromethoxy, trifluoromethoxy,
- 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl,
- $C_{3-6}$-cycloalkyl, $C_{3-6}$-cycloalkyloxy,
- hydroxy-$C_{4-6}$-cycloalkyl, $C_{1-3}$-alkyloxy-$C_{3-6}$-cycloalkyl,
- $C_{3-6}$-cycloalkyl-$C_{1-3}$-alkyl, $C_{3-6}$-cycloalkyl-$C_{1-3}$-alkyloxy,
- (het)aryl, (het)aryloxy, (het)aryl-$C_{1-3}$-alkyl, (het)aryl-$C_{1-3}$-alkyloxy, (het)aryloxy-$C_{1-3}$-alkyl, or
- tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy, wherein the above-mentioned (het)aryl is defined as described for $R^4$ hereinbefore, $R^8$ and $R^9$, which may be identical or different, are halogen, $C_{1-3}$-alkyl, trifluormethyl, hydroxy, $C_{1-3}$-alkyloxy, cyano, or $R^8$ together with $R^9$, if bound to adjacent carbon atoms, may additionally be methylenedioxy, difluoromethylenedioxy, ethylenedioxy, $C_{3-5}$-alkylene, or $R^{10}$ is $R^{10'}$ or $R^{10''}$ and $R^{10'}$ denotes halogen, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, or trifluoromethoxy, $R^{10''}$ denotes pyrrolyl, furanyl, thienyl, pyridyl, wherein in any of these groups 1 or 2 CH optionally are replaced by N atoms, or indolyl, benzofuranyl, benzothiophenyl, quinolinyl, isoquinolinyl, wherein in any of these groups 1 to 3 CH optionally are replaced by N atoms, or phenyl, naphthyl, tetrazolyl, 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-qui-noxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, or 3,4-dihydro-3-oxo-2H-benzo[1,4]oxazinyl, and wherein any of the groups mentioned hereinbefore under $R^{10''}$ optionally are substituted independently with one or two groups selected from halogen, $C_{1-3}$-alkyl, difluoromethyl, trifluoromethyl, cyano, nitro, amino, acetylamino, methylsulfonylamino, carboxy, $C_{1-4}$-alkyl-oxycarbonyl, aminocarbonyl, $C_{1-3}$-alkylaminocarbonyl, di-($C_{1-3}$-alkyl)-aminocarbonyl, aminosulfonyl, methylsulfanyl, methylsulfinyl, methylsulfonyl, hydroxy, $C_{1-3}$-alkyloxy, difluoromethoxy, and trifluoromethoxy, X denotes CH, m, n, o are each 1, and wherein the bicyclic core structure of formula I is optionally substituted independently with $R^{11}$ to $R^{14}$, wherein $R^{11}$ denotes fluorine, $C_{1-4}$-alkyl, (het)aryl, hydroxy, $C_{1-4}$-alkyloxy, cyano, carboxy, $C_{1-4}$-alkyloxycarbonyl, aminocarbonyl, $C_{1-4}$-alkylamino-carbonyl, di-($C_{1-4}$-alkyl)-aminocarbonyl, hydroxy-$C_{1-4}$-alkyl or $C_{1-3}$-alkyloxy-$C_{1-4}$-alkyl, wherein (het)aryl is as described for $R^4$ hereinbefore, $R^{12}$ denotes fluorine or $C_{1-4}$-alkyl, and $R^{13}$ and $R^{14}$, which may be identical or different, denote $C_{1-4}$-alkyl, and wherein the above-mentioned alkyl or alkylene moieties are branched or unbranched, or a physiologically acceptable salt with an inorganic or organic acid or base or a salt thereof wherein the patient is suffering from a metabolic disorder selected from the group consisting of type 1 and type 2 diabetes mellitus, retinopathy, nephropathy or neuropathies, diabetic foot, ulcers, macroangiopathies, slow or poor wound healing, metabolic acidosis or ketosis, reactive hypoglycaemia, hyperinsulinaemia, glucose metabolic disorder, insulin resistance, metabolic syndrome, dyslipidaemias of different origins, atherosclerosis obesity, high blood pressure, chronic heart failure, edema and hyperuricaemia.

9. A process for preparing a pharmaceutical composition, comprising incorporating a compound according to claim 1 or a physiologically acceptable salt with an inorganic or organic acid or base in one or more inert carriers and/or diluents by a non-chemical method.

* * * * *